(12) United States Patent
Shinohara et al.

(10) Patent No.: US 10,342,819 B2
(45) Date of Patent: Jul. 9, 2019

(54) OLIGONUCLEOTIDE HAVING NON-NATURAL NUCLEOTIDE AT 5'-TERMINAL THEREOF

(71) Applicant: Kyowa Hakko Kirin Co., Ltd., Tokyo (JP)

(72) Inventors: Fumikazu Shinohara, Tokyo (JP); Asana Makino, Tokyo (JP); Junichiro Yamamoto, Tokyo (JP); Takahiro Nakajima, Tokyo (JP); Taiji Oashi, Tokyo (JP); Michihiko Suzuki, Tokyo (JP); Jun-ichi Saito, Tokyo (JP); Tomoyuki Nishikawa, Tokyo (JP); Masayoshi Nakoji, Tokyo (JP); Yuichi Takahashi, Tokyo (JP); Yasuo Kouda, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 177 days.

(21) Appl. No.: 15/123,438

(22) PCT Filed: Mar. 3, 2015

(86) PCT No.: PCT/JP2015/056249
§ 371 (c)(1),
(2) Date: Sep. 2, 2016

(87) PCT Pub. No.: WO2015/133491
PCT Pub. Date: Sep. 11, 2015

(65) Prior Publication Data
US 2017/0354673 A1 Dec. 14, 2017

(30) Foreign Application Priority Data
Mar. 3, 2014 (JP) .................. 2014-040872

(51) Int. Cl.
A61K 31/7115 (2006.01)
A61K 31/7076 (2006.01)
(Continued)

(52) U.S. Cl.
CPC ...... A61K 31/7115 (2013.01); A61K 31/5377 (2013.01); A61K 31/7076 (2013.01);
(Continued)

(58) Field of Classification Search
CPC ......... C07H 19/06; C07H 19/10; C07H 19/16
See application file for complete search history.

(56) References Cited
U.S. PATENT DOCUMENTS
5,906,918 A 5/1999 Box et al.
2011/0087015 A1 4/2011 Hirano et al.
(Continued)

FOREIGN PATENT DOCUMENTS
JP 53-63399 6/1978
JP 59-156297 9/1984
(Continued)

OTHER PUBLICATIONS
Millington (Nucleosides, Nucleotides and nucleic acid; 31; 328-338, 2012).*
(Continued)

Primary Examiner — Pancham Bakshi
(74) Attorney, Agent, or Firm — Wenderoth, Lind & Ponack, L.L.P.

(57) ABSTRACT
An oligonucleotide having a nucleotide residue or a nucleoside residue represented by formula (I) {wherein $X^1$ is an oxygen atom or the like, $R^1$ is formula (IIA) (wherein $R^{5A}$ is halogen or the like, and $R^{6A}$ is a hydrogen atom or the like), formula (IVA) (wherein $Y^{3A}$ is a nitrogen atom or the like, and $Y^{4A}$ is CH or the like), or the like, $R^2$ is a hydrogen atom, hydroxy, halogen, or optionally substituted lower alkoxy, and $R^3$ is a hydrogen atom or the like, or formula (VI) (wherein n2 is 1, 2 or 3)} at the 5' end thereof, wherein the nucleotide residue or the nucleoside residue binds to an adjacent nucleotide residue through the oxygen atom at position 3, is provided.

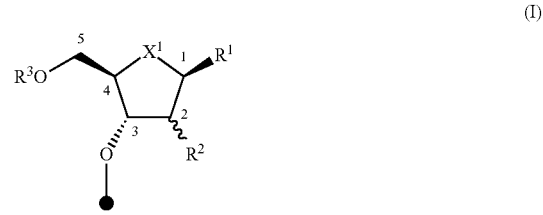

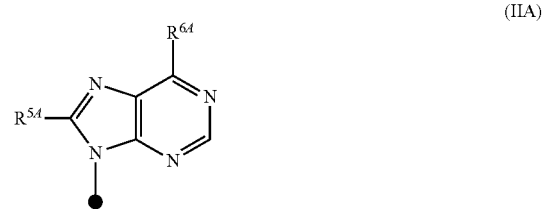

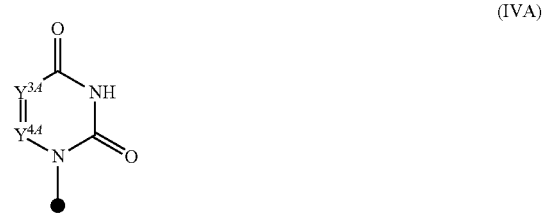

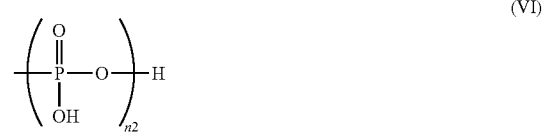

26 Claims, 12 Drawing Sheets
Specification includes a Sequence Listing.

(51) Int. Cl.
| | |
|---|---|
| A61K 31/713 | (2006.01) |
| C07H 19/16 | (2006.01) |
| C07H 19/167 | (2006.01) |
| C07H 19/173 | (2006.01) |
| C07H 19/20 | (2006.01) |
| C07H 19/06 | (2006.01) |
| C07H 19/10 | (2006.01) |
| C07H 21/00 | (2006.01) |
| C07H 23/00 | (2006.01) |
| C12N 15/113 | (2010.01) |
| A61K 31/5377 | (2006.01) |
| C12N 15/11 | (2006.01) |

(52) U.S. Cl.
CPC ........... A61K 31/713 (2013.01); C07H 19/06 (2013.01); C07H 19/10 (2013.01); C07H 19/16 (2013.01); C07H 19/167 (2013.01); C07H 19/173 (2013.01); C07H 19/20 (2013.01); C07H 21/00 (2013.01); C07H 23/00 (2013.01); C12N 15/113 (2013.01); C12N 15/111 (2013.01); C12N 2310/14 (2013.01); C12N 2310/32 (2013.01); C12N 2310/33 (2013.01); C12N 2320/31 (2013.01)

(56) References Cited

U.S. PATENT DOCUMENTS

| | | |
|---|---|---|
| 2013/0102652 A1 | 4/2013 | Burrows et al. |
| 2014/0330004 A1 | 11/2014 | Shinohara et al. |
| 2014/0343129 A1 | 11/2014 | de Fougerolles et al. |
| 2015/0376611 A1 | 12/2015 | Shinohara et al. |

FOREIGN PATENT DOCUMENTS

| | | |
|---|---|---|
| WO | 95/21184 | 8/1995 |
| WO | 03/004603 | 1/2003 |
| WO | 2011/119674 | 9/2011 |
| WO | 2012/158736 | 11/2012 |
| WO | 2013/090186 | 6/2013 |
| WO | 2014/034934 | 3/2014 |

OTHER PUBLICATIONS

Partial Supplementary European Search Report dated Jul. 3, 2017 issued in European counterpart Application No. EP 15758130.7.
Yoshihiro Iijima et al., "Modified oligodeoxynucleotide primers for reverse-transcription of target RNAs that can discriminate among length variants at the 3'-terminus", Organic & Biomolecular Chemistry, vol. 11, No. 47, 2013, pp. 8276-8272.
Christopher L. Millington, et al., "Convenient and Efficient Syntheses of Oligodeoxyribonucleotides Containing $O^6$-(Carboxymethyl)Guanine and $O^6$-(4-Oxo-4-(3-Pyridyl)Butyl)Guanine", Nucleosides, Nucleotides and Nucleic Acids, vol. 31, No. 4, 2012, pp. 328-338.
LászlóÖtvös, et al., "Synthesis and Enzymatic Characterization of $P_1$-Thio-$P_2$-Oxo Trideoxynucleoside Diphosphates Having AZT, FdU, or dT at the 3'-Position", Nucleosides, Nucleotides and Nucleic Acid, vol. 21. No. 1, 2002, pp. 79-82.
Denise M. Kenski et al., "siRNA-optimized Modifications for Enhanced In Vivo Activity", Molecular Therapy—Nucleic Acids, vol. 1, e5, 2012, pp. 1-8.
Sayda M. Elbashir et al., "Duplexes of 21-nucleotide RNAs mediate RNA interference in cultured mammalian cells", Nature, vol. 411, May 24, 2011, pp. 494-498.
Chad V. Pecot et al., "RNA interference in the clinic: challenges and future directions", Nature Reviews, vol. 11, Jan. 2011, pp. 59-67.
Tomoko Kawamata et al., "Making RISC", Trends in Biochemical Sciences, vol. 35, 2010, pp. 368-376.
James S. Parker, "How to slice: snapshots of Argonaute in action", Silence, vol. 1, No. 3, 2010, pp. 1-10.
Nicole T. Schirle et al., "The Crystal Structure of Human Argonaute2", Science, vol. 336, May 25, 2012, pp. 1037-1040.
R. Vijayakrishnan, "Structure-based drug design and modern medicine", Journal of Postgraduate Medicine, vol. 55, Issue 4, 2009, pp. 301-304.
Jia Liu et al., "Synthesis of Photoactive DNA: Incorporation of 8-Bromo-2'-Deoxyadenosine into Synthetic Oligodeoxynucleotides", Tetrahedron Letters, vol. 33, No. 30, 1992, pp. 4265-4268.
Shinya Shibutani et al., "Translesional Biochemistry on DNA Templates Containing 8-Oxo-7,8-dihydrodeoxyadenosine", Biochemistry, vol. 32, 1993, pp. 4615-4621.
József Béres et al., "Synthesis, Structure, and Antitumor and Antiviral Activities of a Series of 5-Halouridine Cyclic 3',5'-Monophosphates", J. Med. Chem., vol. 29, 1986, pp. 488-493.
Justine Michel et al., "Triplex Stability of Oligodeoxynucleotides Containing Substituted quinazoline-2,4-(1H,3H)-dione", Tetrahedron, vol. 53, No. 25, 1997, pp. 8457-8478.
Yitzhak Tor et al., "Designing new isomorphic fluorescent nucleobase analogues: the thieno[3,2-d]pyrimidine core", Tetrahedron, vol. 63, 2007, pp. 3608-3614.
Hervé Seitz et al., "A 5'-uridine amplifies miRNA/miRNA* asymmetry in *Drosophila* by promoting RNA-induced silencing complex formation", Silence, vol. 2, No. 4, pp. 1-10.
Filipp Frank et al., "Structural basis for 5'-nucleotide base-specific recognition of guide RNA by human AGO2", Nature, vol. 465, Jun. 10, 2010, pp. 818-822.
Hayden Peacock et al., "Chemical Modification of siRNA Bases to Probe and Enhance RNA Interference", The Journal of Organic Chemistry, vol. 76, 2011, pp. 7295-7300.
Glen F. Deleavey et al., "Designing Chemically Modified Oligonucleotides for Targeted Gene Silencing", Chemistry & Biology, vol. 19, Aug. 24, 2012, pp. 937-954.
Walt F. Lima et al., "RNA: Processing and Catalysis: Binding and Cleavage Specificities of Human Argonaute2", The Journal of Biological Chemistry, vol. 284, Jul. 22, 2009, pp. 26017-26028.
Piet Herdewijn, "Heterocyclic Modifications of Oligonucleotides and Antisense Technology", Antisense & Nucleic Acid Drug Development, vol. 10, 2000, pp. 297-310
Ya-Lin Chiu et al., "siRNA function in RNAi: A chemical modification analysis", Cold Spring Harbor Laboratory Press., vol. 9, 2003, pp. 1034-1048.
Montserrat Terrazas et al., "RNA major groove modifications improve siRNA stability and biological activity", Nucleic Acids Research, vol. 37, No. 2, 2009, pp. 346-353.
Haripriya Addepalli et al., "Modulation of thermal stability can enhance the potency of siRNA", Nucleic Acids Research, vol. 38, No. 20, 2010, pp. 7320-7331.
Hayden Peacock et al., "$N^2$-Modified 2-aminopurine ribonucleosides as minor-groove-modulating adenosine replacements in duplex RNA", Organic Letters, vol. 12, No. 5, 2010, pp. 1044-1047.
Hayden Peacock et al., "Minor-Groove-Modulating Adenosine Replacements Control Protein Binding and RNAi Activity in siRNAs", ACS Chemical Biology, vol. 5, No. 12, Sep. 23, 2010, pp. 1115-1124.
Vera Mikat et al., "Light-dependent RNA interference with nucleobased-caged siRNAs", RNA, vol. 13, 2007, pp. 2341-2347.
Florian Eberle et al., "Modifications in Small Interfering RNA That Separate Immunostimulation from RNA Interference", The Journal of Immunology, vol. 180, 2008, pp. 3229-3237.
Armando R. Hernández et al., "Steric Restrictions of RISC in RNA Interference Identified with Size-Expanded RNA Nucleobases", ACS Chem. Biol., vol. 7, 2012, pp. 1454-1461.
Kazumitsu Onizuka et al., "Short Interfering RNA Guide Strand Modifiers from Computational Screening", The Journal of the American Chemical Society, vol. 135, 2013, pp. 17069-17077.
Jose M. Ibarra-Soza et al., "7-Substituted 8-aza-7-deazaadenosines for modification of the siRNA major groove", Org. Biomol. Chem., vol. 10, No. 32, Aug. 28, 2012, pp. 6491-6497.
Jie Xia et al., "Gene Silencing Activity of siRNAs with a Ribodifluorotoluyl Nucleotide", ACS Chemical Biology, vol. 1, No. 3, Apr. 17, 2006, pp. 176-183.

(56) References Cited

OTHER PUBLICATIONS

Yogesh S. Sanghvi et al., "Antisense oligodeoxynucleotides: synthesis, biophysical and biological evaluation of oligodeoxynucleotides: containing modified pyrimidines", Nucleic Acids Research, vol. 21, No. 14, 1993, pp. 3197-3203.
Susan M. Freier et al., "The ups and downs of nucleic acid duplex stability: structure-stability studies on chemically-modified DNA:RNA duplexes", Nucleic Acids Research, vol. 25, No. 22, 1997, pp. 4429-4443.
Brian C. Froehler et al., "Oligodeoxynucleotides Containing C-5 Propyne Analogs of 2'-Deoxyuridine and 2'-Deoxycytidine", Tetrahedron Letters, vol. 33, No. 37, 1992, pp. 5307-5310.
Richard W. Wagner et al., "Antisense Gene Inhibition by Oligonucleotides Containing C-5 Propyne Pyrimidines", Science, vol. 260, Jun. 4, 1993, pp. 1510-1513.
Courtney Moulds et al., "Site and Mechanism of Antisense Inhibition by C-5 Propyne Oligonucleotides", Biochemistry, vol. 34, 1995, p. 5044-5053.
John W. Stuart et al., "Structure of the Trinucleotide D-acp$^3$U-A with Coordinated Mg$^{2+}$ Demonstrates that Modified Nucleosides Contribute to Regional Conformations of RNA", Nucleosides and Nucleotides, vol. 15, No. 5, Aug. 15, 2006, pp. 1009-1028.

International Search Report dated May 12, 2015 in corresponding International Application No. PCT/JP2015/056249.
Holmes et al., "Synthesis and Oligonucleotide Incorporation of Nucleotide Analogues Containing Pendant Imidazolyl or Amino Functionalities—The Search for Sequence-Specific Artifical Ribonucleases", European Journal of Organic Chemistry, 2005, vol. 2005, No. 24, pp. 5171-5183.
Haouz et al., "Enzymatic and Structural Analysis of Inhibitors Designed against *Mycobacterium tuberculosis* Thymidylate Kinase", The Journal of Biological Chemistry, 2002, vol. 278, No. 7, pp. 4963-4971.
Rodrigues-Correia et al., "Comparison of the duplex-destabilizing effects of nucleobase-caged oligonucleotides", Analytical and Bioanalytical Chemistry, 2010, vol. 399, No. 1, pp. 441-447.
Ferentz, A.E. et al., "Aminolysis of 2'-deoxyinosine aryl ethers: nucleoside model studies for the synthesis of functionally tethered oligonucleotides", Nucleosides & Nucleotides, 1992, vol. 11, No. 10, pp. 1749-1763.
Hayatsu, H. et al., "N-Sulfomethylation of guanine, adenine and cytosine with formaldehyde-bisulfite. A selective modification of guanine in DNA", Nucleic Acids Research, 1982, vol. 10, No. 20, pp. 6281-6293.

\* cited by examiner

[Fig. 1]
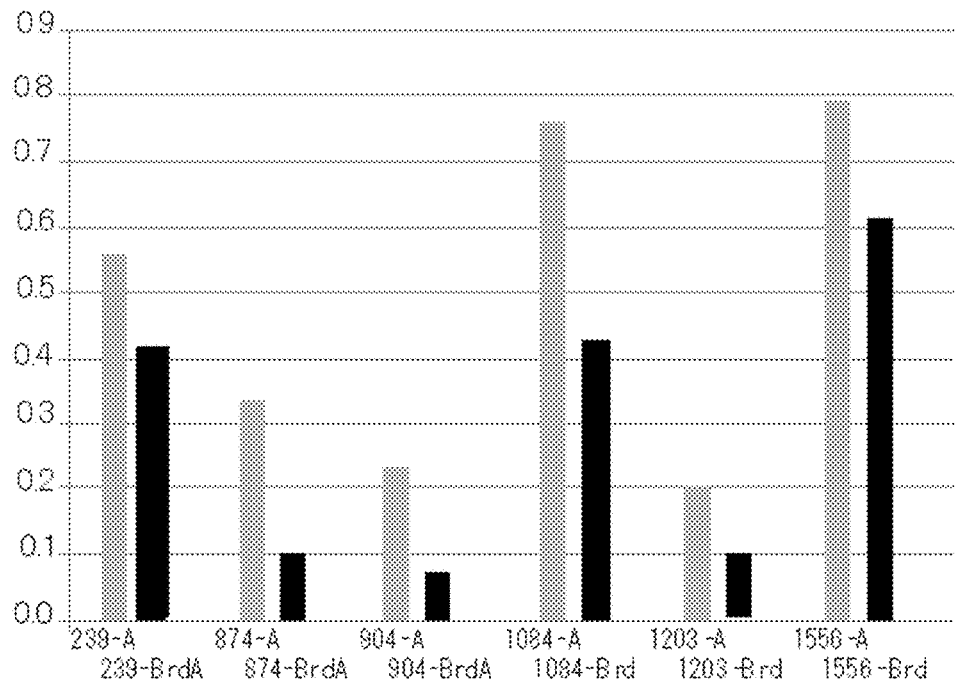
[Fig. 2]
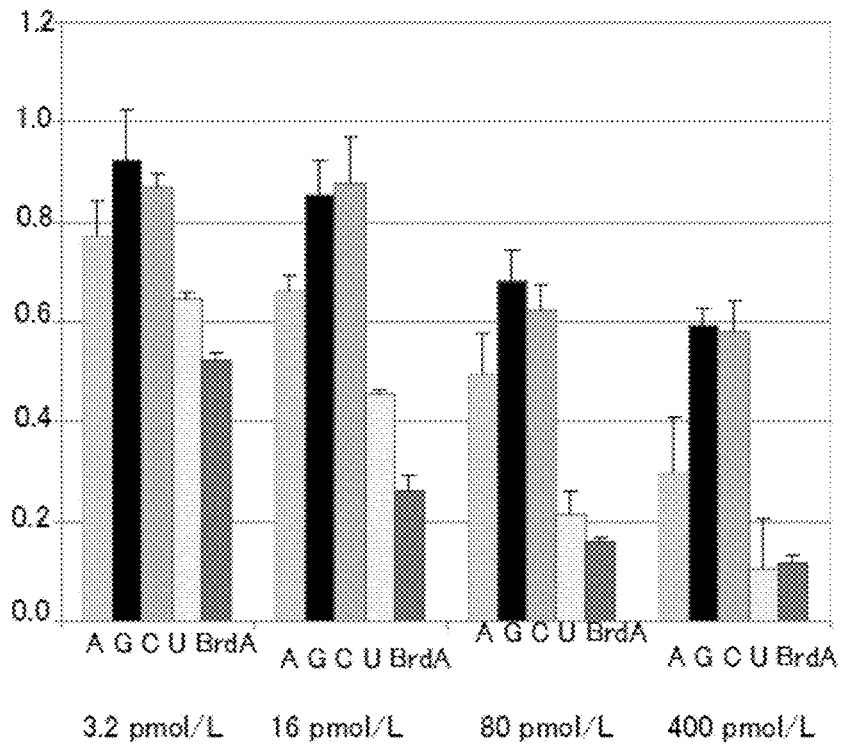

[Fig. 3]
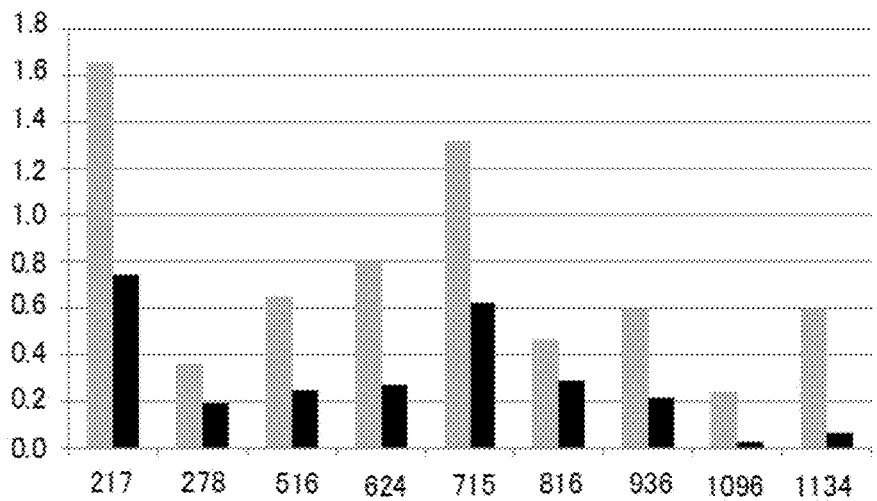
[Fig. 4]
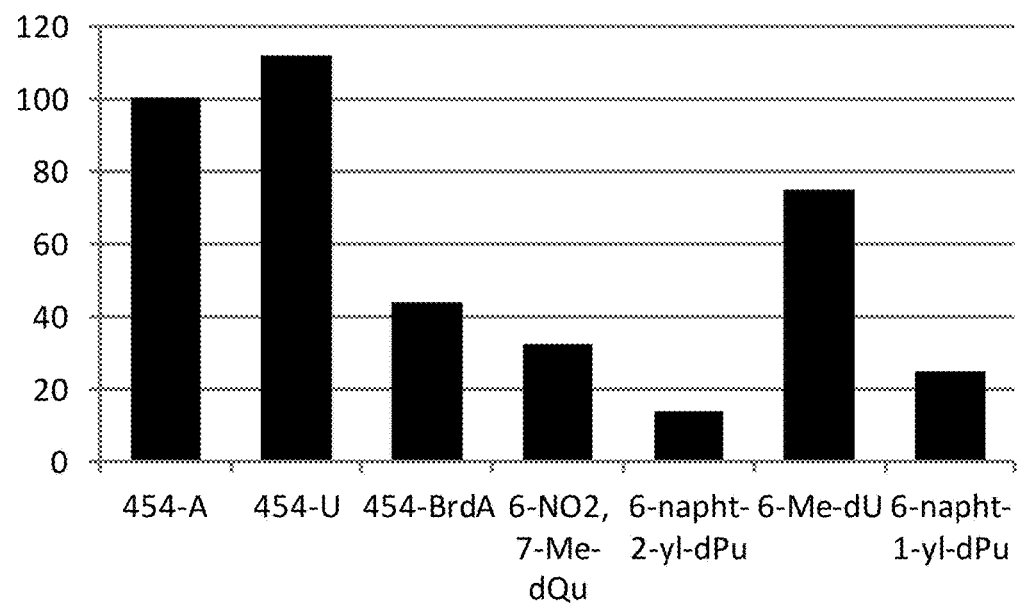

[Fig. 5]
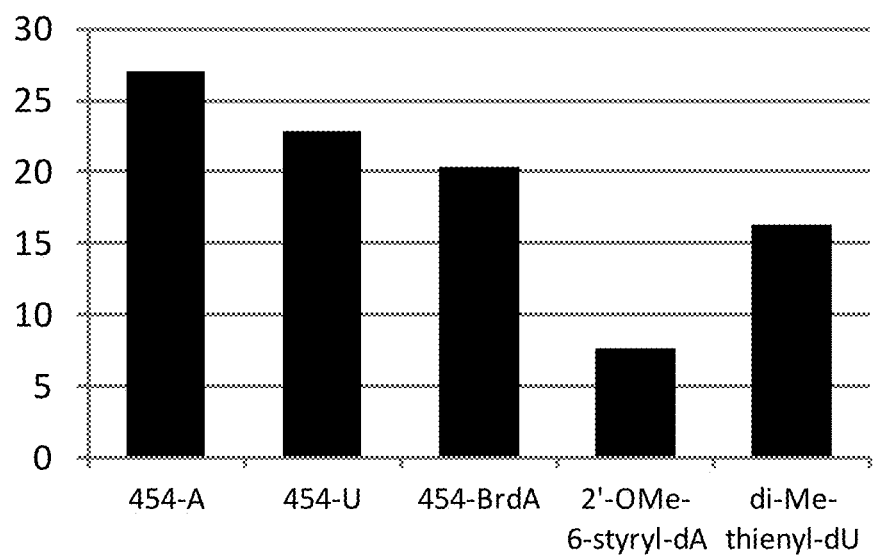
[Fig. 6]
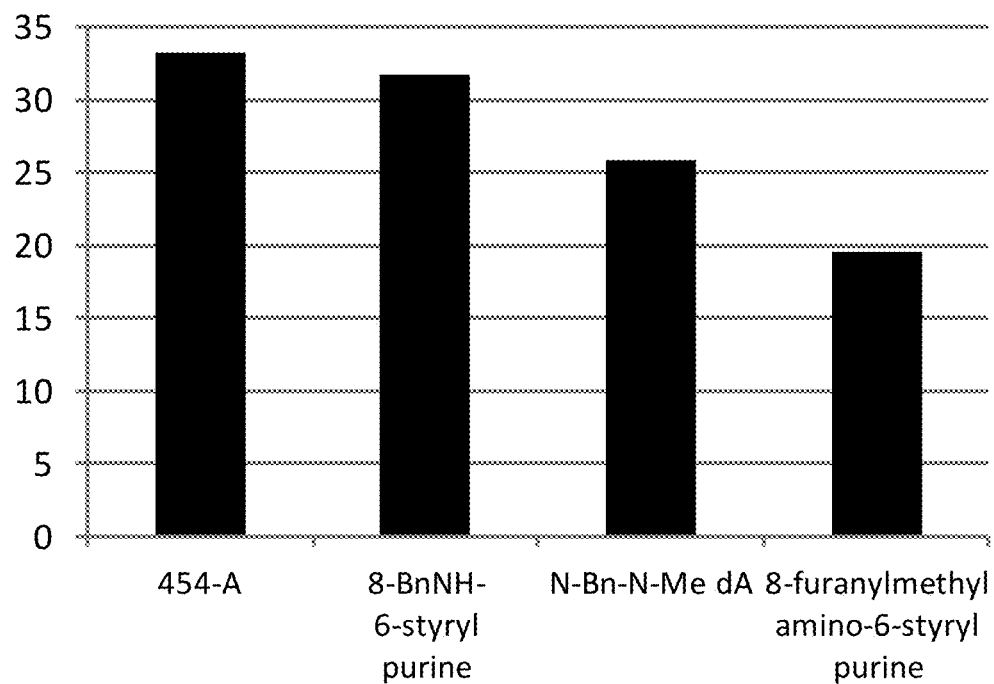

[Fig. 7]
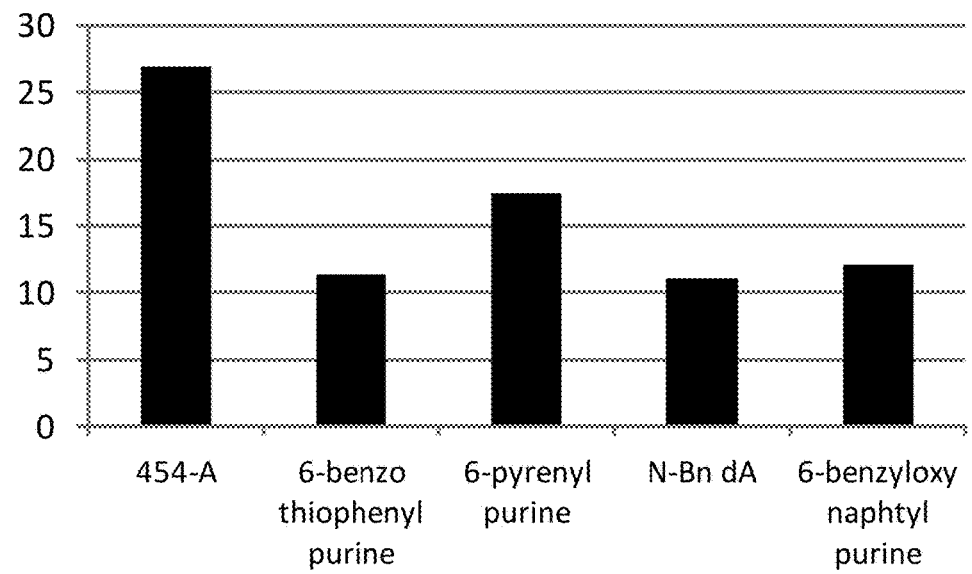
[Fig. 8]
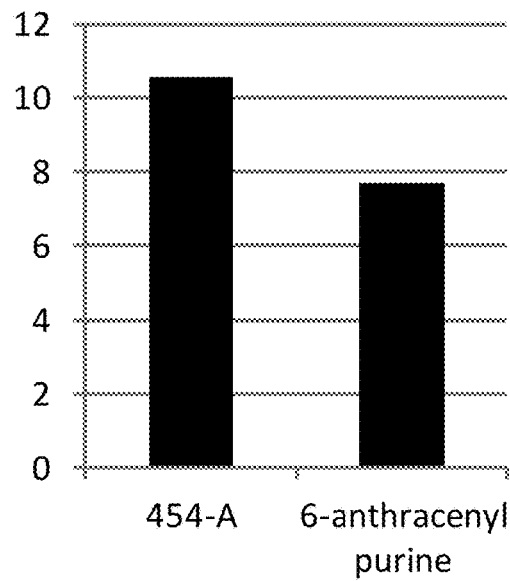

[Fig. 9]
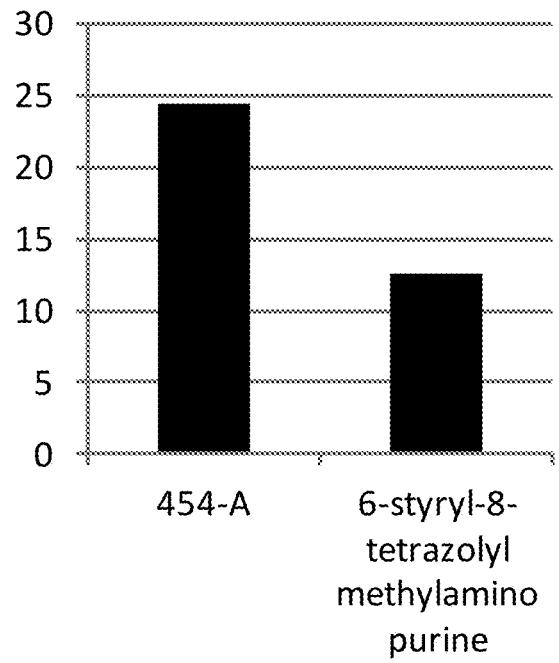
[Fig. 10]
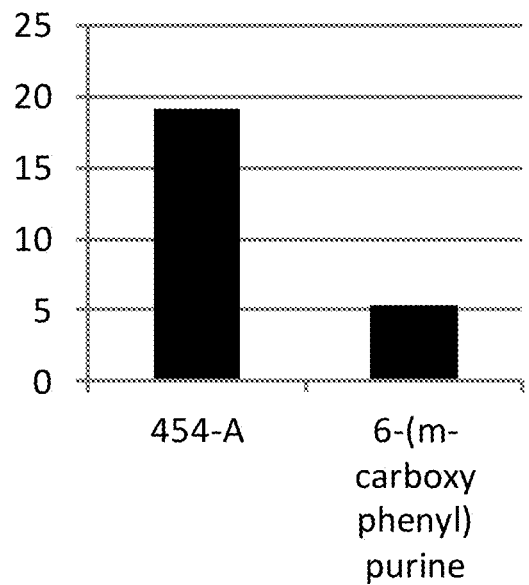

[Fig. 11]
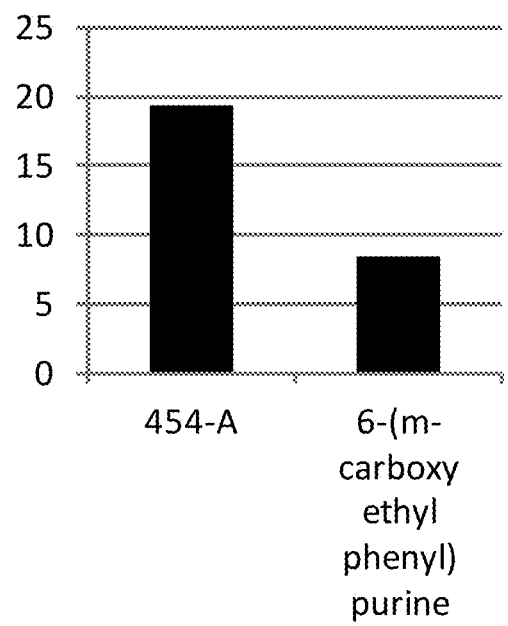
[Fig. 12]
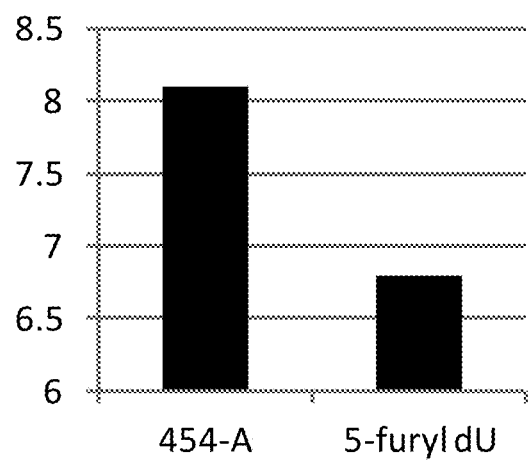

[Fig. 13]
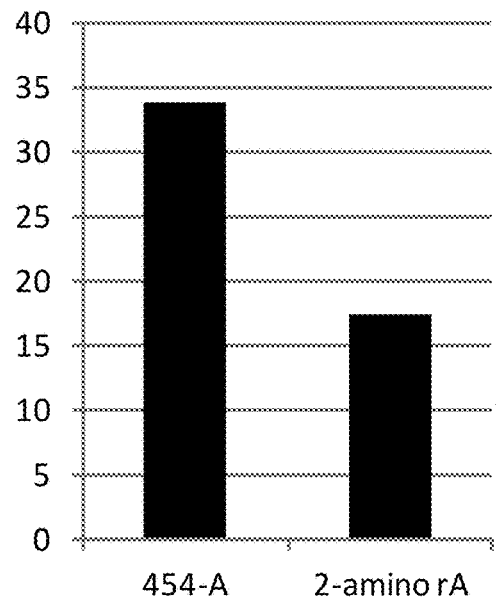
[Fig. 14]
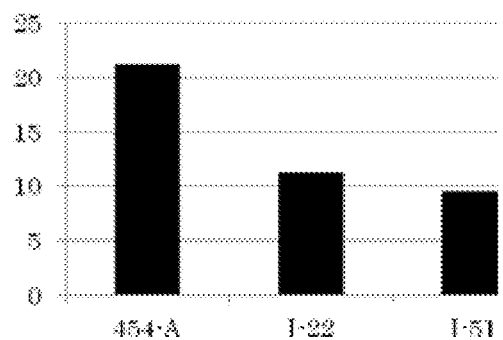
[Fig. 15]
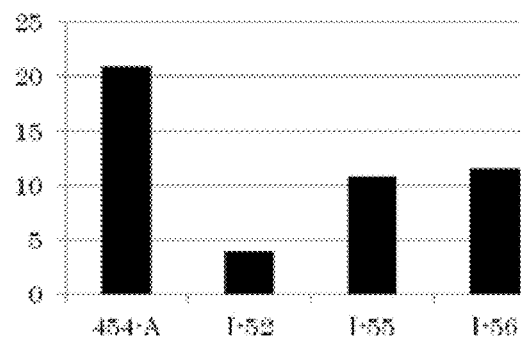

[Fig. 16]
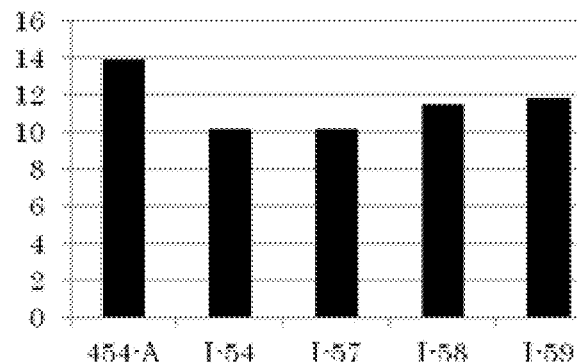
[Fig. 17]
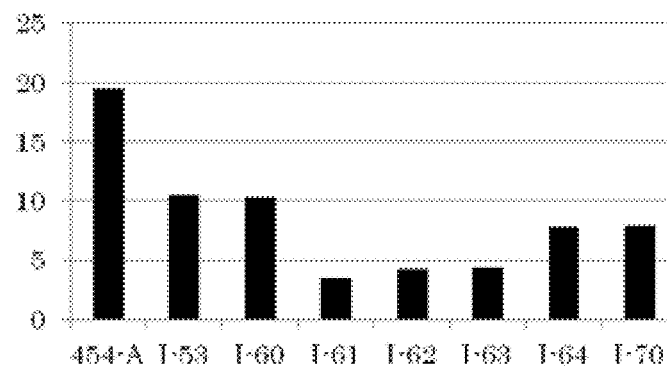
[Fig. 18]
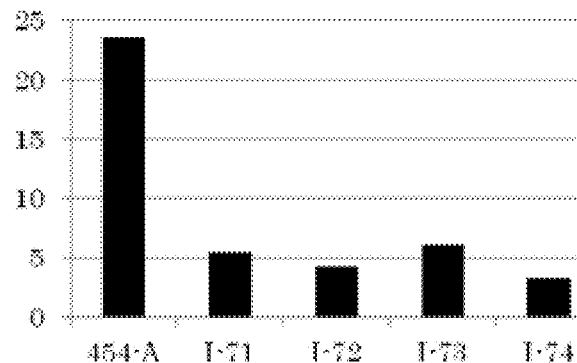

[Fig. 19]
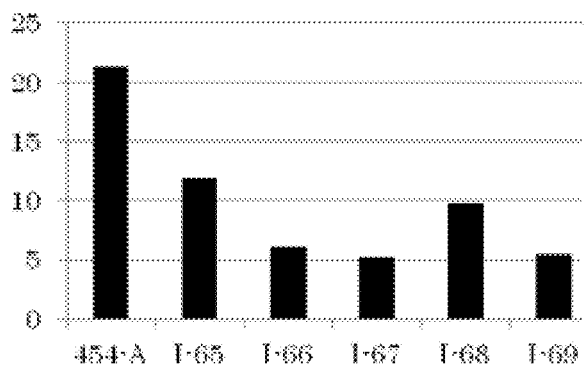
[Fig. 20]
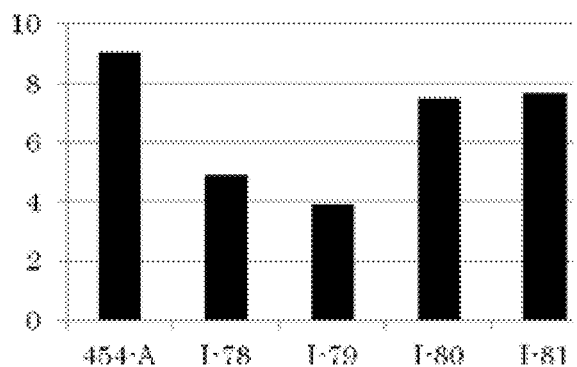
[Fig. 21]
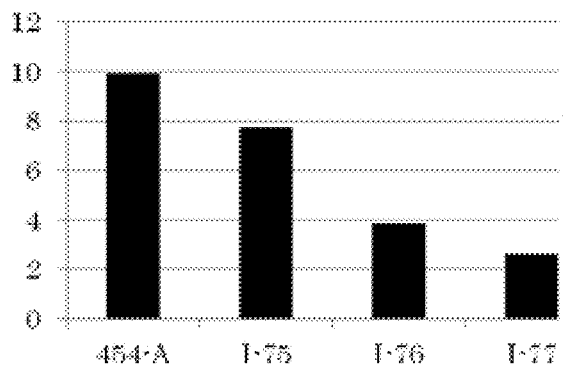

[Fig. 22]
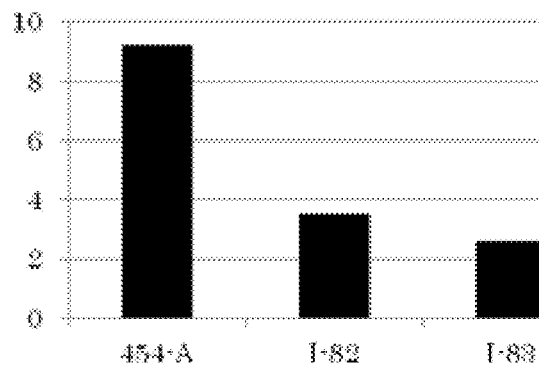
[Fig. 23]
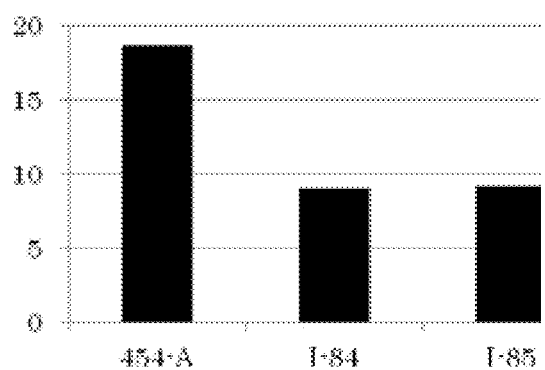
[Fig. 24]
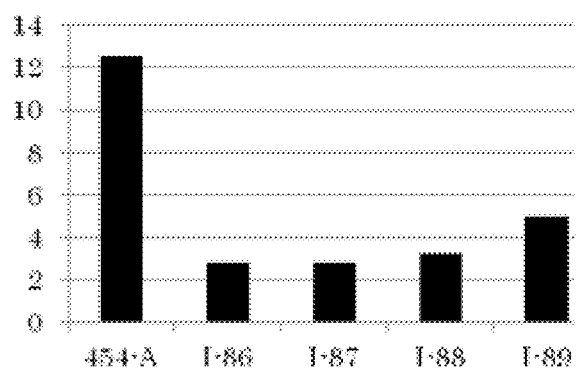

[Fig. 25]
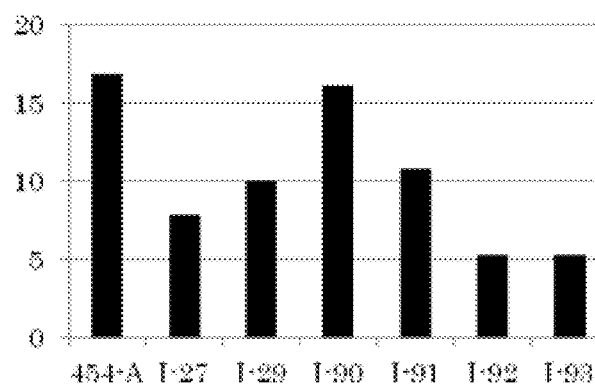
[Fig. 26]
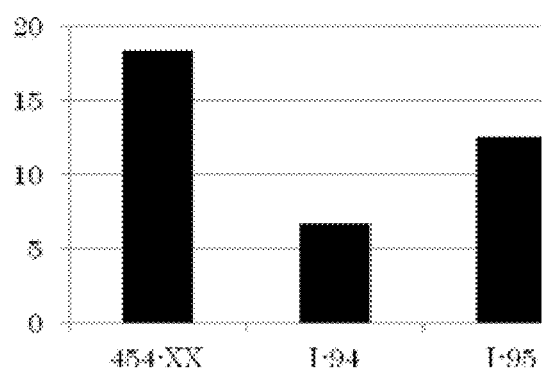
[Fig. 27]
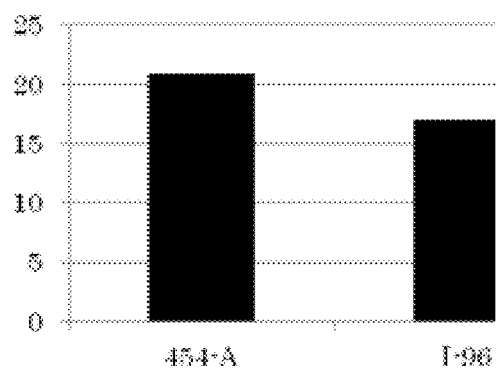

[Fig. 28]
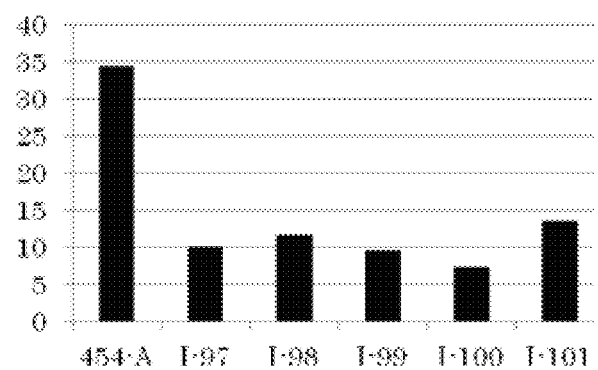

SEQUENCE LISTING

<160> NUMBER OF SEQ ID NOS: 69

<210> SEQ ID NO 1
<211> LENGTH: 21
<212> TYPE: RNA
<213> ORGANISM: Artificial Sequence
<220> FEATURE:
<223> OTHER INFORMATION: 239-BrdA sense

<400> SEQUENCE: 1
ugcagcgaga auagcuugua g                                              21

<210> SEQ ID NO 2
<211> LENGTH: 21
<212> TYPE: RNA
<213> ORGANISM: Artificial Sequence
<220> FEATURE:
<223> OTHER INFORMATION: 239-BrdA antisense
<220> FEATURE:
<221> NAME/KEY: misc_feature
<222> LOCATION: (1)..(1)
<223> OTHER INFORMATION: n is 8-bromo-2'-deoxyadenosine monophosphate

<400> SEQUENCE: 2
ncaagcuauu cucgcugcac a                                              21

<210> SEQ ID NO 3
<211> LENGTH: 21
<212> TYPE: RNA
<213> ORGANISM: Artificial Sequence
<220> FEATURE:
<223> OTHER INFORMATION: 874-BrdA sense

<400> SEQUENCE: 3
uagcuucuuc gcuaagagua c                                              21

<210> SEQ ID NO 4
<211> LENGTH: 21
<212> TYPE: RNA
<213> ORGANISM: Artificial Sequence
<220> FEATURE:
<223> OTHER INFORMATION: 874-BrdA antisense
<220> FEATURE:
<221> NAME/KEY: misc_feature
<222> LOCATION: (1)..(1)
<223> OTHER INFORMATION: n is 8-bromo-2'-deoxyadenosine monophosphate or
      5-fluoro-2'-deoxyuridine monophosphate

<400> SEQUENCE: 4
ncucuuagcg aagaagcuaa a                                              21

<210> SEQ ID NO 5
<211> LENGTH: 21
<212> TYPE: RNA
<213> ORGANISM: Artificial Sequence
<220> FEATURE:
<223> OTHER INFORMATION: 904-BrdA sense

<400> SEQUENCE: 5
caaguacgac cuaagcaauu u                                              21

<210> SEQ ID NO 6
<211> LENGTH: 21
<212> TYPE: RNA
<213> ORGANISM: Artificial Sequence
<220> FEATURE:
<223> OTHER INFORMATION: 904-BrdA antisense
<220> FEATURE:

```
<221> NAME/KEY: misc_feature
<222> LOCATION: (1)..(1)
<223> OTHER INFORMATION: n is 8-bromo-2'-deoxyadenosine monophosphate

<400> SEQUENCE: 6
nuugcuuagg ucguacuugu c                                              21

<210> SEQ ID NO 7
<211> LENGTH: 21
<212> TYPE: RNA
<213> ORGANISM: Artificial Sequence
<220> FEATURE:
<223> OTHER INFORMATION: 1084-BrdA sense

<400> SEQUENCE: 7
aggcaaggug gugcccuuuu u                                              21

<210> SEQ ID NO 8
<211> LENGTH: 21
<212> TYPE: RNA
<213> ORGANISM: Artificial Sequence
<220> FEATURE:
<223> OTHER INFORMATION: 1084-BrdA antisense
<220> FEATURE:
<221> NAME/KEY: misc_feature
<222> LOCATION: (1)..(1)
<223> OTHER INFORMATION: n is 8-bromo-2'-deoxyadenosine monophosphate

<400> SEQUENCE: 8
naagggcacc accuugccua c                                              21

<210> SEQ ID NO 9
<211> LENGTH: 21
<212> TYPE: RNA
<213> ORGANISM: Artificial Sequence
<220> FEATURE:
<223> OTHER INFORMATION: 1203-BrdA sense

<400> SEQUENCE: 9
uuaacaaccc cgaggcuaua a                                              21

<210> SEQ ID NO 10
<211> LENGTH: 21
<212> TYPE: RNA
<213> ORGANISM: Artificial Sequence
<220> FEATURE:
<223> OTHER INFORMATION: 1203-BrdA antisense
<220> FEATURE:
<221> NAME/KEY: misc_feature
<222> LOCATION: (1)..(1)
<223> OTHER INFORMATION: n is 8-bromo-2'-deoxyadenosine monophosphate

<400> SEQUENCE: 10
nuagccucgg gguuguuaac g                                              21

<210> SEQ ID NO 11
<211> LENGTH: 21
<212> TYPE: RNA
<213> ORGANISM: Artificial Sequence
<220> FEATURE:
<223> OTHER INFORMATION: 1556-BrdA sense

<400> SEQUENCE: 11
gacgaggugc cuaaaggauu g                                              21

<210> SEQ ID NO 12
<211> LENGTH: 21
```

```
<212> TYPE: RNA
<213> ORGANISM: Artificial Sequence
<220> FEATURE:
<223> OTHER INFORMATION: 1556-BrdA antisense
<220> FEATURE:
<221> NAME/KEY: misc_feature
<223> OTHER INFORMATION: n is 8-bromo-2'-deoxyadenosine monophosphate or
      5-fluoro-2'-deoxyuridine monophosphate
<220> FEATURE:
<221> NAME/KEY: misc_feature
<222> LOCATION: (1)..(1)
<223> OTHER INFORMATION: n is a, c, g, or u

<400> SEQUENCE: 12
nuccuuuagg caccucgucc a                                              21

<210> SEQ ID NO 13
<211> LENGTH: 21
<212> TYPE: RNA
<213> ORGANISM: Artificial Sequence
<220> FEATURE:
<223> OTHER INFORMATION: 239-A antisense

<400> SEQUENCE: 13
acaagcuauu cucgcugcac a                                              21

<210> SEQ ID NO 14
<211> LENGTH: 21
<212> TYPE: RNA
<213> ORGANISM: Artificial Sequence
<220> FEATURE:
<223> OTHER INFORMATION: 874-A antisense

<400> SEQUENCE: 14
acucuuagcg aagaagcuaa a                                              21

<210> SEQ ID NO 15
<211> LENGTH: 21
<212> TYPE: RNA
<213> ORGANISM: Artificial Sequence
<220> FEATURE:
<223> OTHER INFORMATION: 904-A antisense

<400> SEQUENCE: 15
auugcuuagg ucguacuugu c                                              21

<210> SEQ ID NO 16
<211> LENGTH: 21
<212> TYPE: RNA
<213> ORGANISM: Artificial Sequence
<220> FEATURE:
<223> OTHER INFORMATION: 1084-A antisense

<400> SEQUENCE: 16
aaagggcacc accuugccua c                                              21

<210> SEQ ID NO 17
<211> LENGTH: 21
<212> TYPE: RNA
<213> ORGANISM: Artificial Sequence
<220> FEATURE:
<223> OTHER INFORMATION: 1203-A antisense

<400> SEQUENCE: 17
auagccucgg gguuguuaac g                                              21

<210> SEQ ID NO 18
```

```
<211> LENGTH: 21
<212> TYPE: RNA
<213> ORGANISM: Artificial Sequence
<220> FEATURE:
<223> OTHER INFORMATION: 1556-A antisense

<400> SEQUENCE: 18
auccuuuagg caccucgucc a                                             21

<210> SEQ ID NO 19
<211> LENGTH: 21
<212> TYPE: RNA
<213> ORGANISM: Artificial Sequence
<220> FEATURE:
<223> OTHER INFORMATION: 874-G sense

<400> SEQUENCE: 19
uagcuucuuc gcuaagagca c                                             21

<210> SEQ ID NO 20
<211> LENGTH: 21
<212> TYPE: RNA
<213> ORGANISM: Artificial Sequence
<220> FEATURE:
<223> OTHER INFORMATION: 874-G antisense

<400> SEQUENCE: 20
gcucuuagcg aagaagcuaa a                                             21

<210> SEQ ID NO 21
<211> LENGTH: 21
<212> TYPE: RNA
<213> ORGANISM: Artificial Sequence
<220> FEATURE:
<223> OTHER INFORMATION: 874-C sense

<400> SEQUENCE: 21
uagcuucuuc gcuaagagga c                                             21

<210> SEQ ID NO 22
<211> LENGTH: 21
<212> TYPE: RNA
<213> ORGANISM: Artificial Sequence
<220> FEATURE:
<223> OTHER INFORMATION: 874-C antisense

<400> SEQUENCE: 22
ccucuuagcg aagaagcuaa a                                             21

<210> SEQ ID NO 23
<211> LENGTH: 21
<212> TYPE: RNA
<213> ORGANISM: Artificial Sequence
<220> FEATURE:
<223> OTHER INFORMATION: 874-U sense

<400> SEQUENCE: 23
uagcuucuuc gcuaagagaa c                                             21

<210> SEQ ID NO 24
<211> LENGTH: 21
<212> TYPE: RNA
<213> ORGANISM: Artificial Sequence
<220> FEATURE:
<223> OTHER INFORMATION: 874-U antisense

<400> SEQUENCE: 24
```

```
ucucuuagcg aagaagcuaa a                                              21

<210> SEQ ID NO 25
<211> LENGTH: 21
<212> TYPE: RNA
<213> ORGANISM: Artificial Sequence
<220> FEATURE:
<223> OTHER INFORMATION: 454-5-F-dU sense

<400> SEQUENCE: 25
ggauagcaag accgacuaac a                                              21

<210> SEQ ID NO 26
<211> LENGTH: 21
<212> TYPE: RNA
<213> ORGANISM: Artificial Sequence
<220> FEATURE:
<223> OTHER INFORMATION: 454-5-F-dU antisense
<220> FEATURE:
<221> NAME/KEY: misc_feature
<222> LOCATION: (1)..(1)
<223> OTHER INFORMATION: n is 5-fluoro-2'-deoxyuridine monophosphate

<400> SEQUENCE: 26
nuagucgguc uugcuaucca u                                              21

<210> SEQ ID NO 27
<211> LENGTH: 21
<212> TYPE: RNA
<213> ORGANISM: Artificial Sequence
<220> FEATURE:
<223> OTHER INFORMATION: 1556-5-F-dU sense

<400> SEQUENCE: 27
gacgaggugc cuaaaggaau g                                              21

<210> SEQ ID NO 28
<211> LENGTH: 21
<212> TYPE: RNA
<213> ORGANISM: Artificial Sequence
<220> FEATURE:
<223> OTHER INFORMATION: 454-U antisense

<400> SEQUENCE: 28
uuagucgguc uugcuaucca u                                              21

<210> SEQ ID NO 29
<211> LENGTH: 21
<212> TYPE: RNA
<213> ORGANISM: Artificial Sequence
<220> FEATURE:
<223> OTHER INFORMATION: 1556-U antisense

<400> SEQUENCE: 29
uuccuuuagg caccucgucc a                                              21

<210> SEQ ID NO 30
<211> LENGTH: 21
<212> TYPE: RNA
<213> ORGANISM: Artificial Sequence
<220> FEATURE:
<223> OTHER INFORMATION: 217-BrdA sense

<400> SEQUENCE: 30
gcgccugguc accagggcug c                                              21
```

```
<210> SEQ ID NO 31
<211> LENGTH: 21
<212> TYPE: RNA
<213> ORGANISM: Artificial Sequence
<220> FEATURE:
<223> OTHER INFORMATION: 217-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 31
ngcccuggug accaggcgcc c                                          21

<210> SEQ ID NO 32
<211> LENGTH: 21
<212> TYPE: RNA
<213> ORGANISM: Artificial Sequence
<220> FEATURE:
<223> OTHER INFORMATION: 278-BrdA sense

<400> SEQUENCE: 32
cccuucauug accucaacua c                                          21

<210> SEQ ID NO 33
<211> LENGTH: 21
<212> TYPE: RNA
<213> ORGANISM: Artificial Sequence
<220> FEATURE:
<223> OTHER INFORMATION: 278-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 33
nguugagguc aaugaagggg u                                          21

<210> SEQ ID NO 34
<211> LENGTH: 21
<212> TYPE: RNA
<213> ORGANISM: Artificial Sequence
<220> FEATURE:
<223> OTHER INFORMATION: 516-BrdA sense

<400> SEQUENCE: 34
gagccaaaag ggucaucauc u                                          21

<210> SEQ ID NO 35
<211> LENGTH: 21
<212> TYPE: RNA
<213> ORGANISM: Artificial Sequence
<220> FEATURE:
<223> OTHER INFORMATION: 516-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 35
nugaugaccc uuuuggcucc c                                          21

<210> SEQ ID NO 36
<211> LENGTH: 21
<212> TYPE: RNA
<213> ORGANISM: Artificial Sequence
<220> FEATURE:
<223> OTHER INFORMATION: 624-BrdA sense
```

```
<400> SEQUENCE: 36
ccugcaccac caacugcuua g                                          21

<210> SEQ ID NO 37
<211> LENGTH: 21
<212> TYPE: RNA
<213> ORGANISM: Artificial Sequence
<220> FEATURE:
<223> OTHER INFORMATION: 624-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 37
nagcaguugg uggugcagga g                                          21

<210> SEQ ID NO 38
<211> LENGTH: 21
<212> TYPE: RNA
<213> ORGANISM: Artificial Sequence
<220> FEATURE:
<223> OTHER INFORMATION: 715-BrdA sense

<400> SEQUENCE: 38
cacugccacc cagaagacug u                                          21

<210> SEQ ID NO 39
<211> LENGTH: 21
<212> TYPE: RNA
<213> ORGANISM: Artificial Sequence
<220> FEATURE:
<223> OTHER INFORMATION: 715-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 39
ngucuucugg guggcaguga u                                          21

<210> SEQ ID NO 40
<211> LENGTH: 21
<212> TYPE: RNA
<213> ORGANISM: Artificial Sequence
<220> FEATURE:
<223> OTHER INFORMATION: 816-BrdA sense

<400> SEQUENCE: 40
aggcuguggg caaggucauc c                                          21

<210> SEQ ID NO 41
<211> LENGTH: 21
<212> TYPE: RNA
<213> ORGANISM: Artificial Sequence
<220> FEATURE:
<223> OTHER INFORMATION: 816-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 41
nugaccuugc ccacagccuu g                                          21

<210> SEQ ID NO 42
```

```
<211> LENGTH: 21
<212> TYPE: RNA
<213> ORGANISM: Artificial Sequence
<220> FEATURE:
<223> OTHER INFORMATION: 936-BrdA sense

<400> SEQUENCE: 42
augaugacau caagaaggug g                                              21

<210> SEQ ID NO 43
<211> LENGTH: 21
<212> TYPE: RNA
<213> ORGANISM: Artificial Sequence
<220> FEATURE:
<223> OTHER INFORMATION: 936-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 43
nccuucuuga ugucaucaua u                                              21

<210> SEQ ID NO 44
<211> LENGTH: 21
<212> TYPE: RNA
<213> ORGANISM: Artificial Sequence
<220> FEATURE:
<223> OTHER INFORMATION: 1096-BrdA sense

<400> SEQUENCE: 44
caagcucauu uccugguaug a                                              21

<210> SEQ ID NO 45
<211> LENGTH: 21
<212> TYPE: RNA
<213> ORGANISM: Artificial Sequence
<220> FEATURE:
<223> OTHER INFORMATION: 1096-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 45
nuaccaggaa augagcuuga c                                              21

<210> SEQ ID NO 46
<211> LENGTH: 21
<212> TYPE: RNA
<213> ORGANISM: Artificial Sequence
<220> FEATURE:
<223> OTHER INFORMATION: 1134-BrdA sense

<400> SEQUENCE: 46
gcaacagggu gguggaccuc a                                              21

<210> SEQ ID NO 47
<211> LENGTH: 21
<212> TYPE: RNA
<213> ORGANISM: Artificial Sequence
<220> FEATURE:
<223> OTHER INFORMATION: 1134-BrdA antisense
<220> FEATURE:
<221> NAME/KEY: misc_feature
<222> LOCATION: (1)..(1)
<223> OTHER INFORMATION: n is 8-oxo-2'-deoxyadenosine monophosphate

<400> SEQUENCE: 47
```
ngguccacca cccuguugcu g    21

<210> SEQ ID NO 48
<211> LENGTH: 21
<212> TYPE: RNA
<213> ORGANISM: Artificial Sequence
<220> FEATURE:
<223> OTHER INFORMATION: 217-A antisense

<400> SEQUENCE: 48
agcccuggug accaggcgcc c    21

<210> SEQ ID NO 49
<211> LENGTH: 21
<212> TYPE: RNA
<213> ORGANISM: Artificial Sequence
<220> FEATURE:
<223> OTHER INFORMATION: 278-A antisense

<400> SEQUENCE: 49
aguugagguc aaugaagggg u    21

<210> SEQ ID NO 50
<211> LENGTH: 21
<212> TYPE: RNA
<213> ORGANISM: Artificial Sequence
<220> FEATURE:
<223> OTHER INFORMATION: 516-A antisense

<400> SEQUENCE: 50
augaugaccc uuuuggcucc c    21

<210> SEQ ID NO 51
<211> LENGTH: 21
<212> TYPE: RNA
<213> ORGANISM: Artificial Sequence
<220> FEATURE:
<223> OTHER INFORMATION: 624-A antisense

<400> SEQUENCE: 51
aagcaguugg uggugcagga g    21

<210> SEQ ID NO 52
<211> LENGTH: 21
<212> TYPE: RNA
<213> ORGANISM: Artificial Sequence
<220> FEATURE:
<223> OTHER INFORMATION: 715-A antisense

<400> SEQUENCE: 52
agucuucugg guggcaguga u    21

<210> SEQ ID NO 53
<211> LENGTH: 21
<212> TYPE: RNA
<213> ORGANISM: Artificial Sequence
<220> FEATURE:
<223> OTHER INFORMATION: 816-A antisense

<400> SEQUENCE: 53
augaccuugc ccacagccuu g    21

<210> SEQ ID NO 54
<211> LENGTH: 21
<212> TYPE: RNA

```
<213> ORGANISM: Artificial Sequence
<220> FEATURE:
<223> OTHER INFORMATION: 936-A antisense

<400> SEQUENCE: 54 accucuuga ugucaucaua u                                               21

<210> SEQ ID NO 55
<211> LENGTH: 21
<212> TYPE: RNA
<213> ORGANISM: Artificial Sequence
<220> FEATURE:
<223> OTHER INFORMATION: 1096-A antisense

<400> SEQUENCE: 55
auaccaggaa augagcuuga c                                              21

<210> SEQ ID NO 56
<211> LENGTH: 21
<212> TYPE: RNA
<213> ORGANISM: Artificial Sequence
<220> FEATURE:
<223> OTHER INFORMATION: 1134-A antisense

<400> SEQUENCE: 56
agguccacca cccuguugcu g                                              21

<210> SEQ ID NO 57
<211> LENGTH: 21
<212> TYPE: RNA
<213> ORGANISM: Artificial Sequence
<220> FEATURE:
<223> OTHER INFORMATION: 1096-5-F-dU sense

<400> SEQUENCE: 57
caagcucauu uccugguaag a                                              21

<210> SEQ ID NO 58
<211> LENGTH: 21
<212> TYPE: RNA
<213> ORGANISM: Artificial Sequence
<220> FEATURE:
<223> OTHER INFORMATION: 1096-U antisense

<400> SEQUENCE: 58
uuaccaggaa augagcuuga c                                              21

<210> SEQ ID NO 59
<211> LENGTH: 21
<212> TYPE: RNA
<213> ORGANISM: Artificial Sequence
<220> FEATURE:
<223> OTHER INFORMATION: 1096-A sense

<400> SEQUENCE: 59
caagcucauu uccugguaug a                                              21

<210> SEQ ID NO 60
<211> LENGTH: 21
<212> TYPE: RNA
<213> ORGANISM: Artificial Sequence
<220> FEATURE:
<223> OTHER INFORMATION: 1096-A antisense

<400> SEQUENCE: 60
auaccaggaa augagcuuga c                                              21
```

<210> SEQ ID NO 61
<211> LENGTH: 21
<212> TYPE: RNA
<213> ORGANISM: Artificial Sequence
<220> FEATURE:
<223> OTHER INFORMATION: 1096-G sense

<400> SEQUENCE: 61
caagcucauu uccugguacg a                                              21

<210> SEQ ID NO 62
<211> LENGTH: 21
<212> TYPE: RNA
<213> ORGANISM: Artificial Sequence
<220> FEATURE:
<223> OTHER INFORMATION: 1096-G antisense

<400> SEQUENCE: 62
guaccaggaa augagcuuga c                                              21

<210> SEQ ID NO 63
<211> LENGTH: 20
<212> TYPE: DNA
<213> ORGANISM: Artificial Sequence
<220> FEATURE:
<223> OTHER INFORMATION: forward primer

<400> SEQUENCE: 63
catgaccgag aaggagatcg                                                20

<210> SEQ ID NO 64
<211> LENGTH: 19
<212> TYPE: DNA
<213> ORGANISM: Artificial Sequence
<220> FEATURE:
<223> OTHER INFORMATION: reverse primer

<400> SEQUENCE: 64
cagcttcttg gcggttgta                                                 19

<210> SEQ ID NO 65
<211> LENGTH: 21
<212> TYPE: RNA
<213> ORGANISM: Artificial Sequence
<220> FEATURE:
<223> OTHER INFORMATION: 454-A sense

<400> SEQUENCE: 65
ggauagcaag accgacuauc a                                              21

<210> SEQ ID NO 66
<211> LENGTH: 21
<212> TYPE: RNA
<213> ORGANISM: Artificial Sequence
<220> FEATURE:
<223> OTHER INFORMATION: 454-A antisense

<400> SEQUENCE: 66
auagucgguc uugcuaucca u                                              21

<210> SEQ ID NO 67
<211> LENGTH: 21
<212> TYPE: RNA
<213> ORGANISM: Artificial Sequence
<220> FEATURE:

```
<223> OTHER INFORMATION: 454-XY sense
<220> FEATURE:
<221> NAME/KEY: misc_feature
<222> LOCATION: (19)..(19)
<223> OTHER INFORMATION: n is zebularine-5-monophosphate

<400> SEQUENCE: 67
ggauagcaag accgacuanc a                                            21

<210> SEQ ID NO 68
<211> LENGTH: 21
<212> TYPE: RNA
<213> ORGANISM: Artificial Sequence
<220> FEATURE:
<223> OTHER INFORMATION: 454-A-dT, Combined DNA/RNA Molecule: Synthetic
      oligonucleotide
<220> FEATURE:
<221> NAME/KEY: misc_feature
<222> LOCATION: (21)..(21)
<223> OTHER INFORMATION: deoxythymidine

<400> SEQUENCE: 68
auagucgguc uugcuaucca n                                            21

<210> SEQ ID NO 69
<211> LENGTH: 20
<212> TYPE: RNA
<213> ORGANISM: Artificial Sequence
<220> FEATURE:
<223> OTHER INFORMATION: 454-Xa-dT, Combined DNA/RNA Molecule: Synthetic
      oligonucleotide
<220> FEATURE:
<221> NAME/KEY: misc_feature
<222> LOCATION: (20)..(20)
<223> OTHER INFORMATION: deoxythymidine

<400> SEQUENCE: 69
uagucggucu ugcuauccan                                              20
```

OLIGONUCLEOTIDE HAVING NON-NATURAL NUCLEOTIDE AT 5'-TERMINAL THEREOF

TECHNICAL FIELD

The present invention relates to an oligonucleotide having a knockdown activity (for example, an RNA interfering activity, or the like.) against a target messenger RNA (mRNA), and the like.

BACKGROUND ART

A small interfering RNA (hereinafter referred to as siRNA) is involved in the RNA interference (hereinafter referred to as RNAi) and is an RNA having a function as a guide for inhibiting the expression of a target gene [Nature, vol. 411, No. 6836, pp. 494-498, 2001]. An siRNA can selectively inhibit (knock down) the expression of the protein which a messenger RNA (mRNA) regulates, through cleavage of the mRNA, and therefore, the application thereof to pharmaceuticals is expected (Nature Reviews Cancer, vol. 11, pp. 59-67, 2011).

An siRNA is generally incorporated into a complex called an RNA induced silencing complex (RISC), and then exhibits its function. A main constituent component of the RISC is a protein called Argonaute 2 (AGO2), and AGO2 binds to an siRNA in the RNAi pathway and cleaves an mRNA (Trends in Biochemical Sciences, vol. 35, No. 7, pp. 368-376, 2010). The siRNA incorporated into the RISC is converted to a single strand of only the antisense strand by cleaving the sense strand, and thereafter binds to a target mRNA complementary to the antisense strand. It is known that the target mRNA is then cleaved by an RNase domain in the AGO2, resulting in inhibiting the expression of the protein (Silence, vol. 1, p. 3, 2010).

On the other hand, in recent years, three-dimensional structure analysis of hAGO2 MID/AMP complex and hAGO2 MID/UMP complex (Nature, vol. 465, pp. 818-822, 2010), and a three-dimensional structure analysis for a complex of hAGO2 and an RNA oligonucleotide (Science, vol. 336, p. 25, 2012) have also been reported.

Further, in recent years, particularly a structural analysis of proteins using an X-ray is actively carried out, and there have been many reports of attempts to elucidate a mode of binding between a protein and a compound targeting the protein at the atomic level on the basis of the obtained structural information and to design a compound which fits the structure (Journal of Postgraduate Medicine, vol. 55, pp. 301-304, 2009).

However, although a possibility of avoiding an off-target effect (Patent Literature 1) and a possibility of enhancing the activity of an siRNA by improving the affinity for AGO2 (Non Patent Literature 1) using an oligonucleotide containing an unnatural nucleotide are suggested, a method for improving the affinity for AGO2 and enhancing the knockdown activity is known (Patent Literature 2).

PRIOR ART

Patent Literature

[Patent Literature 1] WO2011/119674
[Patent Literature 2] WO2014/034934

Non Patent Literature

[Non Patent Literature 1] Molecular Therapy-Nucleic Acids vol. 1, p. e5, 2012

DISCLOSURE OF THE INVENTION

Problems to be Solved by the Invention

An object of the present invention is to provide an oligonucleotide which improves affinity for AGO2, and the like.

Means for Solving the Problems

The present invention relates to the following (1) to (77).

(1) An oligonucleotide, comprising a nucleotide residue or a nucleoside residue represented by formula (I) at the 5' end thereof, wherein the nucleotide residue or the nucleoside residue binds to an adjacent nucleotide residue through the oxygen atom at position 3:

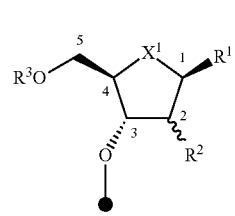

{wherein $X^1$ is an oxygen atom, a sulfur atom, a selenium atom, or $NR^4$ (wherein $R^4$ is a hydrogen atom, optionally substituted lower alkyl, optionally substituted lower alkenyl, optionally substituted lower alkynyl, optionally substituted lower alkanoyl, optionally substituted lower alkylsulfonyl, optionally substituted aralkyl, optionally substituted aryl, optionally substituted aroyl, or optionally substituted aromatic heterocyclic carbonyl), $R^1$ is formula (II):

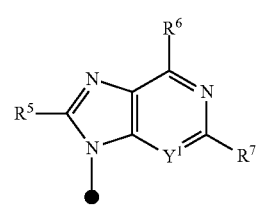

{wherein $Y^1$ is a nitrogen atom or $CR^8$ [wherein $R^8$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted aryl, optionally substituted aralkyl, an optionally substituted aromatic heterocyclic group, optionally substituted aromatic heterocyclic alkyl, $-NR^{9a}R^{9b}$ (wherein $R^{9a}$ and $R^{9b}$ may be the same or different, and each is a hydrogen atom, optionally substituted lower alkyl, or optionally substituted aralkyl), or $-CONR^{9c}R^{9d}$ (wherein $R^{9c}$ and $R^{9d}$ may be the same or different, and each is a hydrogen atom or optionally substituted lower alkyl)], R⁵ is a hydrogen atom, halogen, cyano, carboxy, optionally substituted lower alkyl, optionally substituted cycloalkyl, optionally substituted lower alkenyl, optionally substituted lower alkynyl, optionally substituted lower alkoxy, optionally substituted lower alkoxycarbonyl, optionally substituted lower alkylthio, optionally substituted lower alkanoyl, optionally substituted aryl, an optionally substituted aromatic heterocyclic group, an optionally substituted aliphatic heterocyclic group, —NR$^{10a}$R$^{10b}$ (wherein R$^{10a}$ and R$^{10b}$ have the same meanings as R$^{9a}$ and R$^{9b}$ described above, respectively), —CONR$^{10c}$R$^{10d}$ (wherein R$^{10c}$ and R$^{10d}$ have the same meanings as R$^{9c}$ and R$^{9d}$ described above, respectively), —N=C—R$^{10e}$ (wherein R$^{10e}$ is a hydrogen atom or optionally substituted lower alkyl), —C=N—R$^{10f}$ (wherein R$^{10f}$ is a hydrogen atom or optionally substituted lower alkyl), or —N=N—R$^{10g}$ (wherein R$^{10g}$ is a hydrogen atom or optionally substituted lower alkyl), R⁶ is a hydrogen atom, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted aralkyloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR$^{11a}$R$^{11b}$ (wherein R$^{11a}$ and R$^{11b}$ may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkylsulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), (wherein R$^{11c}$ and R$^{11d}$ may be the same or different, and each is a hydrogen atom, optionally substituted lower alkyl, optionally substituted aryl, or an optionally substituted aromatic heterocyclic group), —NHCONR$^{11e}$R$^{11f}$ (wherein R$^{11e}$ and R$^{11f}$ may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO₂R$^{11g}$ (wherein R$^{11g}$ is optionally substituted lower alkyl, optionally substituted aralkyl, optionally substituted aromatic heterocyclic alkyl, optionally substituted aryl, or an optionally substituted aromatic heterocyclic group), —N=C—R$^{11h}$ (wherein R$^{11h}$ is a hydrogen atom or optionally substituted lower alkyl), (wherein R$^{11i}$ is a hydrogen atom or optionally substituted lower alkyl), or —N=N—R$^{11j}$ (wherein R$^{11j}$ is a hydrogen atom or optionally substituted lower alkyl), R⁷ is a hydrogen atom, an isostere of a hydrogen atom in the nucleic acid field, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR$^{11a}$R$^{11b}$ (wherein R$^{11a}$ and R$^{11b}$ may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkylsulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), —CONR$^{11c}$R$^{11d}$ (wherein R$^{11c}$ and R$^{11d}$ may be the same or different, and each is a hydrogen atom, optionally substituted lower alkyl, optionally substituted aryl, or an optionally substituted aromatic heterocyclic group), —NHCONR$^{11e}$R$^{11f}$ (wherein R$^{11e}$ and R$^{11f}$ may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO₂R$^{11g}$ (wherein R$^{11g}$ is optionally substituted lower alkyl, optionally substituted aralkyl, optionally substituted aromatic heterocyclic alkyl, optionally substituted aryl, or an optionally substituted aromatic heterocyclic group), provided that when Y¹ is a nitrogen atom, R⁵ is a hydrogen atom, R⁶ is —NR$^{11a}$R$^{11b}$, and R⁷ is a hydrogen atom, R$^{11a}$ and R$^{11b}$ are not simultaneously hydrogen atoms}, formula (III):

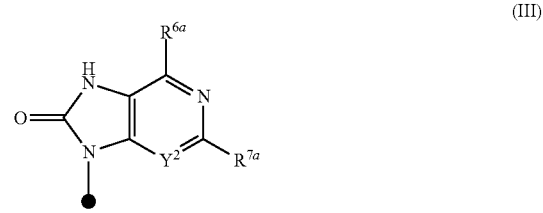

(III)

(wherein Y², R$^{6a}$, and R$^{7a}$ have the same meanings as Y¹, R⁶, and R⁷ described above, respectively), formula (IV):

(IV)

[wherein R¹² is a hydrogen atom, an isostere of a hydrogen atom in the nucleic acid field, optionally substituted lower alkyl, optionally substituted lower alkenyl, optionally substituted lower alkynyl, optionally substituted aralkyl, optionally substituted aromatic heterocyclic alkyl, optionally substituted lower alkanoyl, or optionally substituted lower alkylsulfonyl,

- - - is a single bond or a double bond,
provided that when - - - is a single bond,
$Y^3$ is $NR^{13a}$ (wherein $R^{13a}$ is a hydrogen atom, optionally substituted lower alkyl, optionally substituted lower alkenyl, optionally substituted lower alkynyl, optionally substituted aralkyl, optionally substituted aromatic heterocyclic alkyl, optionally substituted lower alkanoyl, or optionally substituted lower alkylsulfonyl), or $CR^{14a}R^{14b}$ (wherein $R^{14a}$ and $R^{14b}$ may be the same or different, and each is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl), and $Y^4$ is $NR^{13b}$ (wherein $R^{13b}$ has the same meaning as $R^{13a}$ described above) or $CR^{14c}R^{14d}$ (wherein $R^{14c}$ and $R^{14d}$ have the same meanings as $R^{14a}$ and $R^{14b}$ described above, respectively), and when - - - is a double bond, $Y^3$ is a nitrogen atom or $CR^{14e}$ (wherein $R^{14e}$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl) and $Y^4$ is a nitrogen atom or $CR^{14f}$ (wherein $R^{14f}$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl), provided that when $R^{12}$ is a hydrogen atom, $Y^3$ is $CR^{14e}$, and $Y^4$ is $CR^{14f}$, the case where $R^{14e}$ and $R^{14f}$ are simultaneously hydrogen atoms or the case where $R^{14e}$ is methyl and $R^{14f}$ is a hydrogen atom is excluded], or formula (V):

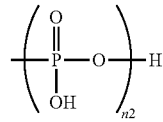

(V)

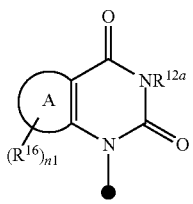

(wherein $R^{12a}$ has the same meaning as $R^{12}$ described above, ring A is an aromatic ring, n1 is an integer of 0 to 4, $R^{16}$ is halogen, hydroxy, sulfanyl, nitro, cyano, carboxy, carbamoyl, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, optionally substituted aromatic heterocyclic alkyl, or optionally substituted lower alkylsulfonyl, provided that when n1 is an integer of 2 to 4, the respective $R^{16}5$ may be the same or different), $R^2$ is a hydrogen atom, hydroxy, halogen, or optionally substituted lower alkoxy, and $R^3$ is a hydrogen atom or $$\left(\begin{array}{c} O \\ \parallel \\ P-O \\ | \\ OH \end{array}\right)_{n2} H$$

(wherein n2 is 1, 2, or 3)}.

(2) The oligonucleotide according to (1), wherein $X^1$ is an oxygen atom.

(3) The oligonucleotide according to (1) or (2), wherein $R^2$ is formula (II).

(4) The oligonucleotide according to (3), wherein $Y^2$ is a nitrogen atom.

(5) The oligonucleotide according to (3) or (4), wherein $R^5$ is a hydrogen atom, halogen, cyano, optionally substituted lower alkyl, optionally substituted cycloalkyl, optionally substituted lower alkenyl, optionally substituted lower alkynyl, optionally substituted lower alkoxy, optionally substituted lower alkanoyl, optionally substituted aryl, an optionally substituted aromatic heterocyclic group, an optionally substituted aliphatic heterocyclic group, $-NR^{10a}R^{10b}$ (wherein $R^{10a}$ and $R^{10b}$ have the same meanings as described above, respectively), $-CONR^{10c}R^{10d}$ (wherein $R^{10c}$ and $R^{10d}$ have the same meanings as described above, respectively), $-N=C-R^{10e}$ (wherein $R^{10e}$ is a hydrogen atom or optionally substituted lower alkyl), $-C=N-R^{10f}$ (wherein $R^{10f}$ is a hydrogen atom or optionally substituted lower alkyl), or $-N=N-R^{10g}$ (wherein $R^{10g}$ is a hydrogen atom or optionally substituted lower alkyl).

(6) The oligonucleotide according to (3) or (4), wherein $R^5$ is a hydrogen atom, halogen, optionally substituted lower alkyl, optionally substituted lower alkenyl, cyano, $-NR^{10a}R^{10b}$ (wherein $R^{10a}$ and $R^{10b}$ have the same meanings as described above, respectively).

(7) The oligonucleotide according to (3) or (4), wherein $R^5$ is optionally substituted lower alkenyl or cyano.

(8) The oligonucleotide according to any one of (3) to (7), wherein $R^6$ is optionally substituted lower alkyl, optionally substituted lower alkenyl, optionally substituted lower alkynyl, optionally substituted aryl, an optionally substituted aromatic heterocyclic group, $-NR^{11a}R^{11b}$ (wherein $R^{11a}$ and $R^{11b}$ have the same meanings as described above, respectively), $-N=C-R^{11h}$ (wherein $R^{11h}$ is a hydrogen atom or optionally substituted lower alkyl), $-C=N-R^{11i}$ (wherein $R^{11i}$ is a hydrogen atom or optionally substituted lower alkyl), or —N═N—$R^{11j}$ (wherein $R^{11j}$ is a hydrogen atom or optionally substituted lower alkyl).

(9) The oligonucleotide according to any one of (3) to (7), wherein $R^6$ is optionally substituted lower alkenyl, optionally substituted aryl, or —$NR^{11a}R^{11b}$ (wherein $R^{11a}$ and $R^{11b}$ have the same meanings as described above, respectively).

(10) The oligonucleotide according to any one of (3) to (7), wherein $R^6$ is —$NR^{11a}R^{11b}$ (wherein $R^{11a}$ and $R^{11b}$ may be the same or different, and each is a hydrogen atom, or optionally substituted lower alkyl).

(11) The oligonucleotide according to any one of (3) to (7), wherein $R^6$ is optionally substituted aryl and the substituent is located at the meta or para position of the aryl.

(12) The oligonucleotide according to any one of (3) to (11), wherein $R^7$ is a hydrogen atom.

(13) The oligonucleotide according to (1) or (2), wherein $R^1$ is formula (III).

(14) The oligonucleotide according to (13), wherein $Y^2$ is a nitrogen atom.

(15) The oligonucleotide according to (13) or (14), wherein $R^{6a}$ is amino, methylamino, or dimethylamino.

(16) The oligonucleotide according to any one of (13) to (15), wherein $R^7$ is a hydrogen atom.

(17) The oligonucleotide according to (1) or (2), wherein $R^4$ is formula (IV).

(18) The oligonucleotide according to (17), wherein $R^{42}$ is a hydrogen atom or an isostere of a hydrogen atom in the nucleic acid field.

(19) The oligonucleotide according to (18), wherein - - - is a double bond, $Y^3$ is $CR^{14e}$ (wherein $R^{14e}$ has the same meaning as described above), and $Y^4$ is a nitrogen atom or $CR^{14f}$ (wherein $R^{14f}$ has the same meaning as described above, provided that the case where $R^{14f}$ is cyano is excluded).

(20) The oligonucleotide according to (19), wherein $R^{14e}$ is a hydrogen atom.

(21) The oligonucleotide according to (19), wherein $R^{14e}$ is halogen, cyano, optionally substituted lower alkenyl, optionally substituted aryl, or an optionally substituted aromatic heterocyclic group, and $R^{14f}$ is a hydrogen atom.

(22) The oligonucleotide according to (19), wherein $R^{14e}$ is a hydrogen atom, and $R^{14f}$ is halogen, optionally substituted lower alkyl, optionally substituted lower alkenyl, optionally substituted aryl, or an optionally substituted aromatic heterocyclic group.

(23) The oligonucleotide according to (1) or (2), wherein $R^1$ is formula (V).

(24) The oligonucleotide according to (23), wherein ring A is formula (A1):

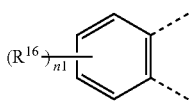
(A1)

(wherein $R^{16}$ and n1 have the same meanings as described above, respectively), formula (A2):

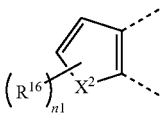
(A2)

(wherein $R^{16}$ has the same meaning as described above, n1 is an integer of 0 to 2, and $X^2$ is NH, an oxygen atom, or a sulfur atom), formula (A3):

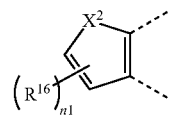
(A3)

(wherein $R^{16}$ and $X^2$ have the same meanings as described above, respectively, and n1 is an integer of 0 to 2), formula (A4):

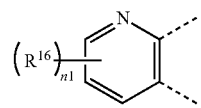
(A4)

(wherein $R^{16}$ has the same meaning as described above, and n1 is an integer of 0 to 3), formula (A5):

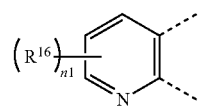
(A5)

(wherein $R^{16}$ has the same meaning as described above, and n1 is an integer of 0 to 3), formula (A6):

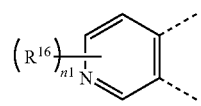
(A6)

(wherein $R^{16}$ has the same meaning as described above, and n1 is an integer of 0 to 3), formula (A7):

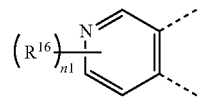
(A7)

(wherein $R^{16}$ has the same meaning as described above, and n1 is an integer of 0 to 3), formula (A8):

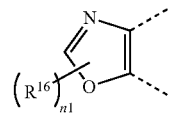
(A8)

(wherein $R^{16}$ has the same meaning as described above, and n1 is 1), formula (A9):

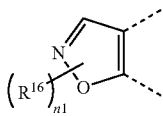

(wherein $R^{16}$ has the same meaning as described above, and n1 is 1), formula (A10):

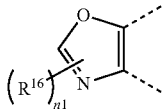

(wherein $R^{16}$ has the same meaning as described above, and n1 is 1), formula (A11):

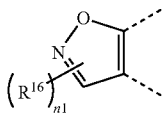

(wherein $R^{16}$ has the same meaning as described above, and n1 is 1).

(25) The oligonucleotide according to (23) or (24), wherein $R^{16}$ is halogen, nitro, optionally substituted lower alkyl, optionally substituted lower alkylamino, or optionally substituted di-lower alkylamino.

(26) The oligonucleotide according to (25), wherein $R^{12a}$ is a hydrogen atom or an isostere of a hydrogen atom in the nucleic acid field.

(27) The oligonucleotide according to any one of (23) to (26), wherein n1 is 1 or 2.

(28) The oligonucleotide according to any one of (1) to (27), wherein $R^3$ is

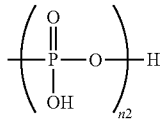

(wherein n2 has the same meaning as described above).

(29) The oligonucleotide according to (28), wherein n2 is 1.

(30) The oligonucleotide according to any one of (1) to (29), wherein $R^2$ is a hydrogen atom, hydroxy, a fluorine atom, or methoxy.

(31) The oligonucleotide according to any one of (1) to (29), wherein $R^2$ is hydroxy.

(32) The oligonucleotide according to (1), wherein $R^2$ is a hydrogen atom, or a fluorine atom.

(33) The oligonucleotide according to (1), wherein $X^1$ is an oxygen atom, and $R^2$ is a hydrogen atom, hydroxy, a fluorine atom, or methoxy.

(34) The oligonucleotide according to (33), wherein $R^1$ is formula (IIA):

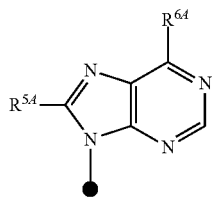

(wherein $R^{5A}$ and $R^{6A}$ have the same meanings as $R^5$ and $R^6$ described above, respectively).

(35) The oligonucleotide according to (34), wherein $R^{5A}$ is halogen, carbamoyl, optionally substituted lower alkyl, optionally substituted cycloalkyl, optionally substituted lower alkenyl, optionally substituted lower alkynyl, optionally substituted lower alkoxy, optionally substituted lower alkanoyl, optionally substituted lower alkylamino, optionally substituted di-lower alkylamino, optionally substituted lower alkylcarbamoyl, optionally substituted di-lower alkylcarbamoyl, optionally substituted aryl, an optionally substituted aromatic heterocyclic group, an optionally substituted aliphatic heterocyclic group or $-NR^{10a}R^{10b}$ (wherein $R^{10a}$ and $R^{10b}$ have the same meanings as described above, respectively).

(36) The oligonucleotide according to (34), wherein $R^{5A}$ is halogen, optionally substituted lower alkyl, optionally substituted lower alkenyl, cyano, or $-NR^{10a}R^{10b}$ (wherein $R^{10a}$ and $R^{10b}$ have the same meanings as described above, respectively).

(37) The oligonucleotide according to any one of (34) to (36), wherein $R^{6A}$ is optionally substituted lower alkyl, optionally substituted lower alkenyl, optionally substituted lower alkynyl, optionally substituted aryl, an optionally substituted aromatic heterocyclic group, or $NR^{11a}R^{11b}$ (wherein $R^{11a}$ and $R^{11b}$ have the same meanings as described above, respectively).

(38) The oligonucleotide according to any one of (34) to (36), wherein $R^{6A}$ is $NR^{11a}R^{11b}$ (wherein $R^{11a}$ and $R^{11b}$ have the same meanings as described above, respectively).

(39) The oligonucleotide according to any one of (34) to (36), wherein $R^{6A}$ is amino, optionally substituted lower alkenyl, or optionally substituted aryl.

(40) The oligonucleotide according to (33), wherein $R^1$ is formula (IVA):

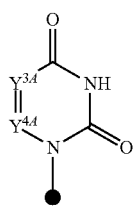

(wherein $Y^{3A}$ and $Y^{4A}$ have the same meanings as $Y^3$ and $Y^4$ described above, respectively, provided that when $Y^{3A}$ and $Y^{4A}$ are $CR^{14e}$ and $CR^{14f}$, and $R^{14e}$ is a hydrogen atom, $R^{14f}$ is not cyano).

(41) The oligonucleotide according to (40), wherein $Y^{3A}$ is $CR^{14e}$ (wherein $R^{14e}$ has the same meaning as described above) and $Y^{4A}$ is $CR^{14f}$ (wherein $R^{14f}$ has the same meaning as described above).

(42) The oligonucleotide according to (41), wherein $R^{14e}$ is a hydrogen atom.

(43) The oligonucleotide according to (41), wherein $R^{14e}$ is halogen, optionally substituted lower alkenyl, optionally substituted aryl, or an optionally substituted aromatic heterocyclic group, and $R^{14f}$ is a hydrogen atom.

(44) The oligonucleotide according to (41), wherein $R^{14e}$ is a hydrogen atom, and $R^{14f}$ is halogen, optionally substituted lower alkyl, optionally substituted lower alkenyl, optionally substituted aryl, or an optionally substituted aromatic heterocyclic group.

(45) The oligonucleotide according to (33), wherein $R^1$ is formula (VA):

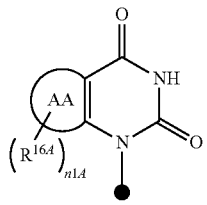

(VA)

(wherein ring AA, n1A, and $R^{16A}$ have the same meanings as ring A, n1, and $R^{16}$ described above, respectively, provided that when n1A is an integer of 2 to 4, the respective $R^{16A}$s may be the same or different, provided that when ring AA is a benzene ring and n1A is 2, $R^{16A}$s are not lower alkoxy, and when ring AA is a benzene ring, n1A is 1, and $R^{16A}$ is a chlorine atom, the case where ring AA is represented by formula (A1'):

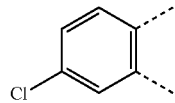

(A1')

is excluded).

(46) The oligonucleotide according to (45), wherein ring AA is a benzene ring or a thiophene ring.

(47) The oligonucleotide according to (45) or (46), wherein $R^{16A}$ is halogen, nitro lower alkyl, optionally substituted lower alkylamino, or optionally substituted di-lower alkylamino.

(48) The oligonucleotide according to any one of (45) to (47), wherein n1A is 1 or 2.

(49) The oligonucleotide according to any one of (33) to (48), wherein $R^3$ is

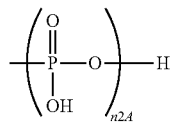

(wherein n2A has the same meaning as described above).

(50) The oligonucleotide according to (49), wherein n2A is 1.

(51) The oligonucleotide according to any one of (33) to (50), wherein $R^2$ is a hydrogen atom, or a fluorine atom.

(52) The oligonucleotide according to any one of (33) to (50), wherein $R^2$ is hydroxy.

(53) The oligonucleotide according to any one of (1) to (52), wherein the oligonucleotide has a length of 10 to 80 bases.

(54) The oligonucleotide according to any one of (1) to (52), wherein the oligonucleotide has a length of 20 to 50 bases.

(55) The oligonucleotide according to any one of (1) to (52), wherein the oligonucleotide has a length of 20 to 30 bases.

(56) The oligonucleotide according to any one of (1) to (52), wherein the oligonucleotide has a length of 21 to 25 bases.

(57) The oligonucleotide according to any one of (1) to (56), wherein the oligonucleotide is a double-stranded oligonucleotide.

(58) The oligonucleotide according to any one of (1) to (56), wherein the oligonucleotide is a single-stranded oligonucleotide.

(59) The oligonucleotide according to any one of (1) to (56), wherein the oligonucleotide is a small interfering RNA (siRNA).

(60) A method for improving the knockdown activity of an oligonucleotide, wherein the oligonucleotide has a knockdown activity against a mRNA encoding a protein involved in a disease, characterized by comprising substituting a base residue at the 5' end of the oligonucleotide with a base residue represented by formula (II):

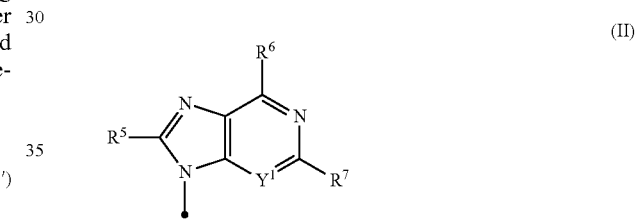

(II)

(wherein $Y^1$, $R^5$, $R^6$, and $R^7$ have the same meanings as described above, respectively), formula (III):

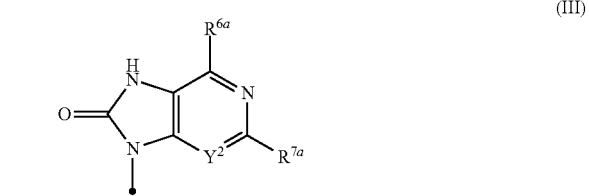

(III)

(wherein $Y^2$, $R^{6a}$, and $R^{7a}$ have the same meanings as described above, respectively), formula (IV):

(IV)

(wherein $R^{12}$, - - - , $Y^3$, and $Y^4$ have the same meanings as described above, respectively), or formula (V):

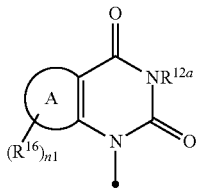

(wherein $R^{12a}$, ring A, n1, and $R^{16}$ have the same meanings as described above, respectively).

(61) A method for improving the knockdown activity of an oligonucleotide, wherein the oligonucleotide has a knockdown activity against a messenger RNA (mRNA) encoding a protein involved in a disease and the base at the 5' end of the oligonucleotide is guanine or cytosine, characterized by comprising substituting the guanine residue or the cytosine residue at the 5' end of the oligonucleotide with an adenine residue (6-aminopurin-9-yl), a thymine residue (5-methyl-1,2,3,4 tetrahydropyrimidine-2,4 dion-1-yl), an uridine residue (pyrimidine-2,4(1H,3H)dion-1-yl), formula (II):

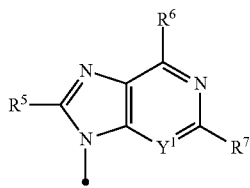

(wherein $Y^1$, $R^5$, $R^6$, and $R^7$ have the same meanings as described above, respectively), formula (III):

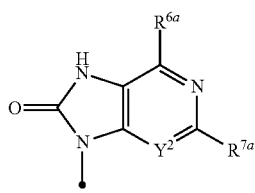

(wherein $Y^2$, $R^{6a}$, and $R^{7a}$ have the same meanings as described above, respectively), formula (IV):

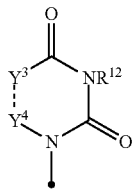

(wherein $R^{12}$, - - -, $Y^3$, and $Y^4$ have the same meanings as described above, respectively), or formula (V):

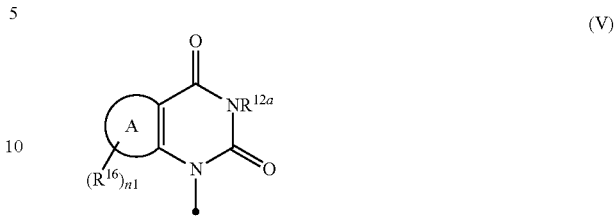

(wherein $R^{12a}$, ring A, n1, and $R^{16}$ have the same meanings as described above, respectively).

(62) The method according to (60) or (61), wherein the oligonucleotide is a small interfering RNA (siRNA).

(63) A nucleic acid pharmaceutical composition, comprising an oligonucleotide, wherein the knockdown activity of the oligonucleotide against a target mRNA is improved by the method according to any one of (60) to (62).

(64) A nucleotide or a nucleoside represented by formula (Ia):

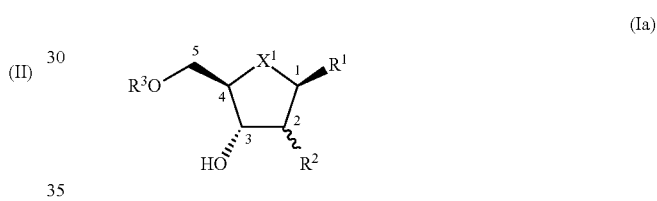

(wherein $X^1$, $R^1$, $R^2$, and $R^3$ have the same meanings as described above, respectively), a compound wherein hydroxy, carboxyl, and/or amino is(are) protected by a protecting group, or an amidite thereof or a salt thereof, for use in substituting a nucleotide residue or a nucleoside residue at the 5' end of the oligonucleotide having a knockdown activity against a mRNA encoding a protein involved in a disease, and for improving the knockdown activity against a target mRNA of the oligonucleotide.

(65) The nucleotide or nucleoside, the compound wherein hydroxy, carboxyl, and/or amino is(are) protected by a protecting group, or an amidite thereof, or a salt thereof according to (63), wherein the oligonucleotide is a small interfering RNA (siRNA).

(66) A nucleotide or nucleoside, comprising a base residue represented by formula (II):

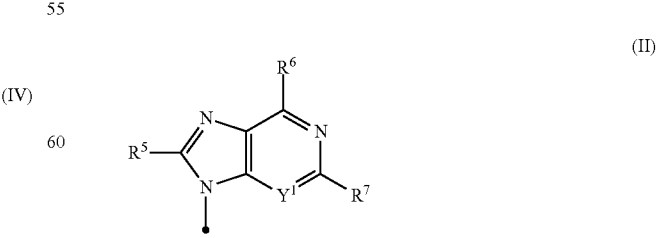

(wherein $Y^1$, $R^5$, $R^6$, and $R^7$ have the same meanings as described above, respectively), formula (III):

(III)

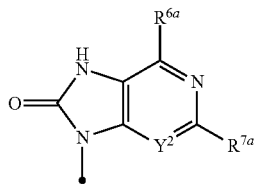

(wherein $Y^2$, $R^{6a}$, and $R^{7a}$ have the same meanings as described above, respectively), formula (IV):

(IV)

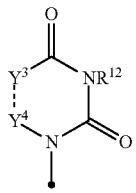

(wherein $R^{12}$, - - -, $Y^3$, and $Y^4$ have the same meanings as described above, respectively), or formula (V):

(V)

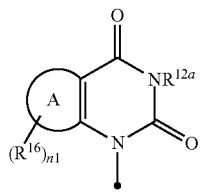

(wherein $R^{12a}$, ring A, n1, and $R^{16}$ have the same meanings as described above, respectively), or a compound wherein hydroxy, carboxyl, and/or amino is(are) protected by a protecting group, or an amidite thereof or a salt thereof, for use in substituting a nucleotide residue or a nucleoside residue at the 5' end of an oligonucleotide having a knockdown activity against a mRNA encoding a protein involved in a disease, and for improving the knockdown activity against a target mRNA of the oligonucleotide.

(67) The nucleotide or nucleoside, or the compound wherein hydroxy, carboxy, and/or amino is(are) protected by a protecting group, or an amidite thereof or a salt thereof according to (66), wherein the oligonucleotide is a small interfering RNA (siRNA).

(68) Use of an oligonucleotide which has a nucleotide residue or a nucleoside residue represented by formula (I) at the 5' end:

(I)

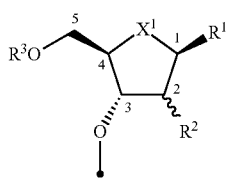

(wherein $X^1$, $R^1$, $R^2$, and $R^3$ have the same meanings as described above, respectively) and has a knockdown activity against a mRNA encoding a protein involved in a disease, for the manufacture of an inhibitor of a target protein expression.

(69) Use of an oligonucleotide introducing a base residue represented by formula (II):

(II)

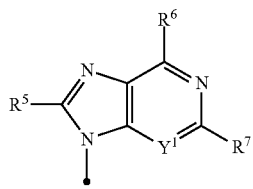

(wherein $Y^1$, $R^5$, $R^6$, and $R^7$ have the same meanings as described above, respectively), formula (III):

(III)

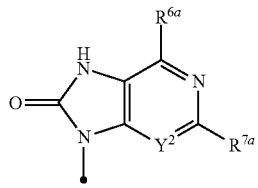

(wherein $Y^2$, $R^{6a}$, and $R^{7a}$ have the same meanings as described above, respectively), formula (IV):

(IV)

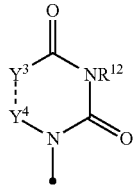

(wherein $R^{12}$, - - -, $Y^3$, and $Y^4$ have the same meanings as described above, respectively), or formula (V):

(V)

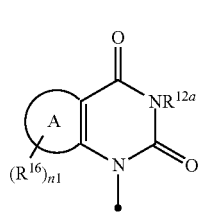

(wherein $R^{12a}$, ring A, n1, and $R^{16}$ have the same meanings as described above, respectively) at the 5' end, wherein the oligonucleotide has a knockdown activity against a mRNA encoding a protein involved in a disease, for the manufacture of an inhibitor of a target protein expression.

(70) The use according to (68) or (69), wherein the oligonucleotide is a small interfering RNA (siRNA).

(71) The oligonucleotide according to any of (1) to (7), wherein $R^2$ is a hydrogen atom, and $R^6$ is optionally substituted lower alkoxy, optionally substituted aryloxy, optionally substituted aralkyloxy, optionally substituted aromatic heterocyclicoxy, optionally substituted lower alkylthio, optionally substituted arylthio, optionally substituted aromatic heterocyclicthio, —NR$^{30}$R$^{31}$ (wherein R$^{30}$ and R$^{31}$ may be the same or different, and each is a hydrogen atom, optionally substituted lower alkyl, optionally substituted lower alkenyl, optionally substituted lower alkynyl, optionally substituted aryl, an optionally substituted aromatic heterocyclic group, optionally substituted aralkyl or optionally substituted aromatic heterocyclic alkyl, provided that the case where R$^{30}$ and R$^{31}$ are simultaneously hydrogen atoms is excluded), optionally substituted aryl or an optionally substituted aromatic heterocyclic group.

(72) The oligonucleotide according to any of (1) to (7), wherein R$^6$ is optionally substituted lower alkoxy, optionally substituted aralkyloxy, optionally substituted lower alkylthio, optionally substituted arylthio, or —NR$^{30A}$R$^{31A}$ (wherein R$^{30A}$ and R$^{31A}$ may be the same or different, and each is optionally substituted lower alkyl, optionally substituted lower alkynyl, optionally substituted aryl or optionally substituted aralkyl, provided that the case where R$^{30A}$ and R$^{31A}$ are simultaneously hydrogen atoms is excluded).

(73) The oligonucleotide according to (71), wherein R$^6$ is lower alkoxy substituted with a substituent containing an acidic functional group, aryloxy substituted with a substituent containing an acidic functional group, aralkyloxy substituted with a substituent containing an acidic functional group, aromatic heterocyclicoxy substituted with a substituent containing an acidic functional group, lower alkylthio substituted with a substituent containing an acidic functional group, arylthio substituted with a substituent containing an acidic functional group, aromatic heterocyclicthio substituted with a substituent containing an acidic functional group, —NR$^{30}$R$^{31}$ (wherein R$^{30}$ and R$^{31}$ may be the same or different, and each is a hydrogen atom, lower alkyl optionally substituted with a substituent containing an acidic functional group, lower alkenyl optionally substituted with a substituent containing an acidic functional group, lower alkynyl optionally substituted with a substituent containing an acidic functional group, aryl optionally substituted with a substituent containing an acidic functional group, an aromatic heterocyclic group optionally substituted with a substituent containing an acidic functional group, aralkyl optionally substituted with a substituent containing an acidic functional group or aromatic heterocyclic alkyl optionally substituted with a substituent containing an acidic functional group), aryl substituted with a substituent containing an acidic functional group, or an aromatic heterocyclic group substituted with a substituent containing an acidic functional group.

(74) The oligonucleotide according to (72), wherein R$^6$ is lower alkoxy substituted with a substituent containing an acidic functional group, aralkyloxy substituted with a substituent containing an acidic functional group, lower alkylthio substituted with a substituent containing an acidic functional group, arylthio substituted with a substituent containing an acidic functional group, or —NR$^{30A}$R$^{31A}$ (wherein R$^{30A}$ and R$^{31A}$ may be the same or different, and each is a lower alkyl optionally substituted with a substituent containing an acidic functional group, lower alkynyl optionally substituted with a substituent containing an acidic functional group, aryl optionally substituted with a substituent containing an acidic functional group, or aralkyl optionally substituted with a substituent containing an acidic functional group, provided that the case where R$^{30A}$ and R$^{31A}$ are simultaneously hydrogen atoms is excluded).

(75) The oligonucleotide according to (73) or (74), wherein the acidic functional group is carboxy and/or —OP(=O)(OH)$_2$.

(76) A nucleotide represented by any one of compound numbers I-39 to I-101 in tables 8 to 21 below, or a salt thereof or a hydrate thereof.

(77) The nucleoside corresponding to a nucleotide according to (76), or a salt thereof or a hydrate thereof.

Effect of the Invention

According to the present invention, an oligonucleotide having improved the affinity for AGO2 and the like are provided.

BRIEF DESCRIPTION OF DRAWING

FIG. 1 is a graph for comparing the levels of luciferase luminescence between an siRNA having 8-Br-dA at the 5' end of the antisense strand and an siRNA having adenosine monophosphate at the 5' end of the antisense strand with respect to luciferase-targeting siRNAs (concentration: 100 pmol/L). The ordinate represents the ratio of luminescence in the case of using each siRNA when the amount of luminescence in a negative control group is taken as 1.

FIG. 2 is a graph for comparing the levels of luciferase luminescence between an siRNA having 8-Br-dA at the 5' end of the antisense strand (874-BrdA) and an siRNA having adenosine monophosphate (874-A), guanosine monophosphate (874-G), cytidine monophosphate (874-C), or uridine monophosphate (874-U) at the 5' end of the antisense strand with respect to luciferase-targeting siRNAs. The ordinate represents the ratio of luminescence in the case of using each siRNA when the amount of luminescence in a negative control group is taken as 1. In the abscissa, A, G, C, U, and BrdA denote 874-A, 874-G, 874-C, 874-U, and 874-BrdA, respectively. The results of the test performed by setting the concentration of each siRNA to 3.2 pmol/L, 16 pmol/L, 80 pmol/L, and 400 pmol/L are shown.

FIG. 3 is a graph for comparing the expression levels of GAPDH mRNA between an siRNA having 8-Br-dA at the 5' end of the antisense strand and an siRNA having adenosine monophosphate at the 5' end of the antisense strand with respect to siRNAs targeting D-glyceraldehyde-3-phosphate dehydrogenase (GAPDH, GenBank Accession No. NM 001256799). The ordinate represents the relative expression level of GAPDH mRNA when the GAPDH mRNA level in a negative control group is taken as 1. The abscissa represents respective siRNAs, more specifically, the left side represents siRNAs having adenosine monophosphate at the 5' end of the antisense strand (217-A, 278-A, 516-A, 624-A, 715-A, 816-A, 936-A, 1096-A, and 1134-A), and the right side represents siRNAs having 8-Br-dA at the 5' end of the antisense strand (217-BrdA, 278-BrdA, 516-BrdA, 624-BrdA, 715-BrdA, 816-BrdA, 936-BrdA, 1096-BrdA, and 1134-BrdA).

FIG. 4 is a graph showing the knockdown activity of each of siRNAs having adenosine monophosphate (454-A), uridine monophosphate (454-U), 8-Br-dA (454-BrdA), I-37 (6-NO2,7-Me-dQu), I-21 (6-napht-2-yl-dPu), I-34 (6-Me-dU), or I-25 (6-napht-1-yl-dPu) at the 5' end of the antisense strand with respect to luciferase-targeting siRNAs. The ordinate represents the 50% inhibitory concentration (IC$_{50}$ (pM)), and the abscissa represents the siRNAs used.

FIG. 5 is a graph showing the knockdown activity of each of siRNAs having adenosine monophosphate (454-A), uridine monophosphate (454-U), 8-Br-dA (454-BrdA), I-32

(2'-OMe-6-styryl-dA), or I-19 (di-Me-thienyl-dU) at the 5' end of the antisense strand with respect to luciferase-targeting siRNAs. The ordinate represents the 50% inhibitory concentration (IC$_{50}$(pM)), and the abscissa represents the siRNAs used.

FIG. 6 is a graph showing the knockdown activity of siRNAs having adenosine monophosphate (454-A), I-45 (8-BnNH-6-styryl purine), I-44 (N-Bn-N-MedA) or I-46 (8-furanylmethylamino-6-styrylpurine) at the 5' end of the antisense strand in luciferase-targeting siRNAs. The ordinate represents the 50% inhibitory concentration (IC$_{50}$ (pM)), and the abscissa represents the siRNAs used.

FIG. 7 is a graph showing the knockdown activity of siRNAs having adenosine monophosphate (454-A), I-39 (6-benzothiophenyl purine), I-41 (6-pyrenylpurine), I-43 (N-Bn dA) or I-40 (6-benzyloxynaphthylpurine) at the 5' end of the antisense strand in luciferase-targeting siRNAs. The ordinate represents the 50% inhibitory concentration (IC$_{50}$ (pM)), and the abscissa represents the siRNAs used.

FIG. 8 is a graph showing the knockdown activity of siRNAs having adenosine monophosphate (454-A) or I-42 (6-anthracenyl purine) at the 5' end of the antisense strand in luciferase-targeting siRNAs. The ordinate represents the 50% inhibitory concentration (IC$_{50}$ (pM)), and the abscissa represents the siRNAs used.

FIG. 9 is a graph showing the knockdown activity of siRNAs having adenosine monophosphate (454-A) or I-47 (6-styryl-8-tetrazolylmethylamino purine) at the 5' end of the antisense strand in luciferase-targeting siRNAs. The ordinate represents the 50% inhibitory concentration (IC$_{50}$ (pM)), and the abscissa represents the siRNAs used.

FIG. 10 is a graph showing the knockdown activity of siRNAs having adenosine monophosphate (454-A) or I-30 (6-(m-carboxyphenyl)purine) at the 5' end of the antisense strand in luciferase-targeting siRNAs. The ordinate represents the 50% inhibitory concentration (IC$_{50}$ (pM)), and the abscissa represents the siRNAs used.

FIG. 11 is a graph showing the knockdown activity of siRNAs having adenosine monophosphate (454-A) or I-48 (6-(m-carboxyethylphenyl)purine) at the 5' end of the antisense strand in luciferase-targeting siRNAs. The ordinate represents the 50% inhibitory concentration (IC$_{50}$ (pM)), and the abscissa represents the siRNAs used.

FIG. 12 is a graph showing the knockdown activity of siRNAs having adenosine monophosphate (454-A) or I-49 (5-furyl dU) at the 5' end of the antisense strand in luciferase-targeting siRNAs. The ordinate represents the 50% inhibitory concentration (IC$_{50}$ (pM)), and the abscissa represents the siRNAs used.

FIG. 13 is a graph showing the knockdown activity of siRNAs having adenosine monophosphate (454-A) or I-50 (2-amino rA) at the 5' end of the antisense strand in luciferase-targeting siRNAs. The ordinate represents the 50% inhibitory concentration (IC$_{50}$ (pM)), and the abscissa represents the siRNAs used.

FIG. 14 is a graph showing the knockdown activity of siRNAs having adenosine monophosphate (454-A), I-22 or I-51 at the 5' end of the antisense strand in luciferase-targeting siRNAs. The ordinate represents the 50% inhibitory concentration (IC$_{50}$ (pM)), and the abscissa represents the siRNAs used.

FIG. 15 is a graph showing the knockdown activity of siRNAs having adenosine monophosphate (454-A), I-52, I-55 or I-56 at the 5' end of the antisense strand in luciferase-targeting siRNAs. The ordinate represents the 50% inhibitory concentration (IC$_{50}$ (pM)), and the abscissa represents the siRNAs used.

FIG. 16 is a graph showing the knockdown activity of siRNAs having adenosine monophosphate (454-A), I-54, I-57, I-58 or I-59 at the 5' end of the antisense strand in luciferase-targeting siRNAs. The ordinate represents the 50% inhibitory concentration (IC$_{50}$ (pM)), and the abscissa represents the siRNAs used.

FIG. 17 is a graph showing the knockdown activity of siRNAs having adenosine monophosphate (454-A), I-53, I-60, I-61, I-62, I-63, I-64 or I-70 at the 5' end of the antisense strand in luciferase-targeting siRNAs. The ordinate represents the 50% inhibitory concentration (IC$_{50}$ (pM)), and the abscissa represents the siRNAs used.

FIG. 18 is a graph showing the knockdown activity of siRNAs having adenosine monophosphate (454-A), I-71, I-72, I-73 or I-74 at the 5' end of the antisense strand in luciferase-targeting siRNAs. The ordinate represents the 50% inhibitory concentration (IC$_{50}$ (pM)), and the abscissa represents the siRNAs used.

FIG. 19 is a graph showing the knockdown activity of siRNAs having adenosine monophosphate (454-A), I-65, I-66, I-67, I-68 or I-69 at the 5' end of the antisense strand in luciferase-targeting siRNAs. The ordinate represents the 50% inhibitory concentration (IC$_{50}$ (pM)), and the abscissa represents the siRNAs used.

FIG. 20 is a graph showing the knockdown activity of siRNAs having adenosine monophosphate (454-A), I-78, I-79, I-80 or I-81 at the 5' end of the antisense strand in luciferase-targeting siRNAs. The ordinate represents the 50% inhibitory concentration (IC$_{50}$ (pM)), and the abscissa represents the siRNAs used.

FIG. 21 is a graph showing the knockdown activity of siRNAs having adenosine monophosphate (454-A), I-75, I-76 or I-77 at the 5' end of the antisense strand in luciferase-targeting siRNAs. The ordinate represents the 50% inhibitory concentration (IC$_{50}$ (pM)), and the abscissa represents the siRNAs used.

FIG. 22 is a graph showing the knockdown activity of siRNAs having adenosine monophosphate (454-A), I-82 or I-83 at the 5' end of the antisense strand in luciferase-targeting siRNAs. The ordinate represents the 50% inhibitory concentration (IC$_{50}$ (pM)), and the abscissa represents the siRNAs used.

FIG. 23 is a graph showing the knockdown activity of siRNAs having adenosine monophosphate (454-A), I-84 or I-85 at the 5' end of the antisense strand in luciferase-targeting siRNAs. The ordinate represents the 50% inhibitory concentration (IC$_{50}$ (pM)), and the abscissa represents the siRNAs used.

FIG. 24 is a graph showing the knockdown activity of siRNAs having adenosine monophosphate (454-A), I-86, I-87, I-88 or I-89 at the 5' end of the antisense strand in luciferase-targeting siRNAs. The ordinate represents the 50% inhibitory concentration (IC$_{50}$ (pM)), and the abscissa represents the siRNAs used.

FIG. 25 is a graph showing the knockdown activity of siRNAs having adenosine monophosphate (454-A), I-27, I-29, I-90, I-91, I-92 or I-93 at the 5' end of the antisense strand in luciferase-targeting siRNAs. The ordinate represents the 50% inhibitory concentration (IC$_{50}$ (pM)), and the abscissa represents the siRNAs used.

FIG. 26 is a graph showing the knockdown activity of siRNAs having adenosine monophosphate (454-A-dT), I-94 or I-95 at the 5' end of the antisense strand in luciferase-targeting siRNAs. The ordinate represents the 50% inhibitory concentration (IC$_{50}$ (pM)), and the abscissa represents the siRNAs used.

FIG. 27 is a graph showing the knockdown activity of siRNAs having adenosine monophosphate (454-A) or I-96 at the 5' end of the antisense strand in luciferase-targeting siRNAs. The ordinate represents the 50% inhibitory concentration ($IC_{50}$ (pM)), and the abscissa represents the siRNAs used.

FIG. 28 is a graph showing the knockdown activity of siRNAs having adenosine monophosphate (454-A), I-97, I-98, I-99, I-100 or I-101 at the 5' end of the antisense strand in luciferase-targeting siRNAs. The ordinate represents the 50% inhibitory concentration ($IC_{50}$ (pM)), and the abscissa represents the siRNAs used.

MODE FOR CARRYING OUT THE INVENTION

Hereinafter, a compound represented by formula (I) is referred to as Compound (I). The compounds having the other formula numbers are referred to in the same manner.

In the definitions of the respective groups in formulae (I), (II), (III), (IV), (V), (IIA), (IIIA), (IVA), (VA), (Ia), and (A1) to (A11), (i) the halogen means each atom of fluorine, chlorine, bromine, and iodine.

(ii) Examples of the lower alkyl and the lower alkyl moieties of the lower alkoxy, the lower alkoxycarbonyl, the lower alkylamino, the di-lower alkylamino, the lower alkylcarbamoyl, the di-lower alkylcarbamoyl, the lower alkylthio, and the lower alkylsulfonyl include linear or branched alkyl having 1 to 10 carbon atom(s). Specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, and the like. The two lower alkyl moieties of the di-lower alkylamino and the di-lower alkylaminocarbamoyl may be the same or different.

(iii) Examples of the cycloalkyl include cycloalkyl having 3 to 10 carbon atoms. Specific examples thereof include cyclopropyl, cyclobutyl, cyclopentyl, cyclohexyl, cycloheptyl, cyclooctyl, cyclodecyl, and the like.

(iv) The alkylene moieties of the aralkyl and the aromatic heterocyclic alkyl have the same meanings as groups in which one hydrogen atom is removed from the lower alkyl described in the above (ii).

(v) Examples of the lower alkenyl include linear or branched alkenyl having 2 to 10 carbon atoms. Specific examples thereof include vinyl, allyl, 1-propenyl, isopropenyl, methacryl, butenyl, crotyl, pentenyl, hexenyl, heptenyl, octenyl, nonenyl, decenyl, and the like.

(vi) Examples of the lower alkynyl include linear or branched alkynyl having 2 to 10 carbon atoms. Specific examples thereof include ethynyl, propargyl, butynyl, pentynyl, hexynyl, heptynyl, octynyl, nonynyl, decynyl, and the like.

(vii) Examples of the lower alkanoyl include linear or branched lower alkanoyl having 1 to 8 carbon atom(s). Specific examples thereof include formyl, acetyl, propionyl, butyryl, isobutyryl, valeryl, isovaleryl, pivaloyl, hexanoyl, heptanoyl, octanoyl, and the like.

(viii) Examples of the aryl and the aryl moieties of the aralkyl, the aroyl, the aryloxy, the arylthio, and the arylsulfonyl include aryl having 6 to 18 carbon atoms. Specific examples thereof include phenyl, naphthyl, indenyl, anthryl, phenanthrenyl, phenalenyl, tetracenyl, pyrenyl, chrysenyl, and the like, and preferred examples thereof include phenyl, naphthyl, anthryl, pyrenyl and the like.

(ix) Examples of the aromatic heterocyclic group and the aromatic heterocyclic group moieties of the aromatic heterocyclic alkyl, the aromatic heterocyclic carbonyl, the aromatic heterocyclicoxy, the aromatic heterocyclicthio, and the aromatic heterocyclic sulfonyl include a 5- or 6-membered monocyclic aromatic heterocyclic group containing at least one atom selected from a nitrogen atom, an oxygen atom, and a sulfur atom, a bicyclic or tricyclic fused-ring aromatic heterocyclic group in which 3- to 8-membered rings are fused and at least one atom selected from a nitrogen atom, an oxygen atom, and a sulfur atom is contained, and the like. Specific examples thereof include pyridyl, pyrazinyl, pyrimidinyl, pyridazinyl, oxopyridazinyl, quinolyl, isoquinolyl, phthalazinyl, quinazolinyl, quinoxalinyl, naphthyridinyl, cinnolinyl, pyrrolyl, pyrazolyl, imidazolyl, triazinyl, triazolyl, tetrazolyl, thienyl, furyl, triazolyl, isothiazolyl, oxazolyl, isoxazolyl, oxadiazolyl, thiadiazolyl, indolyl, isoindolyl, indazolyl, benzofuryl, isobenzofuryl, benzothienyl, benzoimidazolyl, benzotriazolyl, benzothiazolyl, benzoxazolyl, pyrazolopyridyl, pyrazolopyrimidinyl, purinyl, dibenzofuranyl, dibenzoazepinyl, and the like, and preferred examples thereof include pyridyl, pyrrolyl, thienyl, oxazolyl, benzofuryl, isobenzofuryl, benzothienyl, and the like.

(x) Examples of the aliphatic heterocyclic group include a 5- or 6-membered monocyclic aliphatic heterocyclic group containing at least one atom selected from a nitrogen atom, an oxygen atom, and a sulfur atom, a bicyclic or tricyclic fused-ring aliphatic heterocyclic group in which 3- to 8-membered rings are fused and at least one atom selected from a nitrogen atom, an oxygen atom, and a sulfur atom is contained, and the like. Specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, and the like, and preferred examples thereof include tetrahydroquinolyl, tetrahydroisoquinolyl, dihydroindolyl, dihydroisoindolyl, dihydrobenzofuranyl, and the like.

(xi) Examples of the aromatic ring include a benzene ring, a naphthalene ring, an aromatic heterocyclic ring, and the like. The aromatic heterocyclic ring has the same meaning as the aromatic heterocyclic moieties of the aromatic heterocyclic group described above.

(xii) The substituents of the optionally substituted lower alkyl, the optionally substituted lower alkenyl, the optionally substituted lower alkynyl, the optionally substituted lower alkoxy, the optionally substituted lower alkoxycarbonyl, the optionally substituted lower alkanoyl, the optionally substituted lower alkylamino, the optionally substituted di-lower alkylamino, the optionally substituted lower alkylcarbamoyl, the optionally substituted di-lower alkylcarbamoyl, the optionally substituted lower alkylthio, and the optionally substituted lower alkylsulfonyl may be the same or different and in number of, for example, 1 to 3, and examples of the substituents include substituents selected from the group consisting of halogen, hydroxy, sulfanyl, nitro, cyano, an acid functional group, carbamoyl, $C_{3-8}$ cycloalkyl, an aliphatic heterocyclic group, $C_{1-10}$ alkoxy, $C_{3-8}$ cycloalkoxy, $C_{6-14}$ aryloxy, $C_{7-16}$ aralkyloxy, $C_{1-8}$ alkanoyloxy, $C_{7-15}$ aroyloxy, $C_{1-10}$ alkylsulfanyl, —$NR^XR^Y$ {wherein $R^X$ and $R^Y$ may be the same or different, and each is selected from the group consisting of a hydrogen atom, optionally substituted $C_{1-10}$ alkyl [examples of the substituent of the optionally substituted $C_{1-10}$ alkyl include an acidic functional group and optionally substituted $C_{6-14}$ aryl (the substituent of the optionally substituted $C_{6-14}$ aryl include hydroxy in the number of 1 to 3)], optionally substituted $C_{3-8}$ cycloalkyl (examples of the substituent of the optionally substituted $C_{3-8}$ cycloalkyl include optionally substituted $C_{1-10}$ alkyl [examples of the substituent of the optionally substituted $C_{1-10}$ alkyl include an acidic functional group, and optionally substituted $C_{6-14}$ aryl (examples of the substituent of the optionally substituted $C_{6-14}$ aryl include hydroxy in the number of 1 to 3) in the number of 1 to 3]), optionally substituted $C_{6-14}$ aryl {examples of the substituent of the optionally substituted $C_{6-14}$ aryl include halogen, hydroxy, nitro, optionally substituted $C_{1-10}$ alkyl [examples of the substituent of the optionally substituted $C_{1-10}$ alkyl include a acidic functional group, and optionally substituted $C_{6-14}$ aryl (examples of the substituent of the optionally substituted $C_{6-14}$ aryl includes hydroxy in the number of 1 to 3) in the number of 1 to 3] in the number of 1 to 3}, an optionally substituted aromatic heterocyclic group (examples of the substituent of the optionally substituted aromatic heterocyclic group includes hydroxy in the number of 1 to 3), $C_{7-16}$ aralkyl, $C_{1-8}$ alkanoyl, $C_{7-15}$ aroyl, $C_{1-10}$ alkoxycarboxyl or $C_{7-16}$ aralkyloxycarbonyl}, aromatic heterocyclicthio, aromatic heterocyclic sulfinyl, aromatic heterocyclic sulfonyl, $C_{1-8}$ alkanoyl, $C_{7-15}$ aroyl, $C_{1-10}$ alkoxycarbonyl, $C_{6-14}$ aryloxycarbonyl, $C_{1-10}$ alkylcarbamoyl and di-$C_{1-10}$ alkylcarbamoyl.

The substituents of the optionally substituted lower alkenyl, the optionally substituted lower alkynyl, the optionally substituted lower alkoxy, the optionally substituted lower alkoxycarbonyl, the optionally substituted lower alkanoyl, the optionally substituted lower alkylamino, the optionally substituted di-lower alkylamino, the optionally substituted lower alkylcarbamoyl, the optionally substituted di-lower alkylcarbamoyl, the optionally substituted lower alkylthio, and the optionally substituted lower alkylsulfonyl may be substituents selected from the group consisting of $C_{6-14}$ aryl optionally substituted with $C_{1-6}$ alkyl substituted with an acidic functional group and an aromatic heterocyclic group in addition to the groups exemplified in the substituents of the above optionally substituted lower alkyl and the like.

(xiii) The substituents of the optionally substituted aryl, the optionally substituted aralkyl, the optionally substituted aralkyloxy, the optionally substituted aryloxy, the optionally substituted arylthio, the optionally substituted arylsulfonyl, the optionally substituted aroyl, the optionally substituted aromatic heterocyclic group, the optionally substituted aromatic heterocyclic alkyl, the optionally substituted aromatic heterocyclic carbonyl, the optionally substituted aromatic heterocyclicoxy, the optionally substituted aromatic heterocyclicthio, the optionally substituted aromatic heterocyclic sulfonyl, and the optionally substituted styryl may be the same or different and in number of, for example, 1 to 3, and examples of the substituents include substituents selected from the group consisting of halogen, hydroxy, sulfanyl, nitro, cyano, an acidic functional group, carbamoyl, optionally substituted $C_{1-10}$ alkyl [examples of the substituent of the optionally substituted $C_{1-10}$ alkyl include hydroxy, cyano, an acidic functional group, $C_{1-10}$ alkylcarbamoyl, and di-$C_{1-10}$ alkylcarbamoyl, for example, in the number of 1 to 3], trifluoromethyl, $C_{3-8}$ cycloalkyl, optionally substituted $C_{6-14}$ aryl (examples of the substituent of the optionally substituted $C_{6-14}$ aryl include hydroxy in the number of 1 to 3), an aliphatic heterocyclic group, an optionally substituted aromatic heterocyclic group (examples of the substituent of the optionally substituted aromatic heterocyclic group include hydroxy in the number of 1 to 3), aromatic heterocyclicthio, aromatic heterocyclic sulfinyl, aromatic heterocyclic sulfonyl, optionally substituted $C_{1-10}$ alkoxy [examples of the substituent of the optionally substituted $C_{1-10}$ alkoxy include an acidic functional group and optionally substituted $C_{6-14}$ aryl (examples of the substituent of the optionally substituted $C_{6-14}$ aryl include hydroxy in the number of 1 to 3) in the number of 1 to 3], $C_{3-8}$ cycloalkoxy, $C_{6-14}$ aryloxy, $C_{7-16}$ aralkyloxy, $C_{1-8}$ alkanoyloxy, $C_{7-15}$ aroyloxy, $C_{1-10}$ alkylsulfanyl, $C_{1-10}$ alkylsulfonyl, —NR$^{Xa}$R$^{Ya}$ (wherein R$^{Xa}$ and R$^{Ya}$ may be the same or different, and each is a hydrogen atom, $C_{1-10}$ alkyl, $C_{3-8}$ cycloalkyl, $C_{6-14}$ aryl, aromatic heterocyclic group, aromatic heterocyclicthio, aromatic heterocyclic sulfinyl, aromatic heterocyclic sulfonyl, optionally substituted $C_{7-16}$ aralkyl (examples of the substituent of the optionally substituted $C_{7-16}$ aralkyl include hydroxy in the number of 1 to 3), $C_{1-8}$ alkanoyl, $C_{7-15}$ aroyl, $C_{1-10}$ alkoxycarbonyl or $C_{7-16}$ aralkyloxycarbonyl), $C_{1-8}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl, carboxy-$C_{1-10}$ alkyl and $C_{1-10}$ alkoxycarbonyl $C_{1-10}$ alkyl, and one substituted halogen, hydroxy, sulfanyl, nitro, cyano, carboxy, $C_{1-3}$ alkyl, trifluoromethyl, $C_{1-3}$ alkoxy or the like is preferred.

Examples of the $C_{1-10}$ alkyl and the $C_{1-10}$ alkyl moieties of the $C_{1-10}$ alkoxy, the $C_{1-10}$ alkylsulfanyl, the $C_{1-10}$ alkylsulfonyl, the $C_{1-10}$ alkoxycarbonyl, the $C_{1-10}$ alkylcarbamoyl, and the di-$C_{1-10}$ alkylcarbamoyl described above include the groups exemplified as the lower alkyl described above. The two $C_{1-10}$ alkyl moieties of the di-$C_{1-10}$ alkylcarbamoyl may be the same or different.

Examples of the $C_{1-8}$ alkanoyl and the $C_{1-8}$ alkanoyl moiety of the $C_{1-8}$ alkanoyloxy include the groups exemplified as the lower alkanoyl described above.

Examples of the $C_{3-8}$ cycloalkyl and the $C_{3-8}$ cycloalkyl moiety of the $C_{3-8}$ cycloalkoxy include cyclopropyl, cyclobutyl, cyclopentyl, cyclohexyl, cycloheptyl, cyclooctyl, and the like.

Examples of the $C_{6-14}$ aryl and the aryl moieties of the $C_{6-14}$ aryloxy, the $C_{7-15}$ aroyl, the $C_{7-15}$ aroyloxy, and the $C_{6-14}$ aryloxycarbonyl include the groups exemplified as the aryl described above.

Examples of the aryl moieties of the $C_{7-16}$ aralkyloxy, the $C_{7-16}$ aralkyl, and the $C_{7-16}$ aralkyloxycarbonyl include the groups exemplified as the aryl described above. Examples of the alkylene moieties include $C_{1-10}$ alkylene, and more specifically include groups in which one hydrogen atom is removed from the groups exemplified as the lower alkyl described above.

The aliphatic heterocyclic group, halogen, aromatic heterocyclicthio, aromatic heterocyclic sulfonyl and aromatic heterocyclic group have the same meanings as described above.

Examples of the aromatic heterocyclic moiety of the aromatic heterocyclic sulfinyl include the groups exemplified as the aromatic heterocyclic group described above.

Examples of the acidic functional group include carboxy, hydroxamoyl, aminophosphonyl, sulfonylaminocarbonyl, phosphonooxy, —SO$_3$H, sulfino, phosphono, phosphino, aminosulfonyl, —OP(=O)(OH)$_2$, —OP(=O)(OH)—OCH$_2$CH$_2$O—P(=O)(OH)$_2$ and the like.

R$_2$ in the formula (I) above is preferably a hydrogen atom or hydroxy, and more preferably a hydrogen atom.

In the formula (II) above, preferably $Y^1$ is a nitrogen atom or the like; $R^5$ is a hydrogen atom, halogen, cyano, optionally substituted lower alkyl, optionally substituted lower alkenyl or —$NR^{10a}R^{10b}$ (wherein each of $R^{10a}$ and $R^{10b}$ has the same meaning as described above) or the like;

$R^6$ is a hydrogen atom, optionally substituted aryl, an optionally substituted aromatic heterocyclic group, optionally substituted lower alkenyl, optionally substituted lower alkoxy, optionally substituted lower alkylthio, optionally substituted arylthio or —$NR^{11a}R^{11b}$ (wherein $R^{11a}$ and $R^{11b}$ have the same meanings as described above) or the like; and $R^7$ is a hydrogen atom or an isostere of a hydrogen atom in the nucleic acid field (such as a deuterium atom, amino, hydroxy or a fluorine atom) or the like (provided that $R^{11a}$ and $R^{11b}$ cannot simultaneously be hydrogen atoms when $Y^1$ is a nitrogen atom, $R^5$ is a hydrogen atom, $R^6$ is —$NR^{11a}R^{11b}$ and $R^7$ is a hydrogen atom).

More preferably, either $Y^1$ in formula (II) above is a nitrogen atom or the like; $R^5$ is halogen or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, an optionally substituted aromatic heterocyclic group or the like; and $R^7$ is a hydrogen atom, amino or the like, or $Y^1$ in formula (II) above is a nitrogen atom or the like; $R^5$ is a hydrogen atom or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, optionally substituted lower alkoxy, optionally substituted lower alkylthio, optionally substituted arylthio, an optionally substituted aromatic heterocyclic group or the like; and $R^7$ is a hydrogen atom, amino or the like (provided that $R^{11a}$ and $R^{11b}$ cannot simultaneously be hydrogen atoms when $Y^1$ is a nitrogen atom, $R^5$ is a hydrogen atom, $R^6$ is —$NR^{11a}R^{11b}$ and $R^7$ is a hydrogen atom), or $Y^1$ in formula (II) above is a nitrogen atom or the like; $R^5$ is a cyano or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, an optionally substituted aromatic heterocyclic group or the like; and $R^7$ is a hydrogen atom, amino or the like, or $Y^1$ in formula (II) above is a nitrogen atom or the like; $R^5$ is optionally substituted lower alkyl or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, an optionally substituted aromatic heterocyclic group or the like; and $R^7$ is a hydrogen atom, or amino or the like, or $Y^1$ in formula (II) above is a nitrogen atom or the like; $R^5$ is —$NR^{11a}R^{11b}$ (wherein $R^{11a}$ and $R^{11b}$ have the same meanings as described above) or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, an optionally substituted aromatic heterocyclic group or the like; and $R^7$ is a hydrogen atom, amino or the like, or $Y^1$ in formula (II) above is a nitrogen atom or the like; $R^5$ is halogen, a hydrogen atom, cyano, optionally substituted lower alkyl, —$NR^{11a}R^{11b}$ (wherein $R^{11a}$ and $R^{11b}$ have the same meanings as described above) or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, optionally substituted lower alkoxy, optionally substituted lower alkylthio, optionally substituted arylthio, an optionally substituted aromatic heterocyclic group or the like; and $R^7$ is a hydrogen atom (provided that $R^{11a}$ and $R^{11b}$ cannot simultaneously be hydrogen atoms when $Y^1$ is a nitrogen atom, $R^5$ is a hydrogen atom, $R^6$ is —$NR^{11a}R^{11b}$ and $R^7$ is a hydrogen atom), or $Y^1$ in formula (II) above is a nitrogen atom or the like; $R^5$ is halogen, a hydrogen atom, cyano, optionally substituted lower alkyl, —$NR^{11a}R^{11b}$ (wherein $R^{11a}$ and $R^{11b}$ have the same meanings as described above) or the like; $R^6$ is a hydrogen atom, —$NR^{11a}R^{11b}$ (wherein $R^{11a}$ and $R^{11b}$ have the same meanings as described above), optionally substituted lower alkenyl, optionally substituted aryl, an optionally substituted aromatic heterocyclic group or the like; and $R^7$ is amino, and still more preferably either $Y^1$ in formula (II) above is a nitrogen atom or the like; $R^5$ is halogen or the like; $R^6$ is a hydrogen atom or —$NR^{11a}R^{11b}$ (wherein $R^{11a}$ and $R^{11b}$ have the same meanings as described above) or the like; and $R^7$ is a hydrogen atom or the like, or $Y^1$ in formula (II) above is a nitrogen atom or the like; $R^5$ is a hydrogen atom or the like; $R^6$ is optionally substituted lower alkenyl or the like; and $R^7$ is a hydrogen atom or the like, or $Y^1$ in formula (II) above is a nitrogen atom or the like; $R^5$ is a cyano or the like; $R^6$ is a hydrogen atom, —$NR^{11a}R^{11b}$ (wherein $R^{11a}$ and $R^{11b}$ have the same meanings as described above) or the like; and $R^7$ is a hydrogen atom or the like, or $Y^1$ in formula (II) above is a nitrogen atom or the like; $R^5$ is halogen or the like; $R^6$ is optionally substituted lower alkenyl or the like; and $R^7$ is a hydrogen atom or the like, or $Y^1$ in formula (II) above is a nitrogen atom or the like; $R^5$ is a hydrogen atom or the like; $R^6$ is optionally substituted aryl or the like; and $R^7$ is a hydrogen atom or the like, or $Y^1$ in formula (II) above is a nitrogen atom or the like; $R^5$ is a hydrogen atom or the like; $R^6$ is an optionally substituted aromatic heterocyclic group or the like; and $R^7$ is a hydrogen atom or the like, or $Y^1$ in formula (II) above is a nitrogen atom or the like; $R^5$ is a hydrogen atom or the like; $R^6$ is —$NR^{11a}R^{11b}$ (wherein $R^{11a}$ and $R^{11b}$ have the same meanings as described above) or the like; and $R^7$ is a hydrogen atom or the like, or $Y^1$ in formula (II) above is a nitrogen atom or the like; $R^5$ is a hydrogen atom or the like; $R^6$ is optionally substituted lower alkoxy or the like; and $R^7$ is a hydrogen atom or the like, or $Y^1$ in formula (II) above is a nitrogen atom or the like; $R^5$ is a hydrogen atom or the like; $R^6$ is optionally substituted lower alkylthio or the like; and $R^7$ is a hydrogen atom or the like, or $Y^1$ in formula (II) above is a nitrogen atom or the like; $R^5$ is a hydrogen atom or the like; $R^6$ is optionally substituted arylthio or the like; and $R^7$ is a hydrogen atom or the like, or $Y^1$ in formula (II) above is a nitrogen atom or the like; $R^5$ is optionally substituted lower alkyl or the like; $R^6$ is optionally substituted lower alkenyl or the like; and $R^7$ is a hydrogen atom or the like, or $Y^1$ in formula (II) above is a nitrogen atom or the like; $R^5$ is a hydrogen atom or the like; $R^6$ is —$NR^{11a}R^{11b}$ (wherein $R^{11a}$ and $R^{11b}$ have the same meanings as described above) or the like; and $R^7$ is an amino or the like, or $Y^1$ in formula (II) above is a nitrogen atom or the like; $R^5$ is —$NR^{10a}R^{10b}$ (wherein $R^{10a}$ and $R^{10b}$ have the same meanings as described above) or the like; $R^6$ is optionally substituted alkenyl or the like; and $R^7$ is a hydrogen atom or the like.

When above-mentioned $R^5$ is —$NR^{11a}R^{11b}$, $R^{11a}$ and $R^{11b}$ may be the same or different, and are preferably either unsubstituted lower alkyls (wherein the lower alkyl has the same meaning as described above) or substituted lower alkyls (wherein the lower alkyl has the same meaning as described above), and examples of the substituent therein include the optionally substituted aryl group and the optionally substituted aromatic heterocyclic group described above and the like. When above-mentioned $R^6$ is a substituted aryl, the substituent is more preferably in the meta-position or para-position of the aryl, and this substituent is preferably carboxymethyl, 2-carboxyethyl, 3-carboxypropyl group or the like.

(a1) When above-mentioned $R^6$ is —$NR^{11a}R^{11b}$, $R^{11a}$ is preferably optionally substituted lower alkyl, optionally substituted lower alkynyl, optionally substituted aralkyl, optionally substituted aryl or the like, and $R^{11b}$ is preferably a hydrogen atom or the like. The substituent of the optionally substituted alkyl is preferably —$SO_3H$, —$N[CH_2CH_2OP(=O)(OH)_2]_2$ or the like. The substituent of the optionally substituted lower alkynyl is preferably —$OP(=O)(OH)_2$, 2-[$CH_2OP(=O)(OH)_2$]phenyl, 3-[$CH_2OP(=O)(OH)_2$]phenyl, 4-[$CH_2OP(=O)(OH)_2$]phenyl, 3,5-[$CH_2OP(=O)(OH)_2]_2$phenyl or the like. The substituent of the optionally substituted aralkyl is preferably hydroxy, carboxy, —$CH_2OP(=O)(OH)_2$, —$CH_2O$—$P(=O)(OH)$—$OCH_2CH_2O$—$P(=O)(OH)_2$ or the like. The substituent of the optionally substituted aryl is preferably —$CH_2OP(=O)(OH)_2$, —$OCH_2CH_2$—$OP(=O)(OH)_2$ or the like.

(a2) When above-mentioned $R^6$ is optionally substituted aryl, the substituent thereof is preferably carboxymethyl, 2-carboxyethyl, 3-carboxypropyl, —$OH_2OP(=O)(OH)_2$, —$(CH_2)_3OP(=O)(OH)_2$ or the like.

(a3) When above-mentioned $R^6$ is optionally substituted lower alkoxy, the substituent thereof is preferably —$OP(=O)(OH)_2$, optionally substituted aryl group or the like. The substituent of the optionally substituted aryl is preferably nitro, a fluorine atom, hydroxy, —$CH_2OP(=O)(OH)_2$ or the like.

(a4) When above-mentioned $R^6$ is optionally substituted lower alkylthio, the substituent thereof is preferably —$OP(=O)(OH)_2$, (1-carboxymethyl)cyclopropan-1-yl or the like.

(a5) When above-mentioned $R^6$ is optionally substituted arylthio, the substituent thereof is preferably hydroxy, —$CH_2OP(=O)(OH)_2$, carboxy, carboxymethyl or the like.

Further, in the above formula (IV), it is preferred that $R^{12}$ be a hydrogen atom, an isostere of a hydrogen atom in the nucleic acid field (for example, a deuterium atom, amino, hydroxy, a fluorine atom, or the like), or the like; - - - be a double bond; $Y^3$ b e $CR^{14e}$; $Y^4$ be a nitrogen atom or $CR^{14f}$; and $R^{14e}$ and $R^{14f}$ be a hydrogen atom, halogen, cyano, optionally substituted lower alkenyl, optionally substituted aryl, an optionally substituted aromatic heterocyclic group, or the like.

Still further, in the above formula (V), it is preferred that $R^{12a}$ be hydrogen, an isostere of a hydrogen atom in the nucleic acid field (for example, a deuterium atom, amino, hydroxy, a fluorine atom, or the like), or the like; ring A be a benzene ring, a thiophene ring, or the like; n1 be 1 or 2; and $R^{16}$ be halogen, nitro, optionally substituted alkyl, optionally substituted lower alkylamino, or optionally substituted di-lower alkylamino.

The oligonucleotide of the present invention means a polymer or an oligomer comprising a nucleotide residue or a nucleoside residue. The oligonucleotide of the present invention includes both of a single-stranded oligonucleotide and a double-stranded oligonucleotide. In a double-stranded oligonucleotide, the base lengths of the respective oligonucleotide strands may be different. Further, the double-stranded oligonucleotide may contain one or more mismatched base pairs. In addition, a complex formed of three or more oligonucleotide strands is also included in the oligonucleotide of the present invention.

The oligonucleotide of the present invention preferably has a knockdown activity against an mRNA encoding, for example, a protein involved in a disease. Here, the "having a knockdown activity" as used in the specification means inhibiting the expression of a gene (target gene) encoding a protein or the like, and it is preferred that the oligonucleotide of the present invention have the knockdown activity preferably 2 times, more preferably 5 times, further more preferably 10 times higher than that of an siRNA containing a corresponding natural nucleotide at the 5' end of the oligonucleotide.

Examples of the double-stranded oligonucleotide include a double-stranded DNA such as a structural gene, a double-stranded RNA such as a small molecule RNA including an siRNA and a miRNA, and the like. However, the present invention is not limited thereto. Examples of the single-stranded oligonucleotide include an antisense oligonucleotide, a microRNA, an aptamer, an antagomir, a single-stranded RNAi agent (such as an siRNA having a hairpin structure), and the like. However, the present invention is not limited thereto.

The length of the oligonucleotide of the present invention is preferably 10 to 100 bases, more preferably 10 to 80 bases, furthermore preferably 10 to 50 bases, particularly preferably 20 to 50 bases, and the most preferably 20 to 30 bases.

In the oligonucleotide of the present invention, in addition to the nucleotide residue or the nucleoside residue at the 5' end, further one or more nucleotide residues may be modified. Such modification may be contained in any site of a base, a sugar, and a phosphate.

A base-modified nucleotide may be any as long as it is a nucleotide in which a part or the whole of the chemical structure of a base of the nucleotide is modified with an arbitrary substituent or is substituted with an arbitrary atom, and examples thereof include a nucleotide in which an oxygen atom in a base is substituted with a sulfur atom, a nucleotide in which a hydrogen atom in a base is substituted with alkyl having 1 to 10 carbon atoms, a nucleotide in which methyl in a base is substituted with a hydrogen atom or alkyl having 2 to 10 carbon atoms, and a nucleotide in which amino is protected by a protecting group such as an alkyl group having 1 to 10 carbon atoms, alkanoyl having 1 to 8 carbon atoms, or the like.

A sugar moiety-modified nucleotide may be any as long as it is a nucleotide in which a part or the whole of the chemical structure of a sugar of the nucleotide is modified with an arbitrary substituent or is substituted with an arbitrary atom. And, a 2'-modified nucleotide is preferably used.

Examples of the 2'-modified nucleotide include a 2'-modified nucleotide in which the 2'-OH of a ribose is substituted with a substituent selected from a hydrogen atom, —OR, —R, —R', —SH, —SR, amino, —NHR, —NR$_2$, N$_3$, cyano, and halogen (wherein R is lower alkyl or aryl, and the lower alkyl, the aryl, and the halogen have the same meanings as described above, respectively). Specific examples thereof include a 2'-modified nucleotide in which the 2'-OH is substituted with a substituent selected from the group consisting of a fluorine atom, methoxy, 2-(methoxy) ethoxy, 3-aminopropoxy, 2-[(N,N-dimethylamino)oxy]ethoxy, 3-(N,N-dimethylamino)propoxy, 2-[2-(N,N-dimethylamino)ethoxy]ethoxy, 2-(methylamino)-2-oxoethoxy, 2-(N-methylcarbamoyl)ethoxy, and 2-cyanoethoxy, and the like.

A phosphate-modified nucleotide may be any as long as it is a oligonucleotide in which a part or the whole of the chemical structure of a phosphodiester bond of the nucleotide is modified with an arbitrary substituent or is substituted with an arbitrary atom, and examples thereof include a nucleotide in which a phosphodiester bond is replaced with an alkyl phosphonate bond, and the like.

As the oligonucleotide which has a knockdown activity against an mRNA encoding a protein involved in a disease, any nucleic acid, for example, An oligonucleotide which contains a base sequence complementary to a partial base sequence of the mRNA of a gene (target gene) encoding a protein or the like and inhibits the expression of the target gene can be used. Specifically, a double-stranded oligonucleotide such as an siRNA (short interference RNA) or a miRNA (micro RNA), a single-stranded oligonucleotide such as an shRNA (short hairpin RNA), an antisense nucleic acid, or a ribozyme may be used. And, a double-stranded oligonucleotide is preferred.

An oligonucleotide strand containing a base sequence complementary to a partial base sequence of the target gene mRNA is referred to as an antisense strand, and an oligonucleotide containing a base sequence complementary to the base sequence of the antisense strand is referred to as a sense strand. The sense strand refers to an oligonucleotide itself consisting of a partial base sequence of the target gene and the like, namely an oligonucleotide which can form a double strand-forming region by pairing with the antisense strand. In a double-stranded oligonucleotide containing a base sequence complementary to a partial base sequence of the target gene mRNA, the 5' end of the oligonucleotide means the 5' end of the antisense strand.

In the oligonucleotide of the present invention, a double strand-forming region formed by base pairing between an antisense strand and a sense strand has generally 15 to 27 base pairs, preferably 15 to 25 base pairs, more preferably 15 to 23 base pairs, further more preferably 15 to 21 base pairs, and particularly preferably 15 to 19 base pairs. The double strand-forming region may be any as long as the bases of each of the antisense strand and the sense strand pair with each other, and base pairs may be formed or mismatched. And the base at the 5' end of the antisense strand and the base of the sense strand to be paired therewith preferably form an adenosine-uracil (A-U) base pair or a mismatched base pair.

The oligonucleotide in either the antisense strand or the sense strand which constitutes a double-stranded oligonucleotide, or both of them which constitute a double-stranded oligonucleotide may have an additional nucleotide which does not form a double strand on the 3' side or the 5' side of the double strand-forming region. Such a region which does not form a double strand is also referred to as a protrusion (overhang).

As the double-stranded oligonucleotide having a protrusion, for example, a double-stranded oligonucleotide having a protrusion consisting of 1 to 4 bases, generally 1 to 3 bases at the 3' end or the 5' end of at least one strand is used. Also, a double-stranded oligonucleotide having a protrusion consisting of 2 bases is preferably used, and a double-stranded oligonucleotide having a protrusion consisting of dTdT or UU is more preferably used. A protrusion may be present on only the antisense strand, only the sense strand, and both of the antisense strand and the sense strand. And, a double-stranded nucleic acid having a protrusion on both of the antisense strand and the sense strand is preferably used.

In addition, a sequence which is contiguous with the double strand-forming region and partially or completely matches the base sequence of the target gene mRNA, or a sequence which is contiguous with the double strand-forming region and partially or completely matches the base sequence of the complementary strand of the target gene mRNA may also be used. Further, as the double-stranded oligonucleotide, for example, a nucleic acid molecule which forms a double-stranded oligonucleotide having a protrusion described above resulted from the action of a ribonuclease such as Dicer (WO2005/089287), at least a double-stranded oligonucleotide which does not have a protrusion at the 3' end or the 5' end, or the like can also be used.

Further, in the above-described double-stranded oligonucleotide, preferably, at least a sequence of bases (nucleosides) at positions 2 to 17 from the 5' end side to the 3' end side of the antisense strand is a base sequence complementary to a sequence of 16 consecutive bases of the target gene mRNA. More preferably, a sequence of bases at positions 2 to 19 from the 5' end side to the 3' end side of the antisense strand is a base sequence complementary to a sequence of consecutive 18 bases of the target gene mRNA, a sequence of bases at positions 2 to 21 is a base sequence complementary to a sequence of 20 consecutive bases of the target gene mRNA, or a sequence of bases at positions 2 to 25 is a base sequence complementary to a sequence of 24 consecutive bases of the target gene mRNA.

The base sequence at the 5' end of the antisense strand may be complementary to or mismatch the base sequence of the target gene mRNA. Further, when the nucleic acid used in the present invention is an siRNA, preferably 10 to 70%, more preferably 15 to 60%, furthermore preferably 20 to 50% of the sugar in the nucleic acid is a 2'-modified nucleotide. The 2'-modified nucleotide of the present invention is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, or the like, further preferably 2'-O-methyl, 2'-O-ethyl, 2'-fluoro, a hydrogen atom, or the like, and most preferably 2'-O-methyl and 2'-fluoro.

Compound (Ia) corresponds to a nucleotide or a nucleoside in which the residual part of a nucleotide residue or a nucleoside residue represented by formula (I) becomes hydroxy. Examples of the preferred embodiment of Compound (Ia) include an nucleotide or an nucleoside corresponding to the nucleotide residues or the nucleoside residues represented by formula (I) according to the above (2) to (52), and examples of the more preferred embodiment thereof include an nucleotide or an nucleoside corresponding to the nucleotide residue or the nucleoside residue represented by formula (I) wherein $X^1$ is an oxygen atom, $R^2$ is a hydrogen atom, hydroxy, a fluorine atom, or methoxy according to the above (32) to (52).

Compound (Ia) can also be obtained as a salt thereof such as an acid addition salt, a metal salt, an ammonium salt, an organic amine addition salt, an amino acid addition salt, or the like.

Examples of the acid addition salt include an inorganic acid salt such as hydrochloride, sulfate, or phosphate, and an organic acid salt such as acetate, maleate, fumarate, citrate, or methanesulfonate. Examples of the metal salt include an alkali metal salt such as a sodium salt or a potassium salt, an alkaline earth metal salt such as a magnesium salt or a calcium salt, an aluminum salt, a zinc salt, and the like. Examples of the ammonium salt include a salt of ammonium, tetramethylammonium, and the like. Examples of the organic amine addition salt include an addition salt of morpholine, piperidine, and the like. Examples of the amino acid addition salt include an addition salt of lysine, glycine, phenylalanine, and the like.

Among Compounds (Ia), some compounds can exist as a stereoisomer such as a geometric isomer or an optical isomer, a tautomer, and the like. All possible isomers and mixtures thereof inclusive of these isomers can be used in the present invention.

Further, Compound (Ia) can exist in the form of an adduct with water or various solvents, and these adducts can also be used in the present invention.

Examples of the amidite of Compound (Ia) include Compound (B) in the below-described production method for an oligonucleotide, and the like. Next, a production method for an oligonucleotide of the present invention is described.

A general synthetic method for an oligonucleotide comprises, for example, a step such as an amidation of a nucleotide, an oligomerization (including a step of deprotection or the like), a duplication by annealing (as needed), or the like.

The oligonucleotide of the present invention can be produced by, for example, the following production method.

(1) General Example of Oligomerization

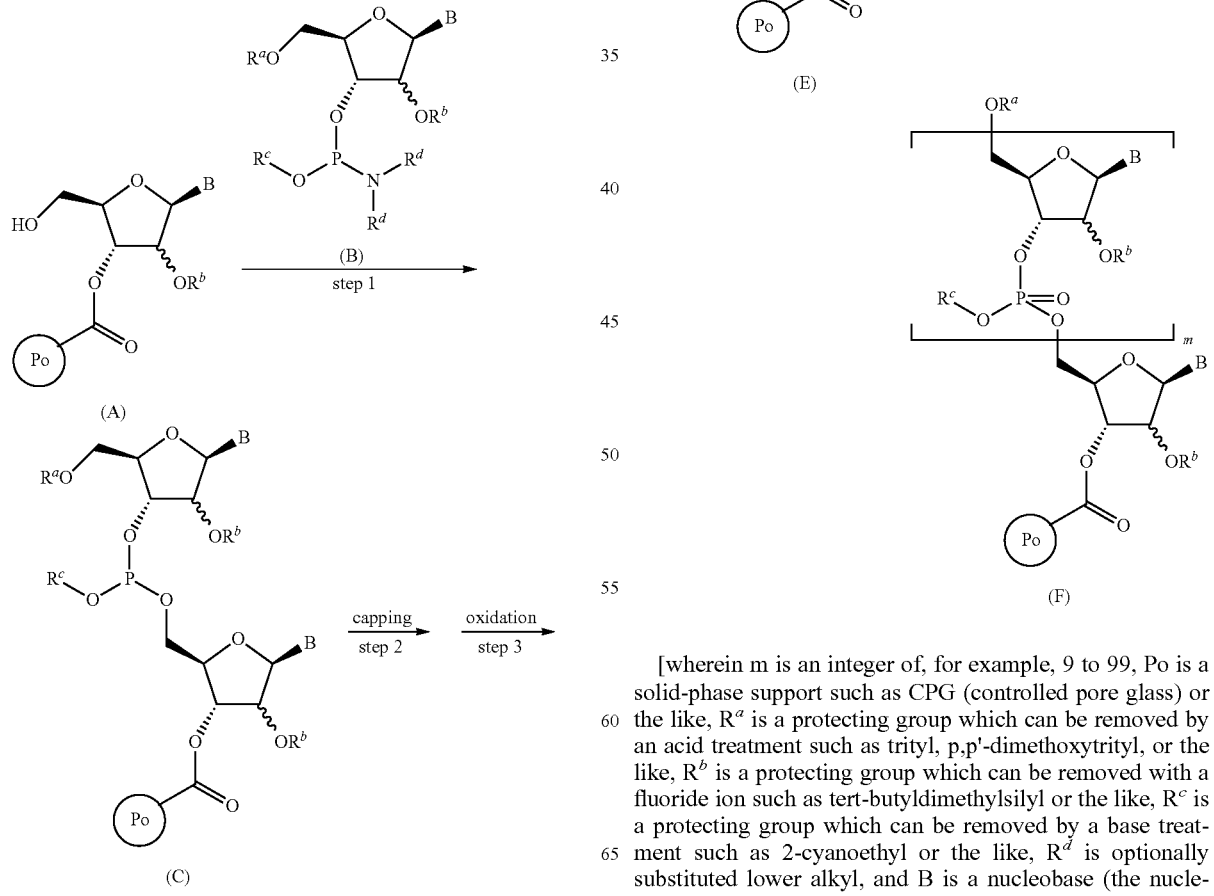

[wherein m is an integer of, for example, 9 to 99, Po is a solid-phase support such as CPG (controlled pore glass) or the like, $R^a$ is a protecting group which can be removed by an acid treatment such as trityl, p,p'-dimethoxytrityl, or the like, $R^b$ is a protecting group which can be removed with a fluoride ion such as tert-butyldimethylsilyl or the like, $R^c$ is a protecting group which can be removed by a base treatment such as 2-cyanoethyl or the like, $R^d$ is optionally substituted lower alkyl, and B is a nucleobase (the nucleobase may be protected by one or more protecting groups as needed, and in the case where the number of the protecting groups is 2 or more, the respective protecting groups may be the same or different). In the case where m is 2 or more, respective Bs in number of m+1, R$^b$s in number of m+1, and R$^c$s in number of m may be the same or different, and R$^a$s in the respective stages may be the same or different. Here, the lower alkyl has the same meaning as described above, and the substituent of the optionally substituted lower alkyl has the same meaning as that of the optionally substituted lower alkyl described above.]

Step 1

Compound (C) can be produced by reacting Compound (A) with Compound (B) in a solvent in the presence of a reaction accelerator at a temperature between 0° C. and 50° C. for 10 seconds to 30 minutes.

Examples of the solvent include dichloromethane, acetonitrile, toluene, ethyl acetate, tetrahydrofuran (THF), 1,4-dioxane, N,N-dimethylformamide (DMF), N-methylpyrrolidone (NMP), water, and the like. These can be used alone or as a mixture thereof.

Examples of the reaction accelerator include 1H-tetrazole, 4,5-dicyanoimidazole, 5-ethylthiotetrazole, 5-benzylthiotetrazole, and the like.

Compound (A) can be obtained as, for example, a commercially available product.

Compound (B) can be produced by, for example, the following method.

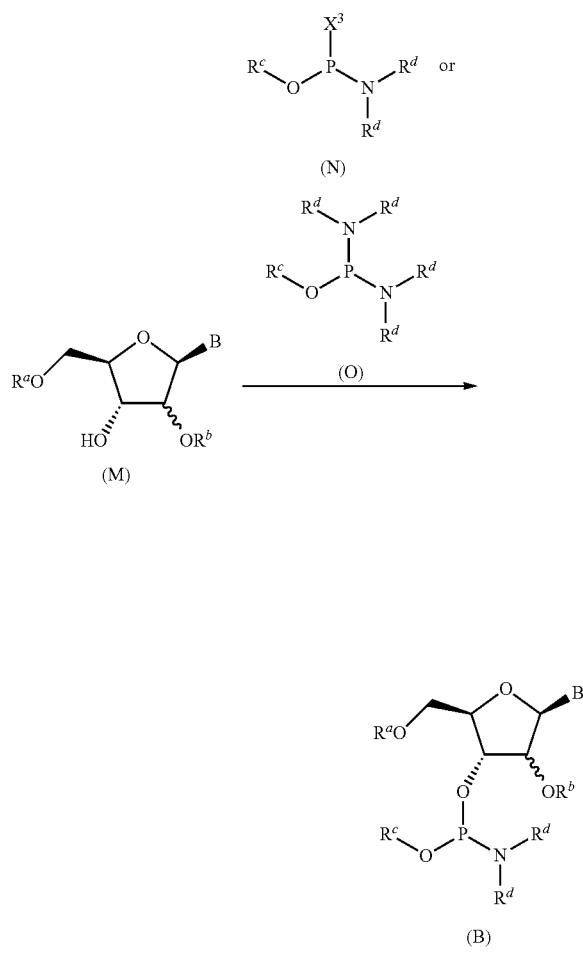

(wherein R$^a$, R$^b$, R$^c$, R$^d$, and B have the same meanings as described above, respectively, and X$^3$ is halogen. The halogen has the same meaning as described above.)

Compound (B) can be produced by reacting Compound (M) with Compound (N) in a solvent in the presence of a base at a temperature between 0° C. and 100° C. for 10 seconds to 24 hours.

Examples of the solvent include dichloromethane, acetonitrile, toluene, ethyl acetate, THF, 1,4-dioxane, DMF, NMP, and the like. These can be used alone or as a mixture thereof.

Examples of the base include triethylamine, N,N-diisopropylethylamine, pyridine, and the like. These can be used alone or as a mixture thereof. Further, Compound (B) can also be produced by reacting Compound (M) with Compound (O) in a solvent in the presence of a reaction accelerator at a temperature between 0° C. and 100° C. for 10 seconds to 24 hours. Examples of the solvent include acetonitrile, THF, and the like. These can be used alone or as a mixture thereof.

Examples of the reaction accelerator include those described above.

Step 2

In Step 1, unreacted Compound (A) can be capped by reacting with an acylation reagent in a solvent in the presence of a base at a temperature between 0° C. and 50° C. for 10 seconds to 30 minutes. At this time, the reaction can also be accelerated by adding a suitable additive.

Examples of the acylation reagent include acetic anhydride and phenoxyacetic anhydride.

Examples of the solvent include dichloromethane, acetonitrile, ethyl acetate, THF, 1,4-dioxane, DMF, and the like. These can be used alone or as a mixture thereof.

Examples of the base include pyridine, 2,6-lutidine, and the like. Examples of the additive include 4-dimethylaminopyridine, 1-methylimidazole, and the like.

Step 3

Compound (D) can be produced by reacting Compound (C) with an oxidizing agent in a solvent in the presence of a base at a temperature between 0° C. and 50° C. for 10 seconds to 30 minutes.

Examples of the oxidizing agent include iodine, an aqueous hydrogen peroxide solution, m-chloroperoxybenzoic acid, peracetic acid, tert-butyl hydroperoxide, (+)-(Camphorsulfonyl)oxaziridine (CSO) and the like. These can be used alone or as a mixture thereof.

Examples of the base and the solvent include those described in the above Step 2, respectively.

Step 4

Compound (E) can be produced by reacting Compound (D) with an acid in a solvent at a temperature between 0° C. and 50° C. for 10 seconds to 30 minutes.

Examples of the acid include dichloroacetic acid, trichloroacetic acid, trifluoroacetic acid, and the like.

Examples of the solvent include dichloromethane, chloroform, and the like.

Steps 1 to 4, and the following Steps 5 and 6 can also be performed by using a nucleic acid synthesizer.

(2) General Example of Introduction of Nucleotide Residue (I) at 5' End
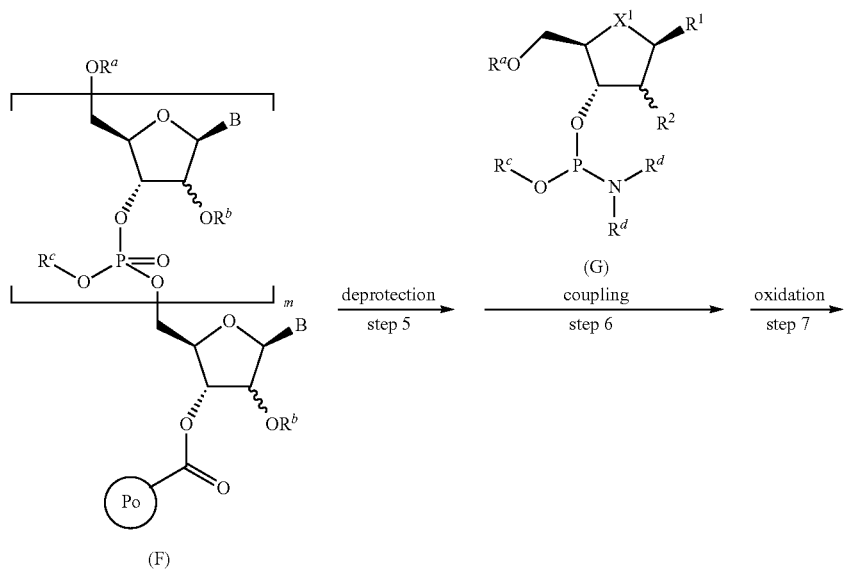
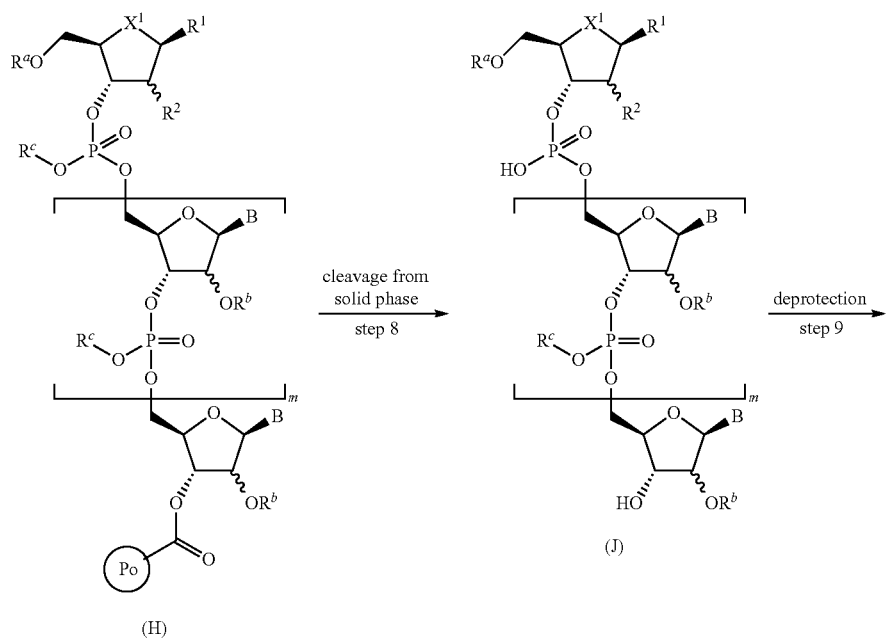

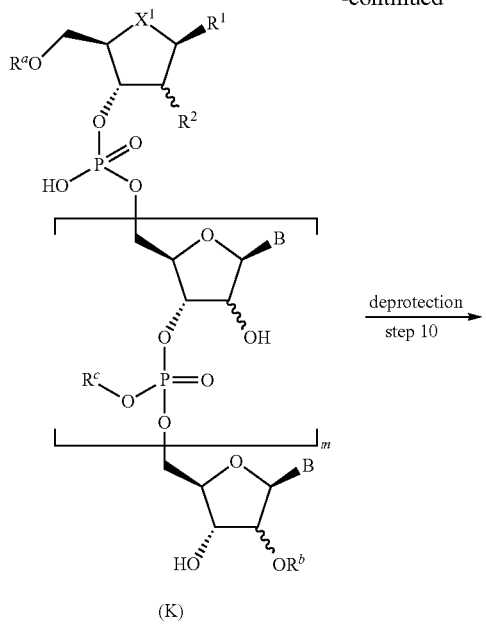
(K)

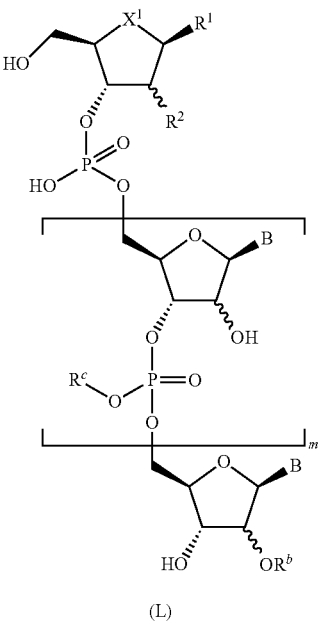
(L)

(wherein B, m, $X^1$, $R^1$, $R^2$, Po, $R^a$, $R^b$, $R^c$, and $R^d$ have the same meanings as described above, respectively.)

Step 5

Step 5 (deprotection of the protecting group $R^a$ of Compound (F)) can be performed in the same manner as the above-described Step 4.

Step 6

Coupling of Compound (F) in which $R^a$ is deprotected in Step 5 (hereinafter referred to as Compound (Fa)) with Compound (G) can be performed by, for example, the following method.

It can be produced by reacting Compound (Fa) with 1 equivalent to a large excess amount of Compound G in a solvent in the presence of a reaction accelerator at a temperature between 0° C. and 50° C. for 10 seconds to 30 minutes.

Examples of the solvent include dichloromethane, acetonitrile, toluene, ethyl acetate, THF, 1,4-dioxane, DMF, NMP, water, and the like. These can be used alone or as a mixture thereof.

Examples of the reaction accelerator include those described above. Compound G can be obtained as, for example, a commercially available product.

Step 7

Compound (H) can be obtained in the same manner as in the above-described Step 3 (oxidation of a phosphorus atom).

Step 8

It can be cleaved from the solid phase by treating with a base to an oligonucleotide supported on a solid phase, the oligonucleotide can be cleaved from the solid phase. That is, Compound (J) can be produced by treating Compound (H) with a base in a solvent at a temperature between −80° C. and 200° C. for 10 seconds to 72 hours.

Examples of the base include ammonia, methylamine, dimethylamine, ethylamine, diethylamine, isopropylamine, diisopropylamine, piperidine, triethylamine, ethlenediamine, 1,8-diazabicyclo[5.4.0]-7-undecene (DBU), potassium carbonate, and the like.

Examples of the solvent include water, methanol, ethanol, THF, and the like.

Incidentally, in this step, deprotection of the protecting group for a nitrogen atom contained in B (nucleobase) is also performed simultaneously.

Moreover, pre-treatment with a poorly nucleophilic base may be performed as pre-treatment in Step 8, and cleavage may be performed following removal of a protecting group such as a phosphate moiety or a carboxyl group.

Examples of the poorly nucleophilic base include DBU, triethylamine, triethylamine, N,N-diisopropylethylamine, diisopropylamine and the like.

Examples of the solvent include acetonitrile, DMF, THF, and the like. These can be used alone or as a mixture thereof.

Step 9

Compound (K) can be produced by reacting Compound (J) with a fluorine reagent in a solvent at a temperature between −80° C. and 200° C. for 10 seconds to 72 hours. At this time, it is also possible to add a base.

Examples of the fluorine reagent include hydrogen fluoride, triethylamine hydrofluoride, tetrabutylammonium fluoride (TBAF), and the like.

Examples of the base include triethylamine, N,N-diisopropylethylamine, and the like.

Examples of the solvent include dichloromethane, chloroform, acetonitrile, toluene, ethyl acetate, THF, 1,4-dioxane, DMF, N,N-dimethylacetamide (DMA), NMP, dimethyl sulfoxide (DMSO), and the like.

Step 10

Compound (L) can be produced by treating Compound (K) with an acid in a solvent or in a column at a temperature between 0° C. and 50° C. for 5 minutes to 100 hours.

Examples of the acid include trifluoroacetic acid and the like. Examples of the solvent include water, methanol, ethanol, acetonitrile, and the like. These can be used alone or as a mixture thereof. Examples of the column include a C18 reverse-phase cartridge column and the like.

(3) General Example of Production of Double-Stranded Oligonucleotide
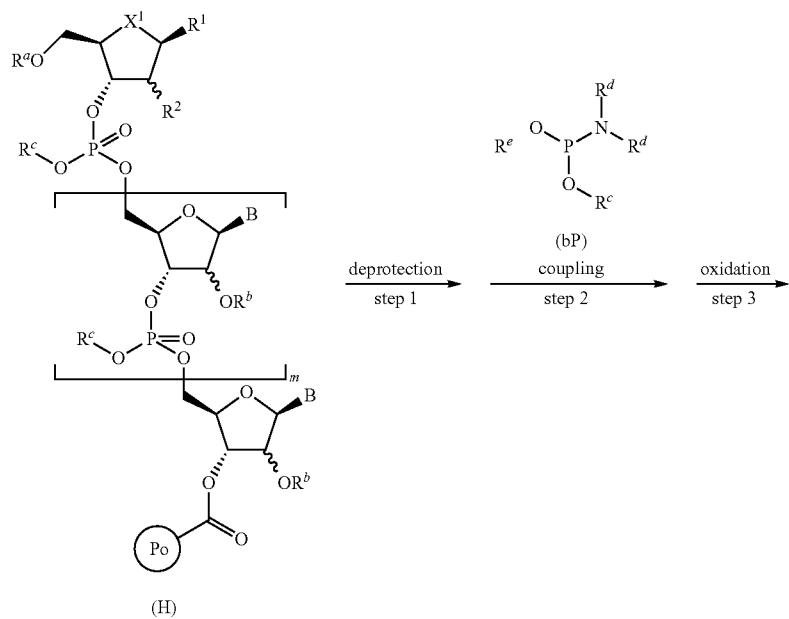
(H)
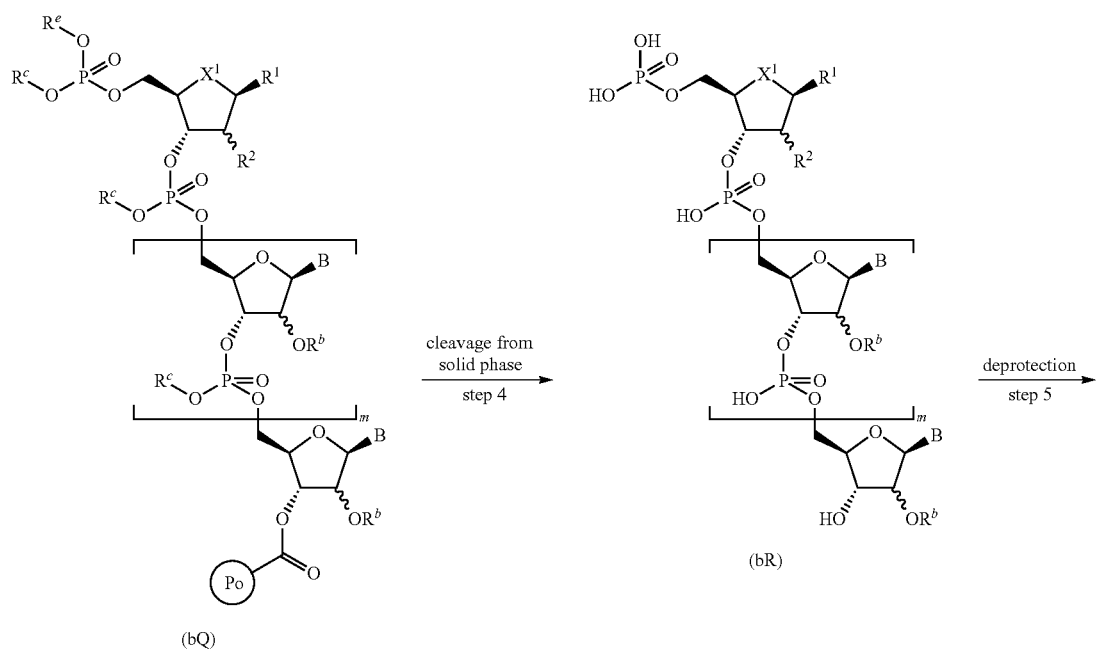
(bQ)    (bR)

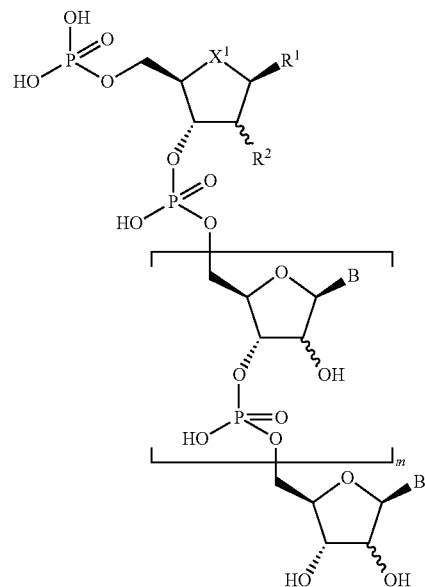

(bS)

[wherein each of B, m, $X^1$, $R^1$, $R^2$, Po, $R^a$, $R^b$, $R^c$ and $R^d$ has the same meaning as described above, and $R^e$ is, for example, a protecting group such as 2-cyanoethyl which can be eliminated by treatment with base, or (3-(4,4'-dimethoxytrityloxy)-2,2-dicarboxyethyl)propyl which can be eliminated by treatment with acid.]

Step 1

Step 1 can be performed in the same manner as in Step 4 of production method (1) using compound (h) obtained in Step 7 of production method (1).

Step 2

Step 2 can be performed in the same manner as in Step 1 of production method (1) using the compound obtained in Step 1 above and compound (bP).

Compound (bP) can be obtained, for example, as a commercial product.

Step 3

Step 3 can be performed in the same manner as in Step 3 of production method (1) using the compound obtained in Step 2 above.

Step 4

Step 4 can be performed in the same manner as in Step 8 of production method (2) using compound (bQ).

Step 5

Step 5 can be performed in the same manner as in Step 9 of production method (2) using compound (bR).

(4) Post-Transformation of Oligonucleic Acid

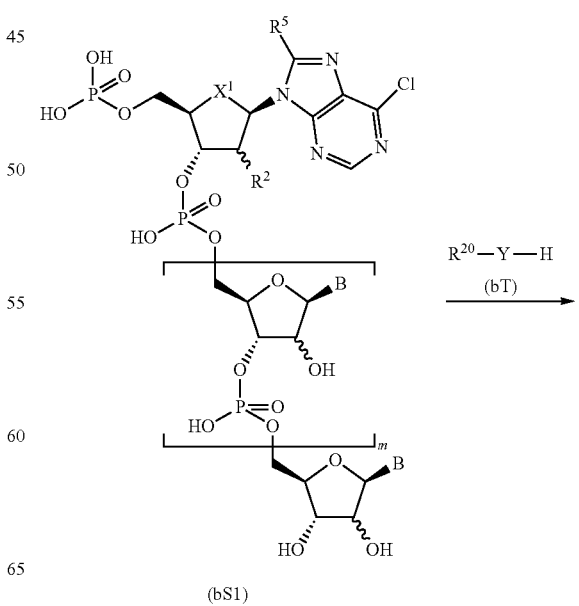

(bS1)

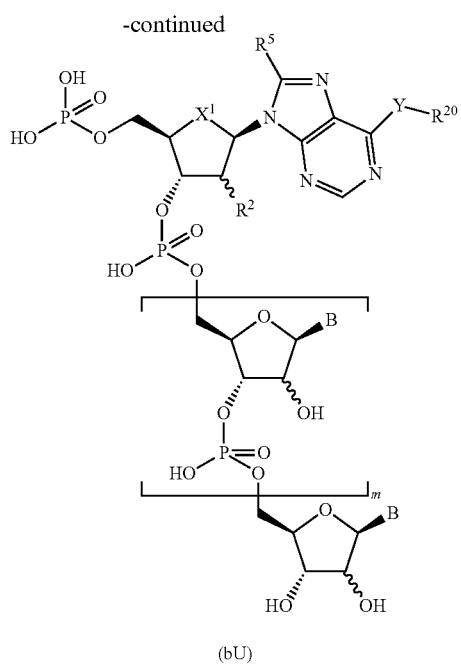

(bU)

(wherein each of $R^2$, $R^5$, $X^1$, B and m has the same meaning as described above, Y is a sulfur atom or $NR^{X1}$ (wherein $R^{X1}$ is a hydrogen atom, lower alkyl or aralkyl, and the the lower alkyl and the aralkyl have the same meanings as described above), $R^{20}$ represents optionally substituted lower alkyl moiety, optionally substituted aryl moiety or optionally substituted aromatic heterocyclic moiety within the optionally substituted lower alkylthio, the optionally substituted arylthio or the optionally substituted aromatic heterocyclicthio defined in $R^6$ described above, respectively. The substituent of the optionally substituted lower alkylthio, optionally substituted arylthio and optionally substituted aromatic heterocyclicthio has the same meaning as the substituent of the optionally substituted lower alkylthio, the optionally substituted arylthio and the optionally substituted aromatic heterocyclicthio described above.)

Compound (bU) can be produced by reacting compound (bS1) and compound (bT) for 10 seconds to 72 hours at a temperature between 0° C. and 150° C. in a solvent, without or with a base.

Examples of the solvent include acetonitrile, N,N-dimethylformamide (DMF), N-methylpyrrolidone (NMP), buffered water and the like. These can be used alone or as a mixture thereof.

Examples of the base include triethylamine, N,N-diisopropylethylamine, DBU, sodium bicarbonate, Tris and the like.

Compound (bS1) can be produced in the same manner as in production method (3).

Compound (bT) can be obtained, for example, as a commercial product.

(5) General Example of Production of Double-Stranded Oligonucleotide

After Compound (L) is reacted with an equimolar amount of a single-stranded oligonucleotide in a solvent at a temperature between 30° C. and 120° C. for 10 seconds to 72 hours, the reaction mixture is gradually cooled to room temperature over 10 minutes to 24 hours, whereby a double-stranded oligonucleotide can be produced.

Examples of the solvent include an acetate buffer, Tris buffer, a citrate buffer, a phosphate buffer, water, and the like. These can be used alone or as a mixture thereof.

The single-stranded oligonucleotide reacted with Compound (L) is an oligonucleotide complementary to Compound (L), but may contain one or more mismatched base pairs. Further, the base length thereof may be different.

In the above-described scheme, by variously changing the nucleobases, the reaction conditions in the respective steps, and the like, a desirable oligonucleotide can be obtained.

These can be performed according to the method described in, for example, (i) Tetrahedron, vol. 48 No. 12, pp. 2223-2311 (1992);

(ii) Current Protocols in Nucleic Acids Chemistry, John Wiley & Sons (2000);

(iii) Protocols for Oligonucleotides and Analogs, Human Press (1993);

(iv) Chemistry and Biology of Artificial Nucleic Acids, Wiley-VCH (2012);

(v) Genome Chemistry, Scientific Approach Using Artificial Nucleic Acids, Kodansha Ltd. (2003);

(vi) New Trend of Nucleic Acid Chemistry, Kagaku-Dojin Publishing Company, Inc. (2011); or the like.

(6) General Method for Producing Nucleotide or Nucleoside Corresponding to Nucleotide Residue or Nucleoside Residue Represented by Formula (I) Hereinafter, a general method for producing a nucleotide or a nucleoside corresponding to a nucleotide residue or a nucleoside residue represented by formula (I) is described. However, the method for producing a nucleotide residue or a nucleoside residue used in the present invention is not limited thereto.

In the production method described below, in the case where the defined group changes under the conditions for the production method or is not suitable for performing the production method, by using a method for introducing and removing a protecting group conventionally used in organic synthetic chemistry [for example, Protective Groups in Organic Synthesis, fourth edition, T. W. Greene, John Wiley & Sons, Inc. (2006), or the like] or the like, a target compound can be produced. Further, it is also possible to change the order of the reaction steps for introducing a substituent and the like as needed.

Production Method 4-1

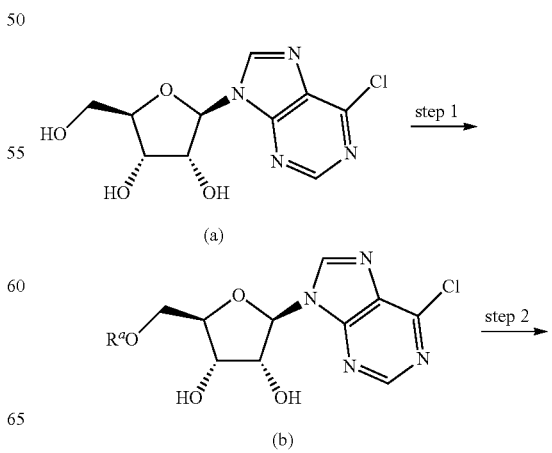

-continued

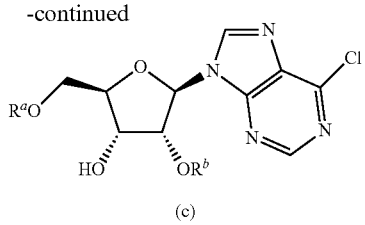

(c)

(wherein $R^a$ and $R^b$ have the same meanings as described above, respectively.)

Step 1

Compound (b) can be produced by reacting Compound (a) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine, N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Compound (a) can be synthesized by, for example, a known method [Journal of Medicinal Chemistry, 2004, 47(6), 1987-1996].

Step 2

Compound (c) can be produced by reacting Compound (b) with a silylating agent in a solvent in the presence of a silver salt and a base at a temperature between 0° C. and 80° C. for 10 minutes to 3 days.

Examples of the solvent include THF, ethylene glycol dimethyl ether (DME), and the like. These can be used alone or as a mixture thereof.

Examples of the silver salt include silver nitrate, silver perchlorate, and the like.

Examples of the base include triethylamine, 1,4-diazabicyclo[2,2,2]octane (DABCO), pyridine, and the like.

Examples of the silylating agent include tert-butyldimethylsilyl chloride and the like.

Production Method 4-2

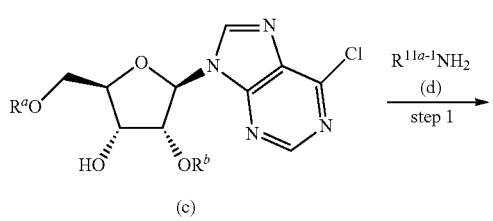

-continued

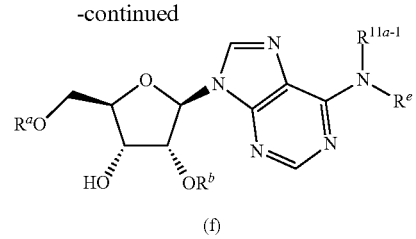

(f)

(wherein $R^a$ and $R^b$ have the same meanings as described above, respectively, $R^e$ is a protecting group which can be removed with a base, for example, acetyl, benzoyl, or the like, and $R^{11a-1}$ is optionally substituted lower alkyl, optionally substituted lower alkenyl, optionally substituted lower alkynyl, optionally substituted aryl, optionally substituted aralkyl, optionally substituted aromatic heterocyclic alkyl, or an optionally substituted aromatic heterocyclic group in the definition of $R^{11a}$ described above.)

Step 1

Compound (e) can be produced by reacting Compound (c) with Compound (d) in a solvent or without a solvent in the presence or absence of a base at a temperature between 0° C. and 150° C. for 1 hour to 1 week.

Examples of the solvent include DMF, pyridine, dichloromethane, THF, ethyl acetate, NMP, acetonitrile, and the like. These can be used alone or as a mixture thereof.

Examples of the base include triethylamine, N-ethyl-N, N-diisopropylamine, and the like.

Step 2

Compound (f) can be produced by reacting Compound (e) with a silylating agent in a solvent at a temperature between 0° C. and 100° C. for 10 minutes to 3 hours, and then, by reacting the resulting product with an acylating agent at a temperature between 0° C. and 100° C. for 1 hour to 72 hours, and by further treating the resulting product with water or an alcohol for 1 hour to 24 hours. The reaction can also be accelerated by allowing a suitable activating agent to coexist with the acylating agent.

Examples of the solvent include pyridine and the like.

Examples of the silylating agent include trimethylsilyl chloride, trifluoromethanesulfonyl trimethylsilyl, N,O-bis(trimethylsilyl)acetamide, 1,1,1,3,3,3-hexamethyldisilazane, and the like.

Examples of the acylating agent include acetic anhydride, acetyl chloride, benzoyl chloride, and the like.

Examples of the alcohol include methanol, ethanol, 1-propanol, and the like.

Examples of the activating agent include 4-dimethylaminopyridine.

Production Method 4-3

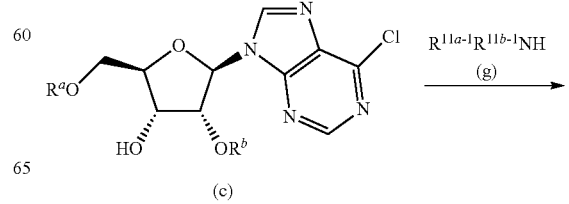

-continued

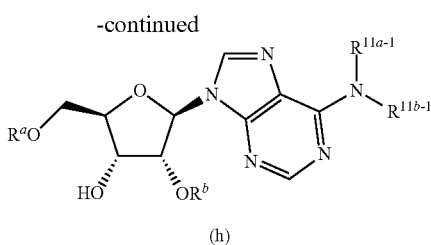

(h)

(wherein $R^a$, $R^b$, and $R^{11a-1}$ have the same meanings as described above, respectively, and $R^{11b-1}$ is optionally substituted lower alkyl, optionally substituted lower alkenyl, optionally substituted lower alkynyl, optionally substituted aryl, optionally substituted aralkyl, optionally substituted aromatic heterocyclic alkyl, or an optionally substituted aromatic heterocyclic group in the definition of $R^{11b}$ described above.)

Compound (h) can be produced by reacting Compound (c) with Compound (g) in a solvent or without a solvent in the presence or absence of a base at a temperature between 0° C. and 150° C. for 1 hour to 1 week.

Examples of the solvent include DMF, pyridine, dichloromethane, THF, ethyl acetate, NMP, acetonitrile, and the like. These can be used alone or as a mixture thereof.

Examples of the base include triethylamine, N-ethyl-N, N-diisopropylamine, and the like.

Production Method 4-4

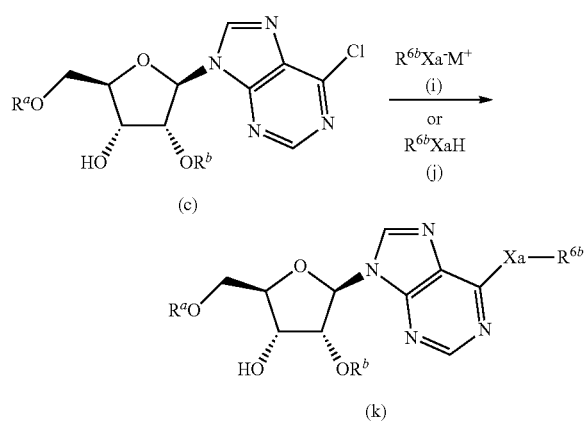

(wherein $R^a$ and $R^b$ have the same meanings as described above, respectively, $R^{6b}$ is optionally substituted lower alkyl, optionally substituted aryl, or an optionally substituted aromatic heterocyclic group, Xa is an oxygen atom or a sulfur atom, and M is an alkali metal atom. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively. The alkali metal atom is a lithium atom, a sodium atom, or a potassium atom.)

Compound (k) can be produced by reacting Compound (c) with Compound (i) in a solvent at a temperature between 0° C. and 100° C. for 10 minutes to 3 days, or by reacting Compound (c) with Compound (j) in a solvent in the presence of a base at a temperature between 0° C. and 120° C. for 10 minutes to 3 days.

Examples of the solvent include methanol, ethanol, 2-propanol, THF, DME, DMF, NMP, and the like. These can be used alone or as a mixture thereof. Examples of the base include sodium hydroxide, potassium hydroxide, sodium carbonate, potassium carbonate, sodium hydride, potassium hydride, tert-butoxy potassium, and the like.

Production Method 4-5

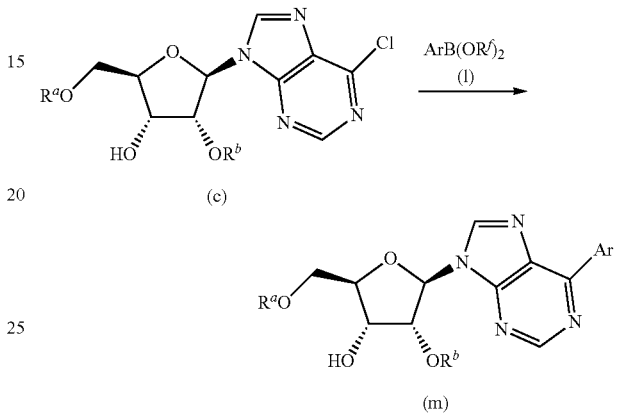

(wherein $R^a$ and $R^b$ have the same meanings as described above, respectively, Ar is optionally substituted aryl or an optionally substituted aromatic heterocyclic group, and $R^f$ is a hydrogen atom or optionally substituted lower alkyl. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively.)

Compound (m) can be produced by reacting Compound (c) with Compound (l) in a solvent in the presence of a base and a palladium catalyst at a temperature between 0° C. and 120° C. for 30 minutes to 72 hours. The reaction can also be accelerated by adding a suitable phosphine.

Compound (l) can be obtained as a commercially available product or according to a known method [for example, Synthesis of Organic Compound VI, organic synthesis using metal, Jikken Kagaku Koza (Encyclopedia of Experimental Chemistry) 18, 5th Ed., p. 97, Maruzen (2005)] or a method according to that.

Examples of the base include potassium carbonate, potassium phosphate, potassium hydroxide, sodium hydroxide, potassium tert-butoxide, triethylamine, diisopropylethylamine, N-methylmorpholine, pyridine, DBU, and the like.

Examples of the palladium catalyst include palladium acetate, tris(dibenzylideneacetone)dipalladium, tetrakis(triphenylphosphine)palladium, 1,1'-bis(diphenylphosphino)ferrocenedichloropalladium/dichloromethane (1:1) adduct, and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water, and the like. These can be used alone or as a mixture thereof.

Examples of the suitable phosphine include 1,2-bis(diphenylphosphino)ethane, 1,3-bis(diphenylphosphino)propane, 4,5'-bis(diphenylphosphino)-9,9'-dimethylxanthene (Xantphos), 2,2'-bis(diphenylphosphino)-1,1'-binaphthyl (BINAP), and the like.

Production Method 4-6

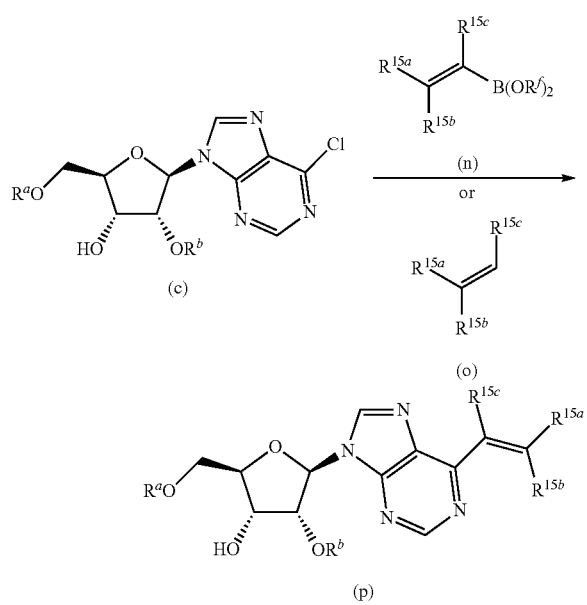

(wherein $R^a$, $R^b$, and $R^f$ have the same meanings as described above, respectively. Each of $R^{15a}$, $R^{15b}$, and $R^{15c}$ is a hydrogen atom, optionally substituted lower alkyl, aryl, or an aromatic heterocyclic group. Here, the lower alkyl, the aryl, and the aromatic heterocyclic group have the same meanings as described above, respectively, and the substituent of the optionally substituted lower alkyl has the same meaning as the substituent of the optionally substituted lower alkyl described above.) Compound (p) can be produced by reacting Compound (c) with Compound (n) in a solvent in the presence of a base and a palladium catalyst at a temperature between 0° C. and 120° C. for 30 minutes to 72 hours. The reaction can also be accelerated by adding a suitable phosphine.

Compound (n) can be obtained as, for example, a commercially available product.

Examples of the base include potassium carbonate, potassium phosphate, potassium hydroxide, sodium hydroxide, potassium tert-butoxide, triethylamine, diisopropylethylamine, N-methylmorpholine, pyridine, DBU, and the like.

Examples of the palladium catalyst include those described above.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water, and the like. These can be used alone or as a mixture thereof.

Further, Compound (p) can also be produced by reacting Compound (c) with Compound (o) in a solvent in the presence of a base and a palladium catalyst at a temperature between 0° C. and 140° C. for 30 minutes to 72 hours.

Examples of the base include potassium acetate, sodium hydrogen carbonate, potassium carbonate, potassium hydroxide, sodium hydroxide, sodium methoxide, potassium tert-butoxide, triethylamine, diisopropylethylamine, N-methylmorpholine, pyridine, DBU, and the like.

Examples of the palladium catalyst include those described above.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the suitable phosphine include 1,2-bis(diphenylphosphino)ethane, 1,3-bis(diphenylphosphino)propane, Xantphos, BINAP, and the like.

Production Method 4-7

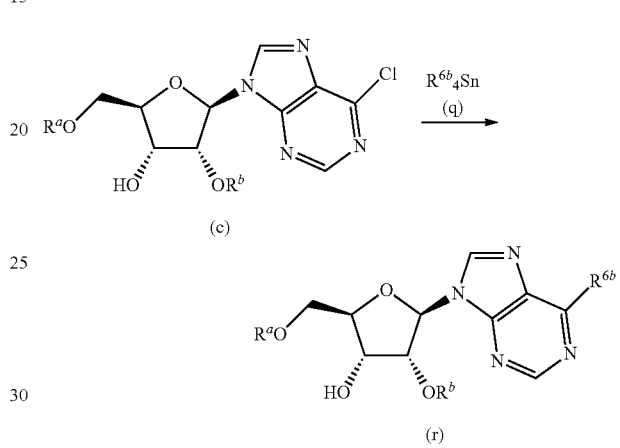

(wherein $R^a$, $R^b$, and $R^{6b}$ have the same meanings as described above, respectively.)

Compound (r) can be produced by reacting Compound (c) with Compound (q) in a solvent in the presence of a palladium catalyst at a temperature between 0° C. and 150° C. The reaction can also be accelerated by adding a suitable additive and/or a suitable phosphine.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Compound (q) can be obtained as, for example, a commercially available product.

Examples of the palladium catalyst include those described above. Examples of the suitable additive include lithium chloride, cesium fluoride, and the like.

Examples of the suitable phosphine include 1,2-bis(diphenylphosphino)ethane, 1,3-bis(diphenylphosphino)propane, Xantphos, BINAP, and the like.

Production Method 4-8

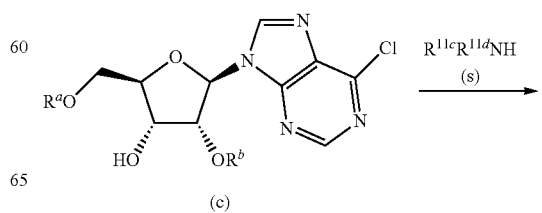

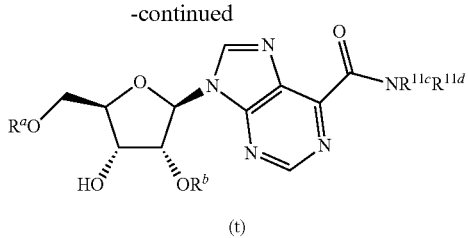

(wherein $R^a$, $R^b$, $R^{11c}$, and $R^{11d}$ have the same meanings as described above, respectively.)

Compound (t) can be produced by reacting Compound (c) with Compound (s) in a solvent under a carbon monoxide atmosphere in the presence of a base and a palladium catalyst at a temperature between room temperature and 120° C. for 1 hour to 72 hours. The reaction can also be accelerated by adding a suitable phosphine.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the base include sodium acetate, potassium acetate, sodium hydrogen carbonate, potassium carbonate, sodium methoxide, potassium tert-butoxide, triethylamine, di isopropylethylamine, N-methylmorpholine, pyridine, DBU, and the like.

Examples of the palladium catalyst include those described above. Examples of the phosphine include 1,2-bis(diphenylphosphino)ethane, 1,3-bis(diphenylphosphino)propane, Xantphos, BINAP, and the like.

Production Method 4-9

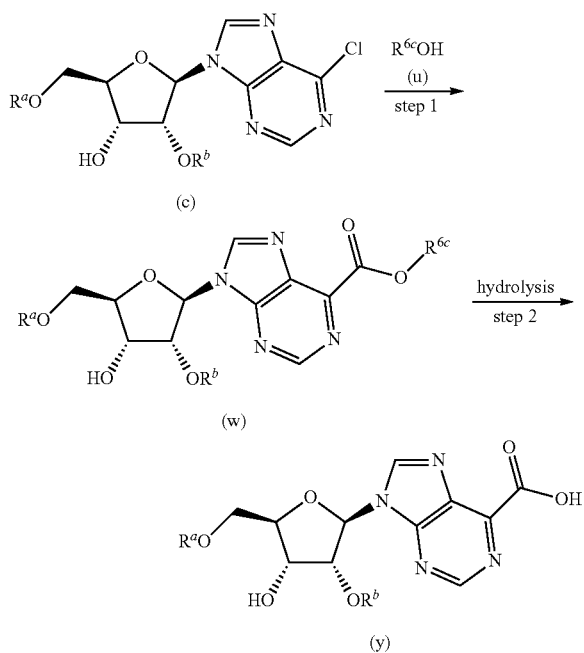

(wherein $R^a$ and $R^b$ have the same meanings as described above, respectively, and $R^{6c}$ is optionally substituted lower alkyl, optionally substituted aryl, or an optionally substituted aromatic heterocyclic group. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively.)

Step 1

Compound (w) can be produced by reacting Compound (c) with Compound (u) in a solvent under a carbon monoxide atmosphere in the presence of a base and a palladium catalyst at a temperature between room temperature and 120° C. for 1 hour to 72 hours. The reaction can also be accelerated by adding a suitable phosphine.

Examples of the solvent include methanol, ethanol, 1-propanol, 2-propanol, 1-butanol, tert-butyl alcohol, dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the base include sodium acetate, potassium acetate, sodium hydrogen carbonate, potassium carbonate, sodium methoxide, potassium tert-butoxide, triethylamine, di isopropylethylamine, N-methylmorpholine, pyridine, DBU, and the like.

Examples of the palladium catalyst include those described above. Examples of the phosphine include 1,2-bis(diphenylphosphino)ethane, 1,3-bis(diphenylphosphino)propane, Xantphos, BINAP, and the like.

Step 2

Compound (y) can be produced by treating Compound (w) in a solvent in the presence of a base at a temperature between 0° C. and 100° C. for 5 minutes to 72 hours.

Examples of the base include potassium carbonate, lithium hydroxide, potassium hydroxide, sodium hydroxide, sodium methoxide, and the like. Examples of the solvent include a solvent containing water, and examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine, and the like. These are used by mixing with water or by mixing with one another and then adding water thereto.

Production Method 4-10

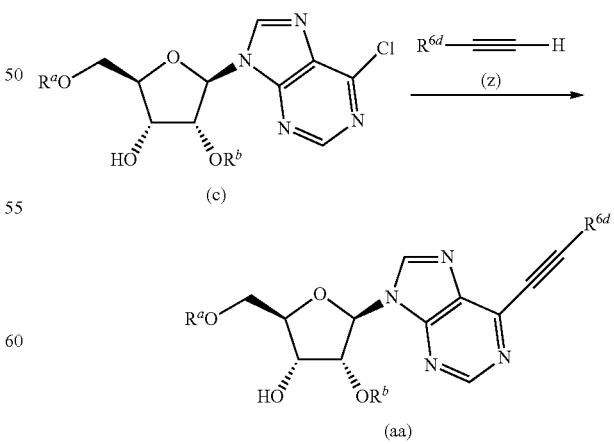

(wherein $R^a$ and $R^b$ have the same meanings as described above, respectively, and $R^{6d}$ is optionally substituted lower alkyl, aryl, or an aromatic heterocyclic group. Here, the lower alkyl, the aryl, and the aromatic heterocyclic group have the same meanings as described above, respectively, and the substituent of the optionally substituted lower alkyl has the same meaning as the substituent of the optionally substituted lower alkyl described above.)

Compound (aa) can be produced by reacting Compound (c) with Compound (z) in a solvent in the presence of a copper salt, a base, and a palladium catalyst at a temperature between room temperature and 150° C. for 1 hour to 72 hours. The reaction can also be accelerated by adding a suitable phosphine.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the copper salt include copper(I) iodide, copper fluoride, copper chloride, copper bromide, copper oxide, copper sulfide, copper selenide, copper acetate, copper cyanide, copper thiocyanate, copper trifluoromethanesulfonate, and the like.

Examples of the base include sodium acetate, potassium acetate, sodium hydrogen carbonate, potassium carbonate, sodium methoxide, potassium tert-butoxide, triethylamine, di isopropylethylamine, N-methylmorpholine, pyridine, DBU, and the like.

Examples of the palladium catalyst include those described above. Examples of the phosphine include 1,2-bis(diphenylphosphino)ethane, 1,3-bis(diphenylphosphino) propane, Xantphos, BINAP, and the like.

Production Method 4-11

By using Compound ae obtained by the following method, a nucleoside used as a starting material for the production of the oligonucleotide of the present invention can be obtained according to the above-described production methods 4-2 to 4-10.

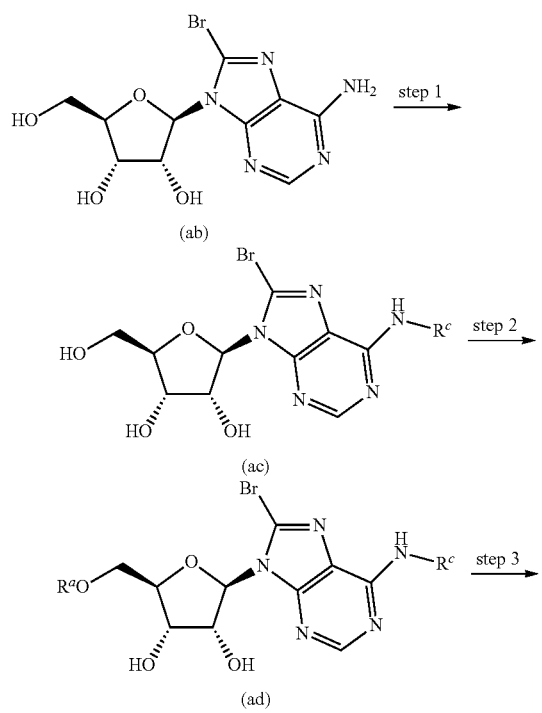

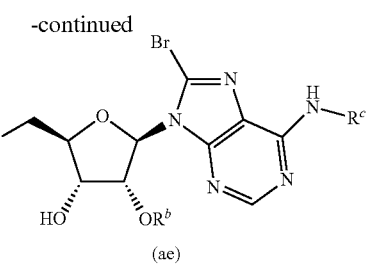

(wherein $R^a$, $R^b$, and $R^c$ have the same meanings as described above, respectively.)

Step 1

Compound (ac) can be produced by reacting Compound (ab) with a silylating agent in a solvent at a temperature between 0° C. and 100° C. for 10 minutes to 3 hours, and then, by reacting with an acylating agent at a temperature between 0° C. and 100° C. for 1 hour to 72 hours, and by further treating with water or an alcohol for 1 hour to 24 hours.

Examples of the solvent include pyridine and the like.

Examples of the silylating agent include trimethylsilyl chloride, trifluoromethanesulfonyl trimethylsilyl, N,O-bis(trimethylsilyl)acetamide, 1,1,1,3,3,3-hexamethyldisilazane, and the like.

Examples of the acylating agent include acetic anhydride, acetyl chloride, benzoyl chloride, and the like.

Examples of the alcohol include methanol, ethanol, 1-propanol, and the like.

Compound (ab) can be synthesized by, for example, a known method [Tetrahedron, 1970, 26, 4251-4259].

Step 2

Compound (ad) can be produced by reacting Compound (ac) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine, N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Step 3

Compound (ae) can be produced by reacting Compound (ad) with a silylating agent in a solvent in the presence of a silver salt and a base at a temperature between 0° C. and 80° C. for 10 minutes to 3 days. Examples of the solvent include THF, DME, and the like. These can be used alone or as a mixture thereof.

Examples of the silver salt include silver nitrate, silver perchlorate, and the like.

Examples of the base include triethylamine, DABCO, pyridine, and the like.

Examples of the silylating agent include tert-butyldimethylsilyl chloride and the like.

Production Method 4-12

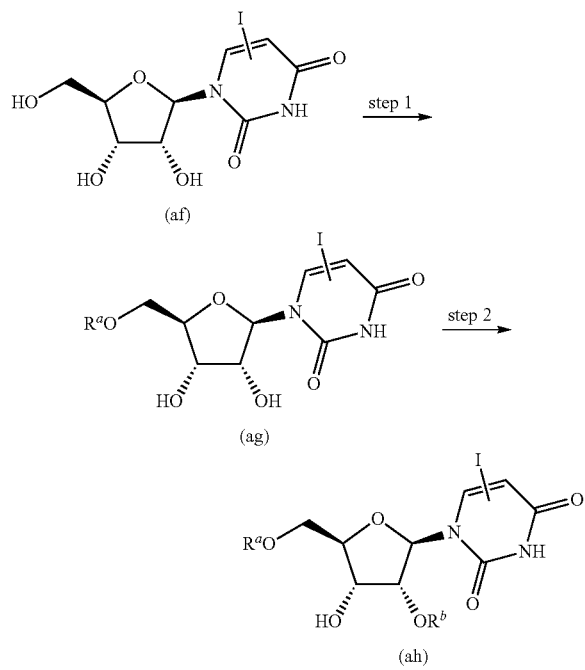

Production Method 4-13

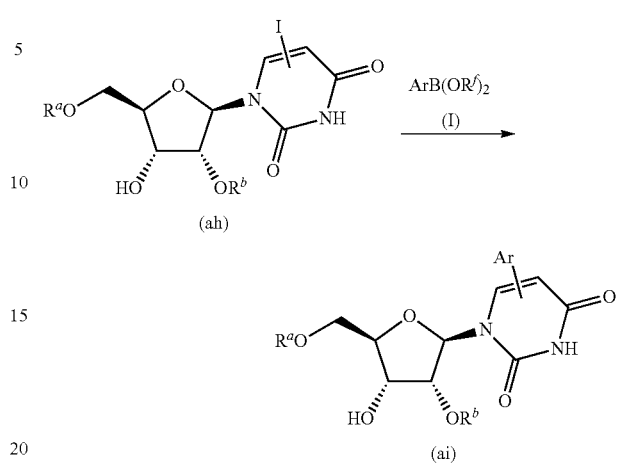

(wherein $R^a$, $R^b$, $R^f$, and Ar have the same meanings as described above, respectively.)

Compound (ai) can be produced according to the production method 4-5 using Compound (ah).

Production Method 4-14

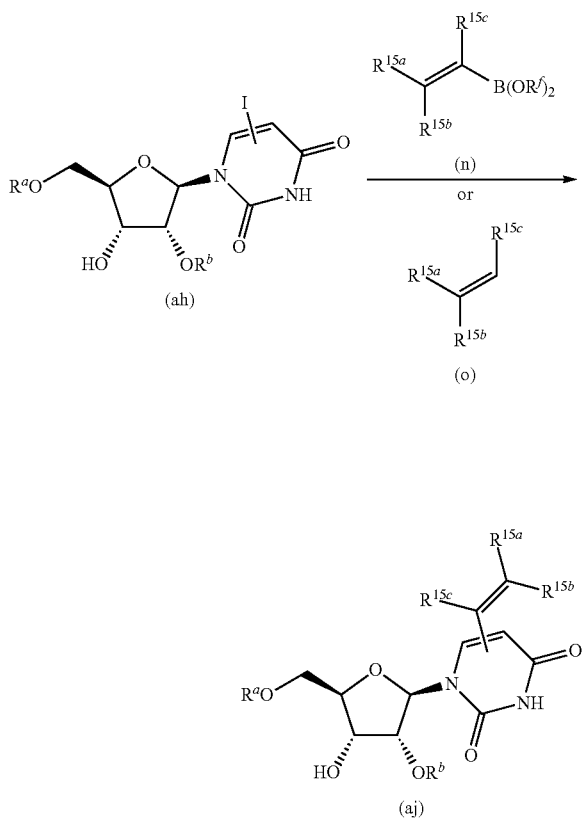

(wherein $R^a$ and $R^b$ have the same meanings as described above, respectively.)

Step 1

Compound (ag) can be produced by reacting Compound (af) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine, N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Compound (af) can be synthesized by, for example, a known method [Journal of Medicinal Chemistry, 2004, 50(5), 915-921 and WO2011/51733].

Step 2

Compound (ah) can be produced by reacting Compound (ag) with a silylating agent in a solvent in the presence of a silver salt and a base at a temperature between 0° C. and 80° C. for 10 minutes to 3 days.

Examples of the solvent include THF, DME, and the like. These can be used alone or as a mixture thereof.

Examples of the silver salt include silver nitrate, silver perchlorate, and the like.

Examples of the base include triethylamine, DABCO, pyridine, and the like.

Examples of the silylating agent include tert-butyldimethylsilyl chloride and the like.

(wherein $R^a$, $R^b$, $R^f$, $R^{15a}$, $R^{15b}$, and $R^{15c}$ have the same meanings as described above, respectively.)

Compound (aj) can be produced according to the production method 4-6 using Compound (ah).

Production Method 4-15

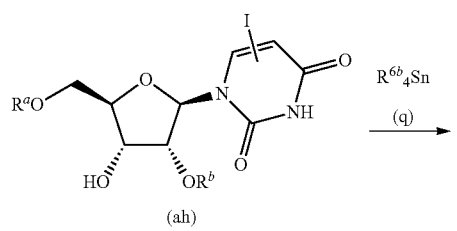

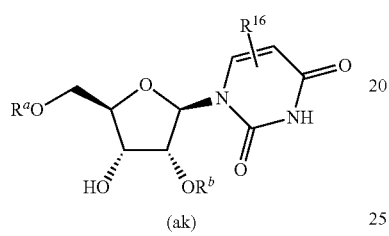

(wherein $R^a$, $R^b$, and $R^{6b}$ have the same meanings as described above, respectively.)

Compound (ak) can be produced according to the production method 4-7 using Compound (ah).

Production Method 4-16

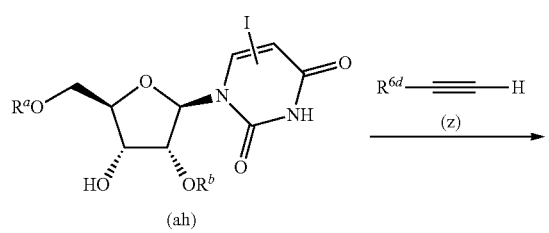

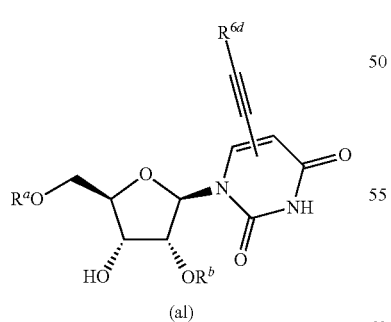

(wherein $R^a$, $R^b$, and $R^{6d}$ have the same meanings as described above, respectively.)

Compound (al) can be produced according to the production method 4-10 using Compound (ah).

Production Method 4-17

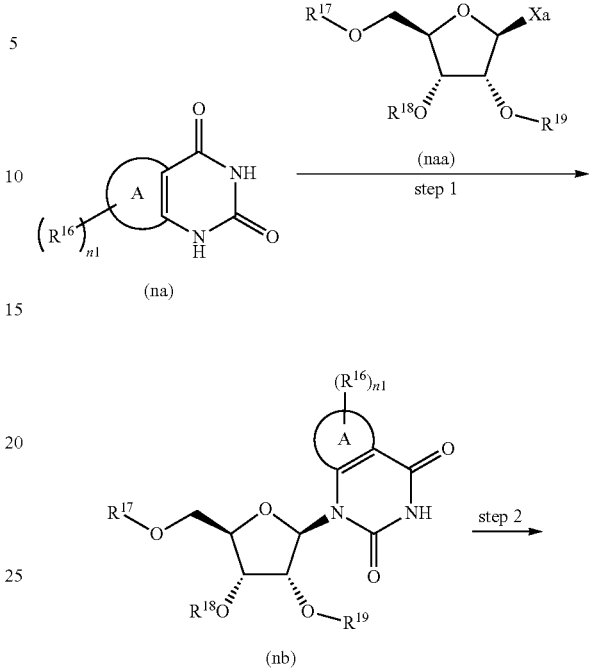

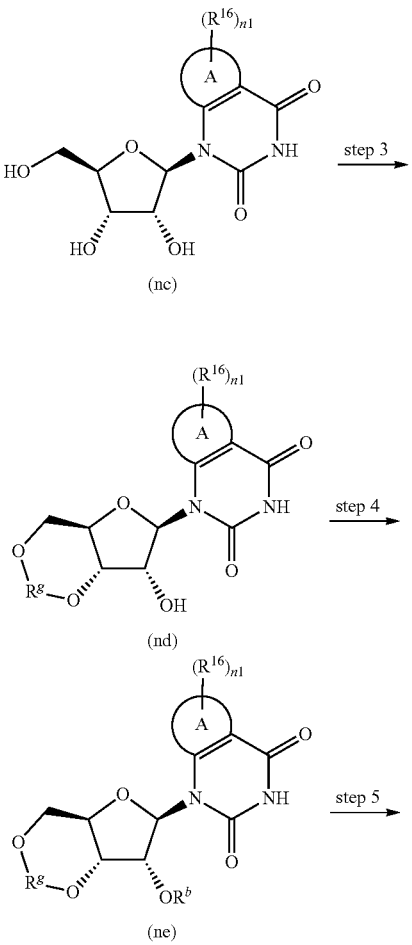

-continued

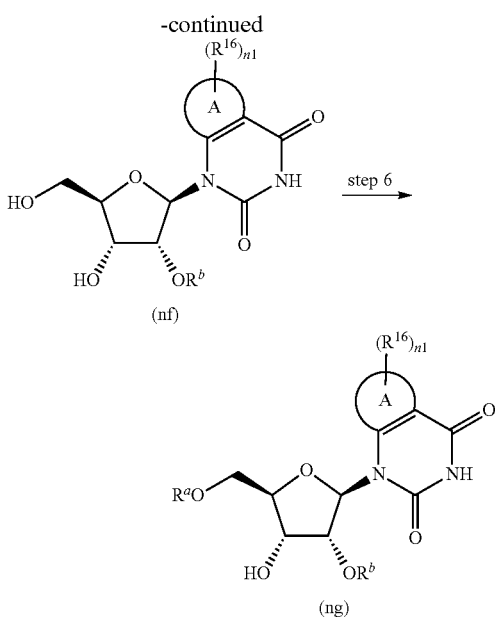

(wherein $R^a$, ring A, $R^{16}$, n1, and $R^b$ have the same meanings as described above, respectively, $R^g$ is a protecting group which can be removed with a fluoride ion, for example, di-tert-butylsilyl or the like, Xa is a leaving group, for example, halogen, an acyloxy group, or the like, and $R^{17}$, $R^{18}$, and $R^{19}$, are each protecting groups which can be deprotected with a base, for example, an acyl group or the like.)

Step 1

Compound (nb) can be produced by reacting Compound (na) with Compound (naa) in a solvent in the presence of a silylating agent at a temperature between 0° C. and 150° C. for 10 minutes to 1 day, and then, by treating in the presence of a Lewis acid at a temperature between 0° C. and 150° C. for 10 minutes to 1 day.

Examples of the solvent include acetonitrile, 1,2-dichloroethane, THF, toluene, and the like. These can be used alone or as a mixture thereof. Examples of the silylating agent include trimethylsilyl chloride, trifluoromethanesulfonyl trimethylsilyl, N,O-bis(trimethylsilyl)acetamide, 1,1,1,3,3,3-hexamethyldisilazane, and the like.

Examples of the Lewis acid include trifluoromethanesulfonyl trimethylsilyl, tin tetrachloride, and the like.

Compound (na) can be obtained as a commercially available product or, for example, by a known method (Tetrahedron, 2012, vol. 68, pp. 8908-8915) or a method according to that.

Step 2

Compound (nc) can be produced by reacting Compound (nb) with a base in a solvent or without a solvent at a temperature between room temperature and 50° C. for 1 hour to 4 days.

Examples of the solvent include methanol, ethanol, THF, DMF, water, and the like. These can be used alone or as a mixture thereof.

Examples of the base include ammonia, methylamine, sodium hydroxide, sodium methoxide, and the like.

Step 3

Compound (nd) can be produced by reacting Compound (nc) with, for example, a corresponding silylating agent in a solvent in the presence of a base at a temperature between 0° C. and 80° C. for 10 minutes to 3 days.

Examples of the solvent include DMF, DMA, NMP, and the like. These can be used alone or as a mixture thereof.

Examples of the base include imidazole, triethylamine, diisopropylethylamine, and the like.

Examples of the silylating agent include di-tert-butylsilyl bis(trifluoromethanesulfonate) and the like.

Step 4

Compound (ne) can be produced by reacting Compound (nd) with, for example, a corresponding silylating agent in a solvent in the presence of a base at a temperature between 0° C. and 80° C. for 10 minutes to 3 days.

Examples of the solvent include dichloromethane, chloroform, 1,2-dichloroethane, DMF, and the like. These can be used alone or as a mixture thereof.

Examples of the base include imidazole, triethylamine, diisopropylethylamine, and the like.

Examples of the silylating agent include tert-butyldimethylsilyl chloride and the like.

Step 5

Compound (nf) can be produced by treating Compound (ne) with a deprotecting reagent in a solvent in the presence of a base at a temperature between 0° C. and 80° C. for 10 minutes to 3 days.

Examples of the solvent include dichloromethane, chloroform, 1,2-dichloroethane, diethyl ether, THF, DME, dioxane, and the like. These can be used alone or as a mixture thereof.

Examples of the base include triethylamine, diisopropylethylamine, pyridine, and the like.

Examples of the deprotecting reagent include hydrogen fluoride-pyridine and the like.

Step 6

Compound (ng) can be produced by reacting Compound (nf) with a corresponding alkylating agent in a solvent in the presence of a base at a temperature between 0° C. and 150° C. for 10 minutes to 3 days. The reaction can also be accelerated by a suitable activating agent.

Examples of the solvent include dichloromethane, chloroform, 1,2-dichloroethane, THF, dioxane, DMF, pyridine, and the like. These can be used alone or as a mixture thereof.

Examples of the base include triethylamine, diisopropylethylamine, pyridine, and the like.

Examples of the alkylating agent include trityl chloride, p,p'-dimethoxytrityl chloride, and the like.

Examples of the activating agent include 4-dimethylaminopyridine and the like.

Production Method 4-18

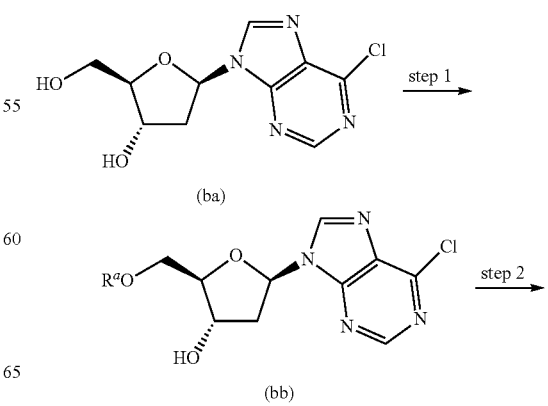

-continued

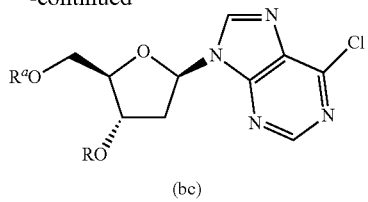

(bc)

(wherein $R^a$ has the same meaning as described above, R is a tri-lower alkylsilyl, and the lower alkyls of the tri-lower alkylsilyl may be the same or different and each has the same meaning as the lower alkyl described above.)

Step 1

Compound (bb) can be produced by reacting compound (ba) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP and the like. These can be used alone or as a mixture thereof.

Examples of the base include pyridine, triethylamine, N,N-diisopropylethylamine, 2,6-lutidine and the like.

Examples of the alkylating agent include trityl chloride, p,p'-dimethoxytrityl chloride and the like.

Examples of the activating agent include 4-dimethylaminopyridine and the like.

Compound (ba) can be obtained, for example, as a commercial product.

Step 2

Compound (bc) can be produced by reacting compound (bb) with a silylating agent in a solvent in the presence of a base at a temperature between 0° C. and 150° C. for 10 minutes to 3 days.

Examples of the solvent include DMF, pyridine, dichloromethane, THF, ethyl acetate, 1,4-dioxane, NMP and the like. These can be used alone or as a mixture thereof.

Examples of the base include imidazole, 2,6-lutidine and the like. Examples of the silylating agent include tert-butylchlorodimethylsilane, tert-butyldimethylsilyl trifluoromethanesulfonate and the like.

Production Method 4-19

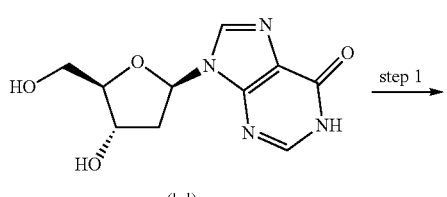

(bd)

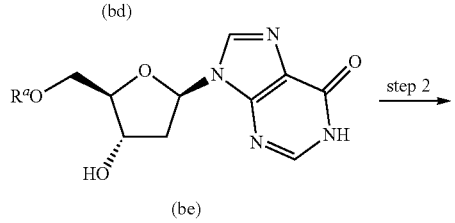

(be)

-continued

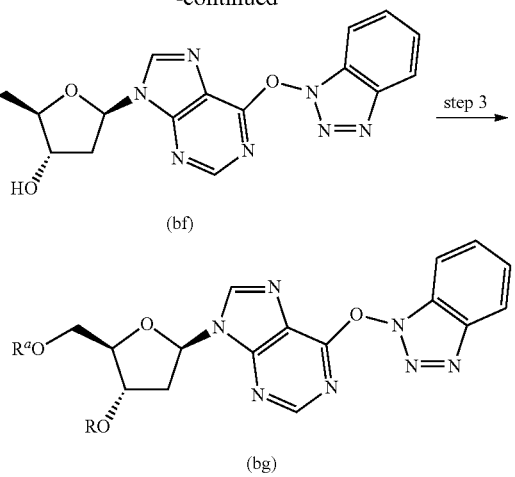

(wherein $R^a$ and R have the same meanings as described above.)

Step 1

Compound (be) can be produced by reacting compound (bd) with an alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP and the like. These can be used alone or as a mixture thereof.

Examples of the base include pyridine, triethylamine, N,N-diisopropylethylamine, 2,6-lutidine and the like.

Examples of the alkylating agent include trityl chloride, p,p'-dimethoxytrityl chloride and the like.

Examples of the activating agent include 4-dimethylaminopyridine and the like.

Compound (bd) can be obtained, for example, as a commercial product.

Step 2

Compound (bf) can be obtained by the methods described in J. Am. Chem. Soc., 2007, Vol. 129, pp. 782-789 using the compound (be).

Step 3

Compound (bg) can be obtained in the same mannner as in Step 2 of Production Method 4-18 using compound (bf).

Production Method 4-20

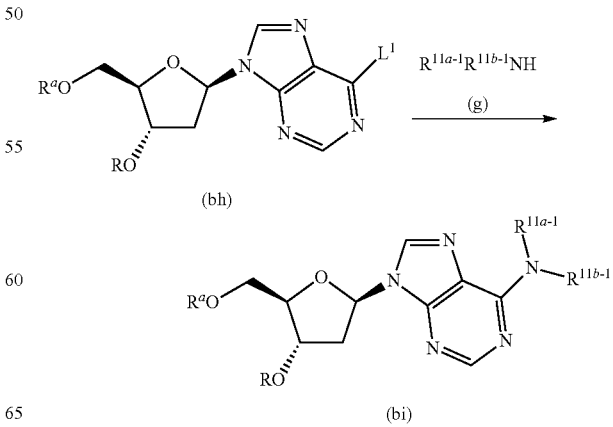

(wherein each of $R^a$, R and $R^{11a-1}$ has the same meaning as described above, and $R^{11b-1}$ is optionally substituted lower alkyl, optionally substituted lower alkenyl, optionally substituted lower alkynyl, optionally substituted aryl, optionally substituted aralkyl, optionally substituted aromatic heterocyclic alkyl or an optionally substituted aromatic heterocyclic group within the definition of $R^{11b}$ above, and $L^1$ is a chlorine atom or 1-benzotriazolyloxy.)

Compound (bi) can be produced by reacting compound (bh) and compound (g) in a solvent or without a solvent in the presence of abase or without a base for 1 hour to 1 week at a temperature between 0° C. and 150° C.

Examples of the solvent include DMF, pyridine, dichloromethane, THF, ethyl acetate, NMP, acetonitrile and the like. These can be used alone or as a mixture thereof.

Examples of the base include triethylamine, N,N-diisopropylethylamine and the like.

Production Method 4-21

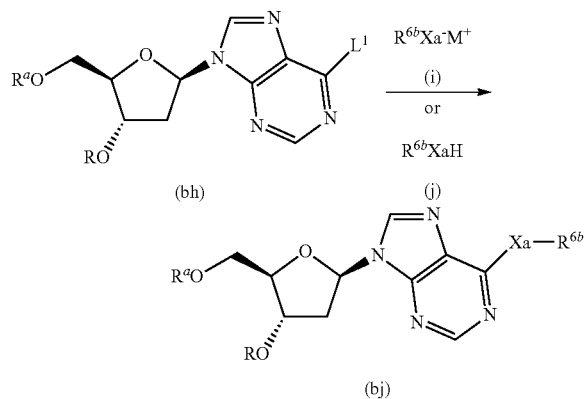

(wherein each of $R^a$, R and $L^1$ has the same meaning as described above, $R^{6b}$ is optionally substituted lower alkyl, optionally substituted aryl or an optionally substituted aromatic heterocyclic group, Xa is an oxygen atom or a sulfur atom, and M is an alkali metal atom. The lower alkyl, aryl and an aromatic heterocyclic group have the same meanings as described above, the substituent of the optionally substituted lower alkyl has the same meaning as the substituent of the optionally substituted lower alkyl described above, the substituent of the optionally substituted aryl and the optionally substituted aromatic heterocyclic group has the same meaning as the substituent of the optionally substituted aryl and the optionally substituted aromatic heterocyclic group described above, and the alkali metal atom is a lithium atom, a sodium atom or a potassium atom.)

Compound (bj) can be produced by reacting compound (bh) and compound (i) in a solvent at a temperature between 0° C. and 100° C. for 10 minutes to 3 days, or by reacting compound (bh) and compound (j) in a solvent in the presence of a base at a temperature between 0° C. and 120° C. for 10 minutes to 3 days.

Examples of the solvent include methanol, ethanol, 2-propanol, THF, DME, DMF, NMP and the like. These can be used alone or as a mixture thereof. Examples of the base include sodium hydroxide, potassium hydroxide, sodium carbonate, potassium carbonate, sodium hydride, potassium hydride, potassium tert-butoxide and the like.

Production Method 4-22

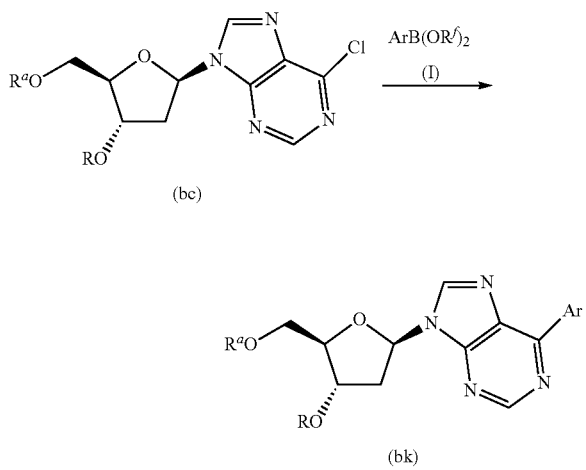

(wherein each of $R^a$ and R has the same meaning as described above, Ar is optionally substituted aryl or an optionally substituted aromatic heterocyclic group, and $R^f$ is a hydrogen atom or optionally substituted lower alkyl. Each of the lower alkyl, the aryl and the aromatic heterocyclic group has the same meaning as described above, the substituent of the optionally substituted lower alkyl has the same meaning as the substituent of the optionally substituted lower alkyl described above, and the substituent of the optionally substituted aryl and the optionally substituted aromatic heterocyclic group have the same meaning as the substituent of the optionally substituted aryl and optionally substituted aromatic heterocyclic group described above. Compound (bk) can be produced by reacting compound (bc) and compound (1) in a solvent in the presence of a base and a palladium catalyst at a temperature between 0° C. and 120° C. for 30 minutes to 72 hours. The reaction can also be accelerated by adding a suitable phosphine.)

Compound (1) can be obtained as a commercially available product oraccording to a method, for example, [Synthesis of Organic Compound VI, organic synthesis using metal, Jikken Kagaku Koza (Encyclopedia of Experimental Chemistry) 18, 5th Ed., p. 97, Maruzen (2005)] or the like. Examples of the base include potassium carbonate, potassium phosphate, potassium hydroxide, sodium hydroxide, potassium tert-butoxide, triethylamine, diisopropylethylamine, N-methylmorpholine, pyridine, DBU and the like.

Examples of the palladium catalyst include palladium acetate, tris(dibenzylideneacetone)dipalladium, tetrakis(triphenylphosphine)palladium, 1,1'-bis(diphenylphosphino)ferrocene-dichloropalladium/dichloromethane 1:1 adduct and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water and the like. These can be used alone or as a mixture thereof.

Examples of the suitable phosphine include 1,2-bis(diphenylphosphino)ethane, 1,3-bis(diphenylphosphino)propane, 4,5'-bis(diphenylphosphino)-9,9'-dimethylxanthene (Xantphos), 2,2'-bis(diphenylphosphino)-1,1'-binaphthyl (BINAP) and the like.

Production Method 4-23

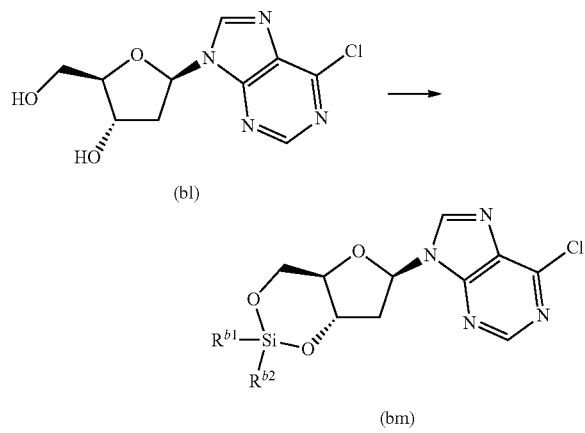

(wherein $R^{b1}$ and $R^{b2}$ may be the same or different, and each is lower alkyl. The lower alkyl has the same meaning as described above.)

Step 1

Compound (bm) can be produced by reacting compound (bl) and a silylating agent in a solvent in the presence of a base at a temperature between 0° C. and 150° C. for 10 minutes to 3 days.

Examples of the solvent include DMF, pyridine, dichloromethane, THF, ethyl acetate, 1,4-dioxane, NMP and the like. These can be used alone or as a mixture thereof.

Examples of the base include imidazole, 2,6-lutidine and the like. Examples of the silylating agent include dichloro di-tert-butylsilane and the like.

Production Method 4-24

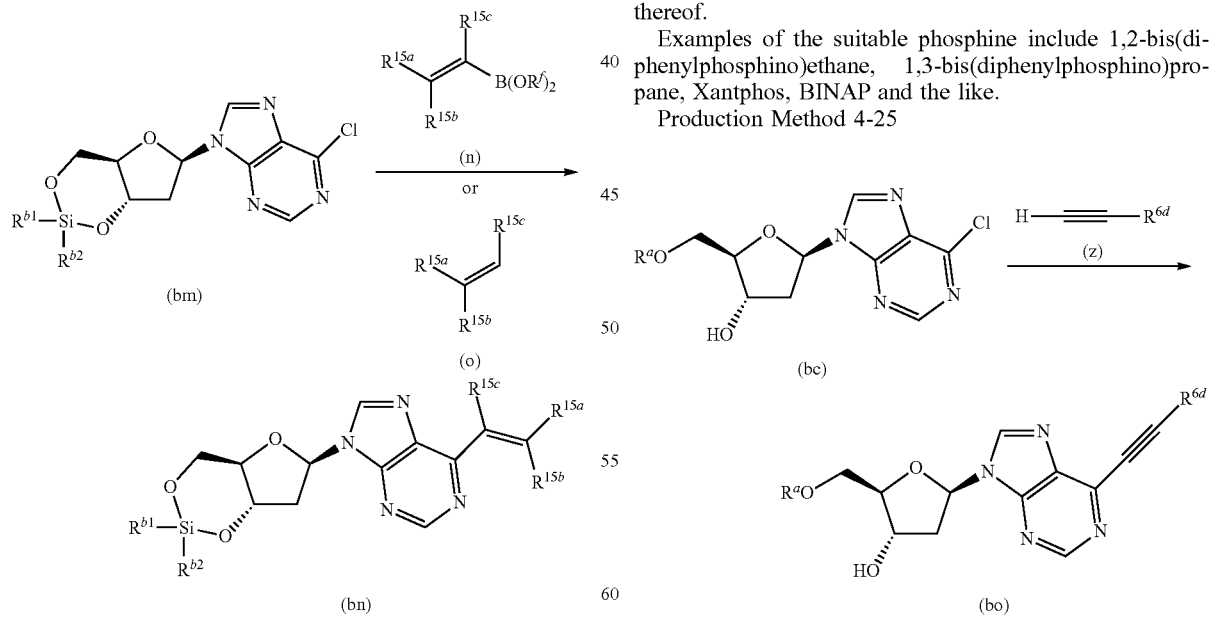

(wherein $R^{b1}$ and $R^{b2}$ have the same meanings as described above, $R^f$ has the same meaning as described above, and $R^{15a}$, $R^{15b}$ and $R^{15c}$ may be the same or different, and each is a hydrogen atom, optionally substituted lower alkyl, aryl, or an aromatic heterocyclic group. Each of the lower alkyl, the aryl and the aromatic heterocyclic group has the same meaning as described above, and the substituent of the optionally substituted lower alkyl has the same meaning as the substituent of the optionally substituted lower alkyl described above.)

Compound (bn) can be produced by reacting compound (bm) and compound (n) in a solvent in the presence of a base and a palladium catalyst at a temperature between 0° C. and 120° C. for 30 minutes to 72 hours. The reaction can be accelerated by adding a suitable phosphine.

Compound (n) can be obtained, for example, as a commercial product. Examples of the base include potassium carbonate, potassium phosphate, potassium hydroxide, sodium hydroxide, potassium tert-butoxide, triethylamine, diisopropylethylamine, N-methylmorpholine, pyridine, DBU and the like.

Examples of the palladium catalyst include those described above.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water and the like, and these can be used alone or as a mixture.

Compound (bn) can also be produced by reacting compound (bm) and compound (o) in a solvent in the presence of a base and a palladium catalyst at a temperature between 0° C. and 140° C. for 30 minutes to 72 hours.

Examples of the base include potassium acetate, sodium bicarbonate, potassium carbonate, potassium hydroxide, sodium hydroxide, sodium methoxide, potassium tert-butoxide, triethylamine, diisopropylethylamine, N-methylmorpholine, pyridine, DBU and the like. Examples of the palladium catalyst include those described above.

Examples of the solvent include dichloromethane, chloroform, 1,2-dichloroethane, toluene, ethyl acetate, acetonitrile, diethyl ether, THF, DME, dioxane, DMF, DMA, NMP and the like. These may be used alone or as a mixture thereof.

Examples of the suitable phosphine include 1,2-bis(diphenylphosphino)ethane, 1,3-bis(diphenylphosphino)propane, Xantphos, BINAP and the like.

Production Method 4-25

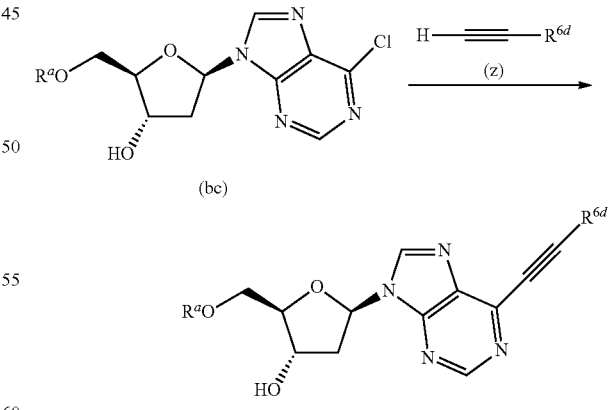

(wherein $R^a$ has the same meaning as described above, and $R^{6d}$ is optionally substituted lower alkyl, aryl or an aromatic heterocyclic group. Each of the lower alkyl, the aryl and the aromatic heterocyclic group has the same meaning as described above, and the substituent of the optionally substituted lower alkyl has the same meaning as the substituent of the optionally substituted lower alkyl described above.)

Compound (bo) can be produced by reacting compound (bc) and compound (z) in a solvent in the presence of a copper salt, a base and a palladium catalyst at a temperature between room temperature and 150° C. for 1 to hours. The reaction can be accelerated by adding a suitable phosphine.

Examples of the solvent include dichloromethane, chloroform, 1,2-dichloroethane, toluene, ethyl acetate, acetonitrile, diethyl ether, THF, DME, dioxane, DMF, DMA, NMP and the like. These may be used alone or as a mixture thereof.

Examples of the copper salt include copper iodide, copper fluoride, copper chloride, copper bromide, copper iodide, copper oxide, copper sulfide, copper selenide, copper acetate, copper cyanide, copper thiocyanate, copper trifluoromethanesulfonate and the like.

Examples of the base include sodium acetate, potassium acetate, sodium bicarbonate, potassium carbonate, sodium methoxide, potassium tert-butoxide, triethylamine, diisopropylethylamine, N-methylmorpholine, pyridine, DBU and the like.

Examples of the palladium catalyst include those described above. Examples of the suitable phosphine include 1,2-bis(diphenylphosphino)ethane, 1,3-bis(diphenylphosphino)propane, Xantphos, BINAP and the like.

The transformation of each group in the compounds included in the above-described respective production methods can also be performed by a known method [for example, Comprehensive Organic Transformations 2nd edition, R. C. Larock, Vch Verlagsgesellscaft Mbh, 1999, or the like] or a method according to those.

A desired nucleotide or nucleoside can be obtained by performing deprotection and phosphorylation of hydroxy of the product obtained by the above-described respective production methods according to a known method [for example, Journal of Medicinal Chemistry, vol. 55, pp. 1478-1489, 2012, or the like].

The intermediate and the target compound in the above-described respective production methods can be isolated and purified by a separation and purification method conventionally used in organic synthetic chemistry, for example, filtration, extraction, washing, drying, concentration, recrystallization, various types of chromatography, or the like. Further, the intermediate can also be subjected to the subsequent reaction particularly without further purification.

The nucleotide or nucleoside above can also be obtained in the form of a salt such as an acid addition salt, a metal salt, an ammonium salt, an organic amine addition salt, an amino acid addition salt, or the like.

Examples of the acid addition salt include an inorganic acid salt such as hydrochloride, sulfate, or phosphate, and an organic acid salt such as acetate, maleate, fumarate, citrate, or methanesulfonate. Examples of the metal salt include an alkali metal salt such as a sodium salt or a potassium salt, an alkaline earth metal salt such as a magnesium salt or a calcium salt, an aluminum salt, a zinc salt, and the like. Examples of the ammonium salt include a salt of ammonium, tetramethylammonium, or the like. Examples of the organic amine addition salt include an addition salt of morpholine, piperidine, or the like. Examples of the amino acid addition salt include a lysine addition salt, a glycine addition salt, a phenylalanine addition salt, and the like.

If it is desirable to obtain a salt of the nucleotide or the nucleoside above, when the nucleotide or the nucleoside is obtained in the form of a salt, it may be directly purified.

Further, when the nucleotide or the nucleoside is obtained in a free form, the nucleotide or the nucleoside may be dissolved or suspended in a suitable solvent, followed by addition of an acid or abase. Then, the resulting salt may be isolated and purified.

Among the nucleotides or the nucleosides above, some nucleotides or nucleosides can exist as a stereoisomer such as a geometric isomer or a optical isomer, a tautomer, or the like. All possible isomers inclusive of these stereoisomers and tautomers and mixtures thereof can be used in the present invention.

Further, the nucleotide or the nucleoside above can exist in the form of an adduct with water or various solvents, and these adducts can also be used in the present invention.

Specific examples of Compound (Ia) are shown in Tables 1 to 21. It should be noted, however, that Compound (Ia) of the present invention and the corresponding nucleotide residue or nucleoside residue represented by formula (I) are not limited to these and the corresponding nucleotide residue or nucleoside residue.

TABLE 1

| Compound No. | structural formula |
|---|---|
| I-1 (8-Br-dA) | |
| I-2 (8-oxo-dA) | |
| I-3 (8-Br-dU) | |
| I-4 (5-F-dU) | |

TABLE 1-continued

| Compound No. | structural formula |
|---|---|
| I-5 reference example 1 | (structure: 6,7-dimethoxy quinazoline-2,4-dione ribose 5'-monophosphate) |
| I-6 reference example 2 | (structure: 5-chloro quinazoline-2,4-dione ribose 5'-monophosphate) |
| I-7 reference example 3 | (structure: 7-chloro quinazoline-2,4-dione ribose 5'-monophosphate) |

TABLE 2

| compound No. | structural formula |
|---|---|
| I-8 reference example 4 | (structure: 8-chloro quinazoline-2,4-dione ribose 5'-monophosphate) |
| I-9 reference example 5 | (structure: thieno[3,2-d]pyrimidine-2,4-dione ribose 5'-monophosphate) |
| I-10 reference example 6 | (structure: 6-styryl purine riboside 5'-monophosphate) |
| I-11 reference example 7 | (structure: 8-bromo-N,N-dimethyladenosine 5'-monophosphate) |
| I-12 reference example 8 | (structure: 8-cyano-N,N-dimethyladenosine 5'-monophosphate) |
| I-13 reference example 9 | (structure: 6-iodouridine 5'-monophosphate) |
| I-14 reference example 10 | (structure: 5-(pyridin-2-yl)uridine 5'-monophosphate) |

TABLE 3
| compound No. | structural formula |
|---|---|
| I-15 reference example 11 | 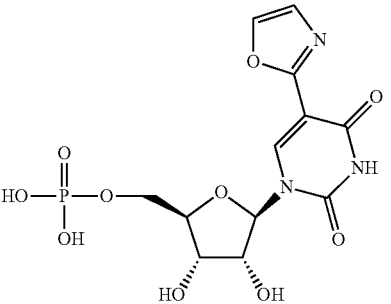 [SMILES: O=c1[nH]c(=O)n([C@@H]2O[C@H](COP(=O)(O)O)[C@@H](O)[C@H]2O)cc1-c1ncco1] |
| I-16 reference example 12 | 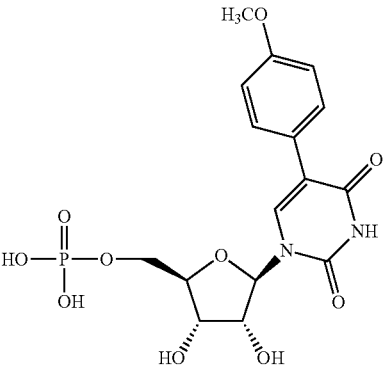 [SMILES: COc1ccc(-c2cn([C@@H]3O[C@H](COP(=O)(O)O)[C@@H](O)[C@H]3O)c(=O)[nH]c2=O)cc1] |
| I-17 reference example 13 | 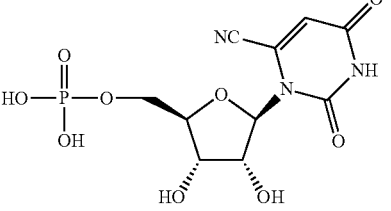 |
| I-18 reference example 14 | 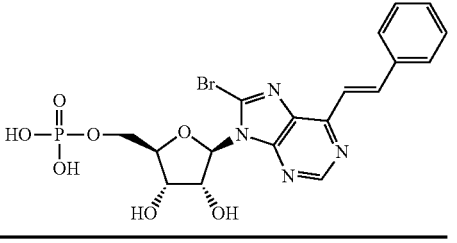 |
TABLE 4
| compound No. | structural formula |
|---|---|
| I-19 reference example 15 | 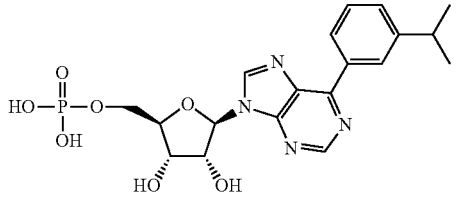 [SMILES: CC(C)c1cccc(-c2ncnc3c2ncn3[C@@H]2O[C@H](COP(=O)(O)O)[C@@H](O)[C@H]2O)c1] |
| I-20 reference example 16 | 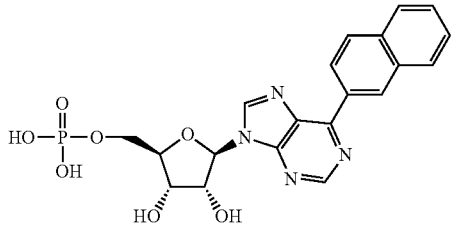 [SMILES: O=P(O)(O)OC[C@H]1O[C@@H](n2cnc3c(-c4ccc5ccccc5c4)ncnc32)[C@H](O)[C@@H]1O] |
| I-21 reference example 17 | 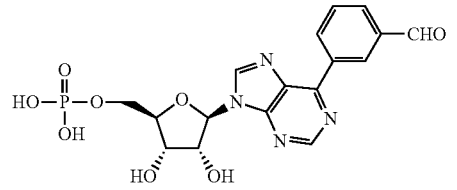 [SMILES: O=Cc1cccc(-c2ncnc3c2ncn3[C@@H]2O[C@H](COP(=O)(O)O)[C@@H](O)[C@H]2O)c1] |
| I-22 reference example 18 | 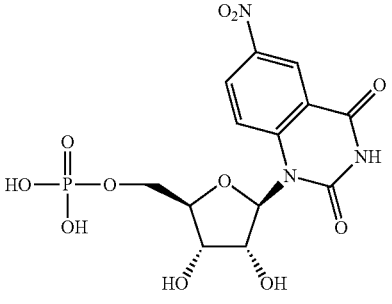 [SMILES: O=c1[nH]c(=O)n([C@@H]2O[C@H](COP(=O)(O)O)[C@@H](O)[C@H]2O)c2ccc([N+](=O)[O-])cc12] |
| I-23 reference example 19 | 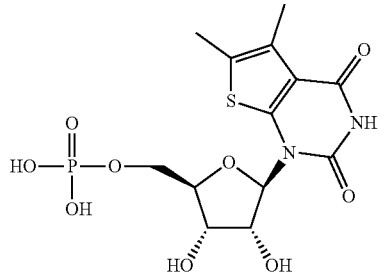 |
| I-24 reference example 20 | 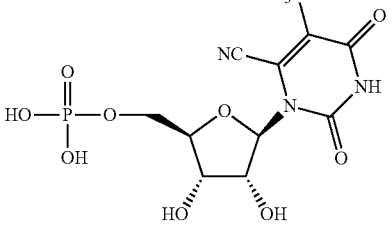 |

TABLE 5

| compound No. | structural formula |
|---|---|
| I-25 reference example 21 | 6-(naphthalen-1-yl)purine riboside 5'-monophosphate |
| I-26 reference example 22 | 6-(biphenyl-3-yl)purine riboside 5'-monophosphate |
| I-27 reference example 23 | 6-(3-aminophenyl)purine riboside 5'-monophosphate |
| I-28 reference example 24 | 6-(3-morpholinophenyl)purine riboside 5'-monophosphate |
| I-29 reference example 25 | 6-(3-benzyloxyphenyl)purine riboside 5'-monophosphate |
| I-30 reference example 26 | 6-(3-carboxyphenyl)purine riboside 5'-monophosphate |

TABLE 6
| compound No. | structural formula |
|---|---|
| I-31 reference example 27 | 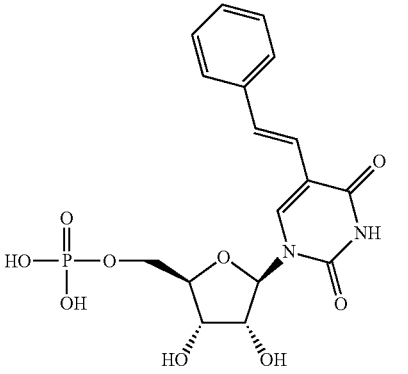 [SMILES: O=c1[nH]c(=O)n([C@@H]2O[C@H](COP(=O)(O)O)[C@@H](O)[C@H]2O)cc1/C=C/c1ccccc1] |
| I-32 reference example 28 | 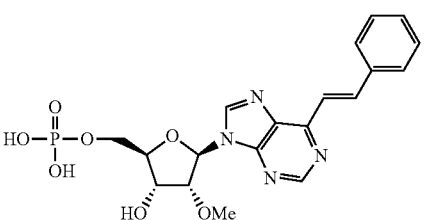 [SMILES: CO[C@@H]1[C@H](O)[C@@H](COP(=O)(O)O)O[C@H]1n1cnc2c(/C=C/c3ccccc3)ncnc21] |
TABLE 6-continued
| compound No. | structural formula |
|---|---|
| I-33 reference example 29 | 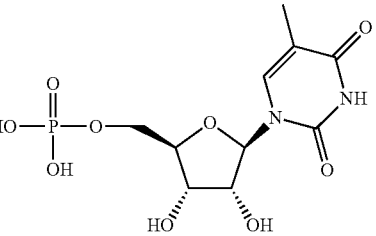 |
| I-34 reference example 30 | 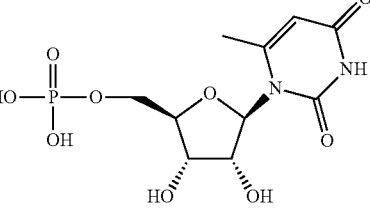 |
TABLE 7
| compound No. | structural formula |
|---|---|
| I-35 reference example 31 | 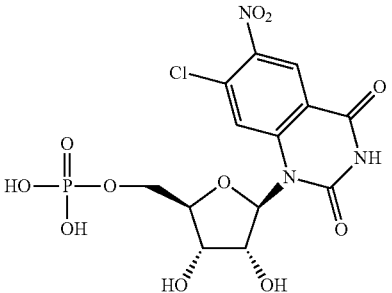 [SMILES: O=c1[nH]c(=O)n([C@@H]2O[C@H](COP(=O)(O)O)[C@@H](O)[C@H]2O)c2cc(Cl)c([N+](=O)[O-])cc12] |
| I-36 reference example 32 | 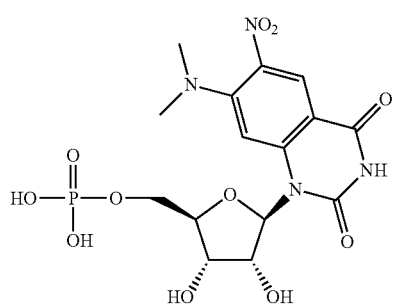 [SMILES: CN(C)c1cc2c(cc1[N+](=O)[O-])c(=O)[nH]c(=O)n2[C@@H]1O[C@H](COP(=O)(O)O)[C@@H](O)[C@H]1O] |

TABLE 7-continued
| compound No. | structural formula |
|---|---|
| I-37 reference example 33 | 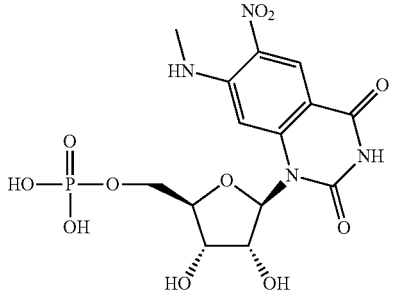 [SMILES: CNc1cc2c(cc1[N+](=O)[O-])c(=O)[nH]c(=O)n2[C@@H]1O[C@H](COP(=O)(O)O)[C@@H](O)[C@H]1O] |
| I-38 reference example 34 | 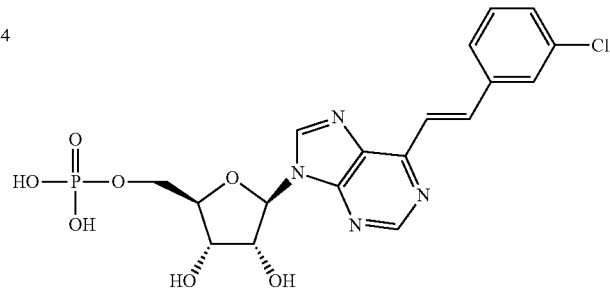 |
TABLE 8
| compound No. | structural formula |
|---|---|
| I-39 reference example 35 | 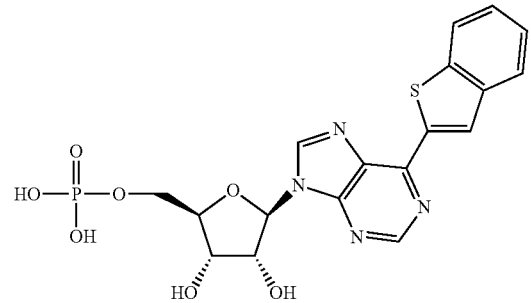 [SMILES: O=P(O)(O)OC[C@H]1O[C@@H](n2cnc3c(-c4cc5ccccc5s4)ncnc32)[C@H](O)[C@@H]1O] |
| I-40 reference example 36 | 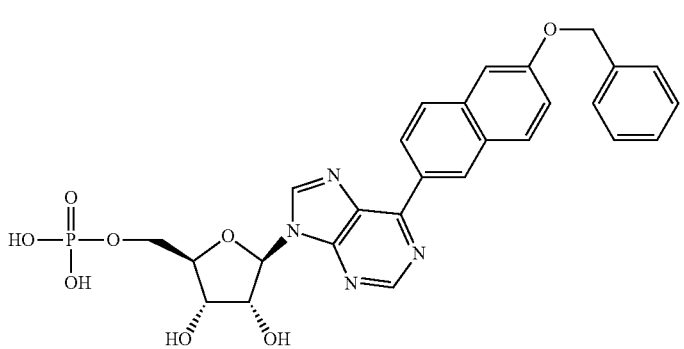 [SMILES: O=P(O)(O)OC[C@H]1O[C@@H](n2cnc3c(-c4ccc5cc(OCc6ccccc6)ccc5c4)ncnc32)[C@H](O)[C@@H]1O] |

TABLE 8-continued

| compound No. | structural formula |
| --- | --- |
| I-41 reference example 37 | |
| I-42 reference example 38 | |
| I-43 reference example 39 | |
| I-44 reference example 40 | |

TABLE 9
| compound No. | structural formula |
|---|---|
| I-45 reference example 41 | 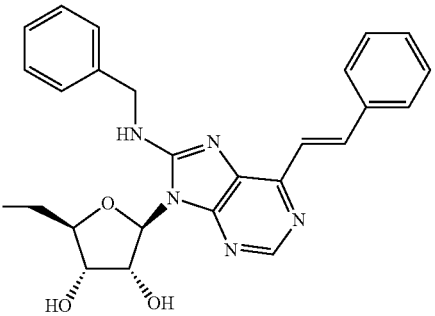 |
| I-46 reference example 42 | 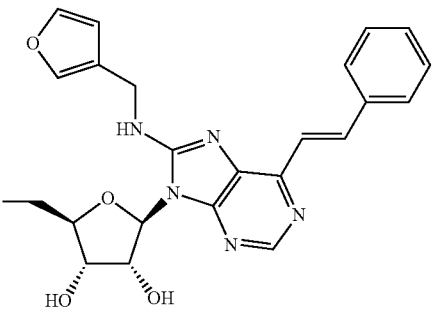 |
| I-47 reference example 43 | 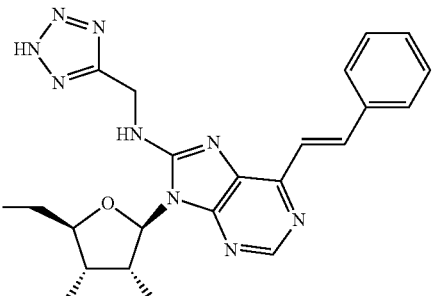 |
| I-48 reference example 44 | 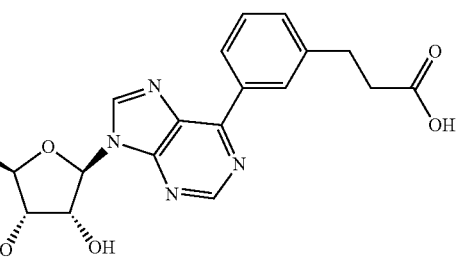 |
| I-49 reference example 45 | 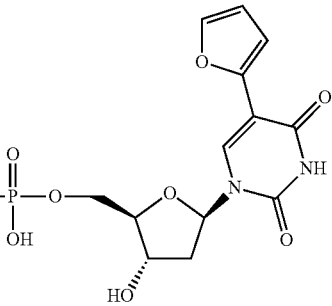 |

TABLE 10

| compound No. | structural formula |
|---|---|
| I-50 reference example 46 | 2-amino-adenosine-5'-monophosphate structure |

TABLE 11

| compound No. | structural formula |
|---|---|
| I-51 reference example 47 | N6-(3-hydroxymethylbenzyl)-2'-deoxyadenosine-5'-monophosphate structure |
| I-52 reference example 48 | N6-(3-phosphoryloxymethylbenzyl)-2'-deoxyadenosine-5'-monophosphate structure |
| I-53 reference example 49 | 6-styryl-2'-deoxypurine-5'-monophosphate structure |
| I-54 reference example 50 | O6-(3-phosphoryloxymethylbenzyl)-2'-deoxyinosine-5'-monophosphate structure |

TABLE 11-continued

| compound No. | structural formula |
| --- | --- |
| I-55<br>reference example 51 | |

TABLE 12

| compound No. | structural formula |
| --- | --- |
| I-56<br>reference example 52 | |
| I-57<br>reference example 53 | |
| I-58<br>reference example 54 | |
| I-59<br>reference example 55 | |

TABLE 12-continued
| compound No. | structural formula |
| --- | --- |
| I-60
reference example 56 | 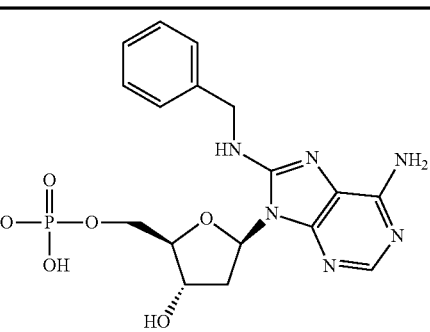 |
TABLE 13
| compound No. | structural formula |
| --- | --- |
| I-61
reference example 57 | 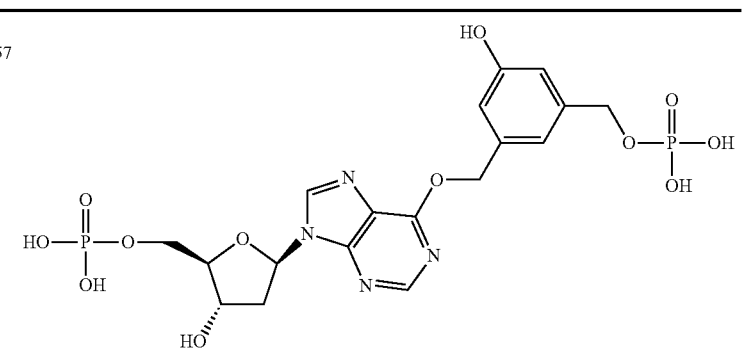 |
| I-62
reference example 58 | 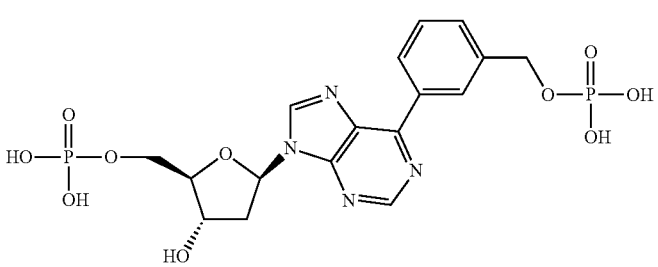 [SMILES: O=P(O)(O)OCc1cccc(-c2ncnc3c2ncn3[C@H]2C[C@H](O)[C@@H](COP(=O)(O)O)O2)c1] |
| I-63
reference example 59 | 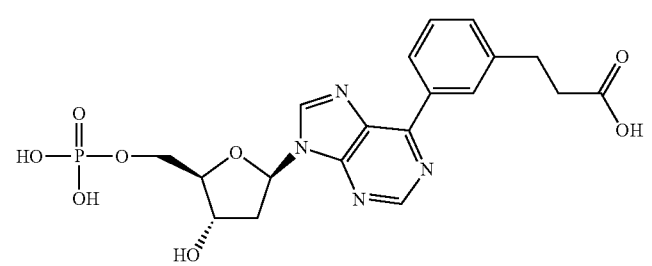 [SMILES: O=C(O)CCc1cccc(-c2ncnc3c2ncn3[C@H]2C[C@H](O)[C@@H](COP(=O)(O)O)O2)c1] |
| I-64
reference example 60 | 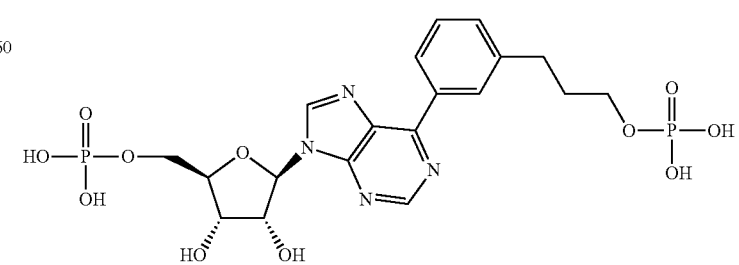 |

TABLE 13-continued
| compound No. | structural formula |
|---|---|
| I-65<br>reference example 61 | 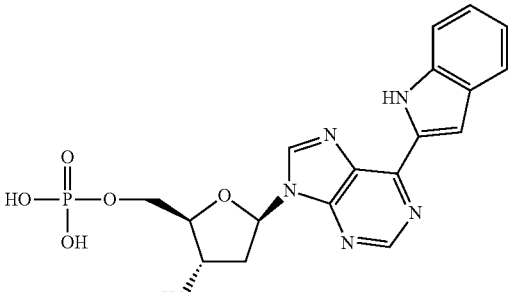 |
TABLE 14
| compound No. | structural formula |
|---|---|
| I-66<br>reference example 62 | 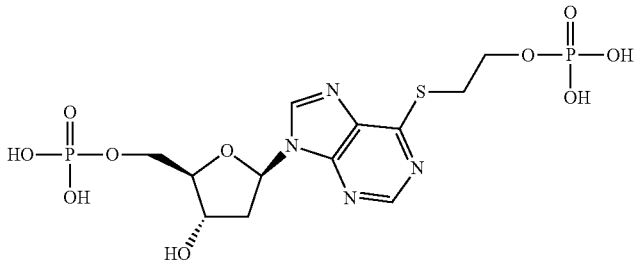 [SMILES: O=P(O)(O)OCCSc1ncnc2c1ncn2[C@H]1C[C@H](O)[C@@H](COP(=O)(O)O)O1] |
| I-67<br>reference example 63 | 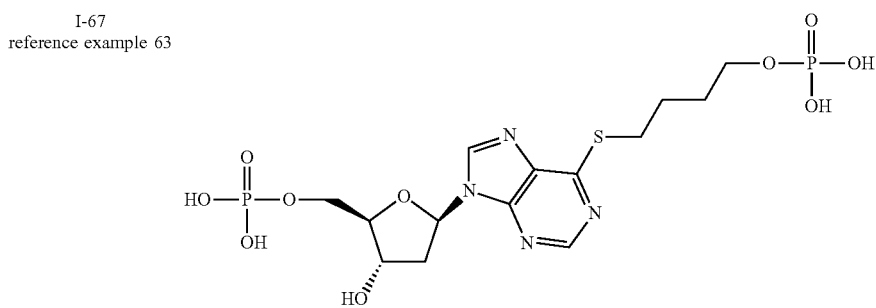 |
| I-68<br>reference example 64 | 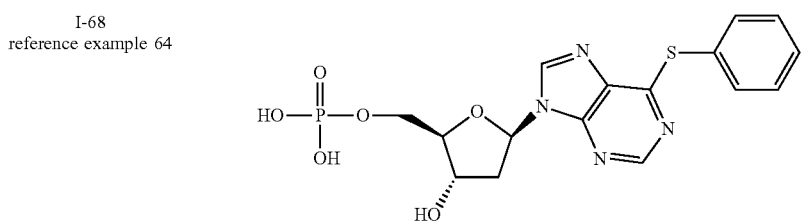 |

TABLE 14-continued
| compound No. | structural formula |
|---|---|
| I-69 reference example 65 | 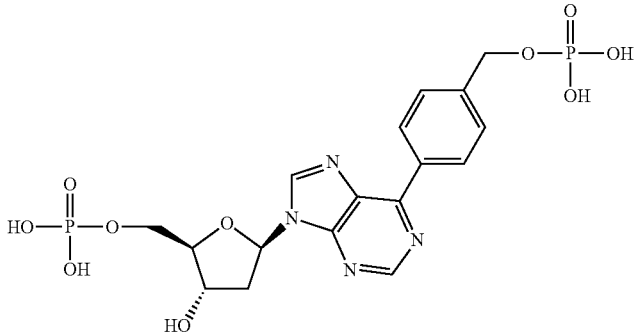 [SMILES: O=P(O)(O)OCc1ccc(-c2ncnc3c2ncn3[C@H]2C[C@H](O)[C@@H](COP(=O)(O)O)O2)cc1] |
| I-70 reference example 51 | 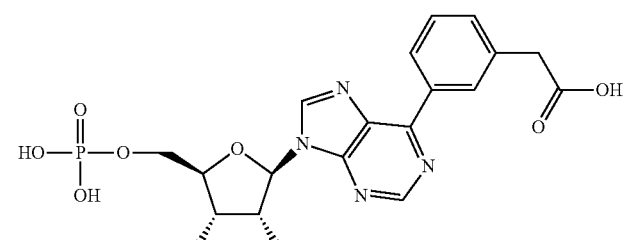 |
TABLE 15
| compound No. | structural formula |
|---|---|
| I-71 reference example 66 | 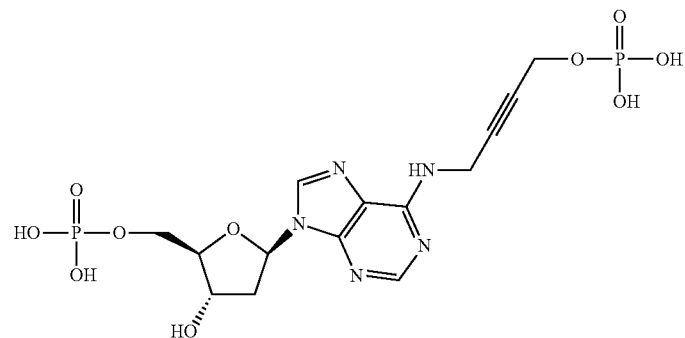 [SMILES: O=P(O)(O)OCC#CCNc1ncnc2c1ncn2[C@H]1C[C@H](O)[C@@H](COP(=O)(O)O)O1] |
| I-72 reference example 67 | 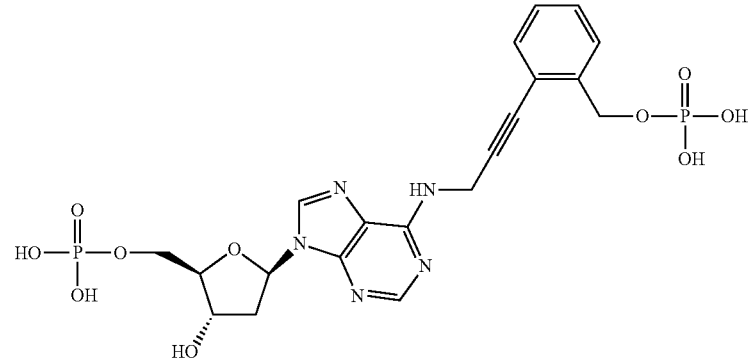 [SMILES: O=P(O)(O)OCc1ccccc1C#CCNc1ncnc2c1ncn2[C@H]1C[C@H](O)[C@@H](COP(=O)(O)O)O1] |

TABLE 15-continued
| compound No. | structural formula |
|---|---|
| I-73 reference example 68 | 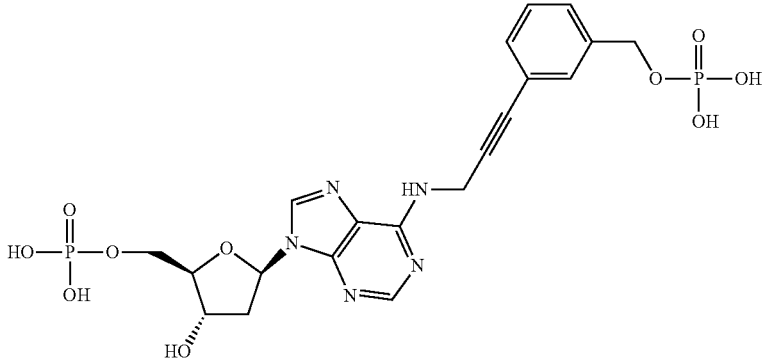 [SMILES: O=P(O)(O)OCc1cccc(C#CCNc2ncnc3c2ncn3[C@H]2C[C@H](O)[C@@H](COP(=O)(O)O)O2)c1] |
| I-74 reference example 69 | 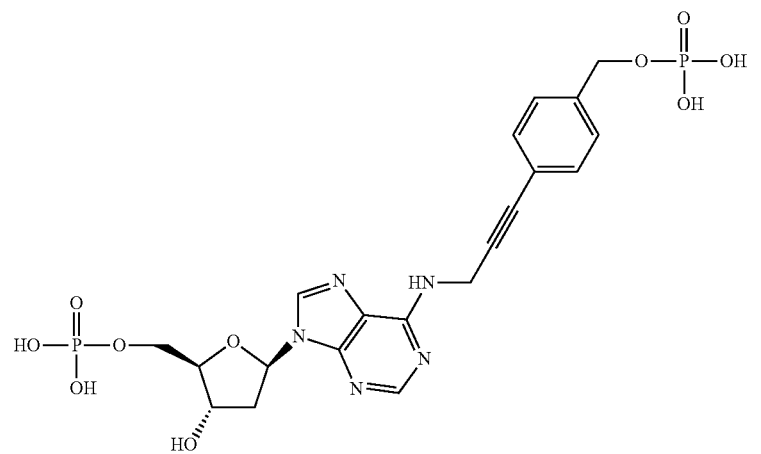 [SMILES: O=P(O)(O)OCc1ccc(C#CCNc2ncnc3c2ncn3[C@H]2C[C@H](O)[C@@H](COP(=O)(O)O)O2)cc1] |
| I-75 reference example 70 | 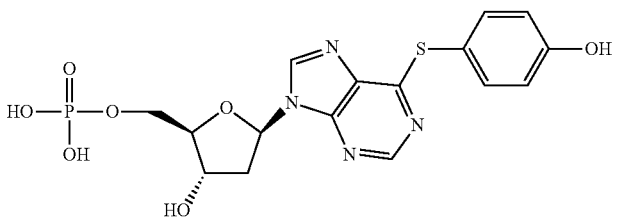 [SMILES: O=P(O)(O)OC[C@H]1O[C@@H](n2cnc3c(Sc4ccc(O)cc4)ncnc32)C[C@@H]1O] |
TABLE 16
| compound No. | stuructural formula |
|---|---|
| I-76 reference example 71 | 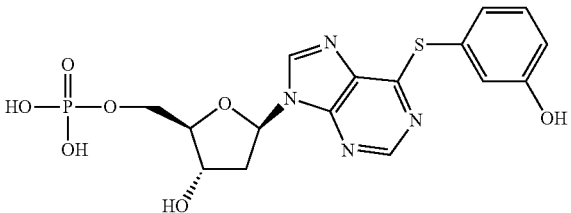 [SMILES: O=P(O)(O)OC[C@H]1O[C@@H](n2cnc3c(Sc4cccc(O)c4)ncnc32)C[C@@H]1O] |

TABLE 16-continued

| compound No. | structural formula |
|---|---|
| I-77<br>reference example 72 | |
| I-78<br>reference example 73 | |
| I-79<br>reference example 73 | |
| I-80<br>reference example 74 | |

TABLE 17

| compound No. | structural formula |
|---|---|
| I-81<br>reference example 75 | |

TABLE 17-continued
| compound No. | structural formula |
| --- | --- |
| I-82<br>reference example 76 | 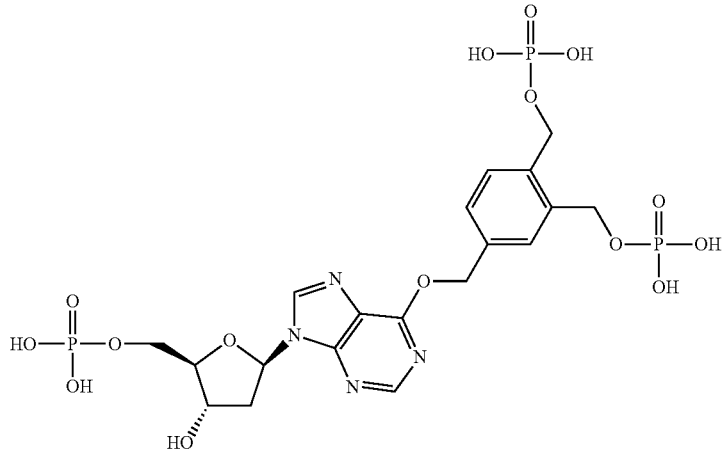 [SMILES: O=P(O)(O)OCc1ccc(COc2ncnc3c2ncn3[C@H]2C[C@H](O)[C@@H](COP(=O)(O)O)O2)cc1COP(=O)(O)O] |
| I-83<br>reference example 77 | 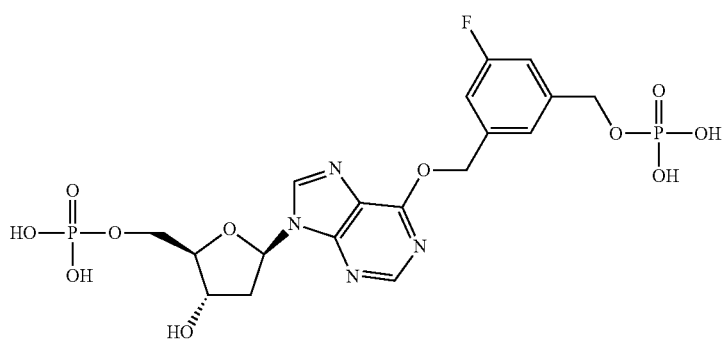 [SMILES: O=P(O)(O)OCc1cc(F)cc(COc2ncnc3c2ncn3[C@H]2C[C@H](O)[C@@H](COP(=O)(O)O)O2)c1] |
| I-84<br>reference example 78 | 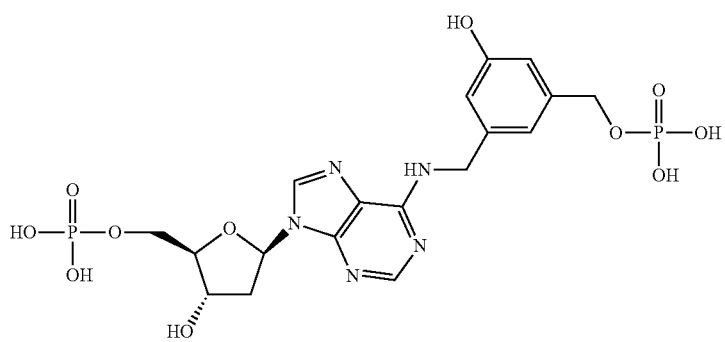 [SMILES: O=P(O)(O)OCc1cc(O)cc(CNc2ncnc3c2ncn3[C@H]2C[C@H](O)[C@@H](COP(=O)(O)O)O2)c1] |
| I-85<br>reference example 79 | 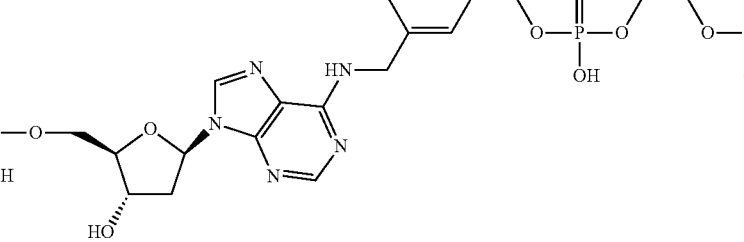 |

TABLE 18
| compound No. | structural formula |
| --- | --- |
| I-86 reference example 80 | 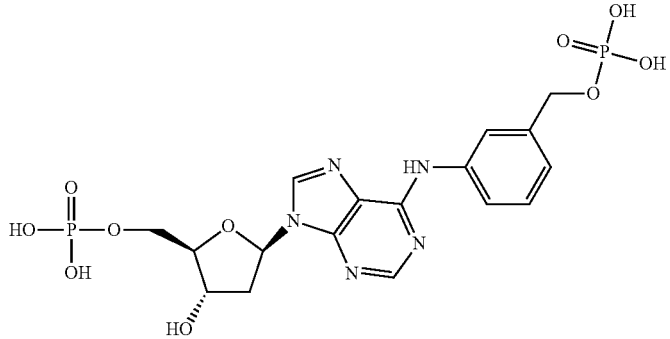 [SMILES: O=P(O)(O)OCc1cccc(Nc2ncnc3c2ncn3[C@H]2C[C@H](O)[C@@H](COP(=O)(O)O)O2)c1] |
| I-87 reference example 81 | 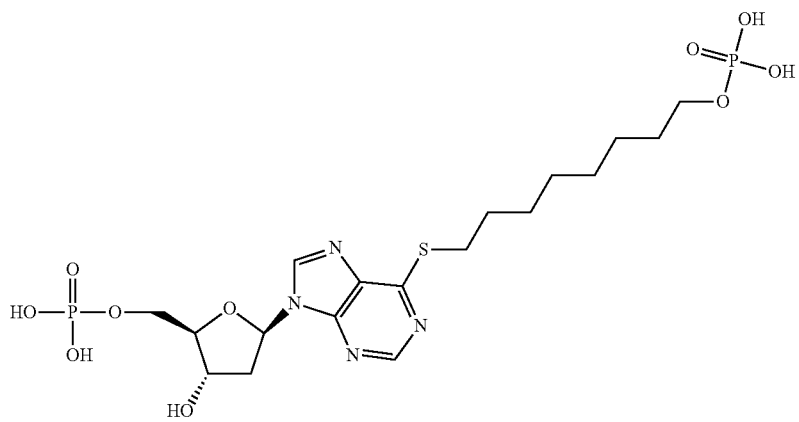 [SMILES: O=P(O)(O)OCCCCCCCCSc1ncnc2c1ncn2[C@H]1C[C@H](O)[C@@H](COP(=O)(O)O)O1] |
| I-88 reference example 82 | 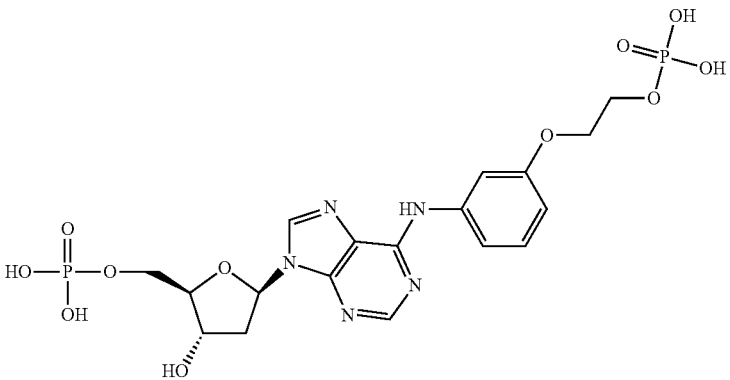 [SMILES: O=P(O)(O)OCCOc1cccc(Nc2ncnc3c2ncn3[C@H]2C[C@H](O)[C@@H](COP(=O)(O)O)O2)c1] |
| I-89 reference example 83 | 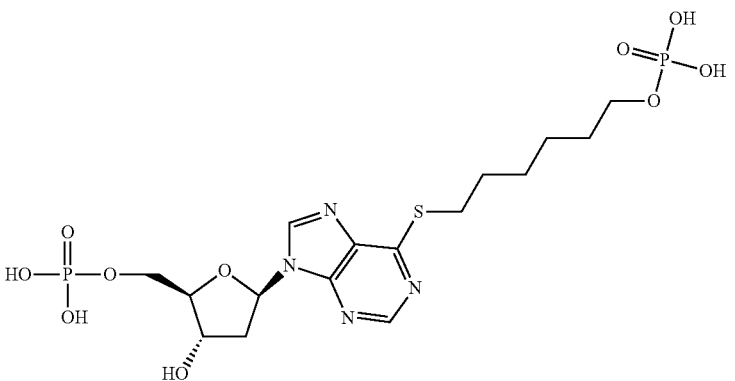 [SMILES: O=P(O)(O)OCCCCCCSc1ncnc2c1ncn2[C@H]1C[C@H](O)[C@@H](COP(=O)(O)O)O1] |

TABLE 18-continued
| compound No. | structural formula |
|---|---|
| I-90 reference example 84 | 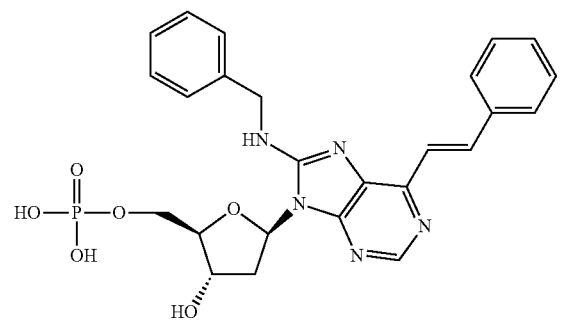 [SMILES: O=P(O)(O)OC[C@H]1O[C@@H](n2c(NCc3ccccc3)nc3c(/C=C/c4ccccc4)ncnc32)C[C@@H]1O] |
TABLE 19
| compound No. | structural formula |
|---|---|
| I-91 reference example 85 | 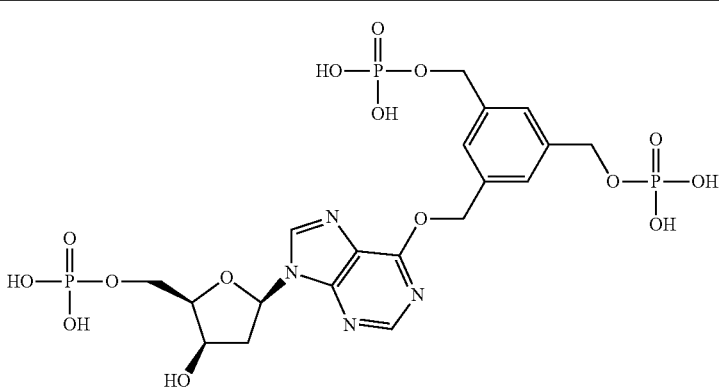 |
| I-92 reference example 86 | 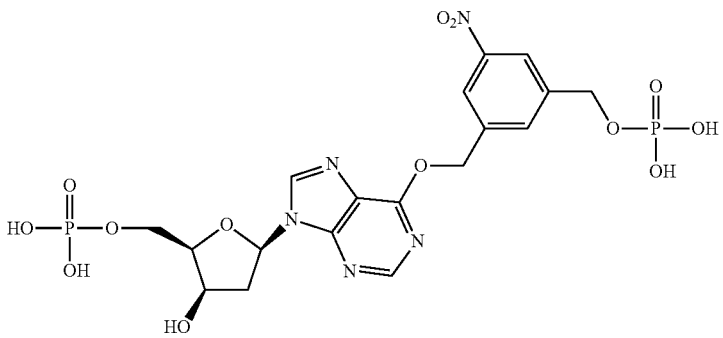 [SMILES: O=[N+]([O-])c1cc(COc2ncnc3c2ncn3[C@H]2C[C@@H](O)[C@@H](COP(=O)(O)O)O2)cc(COP(=O)(O)O)c1] |
| I-93 reference example 87 | 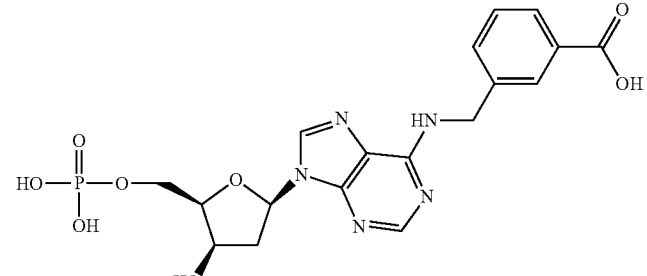 |

TABLE 19-continued
| compound No. | structural formula |
|---|---|
| I-94 reference example 88 | 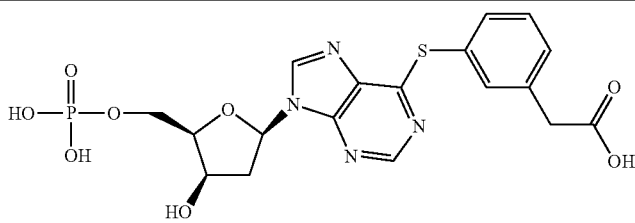 |
| I-95 reference example 89 | 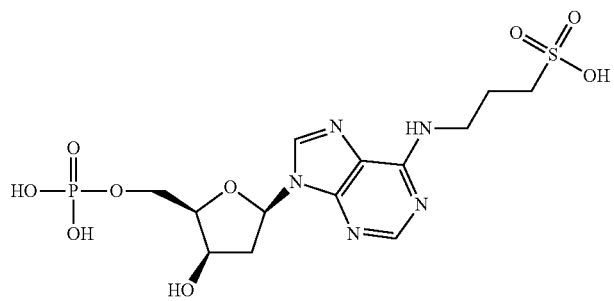 [SMILES: O=P(O)(O)OC[C@H]1O[C@@H](n2cnc3c(NCCCS(=O)(=O)O)ncnc32)C[C@H]1O] |
TABLE 20
| compound No. | structural formula |
|---|---|
| I-96 reference example 89 | 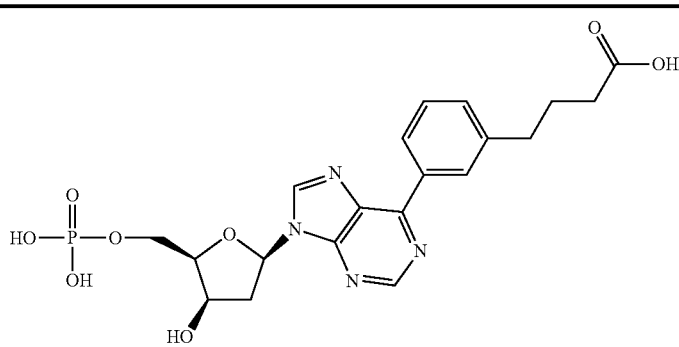 |
| I-97 reference example 90 | 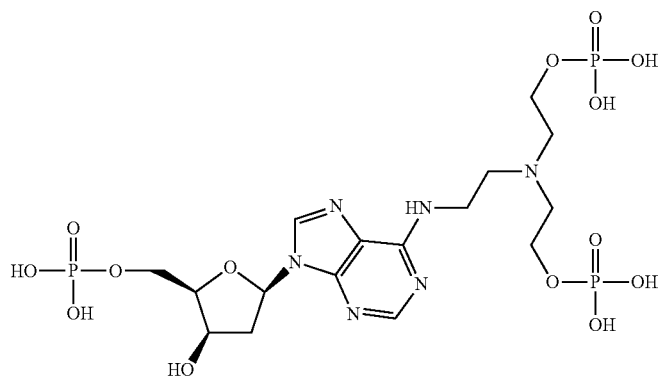 [SMILES: O=P(O)(O)OCCN(CCNc1ncnc2c1ncn2[C@H]1C[C@@H](O)[C@@H](COP(=O)(O)O)O1)CCOP(=O)(O)O] |

TABLE 20-continued
| compound No. | structural formula |
|---|---|
| I-98 reference example 91 | 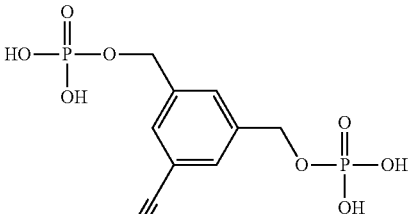 |
| I-99 reference example 92 | 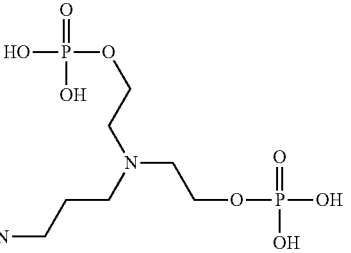 |
| I-100 reference example 93 | 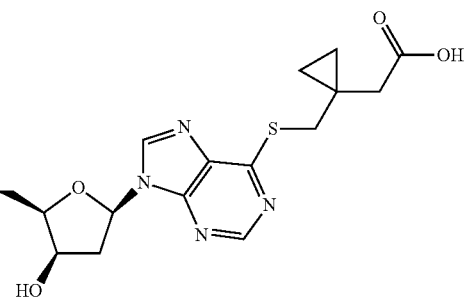 |
TABLE 21
| compound No. | structural formula |
|---|---|
| I-101 reference example 94 | 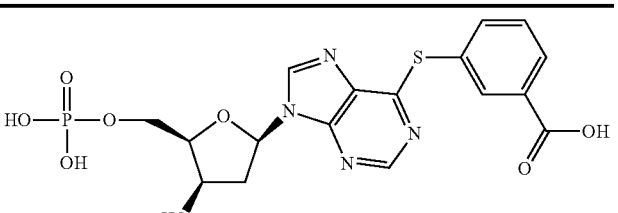 |

The oligonucleotide of the present invention can be introduced into a cell by using a carrier for transfection, preferably a cationic carrier such as a cationic liposome. Further, it can also be directly introduced into a cell by a calcium phosphate method, an electroporation method, a microinjection method, and the like.

For example, an siRNA can selectively inhibit the expression of any protein through cleavage of an mRNA, and therefore, the application thereof to pharmaceuticals is expected. In an oligonucleotide (for example, an siRNA) having a knockdown activity against an mRNA encoding a protein involved in a disease, by substituting a nucleotide residue or a nucleoside residue at the 5' end of the oligonucleotide with a nucleotide residue or a nucleoside residue represented by formula (I), improving the knockdown activity against a target mRNA is expected.

Further, in an oligonucleotide (for example, an siRNA) having a knockdown activity against an mRNA encoding a protein involved in a disease, by substituting a base residue at the 5' end of the oligonucleotide with a base residue represented by any of formulae (II) to (V), the affinity of the oligonucleotide for AGO2 is improved and the oligonucleotide has a higher knockdown activity against a target mRNA. Further, in an oligonucleotide in which a base at the 5' end is guanine or cytosine, by substituting the guanine residue or the cytosine residue at the 5' end of the oligonucleotide with an adenine residue (6-aminopurin-9-yl), a thymine residue (5-methyl-1,2,3,4-tetrahydropyrimidine-2, 4-dion-1-yl), an uridine residue (pyrimidin-2,4(1H,3H)-dion-1-yl), or abase residue represented by any of formulae (II) to (V), the affinity of the oligonucleotide for AGO2 is improved and the oligonucleotide has a higher knockdown activity against a target mRNA.

The phosphate moiety at the 5' end or the sugar moiety of the oligonucleotide having a high knockdown activity against a target mRNA obtained according to the present invention may be the same as or different from that of formula (I).

In the present invention, examples of the preferred embodiment of base residues represented by formulae (II) to (V) include base residues represented by formulae (II) to (V) according to the above (4) to (12), (14) to (16), (18) to (22), (24) to (27), (71) and (72), and examples of the more preferred embodiment thereof include base residues represented by formulae (IIA) to (VA), and (71) and (72) according to the above (35) to (39), (41) to (44), and (46) to (48).

The oligonucleotide of the present invention and the oligonucleotide having a knockdown activity against a target mRNA improved by the method of the present invention can be administered alone as it is. However, usually, it is preferably provided in various pharmaceutical formulations. Further, these pharmaceutical formulations are used for animals and humans.

The pharmaceutical formulations relating to the present invention can contain, as the active ingredient, the oligonucleotide of the present invention alone or as a mixture with any other active ingredient for treatment. Further, these pharmaceutical formulations are prepared by mixing the active ingredient with one or more pharmaceutically acceptable carriers and then produced by any method well known in the technical field of pharmaceutics. Examples of the production method for the pharmaceutical formulation of the present invention include a calcium phosphate method, a DEAE-dextran method, electroporation and microinjection, a virus method, a method using a cationic liposome, and the like (Graham, F. L. and van der Eb, A. J. (1973) Virol. 52, 456; McCutchan, J. H. and Pagano, J. S. (1968) J. Natl. Cancer Inst. 41, 351, Chu, G. et al., (1987) Nucl. Acids Res. 15, 1311, Fraley, R. et al., (1980) J. Biol. Chem. 255, 10431; Capechi, M. R. (1980) Cell, 22, 479, Felgner, P. L. et al., (1987), Proc. Natl. Acad. Sci. USA, 84, 7413). Further, a method using a nucleic acid-containing cationic lipid particle or cationic polymer, a nucleic acid-encapsulated lipid particle, and the like is included. In addition, modification of the surface of a lipid particle and the like with a water-soluble polymer such as polyethylene glycol (PEG) is generally performed, and also the above-described nucleic acid-containing cationic lipid particle or cationic polymer, nucleic acid-encapsulated lipid particle, and the like described above can be transformed into a PEG-modified lipid particle.

As for the administration route, it is preferred to select the most effective administration route in the treatment. Examples of the administration route include oral administration or parenteral administration such as intravenous administration. Examples of the dosage form include a tablet, an injection, and the like. A suitable dosage form for the oral administration, for example, a tablet or the like, can be produced by using an excipient such as lactose, a disintegrator such as starch, a lubricant such as magnesium stearate, a binder such as hydroxypropyl cellulose, and the like.

A suitable dosage form for the parenteral administration, for example, a injection, can be produced by using a salt solution, a glucose solution, or a mixed liquid of a salt solution and a glucose solution, and the like.

The dose and the frequency of administration of the oligonucleotide of the present invention may vary depending upon dosage form, age and body weight of a patient, nature or seriousness of the symptom to be treated, and the like. In general, in the parenteral administration such as intravenous administration a dose of 0.001 to 100 mg, preferably, 0.01 to 10 mg, is administered to an adult once or several times a day. However, these doses and frequencies of administration vary according to the various conditions described above.

Hereinafter, embodiments of the present invention are described with reference to Examples and Reference Examples. Unless otherwise stated, starting materials and reagents used were obtained as commercially available products, or according to known methods. Incidentally, the present invention is not limited to these Examples and Reference Examples.

Example 1

Example 1

The synthesis of luciferase-targeting siRNAs having 8-bromo-2'-deoxyadenosine monophosphate (8-Br-dA) at the 5' end of each of the antisense strands shown in Table 8 (X contained in the sequence of each of the antisense strands denotes 8-Br-dA) were performed on a scale of 0.5 µmol using a nucleic acid synthesizer (Ultra Fast Parallel Synthesizer, Sigma Co., Ltd., hereinafter referred to as UFPS). As a solid-phase support, CPG 500 angstrom, rA.rG(tac), SAFC-PROLIGO was used. Each of DMT-2'-O-TBDMS-rA(tac) amidite (SAFC-PROLIGO), DMT-2'-O-TBDMS-rG (tac) amidite (SAFC-PROLIGO), DMT-2'-O-TBDMS-rC (tac) amidite (SAFC-PROLIGO), and DMT-2'-O-TBDMS-rU amidite (SAFC-PROLIGO) was prepared into a 0.1 mol/L acetonitrile solution, 8-Br-dA-CE phosphoramidite (Glen ResearchCorporation) was prepared into a 0.1 mol/L acetonitrile solution, Chemical Phosphorylation Reagent II (Glen Research Corporation) was prepared into a 0.06 mol/L acetonitrile solution, and these were used for a condensation reaction. As an activating agent of phosphoramidites, 5-benzylthio-1H-tetrazole (SAFC-PROLIGO) was used, and the condensation time was set to 10 minutes in each case. After synthesis in trityl-off mode, it was immersed in a 28% ammonia solution, and the resulting mixture was allowed to stand at 55° C. for 4 hours. After the reaction mixture was concentrated under the reduced pressure, 31% triethylamine trihydrofluoride was added thereto, and the resulting mixture was allowed to stand at 65° C. for 3 hours. Thereafter, 1-butanol was added thereto to stop the reaction. The resulting product was purified by reverse-phase liquid chromatography (SHISEIDO, CAPSELL PAK C18, SG300, 6.0 mm×75 mm, 5% acetonitrile/0.1% triethylammonium acetate buffer, gradient by B solution: 50% acetonitrile/water), whereby a target oligonucleotide was obtained.

The single-stranded oligonucleotide obtained was dissolved in a mixed buffer [100 mmol/L potassium acetate, 30 mmol/L 2-[4-(2-hydroxyethyl)piperazin-1-yl]ethanesulfonic acid (HEPES)-KOH (pH 7.4), and 2 mmol/L magnesium acetate] to give a concentration of 50 μmol/L. Equal amounts of sense and antisense strands were mixed with each other and the resulting mixture was allowed to stand at 80° C. for 10 minutes. The temperature of the mixture was gradually decreased, and the mixture was allowed to stand at 37° C. for 1 hour, whereby a double-stranded oligonucleotide was obtained.

solution, and allowed to stand at room temperature for 4 hours. The reaction mixture was concentrated under reduced pressure, 31% triethylamine trihydrofluoride was added thereto, and the resulting mixture was allowed to stand at 65° C. for 3 hours. To the mixture were added 1-butanol and sodium acetate aqueous solution. Following centrifugation the supernatant was removed, and the residue obtained was washed twice with ethanol. The residue was redissolved in water and purified by reverse-phase liquid chromatography (SHISEIDO, CAPSELL PAK C18, SG300, 6.0 mm×75 mm, gradient by A solution:5% acetonitrile/0.1% triethylammonium acetate buffer, and B solution: 50% acetonitrile/water) to obtain a target oligonucleotide.

The resulting single-stranded oligonucleotide was dissolved in a mixed buffer [100 mmol/L potassium acetate, 30 mmol/L 2-[4-(2-hydroxyethyl)piperazin-1-yl]ethanesulfonic acid (HEPES)-KOH (pH 7.4), 2 mmol/L magnesium acetate] to give a concentration of 50 μmol/L. Equal amounts of sense and antisense strands were mixed with each other and allowed to stand at 80° C. for 10 minutes. The temperature was gradually decreased, and the mixture was allowed to stand at 37° C. for 1 hour to obtain a double-stranded oligonucleotide.

TABLE 22

| | sense strand | | antisense strand | |
|---|---|---|---|---|
| | sequence (5'→3') | SEQ ID NO | sequence (5'→3') | SEQ ID NO |
| 239-BrdA | UGCAGCGAGAAUAGCUUGUAG | 1 | XCAAGCUAUUCUCGCUGCACA | 2 |
| 874-BrdA | UAGCUUCUUCGCUAAGAGUAC | 3 | XCUCUUAGCGAAGAAGCUAAA | 4 |
| 904-BrdA | CAAGUACGACCUAAGCAAUUU | 5 | XUUGCUUAGGUCGUACUUGUC | 6 |
| 1084-BrdA | AGGCAAGGUGGUGCCCUUUUU | 7 | XAAGGGCACCACCUUGCCUAC | 8 |

Example 1-1

Luciferase-targeting siRNAs having 8-bromo-2'-deoxyadenosine monophosphate (8-Br-dA) at the 5' ends of each of the antisense strands shown in Tables 22 and 40 (X contained in the sequence of each antisense strand denotes 8-Br-dA) were synthesized on a scale of 0.5 μmol using a nucleic acid synthesizer (Ultra Fast Parallel Synthesizer, Sigma Co., Ltd., hereinafter referred to as UFPS). As a solid-phase support, CPG 500 angstrom, rA.rG(tac), SAFC-PROLIGO was used. Each of DMT-2'-O-TBDMS-rA(tac) amidite (SAFC-PROLIGO), DMT-2'-O-TBDMS-rG(tac) amidite (SAFC-PROLIGO), DMT-2'-O-TBDMS-rC(tac) amidite (SAFC-PROLIGO), and DMT-2'-O-TBDMS-rU amidite (SAFC-PROLIGO) was prepared into a 0.1 mol/L acetonitrile solution, 8-Br-dA-CE phosphoramidite (Glen Research Corporation) was prepared into a 0.1 mol/L acetonitrile solution, Chemical Phosphorylation Reagent II (Glen Research Corporation) was prepared into a 0.06 mol/L acetonitrile solution, and these were used for a condensation reaction. 5-benzylthio-1H-tetrazole (SAFC-PROLIGO) was used as a phosphoramidite activator, and the condensation time was set to 10 minutes in each case. After synthesis in trityl-off mode, this was immersed in a 28% ammonia

Test Example 1: RNAi Activity of Luciferase-Targeting siRNA

The RNAi activity of the luciferase-targeting siRNA having 8-Br-dA at the 5' end of the antisense strand obtained in Example 1 was evaluated by using the level of inhibition of luciferase luminescence as an index as described below.

In a culture dish (Assay plate, 96-well, with Lid, Cat. No. 3917, manufactured by Costar Co., Ltd.), human cervical cancer-derived cell line Hela cells (CCL-2, purchased from ATCC) transfected with a luciferase expression vector (pGL4.50 [luc2/CMV/Hygro] Vector, Promega Corporation) were suspended in RPMI medium (Invitrogen Life Technologies, 11875093) containing 10% fetal bovine serum, and the cell suspension was inoculated into each well at 50 μL/well to give 5000 cells/well.

An siRNA was diluted with OPTI-MEM (Invitrogen Life Technologies, 31985-070). Lipofectamine RNAiMAX (Invitrogen Life Technologies, 13778-075) was diluted with OPTI-MEM. These prepared dilute liquids were mixed with each other to form an siRNA-lipofectamine RNAiMAX complex. Ten microliter of a solution of the prepared siRNA-Lipofectamine RNAiMAX (Invitrogen Life Technologies, 13778-075) complex was added to each well containing the cell suspension, so that the siRNA was introduced into the Hela cells. The final concentration of the siRNA was set to one level: 100 pmol/L, or the following four levels: 3.2 pmol/L, 16 pmol/L, 80 pmol/L, and 400 pmol/L, and N was set to 6. Further, as a negative control group, cells to which only Lipofectamine RNAiMAX was added were inoculated. Further, for comparison, a test was performed in the same manner also for siRNAs having adenosine monophosphate at a position corresponding to 8-Br-dA of each siRNA (referred to as 239-A, 874-A, 904-A, 1084-A, 1203-A, and 1556-A, respectively, shown in Table 23). Further, a test was performed in the same manner also for siRNAs having guanosine monophosphate, cytidine monophosphate, or uridine monophosphate at a position corresponding to 8-Br-dA of 874-BrdA (referred to as 874-G, 874-C, and 874-U, respectively, shown in Table 24).

or uridine monophosphate at a position corresponding to 8-Br-dA in the sequence thereof at final concentrations of 3.2 pmol/L, 16 pmol/L, 80 pmol/L, and 400 pmol/L (in FIGS. 1 and 2, the ordinate represents the ratio of the amount of luminescence when the amount of luminescence in the negative control group was taken as 1). Additionally, by the Kruskal-Wallis test, it was determined whether or not there is a significant difference. In the statistical analysis, statistical analysis software SAS (Release 9.2, SAS Institute, Inc.) was used. In Table 25, the results of the significant difference test for comparison between the ratio of inhibition of lumi-

TABLE 23

| | sense strand | | antisense strand | |
|---|---|---|---|---|
| | sequence (5'→3') | SEQ ID NO | sequence (5'→3') | SEQ ID NO |
| 239-A | UGCAGCGAGAAUAGCUUGUAG | 1 | ACAAGCUAUUCUCGCUGCACA | 13 |
| 874-A | UAGCUUCUUCGCUAAGAGUAC | 3 | ACUCUUAGCGAAGAAGCUAAA | 14 |
| 904-A | CAAGUACGACCUAAGCAAUUU | 5 | AUUGCUUAGGUCGUACUUGUC | 15 |
| 1084-A | AGGCAAGGUGGUGCCCUUUUU | 7 | AAAGGGCACCACCUUGCCUAC | 16 |
| 1203-A | UUAACAACCCCGAGGCUAUAA | 9 | AUAGCCUCGGGGUUGUUAACG | 17 |
| 1556-A | GACGAGGUGCCUAAAGGAUUG | 11 | AUCCUUUAGGCACCUCGUCCA | 18 |

TABLE 24

| | sense strand | | antisense strand | |
|---|---|---|---|---|
| | sequence (5'→3') | SEQ ID NO | sequence (5'→3') | SEQ ID NO |
| 874-G | UAGCUUCUUCGCUAAGAGCAC | 19 | GCUCUUAGCGAAGAAGCUAAA | 20 |
| 874-C | UAGCUUCUUCGCUAAGAGGAC | 21 | CCUCUUAGCGAAGAAGCUAAA | 22 |
| 874-U | UAGCUUCUUCGCUAAGAGAAC | 23 | UCUCUUAGCGAAGAAGCUAAA | 24 |

The cells after introduction of each of the siRNAs were cultured under the conditions of 37° C. and 5% $CO_2$ for 24 hours.

To the cells after culture, 40 μL of Steady-Glo Luciferase Assay System (Promega E2520), which is a commercially available luciferase assay reagent, was added to each well according to the attached protocol. After the cells were incubated for 10 minutes, the amount of luminescence (cps) per second in each well was measured using ARVO (PerkinElmer) according to the protocol.

By also performing the measurement of the amount of luminescence in the negative control group simultaneously with the measurement of the amount of luminescence in the luciferase-targeting siRNA treated group, the RNAi effect on each of the siRNA-introduced samples was expressed as a relative ratio when the amount of luminescence in the siRNA-unintroduced group (negative control group) was taken as 1. The results of this test are shown in FIGS. 1 and 2. FIG. 1 is a graph showing comparison between the siRNA of the present invention and the siRNA having adenosine monophosphate at a position corresponding to 8-Br-dA in the sequence thereof at a final concentration of 100 pmol/L. FIG. 2 is a graph showing comparison between 874-BrdA, which is the siRNA of the present invention, and 874-A, 874-G, 874-C, and 874-U having adenosine monophosphate, guanosine monophosphate, cytidine monophosphate, or uridine monophosphate at a position corresponding to 8-Br-dA in the sequence thereof at final concentrations of 3.2 pmol/L, 16 pmol/L, 80 pmol/L, and 400 pmol/L (in FIGS. 1 and 2, the ordinate represents the ratio of the amount of luminescence when the amount of luminescence in the negative control group was taken as 1). Additionally, by the Kruskal-Wallis test, it was determined whether or not there is a significant difference. In the statistical analysis, statistical analysis software SAS (Release 9.2, SAS Institute, Inc.) was used. In Table 25, the results of the significant difference test for comparison between the ratio of inhibition of luminescence by 239-BrdA, 874-BrdA, 904-BrdA, 1084-BrdA, 1203-BrdA, and 1556-BrdA and the ratio of inhibition of luminescence by 239-A, 874-A, 904-A, 1084-A, 1203-A, and 1556-A, respectively, are shown. A p-value of 0.05 or less was obtained in all the cases, and it is found that the ratio of inhibition of luminescence was significantly improved in the case of the siRNA in which adenosine monophosphate was substituted with 8-Br-dA.

TABLE 25

| | 239-BrdA | 874-BrdA | 904-BrdA | 1084-BrdA | 1203-BrdA | 1556-BrdA |
|---|---|---|---|---|---|---|
| p | 0.01 | 0.004 | 0.004 | 0.01 | 0.02 | 0.04 |

Test Example 2: RNAi Activity of Luciferase-Targeting siRNA

The RNAi activity of the luciferase-targeting siRNA having 8-Br-dA at the 5' end of the antisense strand obtained in Example 1 was evaluated by measuring the inhibitory effect on the expression of Luciferase GL4 mRNA (GenBank Accession No. EU921840) as described below.

In a culture dish (Multidish 24 wells, Cat. No. 142475, manufactured by Nunc, Inc.), human cervical cancer-derived cell line Bela cells (CCL-2, purchased from ATCC) were suspended in RPMI medium (Invitrogen Life Technologies, 11875093) containing 10% fetal bovine serum, and 500 μL of the resulting cell suspension was inoculated into each well to give 50000 cells/well. Thereto, 100 μL of a solution of an siRNA-Lipofectamine RNAiMAX (Invitrogen Life Technologies, 13778-075) complex mixed in OPTI-MEM (Invitrogen Life Technologies, 31985-070) was added, whereby the siRNA was introduced into the Hela cells. The final concentration of the siRNA was set to the following seven levels: 10000 pmol/L, 2000 pmol/L, 400 pmol/L, 80 pmol/L, 16 pmol/L, 3.2 pmol/L, and 0.64 pmol/L. Further, as a negative control group, cells to which only Lipofectamine RNAiMAX was added were inoculated.

The cells after introduction of the siRNA were cultured under the conditions of 37° C. and 5% $CO_2$ for 24 hours. In order to collect RNA, an RNA extraction kit (RNeasy 74106) of Qiagen, Inc. was used. The cells after culture were washed once with phosphate buffer, and then lysed with RLT buffer (attached to Rneasy) attached to the RNeasy kit and collected. Then, the total RNA was collected according to the instruction attached to the kit. By using the total RNA (1 μg) as a template, a reverse transcription reaction was performed by using Transcriptor First Strand cDNA Synthesis Kit (Roche, 4897030001), whereby a cDNA was prepared. By using this cDNA as a template for the PCR reaction, a GL4 (GenBank Accession No. EU921840) gene and, as a control, D-glyceraldehyde-3-phosphate dehydrogenase (GAPDH, GenBank Accession No. NM_001256799) were subjected to the PCR reaction by the Taqman probe method using ABI 7900HT Fast (Applied Biosystems, Inc. (ABI)), and each level of amplified mRNAs was measured. Then, a semi-quantitative level of mRNA of GL4 was calculated using the level of the amplified mRNA of GAPDH as an internal control. In the measurement of GAPDH, Taqman probe Hs99999905 m1 (Applied Biosystems, Inc. (ABI)) was used. In the measurement of GL4, the probe #20 in the universal probe library (Roche, 04686934001), and as the amplification primers, a DNA having a base sequence represented by SEQ ID NO: 63 (forward primer) and a DNA having a base sequence represented by SEQ ID NO: 64 (reverse primer) were used. Further, in the negative control group, the level of mRNA of GL4 and the level of the amplified mRNA of GAPDH were measured in the same manner, respectively, and a semi-quantitative level of mRNA of GL4 was calculated using the level of amplified mRNA of GAPDH as an internal control.

The level of the target mRNA in the siRNA-introduced sample was represented as a relative ratio when the level of the mRNA of GL4 in the siRNA-unintroduced group (negative control group) was taken as 1.

An $IC_{50}$ value was calculated by the Logit method. A statistical analysis was performed using statistical analysis software SAS (Release 9.2, SAS Institute, Inc.)

In Table 26, the $IC_{50}$ values of 874-BrdA, which is the siRNA of the present invention, and 874-A and 874-U, which have adenosine monophosphate or uridine monophosphate at a position corresponding to 8-Br-dA in the sequence thereof as a comparison, are shown.

TABLE 26

|  | 874-BrdA | 874-U | 874-A |
|---|---|---|---|
| $IC_{50}$ (pmol/L) | 1.8 | 3.3 | 13.3 |

From the results of Test Examples 1 and 2, it is found that the siRNA having 8-Br-dA at the 5' end of the antisense strand (874-BrdA) shows a higher knockdown activity against the expression of luciferase than the siRNA having a corresponding natural nucleotide at the 5' end of the antisense strand.

Example 2

A luciferase-targeting siRNA having 8-oxo-2'-deoxyadenosine monophosphate at the 5' end of the antisense strand shown in Table 27 (referred to as 874-8-oxo-dA, X which is contained in the sequence of the antisense strand denotes 8-oxo-2'-deoxyadenosinemonophosphate) was obtained by synthesis in the same manner as in Example 1 using a commercially available 8-oxo-dA-CE phosphoramidite.

Example 3

An siRNA having 5-bromo-2'-deoxyuridine monophosphate at the 5' end of the antisense strand shown in Table 27 (referred to as 874-5-Br-dU, X which is contained in the sequence of the antisense strand denotes 5-bromo-2'-deoxyuridinemonophosphate) was obtained by synthesis in the same manner as in Example 1 using a commercially available 5-Br-dU-CE phosphoramidite.

Example 4 siRNAs having 5-fluoro-2'-deoxyuridine monophosphate at the 5' end of the antisense strand shown in Table 27 (referred to as 454-5-F-dU and 1556-5-F-dU, X which is contained in the sequence of each of the antisense strands denotes 5-fluoro-2'-deoxyuridine monophosphate) were obtained by synthesis in the same manner as in Example 1 using a commercially available 5-F-dU-CE phosphoramidite.

MALDI-TOF/MS 454-5-F-dU (antisense strand): theoretical value: 6668.85 (M-H), actual value: 6673.35

1556-5-F-dU (antisense strand): theoretical value: 6669.03 (M-H), actual value: 6671.33

TABLE 27

|  | sense strand | | antisense strand | |
|---|---|---|---|---|
|  | sequence (5'→3') | SEQ ID NO | sequence (5'→3') | SEQ ID NO |
| 874-8-oxo-dA | UAGCUUCUUCGCUAAGAGUAC | 3 | XCUCUUAGCGAAGAAGCUAAA | 4 |
| 874-5-Br-dU | UAGCUUCUUCGCUAAGAGAAC | 23 | XCUCUUAGCGAAGAAGCUAAA | 4 |

TABLE 27-continued

| | sense strand | | antisense strand | |
|---|---|---|---|---|
| | sequence (5'→3') | SEQ ID NO | sequence (5'→3') | SEQ ID NO |
| 454-5-F-dU | GGAUAGCAAGACCGACUAACA | 25 | XUAGUCGGUCUUGCUAUCCAU | 26 |
| 1556-5-F-dU | GACGAGGUGCCUAAAGGAAUG | 27 | XUCCUUUAGGCACCUCGUCCA | 12 |

Test Example 3: RNAi Activity of Luciferase-Targeting siRNA

The RNAi activity of each of the luciferase-targeting siRNAs obtained in Example 4 (Table 27, having 5-F-dU at the position of X) was measured and evaluated in the same manner as in Test Example 2. Each of them was compared with an siRNA having a corresponding natural nucleotide at the 5' end of the antisense strand (Table 28).

In Table 29, the respective $IC_{50}$ values are shown.

TABLE 28

| | sense strand | | antisense strand | |
|---|---|---|---|---|
| | sequence (5'→3') | SEQ ID NO | sequence (5'→3') | SEQ ID NO |
| 454-U | GGAUAGCAAGACCGACUAACA | 25 | UUAGUCGGUCUUGCUAUCCAU | 28 |
| 1556-U | GACGAGGUGCCUAAAGGAAUG | 27 | UUCCUUUAGGCACCUCGUCCA | 29 |

TABLE 29

| | KD (Luc assay) $IC_{50}$ (pM) |
|---|---|
| 454-U | 85 |
| 454-5-F-dU | 49 |
| 1556-U | 300 |
| 1556-5-F-dU | 132 |

From the results of Test Example 3, it is found that the siRNAs having 5-fluoro-2'-deoxyuridine monophosphate at the 5' end of the antisense strand (454-5-F-dU and 1556-5-F-dU) show a higher knockdown activity against the expression of luciferase than the siRNAs having a corresponding natural nucleotide at the 5' end of the antisense strand, respectively.

Example 5

D-Glyceraldehyde-3-phosphate dehydrogenase (GAPDH)-targeting siRNAs having 8-oxo-2'-deoxyadenosine monophosphate at the 5' end of each of the antisense strands shown in Table 30 (X contained in the sequence of each of the antisense strands denotes 8-oxo-2'-deoxyadenosine monophosphate) were obtained by synthesis in the same manner as in Example 1.

TABLE 30

| | sense strand | | antisense strand | |
|---|---|---|---|---|
| | sequence (5'→3') | SEQ ID NO | sequence (5'→3') | SEQ ID NO |
| 217-BrdA | GCGCCUGGUCACCAGGGCUGC | 30 | XGCCCUGGUGACCAGGCGCCC | 31 |
| 278-BrdA | CCCUUCAUUGACCUCAACUAC | 32 | XGUUGAGGUCAAUGAAGGGGU | 33 |
| 516-BrdA | GAGCCAAAAGGGUCAUCAUCU | 34 | XUGAUGACCCUUUUGGCUCCC | 35 |
| 624-BrdA | CCUGCACCACCAACUGCUUAG | 36 | XAGCAGUUGGUGGUGCAGGAG | 37 |
| 715-BrdA | CACUGCCACCCAGAAGACUGU | 38 | XGUCUUCUGGGUGGCAGUGAU | 39 |
| 816-BrdA | AGGCUGUGGGCAAGGUCAUCC | 40 | XUGACCUUGCCCACAGCCUUG | 41 |
| 936-BrdA | AUGAUGACAUCAAGAAGGUGG | 42 | XCCUUCUUGAUGUCAUCAUAU | 43 |
| 1096-BrdA | CAAGCUCAUUUCCUGGUAUGA | 44 | XUACCAGGAAAUGAGCUUGAC | 45 |
| 1134-BrdA | GCAACAGGGUGGUGGACCUCA | 46 | XGGUCCACCACCCUGUUGCUG | 47 |

Test Example 4: RNAi Activity of D-Glyceraldehyde-3-Phosphate Dehydrogenase (GAPDH)-Targeting siRNA The RNAi activity of a GAPDH-targeting siRNA having 8-Br-dA at the 5' end of the antisense strand was evaluated by measuring an inhibitory effect on the expression of mRNA of GAPDH as described below. In a culture dish (Multidish 24 wells, Cat. No. 142475, manufactured by Nunc, Inc.), human cervical cancer-derived cell line Hela cells (CCL-2, purchased from ATCC) were suspended in RPMI medium (Invitrogen Life Technologies, 11875093) containing 10% fetal bovine serum, and 500 µL of the resulting cell suspension was inoculated into each well to give 50000 cells/well. Thereto, 100 µL of a solution of an siRNA-Lipofectamine RNAiMAX (Invitrogen Life Technologies, 13778-075) complex mixed in OPTI-MEM (Invitrogen Life Technologies, 31985-070) was added, whereby the siRNA was introduced into the Hela cells. The final concentration of the siRNA was set to one level: 100 pmol/L. Further, as a negative control group, cells to which only Lipofectamine RNAiMAX was added were inoculated.

The cells after introduction of the siRNA were cultured under the conditions of 37° C. and 5% CO$_2$ for 24 hours. In order to collect RNA, an RNA extraction kit (RNeasy 74106) of Qiagen, Inc. was used. The cells after culture were washed once with phosphate buffer, and then lysed with RLT buffer (attached to RNeasy) attached to the RNeasy kit and collected. Then, the total RNA was collected according to the instruction attached to the kit. By using the total RNA (1 µg) as a template, a reverse transcription reaction was performed using Transcriptor First Strand cDNA Synthesis Kit (Roche, 4897030001), whereby the cDNA was prepared. By using this cDNA as a template for a PCR reaction, a GADPH gene and, as a control, a pepytidyl-prolyl cis-trans isomerase B (PPIB) gene (GenBankAccession No. NM_000942) were subjected to a PCR reaction by the Taqman probe method using ABI 7900HT Fast (ABI), and the levels of amplified mRNAs of the respective genes were measured. Then, a semi-quantitative level of mRNA of GAPDH was calculated using the level of the amplified mRNA of PPIB as an internal control. In the measurement of GAPDH, Taqman probe Hs99999905 ml (Applied Biosystems, Inc. (ABI)) was used. In the measurement of PPIB, Hs01018502 ml (Applied Biosystems, Inc. (ABI)) was used.

Further, in the negative control group, the level of the mRNA of GAPDH and the level of the amplified mRNA of PPIB were measured in the same manner, respectively, and a semi-quantitative level of the mRNA of GAPDH was calculated using the level of the amplified mRNA of PPIB as an internal control.

The level of the target mRNA in the siRNA-introduced sample was represented as a relative ratio when the level of the mRNA of GAPDH in the siRNA-unintroduced group (negative control group) was taken as 1. Further, for comparison, a test was performed in the same manner also for siRNAs having adenosine monophosphate at a position corresponding to 8-Br-dA of each siRNA (Table 31).

The results of this test are shown in Table 32 and FIG. 3.

| | sense strand | | antisense strand | |
|---|---|---|---|---|
| | sequence (5'→3') | SEQ ID NO | sequence (5'→3') | SEQ ID NO |
| 217-A | GCGCCUGGUCACCAGGGCUGC | 30 | AGCCCUGGUGACCAGGCGCCC | 48 |
| 278-A | CCCUUCAUUGACCUCAACUAC | 32 | AGUUGAGGUCAAUGAAGGGGU | 49 |
| 516-A | GAGCCAAAAGGGUCAUCAUCU | 34 | AUGAUGACCCUUUUGGCUCCC | 50 |
| 624-A | CCUGCACCACCAACUGCUUAG | 36 | AAGCAGUUGGUGGUGCAGGAG | 51 |
| 715-A | CACUGCCACCCAGAAGACUGU | 38 | AGUCUUCUGGGUGGCAGUGAU | 52 |
| 816-A | AGGCUGUGGGCAAGGUCAUCC | 40 | AUGACCUUGCCCACAGCCUUG | 53 |
| 936-A | AUGAUGACAUCAAGAAGGUGG | 42 | ACCUUCUUGAUGUCAUCAUAU | 54 |
| 1096-A | CAAGCUCAUUUCCUGGUAUGA | 44 | AUACCAGGAAAUGAGCUUGAC | 55 |
| 1134-A | GCAACAGGGUGGUGGACCUCA | 46 | AGGUCCACCACCCUGUUGCUG | 56 |

TABLE 32

| siRNA | level of target mRNA |
|---|---|
| 217-BrdA | 0.743 |
| 217-A | 1.654 |
| 278-BrdA | 0.189 |
| 278-A | 0.361 |
| 516-BrdA | 0.246 |
| 516-A | 0.648 |
| 624-BrdA | 0.273 |
| 624-A | 0.798 |
| 715-BrdA | 0.627 |
| 715-A | 1.321 |
| 816-BrdA | 0.291 |
| 816-A | 0.464 |
| 936-BrdA | 0.217 |
| 936-A | 0.602 |
| 1096-BrdA | 0.027 |
| 1096-A | 0.241 |
| 1134-BrdA | 0.067 |
| 1134-A | 0.597 |

From the results of Test Example 4, it is found that the D-glyceraldehyde-3-phosphate dehydrogenase (GAPDH)-targeting siRNA having 8-Br-dA at the 5' end of the antisense strand shows a higher knockdown activity against the expression of GAPDH than the siRNA having a corresponding natural nucleotide at the 5' end of the antisense strand.

Example 6

It was synthesized using a D-glyceraldehyde-3-phosphate dehydrogenase (GAPDH)-targeting siRNA having 5-fluoro- 2'-deoxyuridine monophosphate at the 5' end of the antisense strand shown in Table 33 (X contained in the sequence of the antisense strand denotes 5-fluoro-2'-deoxyuridine monophosphate) in the same manner as in Example 1.
MALDI-TOF/MS
1096-5-F-dU (antisense strand): theoretical value: 6801.03 (M-H), actual value: 6797.74

TABLE 33

| | sense strand | | antisense strand | |
|---|---|---|---|---|
| | sequence (5'→3') | SEQ ID NO | sequence (5'→3') | SEQ ID NO |
| 1096-5-F-dU | CAAGCUCAUUUCCUGGUAAGA | 57 | XUACCAGGAAAUGAGCUUGAC | 55 |
| 1096-U | CAAGCUCAUUUCCUGGUAAGA | 57 | UUACCAGGAAAUGAGCUUGAC | 58 |
| 1096-A | CAAGCUCAUUUCCUGGUAUGA | 59 | AUACCAGGAAAUGAGCUUGAC | 60 |
| 1096-G | CAAGCUCAUUUCCUGGUACGA | 61 | GUACCAGGAAAUGAGCUUGAC | 62 |

Test Example 5: RNAi Activity of D-Glyceraldehyde-3-Phosphate Dehydrogenase (GAPDH)-Targeting siRNA The activity of the GAPDDH-targeting siRNA obtained in Example 6 was evaluated by measuring an inhibitory effect on the expression of mRNA of GAPDH in the same manner as in Test Example 4.

The level of the target mRNA in the siRNA-introduced sample was represented as a relative ratio when the level of mRNA of GAPDH in the siRNA-unintroduced group (negative control group) was taken as 1. The level of mRNA of GAPDH was calculated using the level of the amplified mRNA of hypoxanthine phosphoribosyltransferase 1 (HPRT1, GenBank Accession No. NM_000194) as an internal control. In the measurement of HPRT1, Taqman probe Hs99999909_m1 (Applied Biosystems, Inc. (ABI)) was used.

Further, for comparison, a test was performed in the same manner also for siRNAs having uracil monophosphate, adenosine monophosphate, or guanine monophosphate at the 5' end of the antisense of each siRNA (Table 33).

The results of this test are shown in Table 34.

TABLE 34

| siRNA | concentration (pM) | level of target mRNA | concentration (pM) | level of target mRNA |
|---|---|---|---|---|
| 1096-5-FU | 10 | 0.059 | 1 | 0.183 |
| 1096-A | 10 | 0.096 | 1 | 0.273 |
| 1096-U | 10 | 0.059 | 1 | 0.238 |
| 1096-G | 10 | 0.102 | 1 | 0.374 |

From the results of Test Example 5, it is found that the D-glyceraldehyde-3-phosphate dehydrogenase (GAPDH)-targeting siRNA having 5-fluoro-2'-deoxyuridine monophosphate at the 5' end of the antisense strand shows a higher knockdown activity against the expression of GAPDH than the siRNA having a corresponding natural nucleotide at the 5' end of the antisense strand.

Reference Example 1.0: Compound I-5

Step 1
Commercially available 6,7-dimethoxyquinazoline-2,4 (1H,3H)-dione (220 mg, 0.991 mmol) and 1-O-acetyl-2,3, 5-tri-O-benzoyl-β-D-ribofuranose (500 mg, 0.991 mmol) were dissolved in acetonitrile (5 mL), and N,O-bis(trimethylsilyl)acetamide (0.735 mL, 2.97 mmol) was added thereto, and the mixture was stirred at 60° C. for 20 minutes. After the reaction solution was cooled to room temperature, methanesulfonyl trimethylsilyl (0.627 mL, 3.47 mmol) was added thereto, and the mixture was stirred at 60° C. for 1 hour. After the reaction solution was cooled to room temperature, a saturated aqueous sodium bicarbonate solution was added thereto, and the mixture was extracted with ethyl acetate. The organic layer was washed with saturated brine, and then dried over sodium sulfate. The residue obtained by evaporating the solvent under reduced pressure was purified by column chromatography (heptane/ethyl acetate) to obtain (2R,3R,4R,5R)-2-((benzoyloxy)methyl)-5-(6,7-dimethoxy-2,4-dioxo-3,4-dihydroquinazolin-1(2H)-yl)tetrahydrofuran-3,4-diyl dibenzoate (599 mg, yield: 91%).

Step 2
(2R,3R,4R,5R)-2-((Benzoyloxy)methyl)-5-(6,7-dimethoxy-2,4-dioxo-3,4-dihydroquinazolin-1(2H)-yl)tetrahydrofuran-3,4-diyl dibenzoate (599 mg, 0.899 mmol) obtained in Step 1 was dissolved in methanol (9 mL), and a methylamine/methanol solution (4.58 mL, 44.9 mmol) was added thereto, and the mixture was stirred overnight at room temperature. To the residue obtained by evaporating the solvent under reduced pressure, diethyl ether was added, and the precipitate was collected by filtration to obtain 1-((2R, 3R,4S,5R)-3,4-dihydroxy-5-(hydroxymethyl)tetrahydrofuran-2-yl)-6,7-dimethoxyquinazoline-2,4(1H,3H)-dione (312 mg, yield: 98%). ESI-MS (m/z): 353 (M−1)

Step 3
1-((2R,3R,4S,5R)-3,4-Dihydroxy-5-(hydroxymethyl)tetrahydrofuran-2-yl)-6,7-dimethoxyquinazoline-2,4(1H,3H)-dione (310 mg, 0.875 mmol) obtained in Step 2 was suspended in acetone (15 mL), and 2,2-dimethoxypropane (0.536 mL, 4.37 mmol) and 4-toluenesulfonic acid monohydrate (183 mg, 0.962 mmol) were added thereto, and the mixture was stirred at room temperature for 2 hours. To the reaction solution was added a saturated aqueous sodium bicarbonate solution, and then, the solvent was evaporated under reduced pressure until the amount of the solvent was decreased to about half, and the resulting residue was purified by column chromatography (chloroform/methanol) to obtain 1-((3aR,4R,6R,6aR)-6-(hydroxymethyl)-2,2-dimethyltetrahydrofuro[3,4-d][1,3]dioxol-4-yl)-6,7-dimethoxyquinazoline-2,4(1H,3H)-dione (315 mg, yield: 91%).
ESI-MS (m/z): 395 (M+1)

Step 4
1-((3aR,4R,6R,6aR)-6-(Hydroxymethyl)-2,2-dimethyltetrahydrofuro[3,4-d][1,3]dioxol-4-yl)-6,7-dimethoxyquinazoline-2,4(1H,3H)-dione (310 mg, 0.786 mmol) obtained in Step 3 was dissolved in dichloromethane (8 mL), and 1H-tetrazole (138 mg, 1.97 mmol) and di-tert-butyl diisopropylphosphoramide (0.522 mL, 1.57 mmol) were added thereto, and the mixture was stirred at room temperature for 5 hours. The reaction solution was cooled to 0° C., and m-chloroperbenzoic acid (452 mg, 1.97 mmol) was added thereto, and the mixture was further stirred at 0° C. for 20 minutes. To the reaction solution was added a saturated aqueous sodium bicarbonate solution, and the mixture was extracted with chloroform and dried over sodium sulfate. The residue obtained by evaporating the solvent under reduced pressure was purified by column chromatography (heptane/ethyl acetate) to obtain di-tert-butyl((3aR,4R,6R,6aR)-6-(6,7-dimethoxy-2,4-dioxo-3,4-dihydroquinazolin-1(2H)-yl)-2,2-dimethyltetrahydrofuro[3,4-d][1,3]dioxol-4-yl)methyl phosphate (259 mg, yield: 56%).

ESI-MS (m/z): 587 (M+1)

Step 5

Di-tert-butyl((3aR,4R,6R,6aR)-6-(6,7-dimethoxy-2,4-dioxo-3,4-dihydroquinazolin-1(2H)-yl)-2,2-dimethyltetrahydrofuro[3,4-d][1,3]dioxol-4-yl)methyl phosphate (77.5 mg, 0.132 mmol) obtained in Step 4 was dissolved in trifluoroacetic acid/water (1:1) (2 mL), and the mixture was stirred at room temperature for 2 hours. After the solvent was evaporated under reduced pressure, acetic acid-triethylamine buffer (pH 6.5) (2 mL) was added thereto, and the solvent was evaporated again under reduced pressure. The resulting residue was dissolved in ethanol, and ethyl acetate was added thereto, and the precipitate was collected by filtration to obtain ((2R,3S,4R,5R)-5-(6,7-dimethoxy-2,4-dioxo-3,4-dihydroquinazolin-1(2H)-yl)-3,4-dihydroxytetrahydrofuran-2-yl)methyl phosphate (Compound I-5) triethylammonium salt (64.9 mg, yield: 92%).

$^1$H-NMR (D$_2$O, 300 MHz) δ: 7.43 (s, 1H), 6.91 (s, 1H), 6.08 (d, J=4.0 Hz, 1H), 4.77-4.58 (m, 1H), 4.38 (t, J=7.3 Hz, 1H), 4.04-4.02 (m, 3H), 3.90 (s, 3H), 3.81 (s, 3H), 3.08 (q, J=7.3 Hz, 6H), 1.16 (t, J=7.3 Hz, 9H).

ESI-MS (m/z): 435 (M+1)

Reference Example 1.1: Compound am-1

Step 1

1-((2R,3R,4S,5R)-3,4-Dihydroxy-5-(hydroxymethyl)tetrahydrofuran-2-yl)-6,7-dimethoxyquinazoline-2,4(1H,3H)-dione (812 mg, 2.29 mmol) obtained in Step 2 of Reference Example 1.0 was dissolved in DMF (10.0 mL), and to the mixture was added di-tert-butylsilyl bis(trifluoromethanesulfonate) (1.00 mL, 2.75 mmol) under ice cooling, and the mixture was stirred under ice cooling for 6 hours. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((4aR,6R,7R,7aS)-2,2-di-tert-butyl-7-hydroxytetrahydro-4H-furo[3, 2-d][1,3,2]dioxasilin-6-yl)-6,7-dimethoxyquinazoline-2,4(1H,3H)-dione (1.08 g, 95.0%).

ESI-MS (m/z): 493 (M−1)

Step 2

1-((4aR,6R,7R,7aS)-2,2-Di-tert-butyl-7-hydroxytetrahydro-4H-furo[3, 2-d][1,3,2]dioxasilin-6-yl)-6,7-dimethoxyquinazoline-2,4(1H,3H)-dione (1.73 mg, 3.50 mmol) obtained in Step 1 was dissolved in DMF (18.0 mL), and imidazole (1.19 g, 17.5 mmol) and tert-butyldimethylsilyl chloride (791 mg, 5.25 mmol) were added thereto, and the mixture was stirred at 60° C. for 3 hours. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6,7-dimethoxyquinazoline-2,4(1H,3H)-dione (1.95 g, 92.0%).

ESI-MS (m/z): 607 (M−1)

Step 3

1-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-6,7-dimethoxyquinazoline-2,4(1H,3H)-dione (500 mg, 0.821 mmol) obtained in Step 2 was dissolved in dichloromethane (8.00 mL), and pyridine (0.531 mL, 6.57 mmol) and hydrogen fluoride-pyridine (0.423 mL, 3.28 mmol) were added thereto under ice cooling, and the mixture was stirred under ice cooling for 1 hour. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((2R,3R,4R,5R)-3-((tert-butyldimethylsilyl)oxy)-4-hydroxy-5-(hydroxymethyl)tetrahydrofuran-2-yl)-6,7-dimethoxyquinazoline-2,4 (1H,3H)-dione (336 mg, 87.0%).

ESI-MS (m/z): 467 (M−1)

Step 4

1-((2R,3R,4R,5R)-3-((Tert-butyldimethylsilyl)oxy)-4-hydroxy-5-(hydroxymethyl)tetrahydrofuran-2-yl)-6,7-dimethoxyquinazoline-2,4 (1H,3H)-dione (85.0 mg, 0.181 mmol) obtained in Step 3 was dissolved in pyridine (2.00 mL), and p,p'-dimethoxytrityl chloride (184 mg, 0.544 mmol) and 4-dimethylaminopyridine (4.43 mg, 0.0360 mmol) were added thereto, and the mixture was stirred at room temperature for 1 hour. To the reaction mixture, a saturated aqueous sodium bicarbonate solution was added, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-6,7-dimethoxyquinazoline-2,4(1H,3H)-dione (138 mg, 99.0%).

ESI-MS (m/z): 769 (M−1)

Step 5

1-((2R,3R,4R,5R)-5-((Bis(4-methoxyphenyl)(phenyl)methoxy)methyl)-3-((tert-butyldimethylsilyl)oxy)-4-hydroxytetrahydrofuran-2-yl)-6,7-dimethoxyquinazoline-2,4 (1H,3H)-dione (74.0 mg, 0.0960 mmol) obtained in Step 4 was dissolved in THF (2.00 mL), and diisopropylamine (0.084 mL, 0.480 mmol) and 2-cyanoethyl chloro(diisopropylamino) phosphinite (0.043 mL, 0.192 mmol) were added thereto under ice cooling, and the mixture was stirred at room temperature for 3 hours. The solvent was evaporated under reduced pressure, and the residue was purified by aminosilica gel column chromatography (ethyl acetate/heptane), and then, further purified by silica gel column chromatography (ethyl acetate/heptane) to obtain (2R,3R,4R, 5R)-2-((bis(4-methoxyphenyl)(phenyl)methoxy)methyl)-4-((tert-butyldimethylsilyl)oxy)-5-(6,7-dimethoxy-2,4-dioxo-3,4-dihydroquinazolin-1(2H)-yl)tetrahydrofuran-3-yl (2-cyanoethyl)diisopropylphosphoramidite (Compound am-1, 63.0 mg, 67.6%).

$^1$H-NMR (CDCl$_3$, 300 MHz) δ: 7.94 (1H, br s), 7.55 (1H, s), 7.47-7.39 (2H, m), 7.38-7.12 (7H, m), 6.93 (1H, s), 6.81-6.70 (4H, m), 5.94-5.89 (1H, m), 5.18-5.08 (1H, m), 4.53-4.38 (1H, m), 4.37-4.26 (1H, m), 3.98-3.69 (12H, m), 3.67-3.48 (4H, m), 3.46-3.23 (2H, m), 2.68-2.52 (1H, m), 2.35-2.27 (1H, m), 1.20-1.00 (12H, m), 0.83, 0.81 (9H, 2s), 0.05, 0.03, −0.09, −0.10 (6H, 4 s).

ESI-MS (m/z): 971 (M+1)

Example 7

An siRNA having Compound I-5 as X at the 5' end of the antisense strand of 454-Xu shown in Table 38 below was synthesized in the same manner as in Example 1 using Compound am-1 obtained in Reference Example 1.1. MALDI-TOF/MS (antisense strand): theoretical value: 6776.96 (M-H), actual value: 6776.21

Reference Example 2.0: Compound I-6

((2R,3S,4R,5R)-5-(6-Chloro-2,4-dioxo-3,4-dihydroquinazolin-1(2H)-yl)-3,4-dihydroxytetrahydrofuran-2-yl)methyl phosphate (Compound I-6) was obtained in the same manner as in Reference Example 1.0 using commercially available 6-chloroquinazoline-2,4(1H,3H)-dione.

$^1$H-NMR (D$_2$O, 300 MHz) δ: 7.88 (d, J=1.8 Hz, 1H), 7.64 (dd, J=9.2, 2.6 Hz, 1H), 7.58 (d, J=9.2 Hz, 1H), 6.14 (d, J=5.5 Hz, 1H), 4.70-4.68 (m, 1H), 4.37 (t, J=5.9 Hz, 1H), 4.09-4.02 (m, 3H).

ESI-MS (m/z): 409 (M+1)

Reference Example 2.1: Compound am-2

(2R,3R,4R,5R)-2-((Bis(4-methoxyphenyl)(phenyl)methoxy)methyl)-4-((tert-butyldimethylsilyl)oxy)-5-(6-chloro-2,4-dioxo-3,4-dihydroquinazolin-1(2H)-yl)tetrahydrofuran-3-yl (2-cyanoethyl) diisopropylphosphoramidite (Compound am-2) is obtained in the same manner as in Reference Example 1.1 using commercially available 6-chloroquinazoline-2,4(1H,3H)-dione.

Example 8

An siRNA having Compound I-6 at the 5' end of the antisense strand is synthesized in the same manner as in Example 1 using Compound am-2 obtained in Reference Example 2.1.

Reference Example 3.0: Compound I-7

((2R,3S,4R,5R)-5-(7-Chloro-2,4-dioxo-3,4-dihydroquinazolin-1(2H)-yl)-3,4-dihydroxytetrahydrofuran-2-yl)methyl phosphate (Compound I-7) was obtained in the same manner as in Reference Example 1.0 using commercially available 7-chloroquinazoline-2,4(1H,3H)-dione.

$^1$H-NMR (D$_2$O, 300 MHz) δ: 7.95 (d, J=8.4 Hz, 1H), 7.61 (s, 1H), 7.30 (d, J=8.4 Hz, 1H), 5.99 (d, J=4.4 Hz, 1H), 4.79 (t, J=5.3 Hz, 1H), 4.38 (t, J=6.4 Hz, 1H), 4.04-3.92 (m, 3H).

ESI-MS (m/z): 409 (M+1)

Reference Example 3.1: Compound am-3

(2R,3R,4R,5R)-2-((Bis(4-methoxyphenyl)(phenyl)methoxy)methyl)-4-((tert-butyldimethylsilyl)oxy)-5-(7-chloro-2,4-dioxo-3,4-dihydroquinazolin-1(2H)-yl)tetrahydrofuran-3-yl (2-cyanoethyl) diisopropylphosphoramidite (Compound am-3) was obtained in the same manner as in Reference Example 1.1 using commercially available 7-chloroquinazoline-2,4(1H,3H)-dione.

$^1$H-NMR (CDCl$_3$, 500 MHz) δ: 8.11 (d, J=8.5 Hz, 1H), 7.67 (7.63) (d, J=1.7 Hz, 1H), 7.45-6.76 (m, 14H), 6.02 (m, 1H), 5.12 (5.07) (m, 1H), 4.45 (m, 1H), 4.32 (4.28) (m, 1H), 3.97-3.25 (m, 12H), 2.70-2.23 (m, 2H), 1.21-1.01 (m, 12H), 0.80 (0.82) (s, 9H), 0.03 (0.05) (s, 3H), −0.12 (s, 3H).

Example 9

An siRNA having Compound I-7 as X at the 5' end of the antisense strand of 454-Xu shown in Table 38 below was synthesized in the same manner as in Example 1 using Compound am-3 obtained in Reference Example 3.1. MALDI-TOF/MS (antisense strand): theoretical value: 6751.35 (M-H), actual value: 6751.83

Reference Example 4.0: Compound I-8

((2R,3S,4R,5R)-5-(5-Chloro-2,4-dioxo-3,4-dihydroquinazolin-1(2H)-yl)-3,4-dihydroxytetrahydrofuran-2-yl)methyl phosphate (Compound I-8) was obtained in the same manner as in Reference Example 1.0 using commercially available 5-chloroquinazoline-2,4(1H,3H)-dione.

$^1$H-NMR (D$_2$O, 300 MHz) δ: 7.66 (d, J=4.8 Hz, 2H), 7.40 (t, J=4.4 Hz, 1H), 6.21 (d, J=5.5 Hz, 1H), 4.80 (t, J=5.9 Hz, 1H), 4.45 (t, J=5.9 Hz, 1H), 4.09 (dd, J=14.5, 7.1 Hz, 3H).

ESI-MS (m/z): 409 (M+1)

Reference Example 4.1: Compound am-4

(2R,3R,4R,5R)-2-((Bis(4-methoxyphenyl)(phenyl)methoxy)methyl)-4-((tert-butyldimethylsilyl)oxy)-5-(5-chloro-2,4-dioxo-3,4-dihydroquinazolin-1(2H)-yl)tetrahydrofuran-3-yl (2-cyanoethyl) diisopropylphosphoramidite (Compound am-4) is obtained in the same manner as in Reference Example 1.1 using commercially available 5-chloroquinazoline-2,4(1H,3H)-dione.

Example 10

An siRNA having Compound I-8 at the 5' end of the antisense strand is synthesized in the same manner as in Example 1 using Compound am-4 obtained in Reference Example 4.1.

Reference Example 5.0: Compound I-9

(2R,3S,4R,5R)-5-(2,4-Dioxo-3,4-dihydrothieno[3,2-d]pyrimidin-1(2H)-yl)-3,4-dihydroxytetrahydrofuran-2-yl)methyl phosphate (Compound I-9) triethylammonium salt was obtained in the same manner as in Reference Example 1.0 using commercially available thieno[3,2-d]pyrimidine-2,4(1H,3H)-dione.

$^1$H-NMR (D$_2$O, 300 MHz) δ: 7.96 (d, J=5.5 Hz, 1H), 7.45 (d, J=4.8 Hz, 1H), 6.14 (d, J=6.2 Hz, 1H), 4.73-4.56 (m, 1H), 4.35 (t, J=5.7 Hz, 1H), 4.09 (brs, 1H), 4.02 (t, J=4.8 Hz, 2H), 3.07 (q, J=7.3 Hz, 6H), 1.15 (t, J=7.3 Hz, 9H).

ESI-MS (m/z): 381 (M+1)

Reference Example 5.1: Compound am-5

(2R,3R,4R,5R)-2-((Bis(4-methoxyphenyl)(phenyl)methoxy)methyl)-4-((tert-butyldimethylsilyl)oxy)-5-(2,4- dioxo-3,4-dihydrothieno [3,2-d]pyrimidin-1(2H)-yl)tetrahydrofuran-3-yl (2-cyanoethyl) diisopropylphosphoramidite (Compound am-5) is obtained in the same manner as in Reference Example 1.1 using commercially available thieno [3,2-d]pyrimidine-2,4(1H,3H)-dione.

Example 11

An siRNA having Compound I-9 at the 5' end of the antisense strand is synthesized in the same manner as in Example 1 using Compound am-5 obtained in Reference Example 5.1.

Reference Example 6.0: Compound I-10

Step 1

(2R,3R,4S,5R)-2-(6-Chloro-9H-purin-9-yl)-5-(hydroxymethyl)tetrahydrofuran-3,4-diol (5.47 g, yield: 72%) was obtained according to the process described in the known method [Journal of Organic Chemistry (J. Org. Chem.), 2002, vol. 67, pp. 6788-6796] using (2R,3R,4R,5R)-2-(acetoxymethyl)-5-(6-chloro-9H-purin-9-yl)tetrahydrofuran-3,4-diyl diacetate (10.9 g, 26.4 mmol) synthesized by the method described in the known method [Journal of Medicinal Chemistry (J. Med. Chem.), 2012, vol. 55, pp. 1478-1489].

(2R,3R,4S,5R)-2-(6-Chloro-9H-purin-9-yl)-5-(hydroxymethyl)tetrahydrofuran-3,4-diol (5.48 g, 19.1 mmol) was suspended in acetone (200 mL), and 2,2-dimethoxypropane (11.7 mL, 95.5 mmol) and 4-toluenesulfonic acid monohydrate (9.09 g, 47.8 mmol) were added thereto, and the mixture was stirred at room temperature for 2 hours. To the reaction solution was added a saturated aqueous sodium bicarbonate solution, and the solvent was evaporated under reduced pressure until the amount of the solvent was decreased to about half. Chloroform was added thereto, and the mixture was extracted with chloroform and dried over sodium sulfate. Then, the residue obtained by evaporating the solvent under reduced pressure was purified by silica gel column chromatography (heptane/ethyl acetate) to obtain ((3aR,4R,6R,6aR)-6-(6-chloro-9H-purin-9-yl)-2,2-dimethyltetrahydrofuro[3,4-d][1,3]dioxol-4-yl)methanol (5.17 g, yield: 83%).

ESI-MS (m/z): 327 (M+1)

Step 2

1,4-Dioxane (2 mL) and water (one drop) were added to ((3aR,4R,6R,6aR)-6-(6-chloro-9H-purin-9-yl)-2,2-dimethyltetrahydrofuro[3,4-d][1,3]dioxol-4-yl)methanol (150 mg, 0.459 mmol) obtained in Step 1, (E)-styrylboronic acid (136 mg, 0.918 mmol), 1,1'-bis(diphenylphosphino)ferrocene-palladium(II) dichloride-dichloromethane complex (37.5 mg, 0.031 mmol), and cesium carbonate (449 mg, 1.38 mmol), and the mixture was stirred at 80° C. for 3 hours under a nitrogen atmosphere. After the reaction solution was cooled to room temperature, saturated brine was added thereto, and the mixture was extracted with ethyl acetate and dried over sodium sulfate. The residue obtained by evaporating the solvent under reduced pressure was purified by column chromatography (heptane/ethyl acetate) to obtain ((3aR,4R,6R,6aR)-2,2-dimethyl-6-(6-((E)-styryl)-9H-purin-9-yl)tetrahydrofuro[3,4-d][1,3]dioxol-4-yl)methanol (90.1 mg, yield: 50%).

ESI-MS (m/z): 395 (M+1)

Step 3

((3aR,4R,6R,6aR)-2,2-Dimethyl-6-(6-styryl-9H-purin-9-yl)tetrahydrofuro[3,4-d][1,3]dioxol-4-yl)methanol (90 mg, 0.228 mmol) obtained in Step 2 was dissolved in dichloromethane (2 mL), and 1H-tetrazole (32.0 mg, 0.456 mmol) and di-tert-butyl diisopropylphosphoramide (0.144 mL, 0.456 mmol) were added thereto, and the resulting solution was stirred at 0° C. for 2 hours. To the reaction solution, m-chloroperbenzoic acid (141 mg, 0.612 mmol) was added, and the mixture was stirred at 0° C. for 15 minutes. To the reaction solution were added a saturated aqueous sodium bicarbonate solution and saturated brine, and the mixture was extracted with chloroform and dried over magnesium sulfate. A residue obtained by evaporating the solvent under reduced pressure was purified by column chromatography (heptane/ethyl acetate) to obtain di-tert-butyl ((3aR,4R,6R,6aR)-2,2-dimethyl-6-(6-styryl-9H-purin-9-yl)tetrahydrofuro[3,4-d][1,3]dioxol-4-yl)methyl phosphate (E/Z geometric isomer mixture, 73.2 mg, yield: 55%).

ESI-MS (m/z): 587 (M+1)

Step 4

Di-tert-butyl ((3aR,4R,6R,6aR)-2,2-dimethyl-6-(6-styryl-9H-purin-9-yl)tetrahydrofuro[3,4-d][1,3]dioxol-4-yl)methyl phosphate (73.0 mg, 0.124 mmol) obtained in Step 3 was dissolved in trifluoroacetic acid/water (1:1) (2 mL), and the mixture was stirred at room temperature for 2 hours. To the residue obtained by evaporating the solvent under reduced pressure was added acetic acid-ammonium acetate buffer (pH 5.7), and then, the residue was purified by preparative HPLC (eluent: a 0.01 mmol/L aqueous ammonium acetate solution/methanol) to give the roughly purified product. To the roughly purified product, 2-propanol was added, and the precipitate was collected by filtration to obtain ((2R,3S,4R,5R)-3,4-dihydroxy-5-(6-((E)-styryl)-9H-purin-9-yl)tetrahydrofuran-2-yl)methyl phosphate (Compound I-10, 21.3 mg, yield: 390).

$^1$H-NMR (D$_2$O, 300 MHz) δ: 8.50 (s, 1H), 8.42 (s, 1H), 7.58 (d, J=15.6 Hz, 1H), 7.19-7.13 (m, 2H), 7.08-6.97 (m, 4H), 5.92 (d, J=4.9 Hz, 1H), 4.60-4.55 (m, 1H), 4.38-4.34 (m, 1H), 4.28-4.23 (m, 1H), 4.10-3.97 (m, 2H).

ESI-MS (m/z): 435 (M+1)

Reference Example 6.1: Compound am-6

Steps 1 to 2

6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine was obtained in the same manner as in Steps 1 to 2 of Reference Example 1.1 using commercial (2R,3R,4S,5R)-2-(6-chloro-9H-purin-9-yl)-5-(hydroxymethyl)tetrahydrofuran-3,4-diol.

Step 3

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-((E)-styryl)-9H-purine was obtained in the same manner as in Step 2 of Reference Example 6.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2.

Steps 4 to 6

(2R,3R,4R,5R)-2-((bis(4-methoxyphenyl)(phenyl)methoxy)methyl)-4-(tert-butyldimethylsilyloxy)-5-(6-((E)-styryl)-9H-purin-9-yl)tetrahydrofuran-3-yl 2-cyanoethyl diisopropylphosphoramidite (Compound am-6) was obtained in the same manner as in Steps 3 to 5 of Reference Example 1.1 using 9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-((E)-styryl)-9H-purine obtained in Step 3.

$^1$H-NMR (CDCl$_3$, 400 MHz) δ: 8.81, 8.79 (1H, 2s), 8.43-8.35 (1H, m), 8.33, 8.29 (1H, 2s), 7.77-7.69 (3H, m), 7.53-7.32 (9H, m), 7.31-7.18 (3H, m), 6.85-6.78 (4H, m), 6.15-6.05 (1H, m), 5.15-5.08 (1H, m), 4.48-4.35 (2H, m), 4.03-3.84 (1H, m), 3.77 (6H, s), 3.70-3.53 (4H, m), 3.38-3.29 (1H, m), 2.72-2.59 (1H, m), 2.37-2.24 (1H, m), 1.23-1.03 (12H, m), 0.76, 0.75 (9H, 2s), −0.02, −0.05, −0.21, −0.21 (6H, 4 s).

Example 12

A luciferase-targeting siRNA having Compound I-10 as X at the 5' end of the antisense strand of 454-Xa shown in Table 38 below was synthesized on a scale of 0.2 μmol using a nucleic acid synthesizer (NS-8, GeneDesign, Inc.). U-RNA-CPG (Glen Research Corporation) was used as a solid-phase support. Each of DMT-2'-O-TBDMS-rA(Pac) amidite (Glen Research Corporation), DMT-2'-O-TBDMS-rG(iPr-Pac) amidite (Glen Research Corporation), DMT-2'-O-TBDMS-rC(ac) amidite (Glen Research Corporation) and DMT-2'-O-TBDMS-rU amidite (Glen Research Corporation) was prepared into an 0.1 mol/L acetonitrile solution, 6-styryl-P phosphoramidite was prepared into an 0.1 mol/L acetonitrile solution, Chemical Phosphorylation Reagent II (Glen Research Corporation) was prepared into an 0.1 mol/L acetonitrile solution, and these were used for a condensation reaction. Using Activator 42 (SAFC-PROLIGO) as a phosphoramidite activator, condensation was performed for 16 minutes under light-shielded conditions. After synthesis in trityl-off mode, this was immersed in a 28% ammonia solution, and allowed to stand at 55° C. for 4 hours. The reaction mixture was concentrated under reduced pressure, 31% triethylamine trihydrofluoride was added thereto, and the resulting mixture was allowed to stand at 65° C. for 2 hours, after which an eluent obtained with NAP-10 (GE Healthcare Sciences (GE) Company) was purified by reverse-phase liquid chromatography (Waters, XBridge C18, 4.6 mm×250 mm, gradient by A solution: 100 mM triethyl amine/acetic acid buffer, and B solution: acetonitrile) to obtain a target oligonucleotide. The structure of the oligonucleotide was determined by polyvalent ion analysis (deconvolution) with LC-MS(ESI-MS).

The resulting single-stranded oligonucleotide was dissolved in a mixed buffer [10 mM Tris, 50 mM sodium chloride, and 1 mM ethylenediamine tetraacetic acid] to give a nucleic acid concentration of 20 μmol/L. Equal amounts of sense and antisense strands were mixed together, and allowed to stand at 80° C. for 10 minutes. The temperature of the mixture was gradually decreased, and the mixture was allowed to stand at 37° C. for 1 hour to obtain a double-stranded oligonucleotide.

ESI-MS (antisense strand): theoretical value: 6777.01, actual value: 6777.19

Reference Example 7.0: Compound I-11

Step 1

(2R,3R,4R,5R)-2-(Acetoxymethyl)-5-(6-chloro-9H-purin-9-yl)tetrahydrofuran-3,4-diyl diacetate (2.00 g, 4.85 mmol) synthesized by the method described in the known method [Journal of Medicinal Chemistry (J. Med. Chem.), 2012, vol. 55, pp. 1478-1489] was dissolved in THF (15 mL), and dimethylamine hydrochloride (1.19 g, 14.5 mmol) and triethylamine (2.70 mL, 19.38 mL) were added thereto, and the mixture was stirred overnight at 60° C. in a sealed tube. To the reaction solution, dimethylamine hydrochloride (1.19 g, 14.5 mmol) and triethylamine (2.70 mL, 19.38 mL) were added, and the mixture was further stirred overnight at 60° C. To the mixture, water was added, and the mixture was extracted with chloroform and concentrated under reduced pressure to obtain (2R,3R,4R,5R)-2-(acetoxymethyl)-5-(6-(dimethylamino)-9H-purin-9-yl)tetrahydrofuran-3,4-diyl diacetate (2.2 g, yield: 108%).

ESI-MS (m/z): 422 (M+1)

Step 2

A 7.0 mol/L ammonia/methanol solution (33.9 mL) was added to (2R,3R,4R,5R)-2-(acetoxymethyl)-5-(6-(dimethylamino)-9H-purin-9-yl)tetrahydrofuran-3,4-diyl diacetate (2.00 g, 4.75 mmol) obtained in Step 1, and the mixture was stirred overnight at room temperature. To the residue obtained by evaporating the solvent under reduced pressure was added an ether/ethyl acetate mixed solution, and the insoluble material was collected by filtration to obtain (2R,3R,4S,5R)-2-(6-(dimethylamino)-9H-purin-9-yl)-5-(hydroxymethyl)tetrahydrofuran-3,4-diol (1.2 g, yield: 86%).

ESI-MS (m/z): 296 (M+1)

Step 3

(2R,3R,4S,5R)-2-(6-(Dimethylamino)-9H-purin-9-yl)-5-(hydroxymethyl)tetrahydrofuran-3,4-diol (1.2 g, 4.06 mmol) obtained in Step 2 was suspended in 0.5 M acetic acid-sodium acetate buffer (pH 4.0) (40 mL), and bromine water (55.8 mL) was added thereto, and the mixture was stirred at room temperature for 4 hours. To the reaction solution, sodium hydrogen sulfate was added until the color of bromine disappeared, and then, the mixture was neutralized with sodium carbonate. The solvent was evaporated under reduced pressure until the amount of the solvent was decreased to about half, and the insoluble material was collected by filtration, washed with water and acetone in order, and then dried under reduced pressure to obtain (2R,3R,4S,5R)-2-(8-bromo-6-(dimethylamino)-9H-purin-9-yl)-5-(hydroxymethyl)tetrahydrofuran-3,4-diol (1.09 g, yield: 72%).

ESI-MS (m/z): 374 (M+1)

Step 4

(2R,3R,4S,5R)-2-(8-Bromo-6-(dimethylamino)-9H-purin-9-yl)-5-(hydroxymethyl)tetrahydrofuran-3,4-diol (2.90 g, 7.75 mmol) obtained in Step 3 was suspended in acetone (39 mL), and 2,2-dimethoxypropane (4.75 mL, 38.8 mmol) and 4-toluenesulfonic acid monohydrate (1.62 g, 38.8 mmol) were added thereto, and the mixture was stirred overnight at room temperature. To the reaction solution were added a saturated aqueous sodium bicarbonate solution and saturated brine, and then, the solvent was evaporated under reduced pressure until the amount of the solvent was decreased to about half. Chloroform was added thereto, and the mixture was extracted with chloroform and dried over sodium sulfate. Thereafter, the mixture was extracted with chloroform and dried over sodium sulfate. The solvent was evaporated under reduced pressure to obtain ((3aR,4R,6R,6aR)-6-(8-bromo-6-(dimethylamino)-9H-purin-9-yl)-2,2-dimethyltetrahydrofuro[3,4-d][1,3]dioxol-4-yl)methanol (1.96 g, yield: 61%) was obtained.

ESI-MS (m/z): 414 (M+1)

Step 5

((3aR,4R,6R,6aR)-6-(8-Bromo-6-(dimethylamino)-9H-purin-9-yl)-2,2-dimethyltetrahydrofuro[3,4-d][1,3]dioxol-4-yl)methanol (200 mg, 0.483 mmol) obtained in Step 4 was dissolved in dichloromethane (2 mL), and 1H-tetrazole (84.6 mg, 1.21 mmol) and di-tert-butyl diisopropylphosphoramidite (0.321 mL, 0.966 mmol) were added thereto, and the mixture was stirred at room temperature for 0.5 hours. The reaction solution was cooled to 0° C., and m-chloroperbenzoic acid (222 mg, 0.966 mmol) was added thereto, and the mixture was further stirred at 0° C. for 15 minutes. To the reaction solution were added a saturated aqueous sodium bicarbonate solution and saturated brine, and the mixture was extracted with chloroform and dried over sodium sulfate. The residue obtained by evaporating the solvent under reduced pressure was purified by column chromatography (heptane/ethyl acetate) to obtain di-tert-butyl ((3aR,4R,6R,6aR)-6-(8-bromo-6-(dimethylamino)-9H-purin-9-yl)-2,2-di methyltetrahydrofuro[3,4-d][1,3]dioxol-4-yl)methyl phosphate (209 mg, yield: 71%).

ESI-MS (m/z): 606 (M+1)

Step 6

Di-tert-butyl ((3aR,4R,6R,6aR)-6-(8-bromo-6-(dimethylamino)-9H-purin-9-yl)-2,2-di methyltetrahydrofuro[3,4-d][1,3]dioxol-4-yl)methyl phosphate (50.0 mg, 0.082 mol)) obtained in Step 5 was dissolved in trifluoroacetic acid/water (1:1) (2 mL), and the mixture was stirred at room temperature for 3 hours. To the residue obtained by evaporating the solvent under reduced pressure, acetic acid-ammonium acetate buffer (pH 5.7) was added, and then, the residue was purified by preparative HPLC (eluent: a 0.01 mmol/L aqueous ammonium acetate solution/methanol) to obtain the roughly purified product. To the roughly purified product, ethanol was added, and the precipitate was collected by filtration to obtain ((2R,3S,4R,5R)-6-(8-bromo-6-(dimethylamino)-9H-purin-9-yl)-3,4-dihydroxytetrahydrofuran-2-yl)methyl phosphate (Compound I-11, 26.2 mg, yield: 70%).

$^1$H-NMR (D$_2$O, 300 MHz) δ: 8.06-7.92 (m, 1H), 5.98-5.93 (m, 1H), 5.15-5.07 (m, 1H), 4.43 (dd, J=5.9, 5.9 Hz, 1H), 4.09 (dd, J=9.8, 4.9 Hz, 1H), 3.99-3.91 (m, 1H), 3.90-3.82 (m, 1H), 3.30-3.12 (m, 6H).

ESI-MS (m/z): 454 (M+1)

Reference Example 7.1: Compound am-7

(2R,3R,4R,5R)-2-((Bis(4-methoxyphenyl)(phenyl)methoxy)methyl)-5-(8-bromo-6-(dimethylamino)-9H-purin-9-yl-4-((tert-butyldimethylsilyl)oxy)tetrahydrofuran-3-yl (2-cyanoethyl) diisopropylphosphoramidite (Compound am-7) is obtained in the same manner as in Reference Example 1.1 using (2R,3R,4S,5R)-2-(8-bromo-6-(dimethylamino)-9H-purin-9-yl)-5-(hydroxymethyl)tetrahydrofuran-3,4-diol obtained in Step 3 of Reference Example 7.0.

Example 13

An siRNA having Compound I-11 at the 5' end of the antisense strand is synthesized in the same manner as in Example 1 using Compound am-7 obtained in Reference Example 7.1.

Reference Example 8.0: Compound I-12

Step 1

Di-tert-butyl ((3aR,4R,6R,6aR)-6-(8-bromo-6-(dimethylamino)-9H-purin-9-yl)-2,2-di methyltetrahydrofuro[3,4-d][1,3]dioxol-4-yl)methyl phosphate (100 mg, 0.165 mmol) obtained in Step 5 of Reference Example 7.0 was dissolved in DMF (1.5 mL), and tetraethylammonium cyanide (129 mg, 0.824 mmol) was added thereto, and the mixture was stirred at 100° C. for 2 hours. After the reaction solution was cooled to room temperature, saturated brine was added thereto, and the mixture was extracted with ethyl acetate and dried over sodium sulfate. The residue obtained by evaporating the solvent under reduced pressure was purified by column chromatography (heptane/ethyl acetate) to obtain di-tert-butyl ((3aR,4R,6R,6aR)-6-(8-cyano-6-(dimethylamino)-9H-purin-9-yl)-2,2-di methyltetrahydrofuro[3,4-d][1,3]dioxol-4-yl)methyl phosphate (52.6 mg, 58%).

ESI-MS (m/z): 558 (M+1)

Step 2

Di-tert-butyl ((3aR,4R,6R,6aR)-6-(8-cyano-6-(dimethylamino)-9H-purin-9-yl)-2,2-di methyltetrahydrofuro[3,4-d][1,3]dioxol-4-yl)methyl phosphate (80.0 mg, 0.145 mmol) obtained in Step 2 was dissolved in trifluoroacetic acid/water (1:1) (4 mL), and the mixture was stirred at room temperature for 3 hours. The residue obtained by evaporating the solvent under reduced pressure was purified by preparative HPLC (eluent: a 0.01 mmol/L aqueous trifluoroacetic acid solution/acetonitrile) to obtain the roughly purified product. To the roughly purified product, ethanol was added, and the precipitate was collected by filtration to obtain ((2R,3S,4R,5R)-6-(8-cyano-6-(dimethylamino)-9H-purin-9-yl)-3,4-dihydroxytetrahydrofuran-2-yl)methyl phosphate (Compound I-12, 8.4 mg, yield: 15%).

$^1$H-NMR (D$_2$O, 300 MHz) δ: 8.05 (s, 1H), 5.97 (d, J=5.9 Hz, 1H), 4.95-4.53 (m, 1H), 4.37-4.29 (m, 1H), 4.24-4.15 (m, 1H), 4.06-3.93 (m, 2H), 3.66-2.83 (m, 6H).

ESI-MS (m/z): 401 (M+1)

Reference Example 8.1: Compound am-8

Steps 1 to 2

8-Bromo-9-((4aR,6R,7R,7aR)-2,2-di-tert-butyl-7-(tert-butyldimethylsilyloxy)tetrahydro-4H-furo[3,2-d][1,3,2]dioxasilin-6-yl)-N,N-dimeth yl-9H-purin-6-amine was obtained in the same manner as in Steps 1 to of Reference Example 1.1 using (2R,3R,4S,5R)-2-(8-bromo-6-(dimethylamino)-9H-purin-9-yl)-5-(hydroxymethyl)tetrahydrofuran-3,4-diol obtained in Step 3 of Reference Example 7.0.

ESI-MS (m/z): 628 (M+1)

Step 3

8-Bromo-9-((4aR,6R,7R,7aR)-2,2-di-tert-butyl-7-(tert-butyldimethylsilyloxy)tetrahydro-4H-furo[3,2-d][1,3,2]dioxasilin-6-yl)-N,N-dimethyl-9H-purin-6-amine (10.0 mg, 0.0160 mmol) obtained in Step 2 was dissolved in DMF (1.00 mL), and sodium cyanide (7.79 mg, 0.159 mmol) and cesium fluoride (7.25 mg, 0.0480 mmol) were added thereto, and the mixture was stirred at 100° C. for 4 hours. To the reaction solution, a saturated aqueous sodium bicarbonate solution was added, and the mixture was extracted with ethyl acetate and dried over sodium sulfate. The residue obtained by evaporating the solvent under reduced pressure was purified by column chromatography (heptane/ethyl acetate) to obtain 9-((4aR,6R,7R,7aR)-2,2-di-tert-butyl-7-((tert-butyldimethylsilyl)ox y)tetrahydro-4H-furo[3,2-d][1,3,2]dioxasilin-6-yl)-6-(dimethylamino)-9H-purin-8-carbonitrile (8.00 mg, yield: 44.8%) was obtained.

ESI-MS (m/z): 575 (M+1)

Steps 4 to 6

(2R,3R,4R,5R)-2-((Bis(4-methoxyphenyl)(phenyl)methoxy)methyl)-4-((tert-butyldimethylsilyl)oxy)-5-(8-cyano-6-(dimethylamino)-9H-purin-9-yl)tetrahydrofuran-3-yl (2-cyanoethyl) diisopropylphosphoramidite (Compound am-8) was obtained in the same manner as in Steps 3 to 5 of Reference Example 1.1 using 9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-(dimethylamino)-9H-purin-8-carbonitrile obtained in Step 3.

$^1$H-NMR (CDCl$_3$, 500 MHz) δ: 8.15-8.12 (1H, m), 7.47-7.46 (2H, m), 7.36-7.34 (4H, m), 7.23-7.20 (3H, m), 6.79-6.77 (4H, m), 6.02-6.00 (1H, m), 5.52-5.37 (1H, m), 4.44-4.40 (2H, m), 4.01-3.30 (19H, m), 3.78-3.77 (7H, m), 2.58-2.42 (2H, m), 1.20-1.14 (13H, m), 0.77-0.73 (9H, m), −0.10 (−0.07) (3H, s), −0.31 (−0.28) (3H, s).

Example 14

An siRNA having Compound I-12 as X of 5' end of the antisense of 454-Xa shown in Table 38 below strand was synthesized in the same manner as in Example 1 using Compound am-8 obtained in Reference Example 8.1. ESI-MS (antisense strand): theoretical value: 6742.95, actual value: 6742.18

Reference Example 9.0: Compound I-13

((2R,3S,4R,5R)-5-(6-Iodo-2,4-dioxo-3,4-dihydropyrimidin-1(2H)-yl)-3,4-dihydroxytetrahydrofuran-2-yl)methyl phosphate triethylamine (Compound I-13) was obtained in the same manner as in Steps 3 to 5 of Reference Example 1.0 using commercially available 1-((2R,3R,4S,5R)-3,4-dihydroxy-5-(hydroxymethyl)tetrahydrofuran-2-yl)-6-iodopyrimidine-2,4(1H,3H)-dione (866 mg, 2.34 mmol).

$^1$H-NMR (D$_2$O, 300 MHz) δ: 6.52 (s, 1H), 5.92 (d, J=3.3 Hz, 1H), 4.69-4.60 (m, 1H), 4.33 (t, J=6.8 Hz, 1H), 4.02-3.86 (m, 3H), 3.07 (q, J=7.3 Hz, 6H), 1.15 (t, J=7.3 Hz, 9H).

ESI-MS (m/z): 451 (M+1)

Reference Example 9.1: Compound am-9

(2R,3R,4R,5R)-2-((Bis(4-methoxyphenyl)(phenyl)methoxy)methyl)-4-((tert-butyldimethylsilyl)oxy)-5-(6-iodo-2,4-dioxo-3,4-dihydropyrimidin-1(2H)-yl)tetrahydrofuran-3-yl (2-cyanoethyl) diisopropylphosphoramidite (Compound am-9) is obtained in the same manner as in Reference Example 1.1 using commercially available 1-((2R,3R,4S,5R)-3,4-dihydroxy-5-(hydroxymethyl)tetrahydrofuran-2-yl)-6-iodopyrimidine-2,4(1H,3H)-dione.

Example 15

An siRNA having Compound I-13 at the 5' end of the antisense strand is synthesized in the same manner as in Example 1 using Compound am-9 obtained in Reference Example 9.1.

Reference Example 10.0: Compound I-14

Step 1
5-Bromo-1-((3aR,4R,6R,6aR)-6-(hydroxymethyl)-2,2-dimethyltetrahydrofuro[3,4-d][1,3]dioxol-4-yl)pyrimidine-2,4(1H,3H)-dione (2.58 g, yield: 69%) was obtained in the same manner as in Step 3 of Reference Example 1.0 using commercially available 5-bromo-1-((2R,3R,4S,5R)-3,4-dihydroxy-5-(hydroxymethyl)tetrahydrofuran-2-yl)pyrimidine-2,4(1H,3H)-dione (3.34 g, 10.3 mmol).

ESI-MS (m/z): 363 (M+1)
Step 2
5-Bromo-1-((3aR,4R,6R,6aR)-6-(hydroxymethyl)-2,2-dimethyltetrahydrofuro[3,4-d][1,3]dioxol-4-yl)pyrimidine-2,4(1H,3H)-dione (200 mg, 0.551 mmol) obtained in Step 1 and tetrakis(triphenylphosphine)palladium (63.6 mg, 0.055 mmol) were dissolved in 1,4-dioxane, and tributyl(2-pyridyl)tin (0.62 mL, 1.93 mmol) was added thereto, and the mixture was stirred overnight at 110° C. After the reaction mixture was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue obtained was purified by column chromatography (chloroform/methanol) to obtain 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H,3H)-dione (45.2 mg, yield: 23%).

ESI-MS (m/z): 362 (M+1)
Steps 3 to 4
((2R,3S,4R,5R)-5-(2,4-Dioxo-5-(pyridin-2-yl)-3,4-dihydropyrimidin-1(2H)-yl)-3,4-dihydroxytetrahydrofuran-2-yl)methyl phosphate (Compound I-14) was obtained in the same manner as in Steps 4 to 5 of Reference Example 1.0 using 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H,3H)-dione obtained in Step 2.

$^1$H-NMR (D$_2$O, 300 MHz) δ: 8.66 (s, 1H), 8.56 (d, J=5.5 Hz, 1H), 8.40 (t, J=7.9 Hz, 1H), 8.20 (d, J=8.4 Hz, 1H), 7.77 (t, J=6.8 Hz, 1H), 5.92 (d, J=4.0 Hz, 1H), 4.35 (t, J=4.2 Hz, 1H), 4.27-4.26 (m, 2H), 4.15 (dd, J=12.1, 2.6 Hz, 1H), 4.04 (dd, J=13.0, 5.7 Hz, 1H).

ESI-MS (m/z): 402 (M+1)

Reference Example 10.1: Compound am-10

Step 1
1-((2R,3R,4S,5R)-3,4-Dihydroxy-5-(hydroxymethyl)tetrahydrofuran-2-yl)-5-(pyridin-2-yl)pyrimidine-2,4 (1H,3H)-dione is obtained in the same manner as in Step 1 of Reference Example 6.1 using 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H,3H)-dione obtained in Step 2 of Reference Example 10.0.

Step 2
(2R,3R,4R,5R)-2-((Bis(4-methoxyphenyl)(phenyl)methoxy)methyl)-4-((tert-butyldimethylsilyl)oxy)-5-(2,4-dioxo-5-(pyridin-2-yl)-3,4-dihydropyrimidin-1(2H)-yl)tetrahydrofuran-3-yl (2-cyanoethyl) diisopropylphosphoramidite (Compound am-10) is obtained in the same manner as in Reference Example 1.1 using 1-((2R,3R,4S,5R)-3,4-dihydroxy-5-(hydroxymethyl)tetrahydrofuran-2-yl)-5-(pyridin-2-yl)pyrimidine-2,4(1H,3H)-dione.

Example 16

An siRNA having Compound I-14 at the 5' end of the antisense strand is synthesized in the same manner as in Example 1 using Compound am-10 obtained in Reference Example 10.1.

Reference Example 11.0: Compound I-15

((2R,3S,4R,5R)-3,4-Dihydroxy-5-(5-(oxazol-2-yl)-2,4-dioxo-3,4-dihydropyrimidin-1(2H)-yl)tetrahydrofuran-2-yl) methyl phosphate (Compound I-15) was obtained in the same manner as in Steps 2 to 4 of Reference Example 10.0 using 2-(tri-n-butylstannyl)oxazole.

$^1$H-NMR (D$_2$O, 300 MHz) δ: 8.52 (s, 1H), 7.84 (s, 1H), 7.19 (s, 1H), 5.93 (d, J=4.9 Hz, 1H), 4.36 (t, J=4.9 Hz, 1H), 4.28-4.24 (m, 2H), 4.11 (dq, J=11.7, 2.0 Hz, 1H), 4.03 (dq, J=11.7, 2.6 Hz, 1H).

ESI-MS (m/z): 392 (M+1)

Reference Example 11.1: Compound am-11

(2R,3R,4R,5R)-2-((Bis(4-methoxyphenyl)(phenyl)methoxy)methyl)-4-((tert-butyldimethylsilyl)oxy)-5-(5-(oxazol-2-yl)-2,4-dioxo-3,4-dihydropyrimidin-1(2H)-yl)tetrahydrofuran-3-yl (2-cyanoethyl) diisopropylphosphoramidite (Compound am-11) is obtained in the same manner as in Reference Example 10.1 using 1-((3aR,4R,6R,6aR)-6-(hydroxymethyl)-2,2-dimethyltetrahydrofuro[3,4-d][1,3]dioxol-4-yl)-5-(oxazol-2-yl)pyrimidine-2,4(1H,3H)-dione synthesized in the same manner as in Step 2 of Reference Example 10.0 using 2-(tri-n-butylstannyl)oxazole.

Example 17

An siRNA having Compound I-15 at the 5' end of the antisense strand is synthesized in the same manner as in Example 1 using Compound am-11 obtained in Reference Example 11.1.

Reference Example 12.0: Compound I-16

Step 1
(2R,3R,4R,5R)-2-((Benzoyloxy)methyl)-5-(5-iodo-2,4-dioxo-3,4-dihydropyrimidin-1(2H)-yl)tetrahydrofuran-3,4-diyl dibenzoate was obtained in the same manner as in Step 1 of Reference Example 1.0 using commercially available 5-iodopyrimidine-2,4(1H,3H)-dione.
ESI-MS (m/z): 683 (M+1)
Step 2
1,4-Dioxane (3 mL) was added to (2R,3R,4R,5R)-2-((benzoyloxy)methyl)-5-(5-iodo-2,4-dioxo-3,4-dihydropyrimidin-1(2H)-yl)tetrahydrofuran-3,4-diyl dibenzoate (200 mg, 0.293 mmol) obtained in Step 1, (4-methoxyphenyl) boronic acid (134.0 mg, 0.879 mmol), 1,1'-bis(diphenylphosphino)ferrocene-palladium(II) dichloride-dichloromethane complex (23.9 mg, 0.029 mmol), and a 2 M aqueous cesium carbonate solution (0.6 mL), and the mixture was stirred at 120° C. for 1 hour. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue obtained was purified by column chromatography (chloroform/methanol) to obtain (2R,3R,4R,5R)-2-((benzoyloxy)methyl)-5-(5-(4-methoxyphenyl)-2,4-dioxo-3,4-dihydropyrimidin-1 (2H)-yl)tetrahydrofuran-3,4-diyl dibenzoate (118 mg, yield: 61%) was obtained.
ESI-MS (m/z): 663 (M+1)
Step 3
((2R,3S,4R,5R)-3,4-Dihydroxy-5-(5-(4-methoxyphenyl)-2,4-dioxo-3,4-dihydropyrimidin-1(2H)-yl)tetrahydrofuran-2-yl)methyl phosphate (Compound I-16) was obtained in the same manner as in Steps 2 to 5 of Reference Example 1.0 using (2R,3R,4R,5R)-2-((benzoyloxy)methyl)-5-(5-(4-methoxyphenyl)-2,4-dioxo-3,4-dihydropyrimidin-1 (2H)-yl)tetrahydrofuran-3,4-diyl dibenzoate obtained in Step 2.
$^1$H-NMR (D$_2$O, 300 MHz) δ: 7.77 (s, 1H), 7.42 (d, J=8.8 Hz, 2H), 7.01 (d, J=8.8 Hz, 2H), 5.97 (d, J=5.5 Hz, 1H), 4.39 (t, J=5.9 Hz, 1H), 4.27 (t, J=4.4 Hz, 1H), 4.22-4.21 (m, 1H), 4.04-4.02 (m, 2H), 3.81 (s, 3H).
ESI-MS (m/z): 431 (M+1)

Reference Example 12.1: Compound am-12

(2R,3R,4R,5R)-2-((Bis(4-methoxyphenyl)(phenyl) methoxy)methyl)-4-((tert-butyldimethylsilyl)oxy)-5-(5-(4-methoxyphenyl)-2,4-dioxo-3,4-di hydropyrimidin-1(2H)-yl)tetrahydrofuran-3-yl (2-cyanoethyl) diisopropylphosphoramidite (Compound am-12) is obtained in the same manner as in Reference Example 1.1 using (2R,3R,4R,5R)-2-((benzoyloxy)methyl)-5-(5-(4-methoxyphenyl)-2,4-dioxo-3,4-dihydropyrimidin-1(2H)-yl)tetrahydrofuran-3,4-diyl dibenzoate obtained in Step 2 of Reference Example 12.0.

Example 18

An siRNA having Compound I-16 at the 5' end of the antisense strand is synthesized in the same manner as in Example 1 using Compound am-12 obtained in Reference Example 12.1.

Reference Example 13.0: Compound I-17

Step 1
Di-tert-butyl ((3aR,4R,6R,6aR)-6-(5-bromo-2,4-dioxo-3,4-dihydropyrimidin-1(2H)-yl)-2,2-dimethyltetrahydrofuro[3,4-d][1,3]dioxol-4-yl)methyl phosphate was obtained in the same manner as in Step 4 of Reference Example 1.0 using 5-bromo-1-((3aR,4R,6R,6aR)-6-(hydroxymethyl)-2,2-dimethyltetrahydro furo[3,4-d][1,3]dioxol-4-yl)pyrimidine-2,4(1H,3H)-dione obtained in Step 1 of Reference Example 10.0.
ESI-MS (m/z): 555 (M+1)
Step 2
Di-tert-butyl ((3aR,4R,6R,6aR)-6-(5-bromo-2,4-dioxo-3,4-dihydropyrimidin-1(2H)-yl)-2,2-dimethyltetrahydrofuro[3,4-d][1,3]dioxol-4-yl)methyl phosphate (200 mg, 0.360 mmol) obtained in Step 1 was dissolved in DMF (7 mL), and sodium cyanide (88.0 mg, 1.801 mmol) was added thereto, and the mixture was stirred overnight at room temperature. To the reaction solution was added a saturated aqueous sodium bicarbonate solution, and the mixture was extracted with ethyl acetate and dried over sodium sulfate. The residue obtained by evaporating the solvent under reduced pressure was purified by column chromatography (heptane/ethyl acetate) to obtain di-tert-butyl ((3aR,4R,6R,6aR)-6-(6-cyano-2,4-dioxo-3,4-dihydropyrimidin-1(2H)-yl)-2,2-dimethyltetrahydrofuro[3,4-d][1,3]dioxol-4-yl)methyl phosphate (150 mg, yield: 83%).
ESI-MS (m/z): 502 (M+1)
Step 3
((2R,3S,4R,5R)-5-(6-Cyano-2,4-dioxo-3,4-dihydropyrimidin-1(2H)-yl)-3,4-dihydroxytetrahydrofuran-2-yl) methyl phosphate (Compound I-17) was obtained in the same manner as in Step 5 of Reference Example 1.0 using di-tert-butyl ((3aR,4R,6R,6aR)-6-(6-cyano-2,4-dioxo-3,4-dihydropyrimidin-1(2H)-yl)-2,2-dimethyltetrahydrofuro[3, 4-d][1,3]dioxol-4-yl)methyl phosphate obtained in Step 2.
$^1$H-NMR (D$_2$O, 300 MHz) δ: 6.51 (d, J=0.7 Hz, 1H), 5.81 (d, J=4.0 Hz, 1H), 4.28 (t, J=6.2 Hz, 1H), 4.01-3.95 (m, 4H).
ESI-MS (m/z): 350 (M+1)

Reference Example 13.1: Compound am-13

Steps 1 to 2
5-Bromo-1-((4aR,6R,7R,7aR)-2,2-di-tert-butyl-7-((tert-butyldimethyl silyl)oxy)tetrahydro-4H-furo[3,2-d][1,3,2]dioxasilin-6-yl)pyrimidine-2,4(1H,3H)-dione was obtained in the same manner as in Steps 1 to 2 of Reference Example 1.1 using commercially available 5-bromo-1-((2R,3R,4S,5R)-3,4-dihydroxy-5-(hydroxymethyl)tetrahydrofuran-2-yl)pyrimidine-2,4(1H,3H)-dione.
ESI-MS (m/z): 577 (M+1)

Step 3

3-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-2,6-dioxo-1,2,3, 6-tetrahydropyrimidine-4-carbonitrile was obtained in the same manner as in Step 2 of Reference Example 13.0 using 5-bromo-1-((4aR,6R,7R,7aR)-2,2-di-tert-butyl-7-((tert-butyldimethyl silyl)oxy)tetrahydro-4H-furo[3,2-d][1,3,2]dioxasilin-6-yl)pyrimidine-2,4(1H,3H)-dione obtained in Step 2.

ESI-MS (m/z): 524 (M+1)

Step 4

(2R,3R,4R,5R)-2-((Bis(4-methoxyphenyl)(phenyl)methoxy)methyl)-4-((tert-butyldimethylsilyl)oxy)-5-(6-cyano-2,4-dioxo-3,4-dihydropyrimidin-1(2H)-yl)tetrahydrofuran-3-yl (2-cyanoethyl) diisopropylphosphoramidite (Compound am-13) was obtained in the same manner as in Steps 3 to 5 of Reference Example 1.1 using 3-((4aR,6R,7R,7aR)-2,2-di-tert-butyl-7-((tert-butyldimethylsilyl)oxy)tetrahydro-4H-furo[3,2-d][1,3,2]dioxasilin-6-yl)-2,6-dioxo-1,2,3, 6-tetrahydropyrimidine-4-carbonitrile obtained in Step 3.

$^1$H-NMR (CDCl$_3$, 500 MHz) δ: 7.47-6.78 (m, 13H), 6.27 (6.26) (s, 1H), 5.84 (m, 1H), 4.95 (4.89) (m, 1H), 4.35-4.19 (m, 2H), 3.96-3.27 (m, 12H), 2.31 (2.59) (m, 2H), 1.19-1.06 (m, 12H), 0.87 (0.88) (s, 9H), 0.06 (0.08) (s, 3H), 0.01 (s, 3H).

Example 19

An siRNA having Compound I-17 as X at the 5' end of the antisense strand of 454-Xu shown in Table 38 below was synthesized in the same manner as in Example 1 using Compound am-13 obtained in Reference Example 13.1. MALDI-TOF/MS (antisense strand): theoretical value: 6691.86 (M-H), actual value: 6691.25

Reference Example 14.0: Compound I-18

Step 1

((3aR,4R,6R,6aR)-2,2-Dimethyl-6-(6-((E)-styryl)-9H-purin-9-yl)tetrahydrofuro[3,4-d][1,3]dioxol-4-yl)methanol (249 mg, 0.631 mmol) obtained in Step 2 of Reference Example 6.0 was dissolved in chloroform (6.00 mL), and imidazole (86 mg, 1.26 mmol) and tert-butyldimethylsilyl chloride (105 mg, 0.694 mmol) were added thereto under ice cooling, and the mixture was stirred at room temperature for 3 hours. Thereafter, imidazole (86 mg, 1.26 mmol) and tert-butyldimethylsilyl chloride (105 mg, 0.694 mmol) were added thereto under ice cooling, and the mixture was further stirred at room temperature for 1 hour. The residue obtained by evaporating the solvent under reduced pressure was purified by column chromatography (heptane/ethyl acetate) to obtain 9-((3aR,4R,6R,6aR)-6-((tert-butyldimethylsilyloxy)methyl)-2,2-dimethyltetrahydrofuro[3,4-d][1,3]dioxol-4-yl)-6-((E)-styryl)-9H-purine (310 mg, 97.0%).

ESI-MS (m/z): 509 (M+1)

Step 2

9-((3aR,4R,6R,6aR)-6-((Tert-butyldimethylsilyloxy)methyl)-2,2-dimethyltetrahydrofuro[3,4-d][1,3]dioxol-4-yl)-6-((E)-styryl)-9H-purine (200 mg, 0.393 mmol) obtained in Step 1 was dissolved in THF (3.00 mL), and lithium diisopropylamide (0.393 mL, 0.786 mmol) was added thereto at −78° C. After stirring the mixture for 30 minutes, the solution obtained by dissolving 1,2-dibromo-1,1,2,2-tetrachloroethane (384 mg, 1.18 mmol) in THF (2.00 mL) was added thereto at −78° C. Thereafter, the temperature of the mixture was raised to room temperature over 1 hour while stirring. To the reaction mixture, a saturated aqueous sodium bicarbonate solution was added, and the mixture was extracted with ethyl acetate and dried over anhydrous sodium sulfate. The residue obtained by evaporating the solvent under reduced pressure was purified by column chromatography (heptane/ethyl acetate) to obtain 8-bromo-9-((3aR,4R,6R,6aR)-6-((tert-butyldimethylsilyloxy)methyl)-2,2-dimethyltetrahydrofuro[3,4-d][1,3]dioxol-4-yl)-6-((E)-styryl)-9H-purine (198 mg, 86.0%).

ESI-MS (m/z): 587 (M+1)

Step 3

8-Bromo-9-((3aR,4R,6R,6aR)-6-((tert-butyldimethylsilyloxy)methyl)-2,2-dimethyltetrahydrofuro[3,4-d][1,3]dioxol-4-yl)-6-((E)-styryl)-9H-purine (198 mg, 0.337 mmol) obtained in Step 2 was dissolved in trifluoroacetic acid/water (1:1) (2 mL), and the mixture was stirred at room temperature for 2 hours. The residue obtained by evaporating the solvent under reduced pressure was purified by column chromatography (heptane/ethyl acetate) to obtain (2R,3R,4S,5R)-2-(8-bromo-6-((E)-styryl)-9H-purin-9-yl)-5-(hydroxymethyl)tetrahydrofuran-3,4-diol (140 mg, 96.0%).

ESI-MS (m/z): 433 (M+1)

Step 4

((3aR,4R,6R,6aR)-6-(8-Bromo-6-((E)-styryl)-9H-purin-9-yl)-2,2-dimethyltetrahydrofuro[3,4-d][1,3]dioxol-4-yl)methanol (66.0 mg, 43.2%) was obtained in the same manner as in Step 3 of Reference Example 1.0 using (2R,3R,4S,5R)-2-(8-bromo-6-((E)-styryl)-9H-purin-9-yl)-5-(hydroxymethyl)tetrahydrofuran-3,4-diol (140 mg, 0.323 mmol) obtained in Step 3.

ESI-MS (m/z): 473 (M+1)

Steps 5 to 6

((2R,3S,4R,5R)-5-(8-Bromo-6-((E)-styryl)-9H-purin-9-yl)-3,4-dihydroxytetrahydrofuran-2-yl)methyl phosphate (Compound I-18, 68.5 mg, 75.0%) was obtained in the same manner as in Steps 3 to 4 of Reference Example 6.0 using ((3aR,4R,6R,6aR)-6-(8-bromo-6-((E)-styryl)-9H-purin-9-yl)-2,2-dimethyltetrahydrofuro[3,4-d][1,3]dioxol-4-yl)methanol (65.0 mg, 0.137 mmol) obtained in Step 4.

$^1$H-NMR (D$_2$O, 400 MHz) δ: 8.45 (1H, s), 7.54 (1H, d, J=15.6 Hz), 7.24-7.17 (2H, m), 7.11-7.00 (3H, m), 6.95 (1H, d, J=15.6 Hz), 5.96 (1H, d, J=4.9 Hz), 5.18 (1H, dd, J=5.4, 5.4 Hz), 4.54 (1H, dd, J=5.4, 5.4 Hz), 4.19-4.13 (1H, m), 4.12-3.95 (2H, m).

ESI-MS (m/z): 513 (M+1)

Reference Example 14.1: Compound am-14

3-((2R,3R,4R,5R)-2-((Bis(4-methoxyphenyl)(phenyl)methoxy)methyl)-5-(8-bromo-6-((E)-styryl)-9H-purin-9-yl)-4-(tert-butyldimethylsilyloxy)tetrahydrofuran-3-yl (2-cyanoethyl) diisopropylphosphoramidite (Compound am-14) is obtained in the same manner as in Reference Example 1.1 using (2R,3R,4S,5R)-2-(8-bromo-6-((E)-styryl)-9H-purin-9-yl)-5-(hydroxymethyl)tetrahydrofuran-3,4-diol obtained in Step 3 of Reference Example 14.0.

Example 20

An siRNA having Compound I-18 at the 5' end of the antisense strand is synthesized in the same manner as in Example 1 using Compound am-14 obtained in Reference Example 14.1.

Reference Example 15.0: Compound I-19 ((2R,3S,4R,5R)-5-(5,6-Dimethyl-2,4-dioxo-3,4-dihydrothieno [2,3-d]pyrimidin-1 (2H)-yl)-3,4-dihydroxytetrahydrofuran-2-yl)methyl phosphate (Compound I-19) triethylammonium salt was obtained in the same manner as in Reference Example 1.0 using commercially available 5,6-dimethylthieno[2,3-d]pyrimidine-2,4(1H,3H)-dione.

$^1$H-NMR (D$_2$O, 300 MHz) δ: 6.10 (d, J=5.5 Hz, 1H), 4.75-4.73 (m, 1H), 4.40 (t, J=5.7 Hz, 1H), 4.24-4.14 (m, 3H), 2.32 (s, 3H), 2.31 (s, 3H). ESI-MS (m/z): 411 (M+1)

Reference Example 15.1: Compound am-15

(2R,3R,4R,5R)-2-((Bis(4-methoxyphenyl)(phenyl)methoxy)methyl)-4-(tert-butyldimethylsilyloxy)-5-(5,6-dimethyl-2,4-dioxo-3,4-dihydrothieno[2,3-d]pyrimidin-1(2H)-yl)tetrahydrofuran-3-yl 2-cyanoethyl diisopropylphosphoramidite (Compound am-15) was obtained in the same manner as in Reference Example 1.1 using commercially available 5,6-dimethylthieno[2,3-d]pyrimidine-2,4(1H,3H)-dione.

$^1$H-NMR (CDCl$_3$, 500 MHz) δ: 7.62 (s, 1H), 7.50-6.78 (m, 13H), 5.98 (m, 1H), 4.92 (m, 1H), 4.34-4.25 (m, 2H), 4.00-3.34 (m, 12H), 2.29 (2.64) (m, 2H), 2.35 (s, 3H), 2.13 (s, 3H), 1.23-1.03 (m, 12H), 0.83 (0.84) (s, 9H), 0.02 (d, J=6.0 Hz, 3H), −0.10 (d, J=5.0 Hz, 3H).

Example 21

An siRNA (referred to as di-Me-thienyl-dU) having Compound I-19 as X at the 5' end of the antisense strand of 454-Xu shown in Table 38 below was synthesized in the same manner as in Example 1 using Compound am-15 obtained in Reference Example 15.1.

MALDI-TOF/MS (antisense strand): theoretical value: 6750.99 (M-H), actual value: 6754.34

Reference Example 16.0: Compound I-20

Step 1

((3aR,4R,6R,6aR)-6-(6-(3-Isopropylphenyl)-9H-purin-9-yl)-2,2-dimethyltetrahydrofuro[3,4-d][1,3]dioxol-4-yl)methanol (167 mg, 133%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and 3-isopropylphenylboronic acid (100 mg, 0.612 mmol).

ESI-MS (m/z): 411 (M+1)

Step 2

Di-tert-butyl ((3aR,4R,6R,6aR)-6-(6-(3-isopropylphenyl)-9H-purin-9-yl)-2,2-dimethyltetrahydrofuro[3,4-d][1,3]dioxol-4-yl)methyl phosphate (96.2 mg, 52.0%) was obtained in the same manner as in Step 3 of Reference Example 6.0 using ((3aR,4R,6R,6aR)-6-(6-(3-isopropylphenyl)-9H-purin-9-yl)-2,2-dimethyltetrahydrofuro[3,4-d][1,3]dioxol-4-yl)methanol (126 mg, 0.307 mmol) obtained in Step 1.

ESI-MS (m/z): 603 (M+1)

Step 3

Di-tert-butyl ((3aR,4R,6R,6aR)-6-(6-(3-isopropylphenyl)-9H-purin-9-yl)-2,2-dimethyltetrahydrofuro[3,4-d][1,3]dioxol-4-yl)methyl phosphate (96.0 mg, 0.159 mmol) obtained in Step 1 was dissolved in trifluoroacetic acid/water (1:1) (2 mL), and the mixture was stirred at room temperature for 3 hours. The residue obtained by evaporating the solvent under reduced pressure was purified by preparative HPLC (eluent: 0.01 mmol/L acetic acid-triethylamine buffer (pH 6.5)/acetonitrile) to obtain ((2R,3S,4R,5R)-3,4-dihydroxy-5-(6-(3-isopropylphenyl)-9H-purin-9-yl)tetrahydrofuran-2-yl)methyl phosphate (Compound I-20) triethylammonium salt (70.0 mg, 80.0%).

$^1$H-NMR (D$_2$O, 300 MHz) δ: 8.72 (2H, d, J=7.0 Hz), 7.97 (1H, s), 7.92-7.83 (1H, m), 7.43-7.33 (2H, m), 6.14 (1H, d, J=5.5 Hz), 4.73-4.64 (14H, m), 4.44-4.38 (1H, m), 4.32-4.25 (1H, m), 4.08-3.93 (2H, m), 3.06 (11H, q, J=7.3 Hz), 2.94-2.81 (1H, m), 1.20-1.08 (22H, m).

ESI-MS (m/z): 451 (M+1)

Reference Example 16.1: Compound am-16

(2R,3R,4R,5R)-2-((Bis(4-methoxyphenyl)(phenyl)methoxy)methyl)-4-(tert-butyldimethylsilyloxy)-5-(6-(3-isopropylphenyl)-9H-purin-9-yl)tetrahydrofuran-3-yl 2-cyanoethyl diisopropylphosphoramidite (Compound am-16) is obtained in the same manner as in Reference Example 6.1 using ((3aR,4R,6R,6aR)-6-(6-(3-isopropylphenyl)-9H-purin-9-yl)-2,2-dimethyltetrahydrofuro[3,4-d][1,3]dioxol-4-yl)methanol obtained in Step 1 of Reference Example 16.0.

Example 22

An siRNA having Compound I-20 at the 5' end of the antisense strand is synthesized in the same manner as in Example 1 using Compound am-16 obtained in Reference Example 16.1.

Reference Example 17.0: Compound I-21

Step 1

((3aR,4R,6R,6aR)-2,2-Dimethyl-6-(6-(naphthalen-2-yl)-9H-purin-9-yl)tetrahydrofuro[3,4-d][1,3]dioxol-4-yl)methanol (147 mg, 114%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and 2-naphthaleneboronic acid (105 mg, 0.612 mmol).

ESI-MS (m/z): 419 (M+1)

Step 2

Di-tert-butyl ((3aR,4R,6R,6aR)-2,2-dimethyl-6-(6-(naphthalen-2-yl)-9H-purin-9-yl)tetrahydrofuro[3,4-d][1,3]dioxol-4-yl)methyl phosphate (90.0 mg, 48.2%) was obtained in the same manner as in Step 3 of Reference Example 6.0 using ((3aR,4R,6R,6aR)-2,2-dimethyl-6-(6-(naphthalen-2-yl)-9H-purin-9-yl)tetrahydrofuro[3,4-d][1,3]dioxol-4-yl)methanol (128 mg, 0.306 mmol) obtained in Step 1.

ESI-MS (m/z): 611 (M+1)

Step 3

((2R,3S,4R,5R)-3,4-Dihydroxy-5-(6-(naphthalen-2-yl)-9H-purin-9-yl)tetrahydrofuran-2-yl)methyl phosphate (Compound I-21) triethylammonium salt (20.0 mg, 29.6%) was obtained in the same manner as in Step 5 of Reference Example 1.0 using di-tert-butyl ((3aR,4R,6R,6aR)-2,2-dimethyl-6-(6-(naphthalen-2-yl)-9H-purin-9-yl)tetrahydrofuro[3,4-d][1,3]dioxol-4-yl)methyl phosphate (77.0 mg, 0.126 mmol) obtained in Step 2.

$^1$H-NMR (D$_2$O, 400 MHz) δ: 8.30 (1H, s), 8.05 (1H, s), 7.80 (1H, s), 7.55-7.40 (1H, m), 7.27-6.92 (5H, m), 5.73 (1H, s), 4.52-4.18 (3H, m), 4.15-3.92 (2H, m), 3.06-2.96 (6H, m), 1.16-1.04 (9H, m).

ESI-MS (m/z): 459 (M+1)

Reference Example 17.1: Compound am-17

Steps 1 to 2

6-Chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine was obtained in the same manner as in Steps 1 to 2 of Reference Example 1.1 using commercially available (2R,3R,4S,5R)-2-(6-chloro-9H-purin-9-yl)-5-(hydroxymethyl)tetrahydrofuran-3,4-diol. ESI-MS (m/z): 541 (M+1)

Step 3

9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(naphthalen-2-yl)-9H-purine was obtained in the same manner as in Step 1 of Reference Example 17.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2.

ESI-MS (m/z): 633 (M+1)

Steps 4 to 6

(2R,3R,4R,5R)-2-((Bis(4-methoxyphenyl)(phenyl)methoxy)methyl)-4-(tert-butyldimethylsilyloxy)-5-(6-(naphthalen-2-yl)-9H-purin-9-yl)tetrahydrofuran-3-yl 2-cyanoethyl diisopropylphosphoramidite (Compound am-17) was obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(naphthalen-2-yl)-9H-purine obtained in Step 3.

$^1$H-NMR (CDCl$_3$, 500 MHz) δ: 9.43 (m, 1H), 8.96 (m, 1H), 8.88 (m, 1H), 8.40 (m, 1H), 8.08 (m, 1H), 8.02 (m, 1H), 7.91 (m, 1H), 7.59-7.52 (m, 2H), 7.52-6.81 (m, 13H), 6.19 (6.13) (m, 1H), 5.11 (m, 1H), 4.50-4.38 (m, 2H), 4.02-3.32 (m, 12H), 2.67 (2.32) (m, 2H), 1.23-1.05 (m, 12H), 0.76 (0.77) (s, 9H), −0.03 (0.00) (s, 3H), −0.19 (−0.17) (s, 3H).

Example 23

An siRNA (referred to as 6-napht-2-yl-dPu) having Compound I-21 as X at the 5' end of the antisense strand of 454-Xa shown in Table 38 below was synthesized in the same manner as in Example 1 using Compound am-17 obtained in Reference Example 17.1.

MALDI-TOF/MS (antisense strand): theoretical value: 6801.03 (M-H), actual value: 6805.40

Reference Example 18.0: Compound I-22

Step 1

((3aR,4R,6R,6aR)-6-(6-(3-Formylphenyl)-9H-purin-9-yl)-2,2-dimethyltetrahydrofuro[3,4-d][1,3]dioxol-4-yl)methanol (216 mg, 89%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (200 mg, 0.612 mmol) obtained in Step 1 of Reference Example 6.0 and 3-formylphenylboronic acid (184 mg, 1.22 mmol).

ESI-MS (m/z): 397 (M+1)

Step 2

Di-tert-butyl ((3aR,4R,6R,6aR)-6-(6-(3-formylphenyl)-9H-purin-9-yl)-2,2-dimethyltetrahydrofuro[3,4-d][1,3]dioxol-4-yl)methyl phosphate (35.0 mg, 11.0%) was obtained in the same manner as in Step 3 of Reference Example 6.0 using ((3aR,4R,6R,6aR)-6-(6-(3-formylphenyl)-9H-purin-9-yl)-2,2-dimethyltetrahydrofuro[3,4-d][1,3]dioxol-4-yl)methanol (215 mg, 0.542 mmol) obtained in Step 1.

ESI-MS (m/z): 589 (M+1)

Step 3

((2R,3S,4R,5R)-3,4-Dihydroxy-5-(6-(3-formylphenyl)-9H-purin-9-yl)tetrahydrofuran-2-yl)methyl phosphate (Compound I-22, 20.0 mg, 29.6%) was obtained in the same manner as in Step 5 of Reference Example 1.0 using di-tert-butyl ((3aR,4R,6R,6aR)-6-(6-(3-formylphenyl)-9H-purin-9-yl)-2,2-dimethyltetrahydrofuro[3,4-d][1,3]dioxol-4-yl) methyl phosphate (33.0 mg, 0.0560 mmol) obtained in Step 1.

$^1$H-NMR (D$_2$O, 300 MHz) δ: 9.93 (1H, s), 8.88 (1H, s), 8.76 (1H, s), 8.67-8.60 (1H, m), 8.47-8.40 (1H, m), 8.06-7.99 (1H, m), 7.74-7.66 (1H, m), 6.20 (1H, d, J=5.5 Hz), 4.76-4.68 (2H, m), 4.46-4.41 (1H, m), 4.34-4.29 (1H, m), 4.12-4.00 (2H, m).

ESI-MS (m/z): 437 (M+1)

Reference Example 18.1: Compound am-18

(2R,3R,4R,5R)-2-((Bis(4-methoxyphenyl)(phenyl)methoxy)methyl)-4-(tert-butyldimethylsilyloxy)-5-(6-(3-formylphenyl)-9H-purin-9-yl)tetra hydrofuran-3-yl 2-cyanoethyl diisopropylphosphoramidite (Compound am-18) is obtained in the same manner as in Reference Example 6.1 using ((3aR,4R,6R,6aR)-6-(6-(3-formylphenyl)-9H-purin-9-yl)-2,2-dimethyltetrahydrofuro[3,4-d][1,3]dioxol-4-yl) methanol obtained in Step 1 of Reference Example 18.0.

Reference Example 18.1: Compound am-18

Step 1

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-formylphenyl)-9H-purine was obtained (826 mg, 73.2%) in the same manner as in Step of Reference Example 18.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (1.00 g, 1.848 mmol) obtained in Step 2 of Reference Example 17.1.

Step 2

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-formylphenyl)-9H-purine (720 mg, 1.179 mmol) obtained in Step 1 was dissolved in dichloromethane (15 mL). To the solution were added 1,3-propanediol (0.427 mL, 5.89 mmol), triethyl orthoformate (0.294 mL, 1.768 mmol) and a dichloromethane solution of titanium tetrachloride (1 mol/L) (0.589 mL, 0.589 mmol) under ice cooling, and the mixture was stirred for 4 hours at room temperature. Saturated sodium bicarbonate solution was added to the reaction mixture, which was then extracted with ethyl acetate, and the organic layer was washed with saturated brine and dried with anhydrous magnesium sulfate. The solvent was evaporated under reduced pressure, and the residue was purified by ethyl acetate/heptane silica gel column chromatography to obtain 6-(3-(1,3-dioxan-2-yl)phenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine (690 mg, 88.0%).

Steps 3 to 5

(2R,3R,4R,5R)-5-(6-(3-(1,3-dioxan-2-yl)phenyl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-18) was obtained in the same manner as in Steps 3 to 5 of Reference Example 1.1 using 6-(3-(1,3-dioxan-2-yl)phenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 2.

Example 24-0

An siRNA having Compound I-22 at the 5' end of the antisense strand is synthesized in the same manner as in Example 1 using Compound am-18 obtained in Reference Example 18.1.

Example 24

Using Compound am-18 obtained in Reference Example 18.1, an oligonucleic acid was synthesized by solid-phase synthesis in the same manner as in Example 1, and then deprotected for 1 hour at room temperature using 80% acetic acid (0.500 mL). The mixture was concentrated under reduced pressure, and annealed in the same manner as in Example 1 to synthesize an siRNA (referred to as 6-(m-formyl)phenyl-Pu) having Compound I-22 as X at the 5' end of the antisense strand of 454 Xa shown in Table 38 below.
ESI-MS (antisense strand) theoretical value: 6778.98 actual value: 6778.23

Reference Example 19.0: Compound I-23

((2R,3S,4R,5R)-3,4-Dihydroxy-5-(6-nitro-2,4-dioxo-3,4-dihydroquinazolin-1(2H)-yl)tetrahydrofuran-2-yl)methyl phosphate (Compound I-23) triethylammonium salt was obtained in the same manner as in Reference Example 1.0 using commercially available 6-nitro-1H-quinazoline-2,4-dione.
$^1$H-NMR (D$_2$O, 300 MHz) δ: 8.82 (d, J=2.9 Hz, 1H), 8.49 (dd, J=9.3, 2.4 Hz, 1H), 7.89 (d, J=9.5 Hz, 1H), 6.27 (d, J=5.9 Hz, 1H), 4.73 (t, J=6.2 Hz, 1H), 4.42 (t, J=5.9 Hz, 1H), 4.09-4.04 (m, 3H), 3.08 (q, J=7.3 Hz, 6H), 1.16 (t, J=7.3 Hz, 9H).
ESI-MS (m/z): 420 (M+1)

Reference Example 19.1: Compound am-19

(2R,3R,4R,5R)-2-((Bis(4-methoxyphenyl)(phenyl)methoxy)methyl)-4-(tert-butyldimethylsilyloxy)-5-(6-nitro-2,4-dioxo-3,4-dihydroquinazolin-1(2H)-yl)tetrahydrofuran-3-yl 2-cyanoethyl diisopropylphosphoramidite (Compound am-19) is obtained in the same manner as in Reference Example 1.1 using commercially available 6-nitro-1H-quinazoline-2,4-dione.

Example 25

An siRNA having Compound I-23 at the 5' end of the antisense strand is synthesized in the same manner as in Example 1 using Compound am-19 obtained in Reference Example 19.1.

Reference Example 20.0: Compound I-24

Steps 1 to 4
Di-tert-butyl ((3aR,4R,6R,6aR)-6-(5,6-dimethyl-2,4-dioxo-3,4-dihydropyrimidin-1(2H)-yl)-2,2-dimethyltetrahydrofuro[3,4-d][1,3]dioxol-4-yl)methyl phosphate was obtained in the same manner as in Steps 1 to 4 of Reference Example 1 using commercially available 5,6-dimethylpyrimidine-2,4(1H,3H)-dione.
ESI-MS (m/z): 505 (M+1)

Step 5
Di-tert-butyl ((3aR,4R,6R,6aR)-6-(5,6-dimethyl-2,4-dioxo-3,4-dihydropyrimidin-1(2H)-yl)-2,2-dimethyltetrahydrofuro[3,4-d][1,3]dioxol-4-yl)methyl phosphate (200 mg, 0.396 mmol) obtained in Step 4 was dissolved in 1,4-dioxane (4.00 mL), and selenium dioxide (440 mg, 3.96 mmol) was added thereto, and the mixture was stirred overnight under reflux. The reaction solution was filtered through Celite, and the residue obtained by evaporating the solvent under reduced pressure was purified by column chromatography (heptane/ethyl acetate) to obtain di-tert-butyl ((3aR,4R,6R,6aR)-6-(6-(hydroxymethyl)-5-methyl 2,4-dioxo-3,4-dihydropyrimidin-1(2H)-yl)-2,2-dimethyltetrahydrofuro[3,4-d][1,3]dioxol-4-yl)methyl phosphate (38.6 mg, yield: 19%) was obtained.
ESI-MS (m/z): 521 (M+1)
Step 6
Di-tert-butyl ((3aR,4R,6R,6aR)-6-(6-(hydroxymethyl)-5-methyl 2,4-dioxo-3,4-dihydropyrimidin-1(2H)-yl)-2,2-dimethyltetrahydrofuro [3,4-d][1,3]dioxol-4-yl)methyl phosphate (38.6 mg, 0.074 mmol) obtained in Step 5 was dissolved in acetonitrile (1.00 mL), and pyridine (0.06 mL, 0.742 mmol) and Dess-Martin periodinane (62.9 mg, 0.148 mmol) were added thereto, and the mixture was stirred overnight at 60° C. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and the solvent was evaporated under reduced pressure. The residue obtained was purified by preparative thin-layer chromatography (hexane/ethyl acetate=20/80) to obtain di-tert-butyl ((3aR,4R,6R,6aR)-6-(6-(hydroxymethyl)-5-methyl-2,4-dioxo-3,4-dihydropyrimidin-1(2H)-yl)-2,2-dimethyltetrahydrofuro[3,4-d][1,3]dioxol-4-yl)methyl phosphate (32.8 mg, yield: 85%).
ESI-MS (m/z): 519 (M+1)
Step 7
Di-tert-butyl ((3aR,4R,6R,6aR)-6-(6-(hydroxymethyl)-5-methyl-2,4-dioxo-3,4-dihydropyrimidin-1(2H)-yl)-2,2-dimethyltetrahydrofuro[3,4-d][1,3]dioxol-4-yl)methyl phosphate (46.0 mg, 0.089 mmol) obtained in Step 6 was dissolved in THF (1.00 mL), and hydroxylamine hydrochloride (30.8 mg, 0.444 mmol) was added thereto, and the mixture was stirred at 60° C. for 2 hours. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and the solvent was evaporated under reduced pressure. The residue was purified by preparative thin-layer chromatography (chloroform/methanol=90/10) to obtain di-tert-butyl ((3aR, 4R,6R,6aR)-6-(6-((E)-(hydroxyimino)methyl)-5-methyl 2,4-dioxo-3,4-dihydropyrimidin-1(2H)-yl)-2,2-dimethyltetrahydrofuro[3,4-d][1,3]dioxol-4-yl)methyl phosphate (33.7 mg, yield: 71%) was obtained.
ESI-MS (m/z): 534 (M+1)
Step 8
Triphenylphosphine oxide (1.76 mg, 0.006 mmol) was dissolved in ethyl acetate (1.00 mL), and oxalyl chloride (0.017 mL, 0.19 mmol) was added thereto, and the mixture was stirred at room temperature for 5 minutes to prepare a reaction mixture. Di-tert-butyl ((3aR,4R,6R,6aR)-6-(6-((E)-(hydroxyimino)methyl)-5-methyl-2,4-dioxo-3,4-dihydropyrimidin-1 (2H)-yl)-2,2-dimethyltetrahydrofuro[3,4-d][1,3] dioxol-4-yl)methyl phosphate (33.7 mg, 0.063 mmol) obtained in Step 7 was dissolved in ethyl acetate (1.00 mL), and the reaction solution was gradually added thereto, and the mixture was stirred overnight at room temperature. The residue obtained by evaporating the solvent was dissolved in trifluoroacetic acid/water (1:1) (2 mL), and the mixture was stirred at room temperature for 2 hours. After the solvent was evaporated under reduced pressure, acetic acid-triethylamine buffer (pH 6.5) (2 mL) was added thereto, and the solvent was evaporated again under reduced pressure. The resulting residue was dissolved in ethanol, and ethyl acetate was added thereto, and the precipitate was collected by filtration to obtain ((2R,3S,4R,5R)-5-(6-cyano-5-methyl-2,4-dioxo-3,4-dihydropyrimidin-1(2H)-yl)-3,4-dihydroxytetrahydrofuran-2-yl)methyl phosphate (Compound I-24) triethylammonium salt (1.6 mg (two batches), yield: 74%) was obtained.

$^1$H-NMR (D$_2$O, 300 MHz) δ: 5.96 (d, J=4.0 Hz, 1H), 4.41 (t, J=6.4 Hz, 1H), 4.19-4.06 (m, 3H), 3.21 (q, J=7.2 Hz, 6H), 2.19 (s, 3H), 1.28 (t, J=7.5 Hz, 9H).

ESI-MS (m/z): 404 (M+1)

Reference Example 20.1: Compound am-20

Step 1

(2R,3R,4R,5R)-2-(Benzoyloxymethyl)-5-(6-(hydroxymethyl)-5-methyl-2, 4-dioxo-3,4-dihydropyrimidin-1(2H)-yl)tetrahydrofuran-3,4-diyl benzoate was obtained in the same manner as in Step 5 of Reference Example 20.0 using (2R,3R,4R,5R)-2-(benzoyloxymethyl)-5-(5,6-dimethyl-2,4-dioxo-3,4-di hydropyrimidin-1 (2H)-yl)tetrahydrofuran-3,4-diyl benzoate obtained in Step 1 of Reference Example 20.0.

ESI-MS (m/z): 601 (M+1)

Step 2

(2R,3R,4R,5R)-2-(Benzoyloxymethyl)-5-(6-formyl-5-methyl-2,4-dioxo-3,4-dihydropyrimidin-1(2H)-yl)tetrahydrofuran-3,4-diyl benzoate was obtained in the same manner as in Step 6 of Reference Example 20.0 using (2R,3R,4R,5R)-2-(benzoyloxymethyl)-5-(6-hydroxymethyl)-5-methyl-2,4-dioxo-3,4-dihydropyrimidin-1(2H)-yl)tetrahydrofuran-3,4-diyl benzoate obtained in Step 1.

ESI-MS (m/z): 599 (M+1)

Step 3

(2R,3R,4R,5R)-2-(Benzoyloxymethyl)-5-(6-((E)-(hydroxyimino)methyl)-5-methyl-2,4-dioxo-3,4-dihydropyrimidin-1(2H)-yl)tetrahydrofuran-3, 4-diyl benzoate was obtained in the same manner as in Step 7 of Reference Example 20.0 using (2R,3R,4R,5R)-2-(benzoyloxymethyl)-5-(6-formyl-5-methyl-2,4-dioxo-3,4-dihydropyrimidin-1 (2H)-yl)tetrahydrofuran-3,4-diyl benzoate obtained in Step 2.

ESI-MS (m/z): 614 (M+1)

Step 4

Triphenylphosphine oxide (11.0 mg, 0.039 mmol) was dissolved in ethyl acetate (5.00 mL), and oxalyl chloride (0.104 mL, 1.183 mmol) was added thereto, and the mixture was stirred at room temperature for 5 minutes to obtain a reaction mixture solution. (2R,3R,4R,5R)-2-(Benzoyloxymethyl)-5-(6-((E)-(hydroxyimino)methyl)-5-methyl-2,4-dioxo-3,4-dihydropyrimidin-1(2H)-yl)tetrahydrofuran-3,4-diyl benzoate (242 mg, 0.394 mmol) obtained in Step 3 was dissolved in ethyl acetate (5.00 mL), and the reaction solution was gradually added thereto, and the mixture was stirred at room temperature for 2 hours. The residue obtained by evaporating the solvent under reduced pressure was purified by column chromatography (heptane/ethyl acetate) to obtain (2R,3R,4R,5R)-2-(benzoyloxymethyl)-5-(6-cyano-5-methyl-2,4-dioxo-3, 4-dihydropyrimidin-1 (2H)-yl)tetrahydrofuran-3,4-diyl benzoate (207 mg, yield: 88%) was obtained.

ESI-MS (m/z): 596 (M+1)

Step 5

3-((2R,3R,4S,5R)-3,4-Dihydroxy-5-(hydroxymethyl)tetrahydrofuran-2-yl)-5-methyl-2,6-dioxo-1,2,3,6-tetrahydropyrimidine-4-carbonitrile was obtained in the same manner as in Step 2 of Reference Example 1.0 using (2R,3R,4R,5R)-2-(benzoyloxymethyl)-5-(6-cyano-5-methyl-2,4-dioxo-3, 4-dihydropyrimidin-1(2H)-yl)tetrahydrofuran-3,4-diyl benzoate obtained in Step 4.

ESI-MS (m/z): 284 (M+1)

Steps 6 to 10

(2R,3R,4S,5R)-2-((Bis(4-methoxyphenyl)(phenyl)methoxy)methyl)-4-(tert-butyldimethylsilyloxy)-5-(6-cyano-5-methyl-2,4-dioxo-3,4-dihydro pyrimidin-1(2H)-yl)tetrahydrofuran-3-yl 2-cyanoethyl diisopropylphosphoramidite (Compound am-20) is obtained in the same manner as in Steps 1 to 5 of Reference Example 1.1 using 3-((2R,3R,4S,5R)-3,4-dihydroxy-5-(hydroxymethyl)tetrahydrofuran-2-yl)-5-methyl-2,6-dioxo-1,2,3,6-tetrahydropyrimidine-4-carbonitrile obtained in Step 5.

Example 26

An siRNA having Compound I-24 at the 5' end of the antisense strand is synthesized in the same manner as in Example 1 using Compound am-20 obtained in Reference Example 20.1.

Reference Example 21.0: Compound I-25

Step 1

((3aR,4R,6R,6aR)-2,2-Dimethyl-6-(6-(naphthalen-1-yl)-9H-purin-9-yl)tetrahydrofuro[3,4-d][1,3]dioxol-4-yl)methanol (150 mg, 117%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and naphthalen-1-yl boronic acid (105 mg, 0.612 mmol).

ESI-MS (m/z): 419 (M+1)

Step 2

Di-tert-butyl ((3aR,4R,6R,6aR)-2,2-dimethyl-6-(6-(naphthalen-1-yl)-9H-purin-9-yl)tetrahydrofuro[3,4-d][1,3]dioxol-4-yl)methyl phosphate (70.0 mg, 37.5%) was obtained in the same manner as in Step 3 of Reference Example 6.0 using ((3aR,4R,6R,6aR)-2,2-dimethyl-6-(6-(naphthylen-1-yl)-9H-purin-9-yl)tetrahydrofuro[3,4-d][1,3]dioxol-4-yl) methanol (128 mg, 0.306 mmol) obtained in Step 1.

ESI-MS (m/z): 611 (M+1)

Step 3

((2R,3S,4R,5R)-3,4-Dihydroxy-5-(6-(naphthalen-1-yl)-9H-purin-9-yl)tetrahydrofuran-2-yl)methyl phosphate (Compound I-25) triethylammonium salt (10.8 mg, 15.3%) was obtained in the same manner as in Step 3 of Reference Example 16.0 using di-tert-butyl ((3aR,4R,6R,6aR)-2,2-dimethyl-6-(6-(naphthalen-1-yl)-9H-purin-9-yl)tetrahydrofuro[3,4-d][1,3]dioxol-4-yl)methyl phosphate (77.0 mg, 0.126 mmol) obtained in Step 2.

$^1$H-NMR (D$_2$O, 300 MHz) δ: 8.87 (1H, s), 8.60 (1H, s), 8.07-7.84 (2H, m), 7.73-7.60 (2H, m), 7.58-7.40 (2H, m), 7.38-7.28 (1H, m), 6.21 (1H, d, J=5.5 Hz), 4.75-4.66 (1H, m), 4.45-4.38 (1H, m), 4.35-4.28 (1H, m), 4.10-3.98 (2H, m), 3.05 (6H, q, J=7.3 Hz), 1.13 (9H, t, J=7.3 Hz).

ESI-MS (m/z): 459 (M+1)

Reference Example 21.1: Compound am-21

Step 1

9-((4aR,6R,7R,7aS)-2,2-Di-tert-butyl-7-(tert-butyldimethylsilyloxy)tetrahydro-4H-furo[3,2-d][1,3,2]dioxasilin-6- yl)-6-(naphthalen-1-yl)-9H-purine was obtained in the same manner as in Step 1 of Reference Example 21.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

ESI-MS (m/z): 633 (M+1)

Steps 2 to 4

(2R,3R,4R,5R)-2-((Bis(4-methoxyphenyl)(phenyl)methoxy)methyl)-4-(tert-butyldimethylsilyloxy)-5-(6-(naphthalen-1-yl)-9H-purin-9-yl)tetrahydrofuran-3-yl 2-cyanoethyl diisopropylphosphoramidite (Compound am-21) was obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(naphthalen-1-yl)-9H-purine obtained in Step 1.

$^1$H-NMR (CDCl$_3$, 500 MHz) δ: 9.04 (m, 1H), 8.34 (m, 1H), 8.20 (m, 1H), 8.04-7.91 (m, 2H), 7.93 (m, 1H), 7.64 (m, 1H), 7.54-7.45 (m, 4H), 7.39-6.79 (m, 11H), 6.21 (6.15) (m, 1H), 5.16 (m, 1H), 4.51-4.39 (m, 2H), 4.04-3.32 (m, 12H), 2.68 (2.32) (m, 2H), 1.25-1.06 (m, 12H), 0.76 (0.77) (s, 9H), −0.01 (0.01) (s, 3H), −0.16 (−0.15) (s, 3H).

Example 27

An siRNA (6-napht-1-yl-dPu) having Compound I-25 as X at the 5' end of the antisense strand of 454-Xa shown in Table 38 below was synthesized in the same manner as in Example 1 using Compound am-21 obtained in Reference Example 21.1.

MALDI-TOF/MS (antisense strand): theoretical value: 6801.03 (M-H), actual value: 6800.94

Reference Example 22.0: Compound I-26

Step 1 ((3aR,4R,6R,6aR)-6-(6-(Biphenyl-3-yl)-9H-purin-9-yl)-2,2-dimethyltetrahydrofuro[3,4-d][1,3]dioxol-4-yl)methanol (130 mg, 95%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (1,1'-biphenyl)-3-yl boronic acid (121 mg, 0.612 mmol).

ESI-MS (m/z): 445 (M+1)

Step 2

Di-tert-butyl ((3aR,4R,6R,6aR)-6-(6-(biphenyl-3-yl)-9H-purin-9-yl)-2,2-dimethyltetrahydrofuro[3,4-d][1,3]dioxol-4-yl)methyl phosphate (107 mg, 59.8%) was obtained in the same manner as in Step 3 of Reference Example 6.0 using ((3aR,4R,6R,6aR)-6-(6-(biphenyl-3-yl)-9H-purin-9-yl)-2,2-dimethyltetrahydrofuro[3,4-d][1,3]dioxol-4-yl)methanol (125 mg, 0.281 mmol) obtained in Step 1.

ESI-MS (m/z): 637 (M+1)

Step 3

((2R,3S,4R,5R)-5-(6-(Biphenyl-3-yl)-9H-purin-9-yl)-3,4-dihydroxytetrahydrofuran-2-yl)methyl phosphate (Compound I-26) (47.0 mg, 61.8%) was obtained in the same manner as in Step 5 of Reference Example 1.0 using di-tert-butyl ((3aR,4R,6R,6aR)-6-(6-(biphenyl-3-yl)-9H-purin-9-yl)-2,2-dimethyltetrahydrofuro[3,4-d][1,3]dioxol-4-yl)methyl phosphate (100 mg, 0.157 mmol) obtained in Step 2.

$^1$H-NMR (DMSO-d$_6$, 300 MHz) δ: 9.14 (1H, s), 9.06 (1H, s), 8.89 (1H, s), 8.82 (1H, d, J=7.7 Hz), 7.89 (1H, d, J=7.7 Hz), 7.79-7.68 (3H, m), 7.58-7.50 (2H, m), 7.47-7.40 (1H, m), 6.15 (1H, d, J=5.5 Hz), 4.72-4.65 (1H, m), 4.27-4.22 (1H, m), 4.20-3.98 (3H, m).

ESI-MS (m/z): 485 (M+1)

Reference Example 22.1: Compound am-22

Step 1

6-(Biphenyl-3-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine (239 mg, 65.4%) was obtained in the same manner as in Step of Reference Example 22.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (300 mg, 0.554 mmol) obtained in Step 2 of Reference Example 17.1.

Steps 2 to 4

(2R,3R,4R,5R)-5-(6-(biphenyl-3-yl)-9H-purin-9-yl)-2-((bis(4-methoxy phenyl)(phenyl)methoxy)methyl)-4-(tert-butyldimethylsilyloxy)tetrahydrofuran-3-yl 2-cyanoethyl diisopropylphosphoramidite (Compound am-22) was obtained in the same manner as in Steps 3 to 5 of Reference Example 1.1 using 6-(biphenyl-3-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

$^1$H-NMR (CDCl$_3$, 400 MHz) δ: 9.05-9.05 (m, 1H), 8.94-8.92 (m, 1H), 8.82-8.80 (m, 1H), 8.36-8.35 (m, 1H), 7.77-7.74 (m, 3H), 7.65-7.63 (m, 1H), 7.49-7.47 (m, 4H), 7.38-7.36 (m, 3H), 7.30-7.21 (m, 5H), 6.83-6.81 (m, 4H), 6.17-6.12 (m, 1H), 5.14-5.13 (m, 1H), 4.45-4.41 (m, 2H), 3.99-3.97 (m, 1H), 3.77-3.77 (m, 6H), 3.66-3.57 (m, 4H), 3.37-3.35 (m, 1H), 2.66-2.65 (m, 1H), 2.32-2.31 (m, 1H), 1.27-1.06 (m, 12H), 0.86-0.76 (m, 9H), −0.04 (−0.01) (s, 3H), −0.21 (−0.19) (s, 3H).

Example 28

An siRNA having Compound I-26 as X at the 5' end of the antisense strand of 454-Xa shown in Table 38 below was synthesized in the same manner as in Example 1 using Compound am-22 obtained in Reference Example 22.1.

ESI-MS (antisense strand): theoretical value: 6827.06, actual value: 6826.60

Reference Example 23.0: Compound I-27

Step 1 ((3aR,4R,6R,6aR)-6-(6-(3-Aminophenyl)-9H-purin-9-yl)-2,2-dimethyltetrahydrofuro[3,4-d][1,3]dioxol-4-yl)methanol (77.2 mg, 65.8%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-aminophenyl)boronic acid (84 mg, 0.612 mmol).

ESI-MS (m/z): 384 (M+1)

Step 2

Di-tert-butyl ((3aR,4R,6R,6aR)-6-(6-(3-aminophenyl)-9H-purin-9-yl)-2,2-dimethyltetrahydrofuro[3,4-d][1,3]dioxol-4-yl)methyl phosphate (38.4 mg, 33.2%) was obtained in the same manner as in Step 3 of Reference Example 6.0 using ((3aR,4R,6R,6aR)-6-(6-(3-aminophenyl)-9H-purin-9-yl)-2,2-dimethyltetrahydrofuro[3,4-d][1,3]dioxol-4-yl)methanol (77.0 mg, 0.201 mmol) obtained in Step 1.

ESI-MS (m/z): 576 (M+1)

Step 3
((2R,3S,4R,5R)-5-(6-(3-Aminophenyl)-9H-purin-9-yl)-3,4-dihydroxytetrahydrofuran-2-yl)methyl phosphate (Compound I-27) (13.0 mg, 43.3%) was obtained in the same manner as in Step 5 of Reference Example 1.0 using di-tert-butyl ((3aR,4R,6R,6aR)-6-(6-(3-aminophenyl)-9H-purin-9-yl)-2,2-dimethyltetrahydrofuro[3,4-d][1,3]dioxol-4-yl)methyl phosphate (38.0 mg, 0.0660 mmol) obtained in Step 2.

$^1$H-NMR (D$_2$O, 300 MHz) δ: 8.82 (1H, s), 8.73 (1H, s), 8.22-8.15 (2H, m), 7.66-7.58 (1H, m), 7.55-7.48 (1H, m), 6.16 (1H, d, J=5.5 Hz), 4.72-4.65 (1H, m), 4.45-4.38 (1H, m), 4.35-4.26 (1H, m), 4.14-3.98 (2H, m).

ESI-MS (m/z): 424 (M+1)

Reference Example 23.1: Compound am-23

Step 1
6-(3-Aminophenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 23.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine obtained in Step 2 of Reference Example 17.1.

Steps 2 to 4
(2R,3R,4R,5R)-5-(6-(3-Aminophenyl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-23) is obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-aminophenyl)-9H-purine obtained in Step 1.

Reference Example 23.1: Compound am-23

Step 1
6-(3-aminophenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine was obtained (622 mg, 56.3%) in the same manner as in Step of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (1.00 g, 1.85 mmol) obtained in Step 2 of Reference Example 17.1 and 3-aminophenyl boronic acid.

Step 2
6-(3-aminophenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine (590 mg, 0.987 mmol) obtained in Step 1 was dissolved in DMF (10 mL). To the mixture was added N,N-dimethylformamide dimethylacetal (1.32 mL, 9.87 mmol), and the mixture was stirred for 21 hours at 60° C. Saturated sodium bicarbonate solution was added to the reaction mixture, which was then extracted with ethyl acetate, and the organic layer was washed with saturated brine and dried with anhydrous magnesium sulfate. The solvent was evaporated under reduced pressure, and the residue was purified by ethyl acetate/heptane silica gel column chromatography to obtain 9-((4aR,6R,7R,7aR)-2,2-di-tert-butyl-7-(tert-butyldimethylsilyloxy)tetrahyro-4H-furo[3,2-d][1,3,2]dioxasilin-6-yl)-6-(3-(((dimethylamino)methylene)amino)phenyl)-9H-purine (514 mg, 80.0%).

Steps 3 to 5
(2R,3R,4R,5R)-2-((bis(4-methoxyphenyl)(phenyl)methoxy)methyl)-4-(tert-buityldimethylsilyloxy)-5-(6-(3-(((dimethylamino)methylene)amino)phenyl)-9H-purin-9-yl)tetrahydrofuran-3-yl 2-cyanoethyl diisopropylphosphoramidite (Compound am-23) was obtained in the same manner as in Steps 3 to 5 of Reference Example 1.1 using 9-((4aR,6R,7R,7aR)-2,2-di-tert-butyl-7-(tert-butyldimethylsilyloxy)tetrahyro-4H-furo[3,2-d][1,3,2]dioxasilin-6-yl)-6-(3-(((dimethylamino)methylene)amino)phenyl)-9H-purine obtained in Step 2.

$^1$H-NMR (CDCl$_3$, 400 MHz) δ: 8.90, 8.88 (1H, 2s), 8.52-8.46 (1H, m), 8.36-8.29 (2H, m), 7.68 (1H, s), 7.52-7.42 (3H, m), 7.41-7.33 (4H, m), 7.32-7.14 (4H, m), 6.85-6.78 (4H, m), 6.17-6.08 (1H, m), 5.16-5.09 (1H, m), 4.49-4.35 (2H, m), 4.03-3.85 (1H, m), 3.76 (6H, s), 3.70-3.53 (4H, m), 3.38-3.27 (1H, m), 3.06 (6H, s), 2.70-2.62 (1H, m), 2.33-2.27 (1H, m), 1.24-1.02 (12H, m), 0.74, 0.72 (9H, 2s), −0.02, −0.06, −0.21, −0.23 (6H, 4 s).

Example 29-0

An siRNA having Compound I-27 at the 5' end of the antisense strand is synthesized in the same manner as in Example 1 using Compound am-23 obtained in Reference Example 23.1.

Example 29

An siRNA having Compound I-27 as X at the 5' end of the antisense strand of 454-Xa shown in Table 38 below was synthesized in the same manner as in Example 1 using Compound am-23 obtained in Reference Example 23.1. ESI-MS (antisense strand): theoretical value: 6765.98, actual value: 6766.80

Reference Example 24.0: Compound I-28

Step 1
((3aR,4R,6R,6aR)-2,2-Dimethyl-6-(6-(3-morpholinophenyl)-9H-purin-9-yl)tetrahydrofuro[3,4-d][1,3]dioxol-4-yl)methanol (127 mg, 92%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-morpholinophenyl)boronic acid (127 mg, 0.612 mmol).

ESI-MS (m/z): 454 (M+1)

Step 2
Di-tert-butyl ((3aR,4R,6R,6aR)-2,2-dimethyl-6-(6-(3-morpholinophenyl)-9H-purin-9-yl)tetrahydrofuro[3,4-d][1,3]dioxol-4-yl)m methyl phosphate (65.0 mg, 38.0%) was obtained in the same manner as in Step 3 of Reference Example 6.0 using ((3aR,4R,6R,6aR)-2,2-dimethyl-6-(6-(3-morpholinophenyl)-9H-purin-9-yl)tetrahydrofuro[3,4-d][1,3]dioxol-4-yl)methanol (120 mg, 0.265 mmol) obtained in Step 1.

ESI-MS (m/z): 646 (M+1)

Step 3
((2R,3S,4R,5R)-3,4-Dihydroxy-5-(6-(3-morpholinophenyl)-9H-purin-9-yl)tetrahydrofuran-2-yl)methyl phosphate (Compound I-28) triethylammonium salt (9.00 mg, 15.5%) was obtained in the same manner as in Step 3 of Reference Example 16.0 using di-tert-butyl ((3aR,4R,6R,6aR)-2,2-dimethyl-6-(6-(3-morpholinophenyl)-9H-purin-9-yl)tetrahydrofuro[3,4-d][1,3]dioxol-4-yl)methyl phosphate (63.0 mg, 0.0980 mmol) obtained in Step 2.

¹H-NMR (D₂O, 300 MHz) δ: 8.83 (1H, s), 8.72 (1H, s), 7.85-7.75 (2H, m), 7.52-7.44 (1H, m), 7.28-7.20 (1H, m), 6.21-6.19 (1H, m), 4.76-4.68 (1H, m), 4.45-4.40 (1H, m), 4.34-4.28 (1H, m), 4.06 (2H, s), 3.88-3.80 (4H, m), 3.23-3.15 (4H, m), 3.08 (6H, q, J=7.3 Hz), 1.16 (9H, t, J=7.3 Hz).
ESI-MS (m/z): 494 (M+1)

Reference Example 24.1: Compound am-24

Step 1
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-morpholinophenyl)-9H-purine is obtained in the same manner as in Step 1 of Reference Example 24.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine obtained in Step 2 of Reference Example 17.1.
Steps 2 to 4
(2R,3R,4R,5R)-2-((Bis(4-methoxyphenyl)(phenyl)methoxy)methyl)-4-(tert-butyldimethylsilyloxy)-5-(6-(3-morpholinophenyl)-9H-purin-9-yl)tetrahydrofuran-3-yl 2-cyanoethyl diisopropylphosphoramidite (Compound am-24) is obtained in the same manner as in Steps 3 to 5 of Reference
Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-morpholinophenyl)-9H-purine obtained in Step 1.

Example 30

An siRNA having Compound I-28 at the 5' end of the antisense strand is synthesized in the same manner as in Example 1 using Compound am-24 obtained in Reference Example 24.1.

Reference Example 25.0: Compound I-29

Step 1 ((3aR,4R,6R,6aR)-6-(6-(3-(Benzyloxy)phenyl)-9H-purin-9-yl)-2,2-dimethyltetrahydrofuro[3,4-d][1,3]dioxol-4-yl)methanol (180 mg, 130%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-(benzyloxy)phenyl)boronic acid (140 mg, 0.612 mmol).
ESI-MS (m/z): 475 (M+1)
Step 2
Di-tert-butyl ((3aR,4R,6R,6aR)-6-(6-(3-(benzyloxy)phenyl)-9H-purin-9-yl)-2,2-dimethyltetrahydrofuro[3,4-d][1,3]dioxol-4-yl)methyl phosphate (95.0 mg, 48.3%) was obtained in the same manner as in Step 3 of Reference Example 6.0 using ((3aR,4R,6R,6aR)-6-(6-(3-(benzyloxy)phenyl)-9H-purin-9-yl)-2,2-dimethyltetrahydrofuro[3,4-d][1,3]dioxol-4-yl)methanol (140 mg, 0.295 mmol) obtained in Step 1.
ESI-MS (m/z): 667 (M+1)
Step 3
((2R,3S,4R,5R)-5-(6-(3-(Benzyloxy)phenyl)-9H-purin-9-yl)-3,4-dihydroxytetrahydrofuran-2-yl)methyl phosphate (Compound I-29) triethylammonium salt (32.0 mg, 36.5%) was obtained in the same manner as in Step 3 of Reference Example 16.0 using di-tert-butyl ((3aR,4R,6R,6aR)-6-(6-(3-(benzyloxy)phenyl)-9H-purin-9-yl)-2,2-dimethyltetrahydrofuro[3,4-d][1,3]dioxol-4-yl)methyl phosphate (95.0 mg, 0.142 mmol) obtained in Step 2.
¹H-NMR (D₂O, 400 MHz) δ: 8.63 (1H, s), 8.59 (1H, s), 7.67-7.55 (2H, m), 7.30-7.16 (6H, m), 6.94-6.88 (1H, m), 6.06 (1H, d, J=5.9 Hz), 4.88 (2H, s), 4.71-4.62 (1H, m), 4.39-4.34 (1H, m), 4.28-4.22 (1H, m), 4.06-3.95 (2H, m), 3.14-2.95 (6H, q, J=7.3 Hz), 1.12 (9H, t, J=7.3 Hz).
ESI-MS (m/z): 515 (M+1)

Reference Example 25.1-A: Compound am-25

Step 1
6-(3-(Benzyloxy)phenyl)-9-((4aR,6R,7R,7aR)-2,2-di-tert-butyl-7-(ter t-butyldimethylsilyloxy)tetrahydro-4H-furo[3,2-d][1,3,2]dioxasilin-6-yl)-9H-purine is obtained in the same manner as in Step 1 of Reference
Example 25.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine obtained in Step 2 of Reference Example 17.1.
Steps 2 to 4
(2R,3R,4R,5R)-5-(6-(3-(Benzyloxy)phenyl-9H-purin-9-yl)-2-((bis(4-methoxyphenyl) (phenyl)methoxy)methyl)-4-(tert-butyldimethylsilyloxy)tetrahydrofuran-3-yl 2-cyanoethyl diisopropylphosphoramidite (Compound am-25) is obtained in the same manner as in Steps 3 to 5 of Reference
Example 1.1 using 6-(3-(benzyloxy)phenyl)-9-((4aR,6R,7R,7aR)-2,2-di-tert-butyl-7-(ter t-butyldimethylsilyloxy)tetrahydro-4H-furo[3,2-d][1,3,2]dioxasilin-6-yl)-9H-purine obtained in Step 1.

Reference Example 25.1: Compound am-25

Step 1
6-(3-(benzyloxy)phenyl)-9-((4aR,6R,7R,7aR)-2,2-di-tert-butyl-7-(ter t-butyldimethylsilyloxy)tetrahydro-4H-furo[3,2-d][1,3,2]dioxasilin-6-yl)-9H-purine was obtained (284 mg, 74.4%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (300 mg, 0.554 mmol) obtained in Step 2 of Reference Example 17.1 and 3-benzyloxyphenylboronic acid.
Steps 2 to 4
(2R,3R,4R,5R)-5-(6-(3-(benzyloxy)phenyl-9H-purin-9-yl)-2-((bis(4-methoxyphenyl) (phenyl)methoxy)methyl)-4-(tert-butyldimethylsilyloxy)tetrahydrofuran-3-yl 2-cyanoethyl diisopropylphosphoramidite was obtained (0.35 g, 98%) in the same manner as in Steps 3 to 5 of Reference
Example 1.1 using 6-(3-(benzyloxy)phenyl)-9-((4aR,6R,7R,7aR)-2,2-di-tert-butyl-7-(ter t-butyldimethylsilyloxy)tetrahydro-4H-furo[3,2-d][1,3,2]dioxasilin-6-yl)-9H-purine obtained in Step 1.
¹H-NMR (CDCl₃, 400 MHz) δ: 8.91-8.90 (1H, m), 8.49-8.45 (2H, m), 8.35-8.34 (1H, m), 7.50-7.47 (5H, m), 7.40-7.20 (10H, m), 7.16-7.14 (1H, m), 6.83-6.81 (4H, m), 6.16-6.11 (1H, m), 5.21 (2H, s), 5.13-5.11 (1H, m), 4.44-4.41 (2H, m), 3.99-3.31 (12H, m), 2.69-2.29 (2H, m), 1.22-1.05 (12H, m), 0.82-0.77 (9H, m), −0.04--0.04 (3H, m), −0.12--0.21 (3H, m).

Example 31-0

An siRNA having Compound I-29 at the 5' end of the antisense strand is synthesized in the same manner as in Example 1 using Compound am-25 obtained in Reference Example 25.1.

Example 31

An siRNA (referred to as 6-(3-benzyloxy)phenyl-Pu) having Compound I-29 as X at the 5' end of the antisense strand of 454-Xa shown in Table 38 below was synthesized in the same manner as in Example 1 using Compound am-25 obtained in Reference Example 25.1.

ESI-MS (antisense strand): theoretical value: 6857.09, actual value: 6857.18

Reference Example 26.0: Compound I-30

Step 1
((3aR,4R,6R,6aR)-6-(6-(3-(Methoxycarbonyl)phenyl)-9H-purin-9-yl)-2, 2-dimethyltetrahydrofuro[3,4-d][1,3]dioxol-4-yl)methanol (160 mg, 123%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-(methoxycarbonyl)phenyl)boronic acid (110 mg, 0.612 mmol).

ESI-MS (m/z): 427 (M+1)

Step 2
Di-tert-butyl ((3aR,4R,6R,6aR)-6-(6-(3-(methoxycarbonyl)phenyl)-9H-purin-9-yl)-2, 2-dimethyltetrahydrofuro[3,4-d][1,3]dioxol-4-yl)methyl phosphate (100 mg, 53.0%) was obtained in the same manner as in Step 3 of Reference Example 6.0 using ((3aR,4R,6R,6aR)-6-(6-(3-(methoxycarbonyl)phenyl)-9H-purin-9-yl)-2, 2-dimethyltetrahydrofuro[3,4-d][1,3]dioxol-4-yl)methanol (130 mg, 0.305 mmol) obtained in Step 1.

ESI-MS (m/z): 619 (M+1)

Step 3
((2R,3S,4R,5R)-5-(6-(3-(Methoxycarbonyl)phenyl)-9H-purin-9-yl)-3,4-dihydroxytetrahydrofuran-2-yl)methyl phosphate (45.0 mg, 87.0%) was obtained in the same manner as in Step 5 of Reference Example 1.0 using di-tert-butyl ((3aR,4R,6R,6aR)-6-(6-(3-(methoxycarbonyl)phenyl)-9H-purin-9-yl)-2, 2-dimethyltetrahydrofuro[3,4-d][1,3]dioxol-4-yl)methyl phosphate (68.7 mg, 0.111 mmol) obtained in Step 2.

ESI-MS (m/z): 467 (M+1)

Step 4
((2R,3S,4R,5R)-5-(6-(3-(Methoxycarbonyl)phenyl)-9H-purin-9-yl)-3,4-dihydroxytetrahydrofuran-2-yl)methyl phosphate (20.0 mg, 0.0430 mmol) obtained in Step 3 was dissolved in a 1 N aqueous sodium hydroxide solution (2 mL), and the mixture was stirred at room temperature for 2 hours.

Acetic acid-triethylamine buffer (pH 6.5) was added thereto, and the residue obtained by evaporating the solvent under reduced pressure was purified by preparative HPLC (eluent: a 0.01 mmol/L aqueous ammonium acetate solution/methanol) to obtain ((2R,3S,4R,5R)-5-(6-(3-(carboxy)phenyl)-9H-purin-9-yl)-3,4-dihydroxytetrahydrofuran-2-yl)methyl phosphate (Compound I-30) triethylammonium salt (10.0 mg, 42.1%) was obtained.

$^1$H-NMR (D$_2$O, 300 MHz) δ: 8.88-8.53 (3H, m), 8.34-8.22 (1H, m), 8.03-7.92 (1H, m), 7.60-7.48 (1H, m), 6.22-6.15 (1H, m), 4.76-4.65 (1H, m), 4.47-4.42 (1H, m), 4.35-4.30 (1H, m), 4.15-4.00 (2H, m), 3.09 (6H, q, J=7.2 Hz), 1.16 (9H, t, J=7.3 Hz).

ESI-MS (m/z): 453 (M+1)

Reference Example 26.1: Compound am-26

Step 1
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-methoxycarbonyl)-9H-purine is obtained in the same manner as in Step 1 of Reference Example 26.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine obtained in Step 2 of Reference Example 17.1.

Step 2
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-carboxyl)-9H-purine is obtained in the same manner as in Step 4 of Reference Example 26.0 using 9-((4aR, 6R,7R,7aS)-2,2-di-tert-butyl-7-(tert-butyldimethylsilyloxy)tetrahydro-4H-furo[3,2-d][1,3,2]dioxasilin-6-yl)-6-(3-methoxycarbonyl)-9H-purine obtained in Step 1.

Steps 3 to 5
(2R,3R,4R,5R)-2-((Bis(4-methoxyphenyl)(phenyl)methoxy)methyl)-4-(tert-butyldimethylsilyloxy)-5-(6-(3-carboxylphenyl)-9H-purin-9-yl)tetrahydrofuran-3-yl 2-cyanoethyl diisopropylphosphoramidite (Compound am-26) is obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-carboxyl)-9H-purine obtained in Step 2.

Reference Example 26.1: Compound am-26

Step 1
9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-methoxycarbonyl)-9H-purine was obtained (0.578 g, 81%) in the same manner as in Step of Reference Example 26.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (0.600 g, 1.11 mmol) obtained in Step 2 of Reference Example 17.1.

Step 2
3-(9-((4aR,6R,7R,7aS)-2,2-di-tert-butyl-7-((tert-butyldimethylsilyl)oxy)tetrahydro-4H-furo[3,2-d][1,3,2]dioxasilin-6-yl)-9H-purin-6-yl)benzoic acid was obtained (0.505 g, 89%) in the same manner as in Step of Reference Example 26.0 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-methoxycarbonyl)-9H-purine (0.578 g, 0.902 mmol) obtained in Step 1.

Step 3
3-(9-((4aR,6R,7R,7aS)-2,2-di-tert-butyl-7-((tert-butyldimethylsilyl) oxy)tetrahydro-4H-furo[3,2-d][1,3,2]dioxasilin-6-yl)-9H-purin-6-yl)benzoic acid (0.897 g, 1.43 mmol) obtained in Step 2 was dissolved in DMF (10 mL). To the mixture were added 3-hydroxypropanenitrile (0.291 mL, 4.29 mmol), 1-(3-dimethylaminopropyl)-3-ethylcarbodiimide hydrochloride (0.411 g, 2.15 mmol), 1-hydroxybenzotriazole hydrate (0.329 g, 2.15 mmol) and diisopropylethylamine (0.750 mL, 4.29 mmol), and the mixture was stirred overnight at room temperature. Saturated sodium bicarbonate solution was added to the reaction solution, which was then extracted twice with ethyl acetate. The organic layer was washed with saturated brine and dried with anhydrous sodium sulfate, and the solvent was evaporated under reduced pressure. The residue obtained was purified by hexane/ethyl acetate silica gel column chromatography to obtain 2-cyanoethyl 3-(9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-9H-purin-6-yl)benzoate (0.373 g, 38%).

Steps 4 to 6

2-Cyanoethyl 3-(9-((2R,3R,4R,5R)-5-((bis(4-methoxyphenyl)(phenyl)methoxy)methyl)-3-((tert-butyldimethylsilyl)oxy)tetrahydrofuran-2-yl)-9H-purin-6-yl benzoate (Compound am-26) was obtained in the same manner as in Steps to 5 of Reference Example 1.1 using 2-cyanoethyl 3-(9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-9H-purin-6-yl)benzoate obtained in Step 3.

Example 32-0

An siRNA having Compound I-30 at the 5' end of the antisense strand is synthesized in the same manner as in Example 1 using Compound am-26 obtained in Reference Example 26.1.

Example 32

An siRNA (referred to as 6-(3-carboxy)phenyl-Pu) having Compound I-30 as X at the 5' end of the antisense strand of 454-Xa shown in Table 38 below was synthesized in the same manner as in Example 1-1 using Compound am-26 obtained in Reference Example 26.1.

ESI-MS (antisense strand): theoretical value: 6794.98, actual value: 6792.84

Reference Example 27.0: Compound I-31

Step 1

1-((3aR,4R,6R,6aR)-6-(Hydroxymethyl)-2,2-dimethyltetrahydrofuro[3,4-d][1,3]dioxol-4-yl)-5-styrylpyrimidine-2,4(1H,3H)-dione (43.8 mg, 41%) was obtained in the same manner as in Step 2 of Reference Example 6.0 using 5-bromo-1-H2R,3R,4S,5R)-3,4-dihydroxy-5-(hydroxymethyl)tetrahydrofuran-2-yl)pyrimidine-2,4(1H,3H)-dione (100 mg, 0.275 mmol) obtained in Step 1 of Reference Example 10.0.

ESI-MS (m/z): 385 (M−1)

Step 2

1-((3aR,4R,6R,6aR)-6-(Hydroxymethyl)-2,2-dimethyltetrahydrofuro[3,4-d][1,3]dioxol-4-yl)-5-styrylpyrimidine-2,4(1H,3H)-dione (16.3 mg, 0.042 mmol) obtained in Step 1 was dissolved in dichloromethane (2 mL), and 1H-tetrazole (7.39 mg, 0.105 mmol) and di-tert-butyl diisopropylphosphoramide (0.028 mL, 0.084 mmol) were added thereto, and the mixture was stirred at room temperature for 2 hours. After the reaction solution was cooled to 0° C., (2R,8aS)-(+)-(camphorylsulfonyl)oxaziridine (19.4 mg, 0.084 mmol) was added thereto, and the mixture was further stirred at 0° C. for 30 minutes. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue was purified by column chromatography (heptane/ethyl acetate) to obtain di-tert-butyl ((3aR,4R,6R,6aR)-6-(2,4-dioxo-5-styryl-3,4-dihydropyrimidin-1(2H)-yl)-2,2-dimethyltetrahydrofuro[3,4-d][1,3]dioxol-4-yl)methyl phosphate (10.0 mg, 41%).

ESI-MS (m/z): 577 (M−1)

Step 3

((2R,3S,4R,5R)-5-(2,4-Dioxo-5-styryl-3,4-dihydropyrimidin-1(2H)-yl)-3,4-dihydroxytetrahydrofuran-2-yl) methyl phosphate (Compound I-31) triethylammonium salt (9.30 mg, 102%) was obtained in the same manner as in Step 5 of Reference Example 1.0 using di-tert-butyl ((3aR,4R,6R,6aR)-6-(2,4-dioxo-5-styryl-3,4-dihydropyrimidin-1 (2H)-yl)-2,2-dimethyltetrahydrofuro[3,4-d][1,3]dioxol-4-yl)methyl phosphate (10.0 mg, 0.017 mmol) obtained in Step 2.

$^1$H-NMR (D$_2$O, 300 MHz) δ: 7.96 (s, 1H), 7.49 (d, J=7.3 Hz, 2H), 7.37-7.19 (m, 3H), 6.88 (d, J=16.5 Hz, 1H), 5.91 (d, J=5.1 Hz, 1H), 4.32 (t, J=5.1 Hz, 1H), 4.26 (t, J=4.8 Hz, 1H), 4.21-4.20 (m, 1H), 4.11-3.99 (m, 2H), 3.09 (q, J=7.3 Hz, 6H), 1.16 (t, J=7.3 Hz, 9H). ESI-MS (m/z): 425 (M−1)

Reference Example 27.1: Compound am-27

Step 1

1-((4aR,6R,7R,7aR)-2,2-Di-tert-butyl-7-((tert-butyldimethylsilyl)ox y)tetrahydro-4H-furo[3,2-d][1,3,2]dioxasilin-6-yl)-5-styrylpyrimidine-2,4(1H,3H)-dione is obtained in the same manner as in Step 1 of Reference Example 27.0 using 5-bromo-1-((4aR,6R,7R,7aR)-2,2-di-tert-butyl-7-((tert-butyldimethyl silyl)oxy)tetrahydro-4H-furo[3,2-d][1, 3,2]dioxasilin-6-yl)pyrimidine-2,4(1H,3H)-dione obtained in Step 2 of Reference Example 13.1.

Step 2

(2R,3R,4R,5R)-2-((Bis(4-methoxyphenyl)(phenyl) methoxy)methyl)-4-((tert-butyldimethylsilyl)oxy)-5-(2,4-dioxo-5-styryl-3,4-dihydropyrimidin-1(2H)-yl)tetrahydrofuran-3-yl (2-cyanoethyl) diisopropylphosphoramidite is obtained in the same manner as in Steps to 5 of Reference Example 1.1 using 1-((4aR,6R,7R,7aR)-2,2-di-tert-butyl-7-((tert-butyldimethylsilyl)ox y)tetrahydro-4H-furo[3,2-d][1, 3,2]dioxasilin-6-yl)-5-styrylpyrimidine-2,4(1H,3H)-dione obtained in Step 1.

Example 33

An siRNA having Compound I-31 at the 5' end of the antisense strand is synthesized in the same manner as in Example 1 using Compound am-27 obtained in Reference Example 27.1.

Reference Example 28.1: Compound am-28

Step 1

Commercially available (2R,3R,4S,5R)-2-(6-chloro-9H-purin-9-yl)-5-(hydroxymethyl)tetrahydrofuran-3,4-diol (5.00 g, 17.4 mmol) was dissolved in pyridine (42 mL), and 1,3-dichloro-1,1,3,3-tetraisopropyldisiloxane (6.70 ml, 20.9 mmol) was added thereto, and the mixture was stirred at room temperature for 2 hours. To the reaction solution, water was added, and the mixture was extracted with ethyl acetate. The organic layer was washed with saturated brine and dried over sodium sulfate. The residue obtained by evaporating the solvent under reduced pressure was purified by column chromatography (hexane/ethyl acetate) to obtain (6aR,8R,9R,9aS)-8-(6-chloro-9H-purin-9-yl)-2,2,4,4-tetraisopropyltetrahydro-6H-furo[3,2-f][1,3,5,2,4]trioxadisilocin-9-ol (8.64 g, yield: 94%).

ESI-MS (m/z): 530 (M+1)

Step 2

(6aR,8R,9R,9aS)-2,2,4,4-Tetraisopropyl-8-(6-((E)-styryl)-9H-purin-9-yl)tetrahydro-6H-furo[3,2-f][1,3,5,2,4] trioxadisilocin-9-ol (4.77 g, yield: 65%) was obtained in the same manner as in Step 2 of Reference Example 6.0 using (6aR,8R,9R,9aS)-8-(6-chloro-9H-purin-9-yl)-2,2,4,4-tetraisopropyltetrahydro-6H-furo[3,2-f][1,3,5,2,4]trioxadisilocin-9-ol (6.50 g, 12.3 mmol) obtained in Step 1.
ESI-MS (m/z): 598 (M+1)
Step 3
(6aR,8R,9R,9aS)-2,2,4,4-Tetraisopropyl-8-(6-((E)-styryl)-9H-purin-9-yl)tetrahydro-6H-furo[3,2-f][1,3,5,2,4]trioxadisilocin-9-ol (4.50 g, 7.54 mmol) obtained in Step 2 was dissolved in N,N-dimethylformamide (50 mL), and 60% sodium hydride (302 mg, 7.54 mmol) and methyl iodide (0.471 mL, 7.54 mmol) were added thereto at 0° C., and the mixture was stirred at room temperature for 2 hours. To the reaction solution, water was added, and the mixture was extracted with ethyl acetate. The organic layer was washed with saturated brine and dried over sodium sulfate. The residue obtained by evaporating the solvent under reduced pressure was purified by column chromatography (hexane/ethyl acetate) to obtain 6-((E)-styryl)-9-((6aR,8R,9R,9aR)-2,2,4,4-tetraisopropyl-9-methoxytetrahydro-6H-furo[3,2-f][1,3,5,2,4]trioxadisilocin-8-yl)-9H-purine (2.09 g, yield: 45%).
ESI-MS (m/z): 612 (M+1)
Step 4
6-((E)-styryl)-9-((6aR,8R,9R,9aR)-2,2,4,4-Tetraisopropyl-9-methoxytetrahydro-6H-furo[3,2-f][1,3,5,2,4]trioxadisilocin-8-yl)-9H-purine (569 mg, 0.931 mmol) obtained in Step 3 was dissolved in tetrahydrofuran (10 mL), and acetic acid (0.117 mL, 2.049 mmol) and a solution of tetrabutylammonium fluoride in tetrahydrofuran (1 mol/L, 2.05 ml, 2.05 mmol) were added thereto, and the mixture was stirred at room temperature for 30 minutes. The reaction solution was concentrated under reduced pressure, and the residue was purified by column chromatography (chloroform/methanol) to obtain (2R,3S,4R,5R)-2-(hydroxymethyl)-4-methoxy-5-(6-((E)styryl)-9H-purin-9-yl)tetrahydrofuran-3-ol (341 mf, yield: 99%).
$^1$H-NMR (CDCl$_3$, 500 MHz) δ: 8.90 (s, 1H), 8.43 (d, J=16.7 Hz, 1H), 8.13 (s, 1H), 7.68-7.75 (m, 3H), 7.37-7.47 (m, 3H), 6.17 (dd, J=2.2, 11.9 Hz, 1H), 5.95 (d, J=7.0 Hz, 1H), 4.77 (dd, J=4.7, 7.4 Hz 1H), 4.61 (d, J=4.4 Hz, 1H)), 4.39-4.41 (m, 1H), 3.99-4.02 (m, 1H), 3.78-3.83 (m, 1H), 3.37 (s, 3H), 2.67 (s, 1H).
ESI-MS (m/z): 369 (M+1)
Step 5
(2R,3R,4R,5R)-2-((Bis(4-methoxyphenyl)(phenyl)methoxy)methyl)-4-met boxy-5-(6-((E)styryl)-9H-purin-9-yl)tetrahydrofuran-3-yl (2-cyanoethyl) diisopropylphosphoramidite (Compound am-28) was obtained in the same manner as in Reference Example 1.1 using ((2R,3S,4R,5R)-2-(hydroxymethyl)-4-methoxy-5-(6-((E)styryl)-9H-purin-9-yl)tetrahydrofuran-3-ol obtained in Step 4. This Compound was used in the subsequent Step without purification.

Example 34

An siRNA (referred to as 2'-OMe-6-styryl-dA) having Compound I-32 as X at the 5' end of the antisense strand of 454-Xa shown in Table 38 below was synthesized in the same manner as in Example 1 using Compound am-28 obtained in Reference Example 28.1.
ESI-MS (m/z): theoretical value: 6792.04 actual value: 6792.18

Reference Example 29.0: Compound I-33

((2R,3S,4R,5R)-3,4-Dihydroxy-5-(5-methyl-2,4-dioxo-3,4-dihydropyrimidin-1(2H)-yl)tetrahydrofuran-2-yl)methyl phosphate (Compound I-33) was obtained in the same manner as in Reference Example 1.0 using commercially available 5-methylpyrimidine-2,4(1H,3H)-dione.
$^1$H-NMR (D$_2$O, 300 MHz) δ: 7.67 (s, 1H), 5.86 (d, J=5.5 Hz, 1H), 4.23 (dt, J=12.8, 4.9 Hz, 2H), 4.13 (dt, J=6.0, 2.6 Hz, 1H), 4.02-3.89 (m, 2H), 1.80 (s, 3H).
ESI-MS (m/z): 337 (M−1)

Reference Example 29.1: Compound am-29

Step 1 (2R,3R,4R,5R)-2-((Bis(4-methoxyphenyl)(phenyl)methoxy)methyl)-4-((tert-butyldimethylsilyl)oxy)-5-(5-methyl-2,4-dioxo-3,4-dihydropyrimidin-1(2H)-yl)tetrahydrofuran-3-yl (2-cyanoethyl) diisopropylphosphoramidite is obtained in the same manner as in Reference Example 1.1 using commercially available 5-methylpyrimidine-2,4(1H,3H)-dione.

Example 35

An siRNA having Compound I-33 at the 5' end of the antisense strand is synthesized in the same manner as in Example 1 using Compound am-29 obtained in Reference Example 29.1.

Reference Example 30.0: Compound I-34

((2R,3S,4R,5R)-3,4-Dihydroxy-5-(6-methyl-2,4-dioxo-3,4-dihydropyrimidin-1(2H)-yl)tetrahydrofuran-2-yl)methyl phosphate (Compound I-34) was obtained in the same manner as in Reference Example 1.0 using commercially available 6-methylpyrimidine-2,4(1H,3H)-dione.
$^1$H-NMR (D$_2$O, 300 MHz) δ: 5.63 (s, 1H), 5.56 (d, J=2.9 Hz, 1H), 4.31 (t, J=6.6 Hz, 1H), 4.05-3.90 (m, 4H), 2.27 (s, 3H), 1.95 (s, 1H).
ESI-MS (m/z): 337 (M−1)

Reference Example 30.1: Compound am-30

(2R,3R,4R,5R)-2-((Bis(4-methoxyphenyl)(phenyl)methoxy)methyl)-4-((tert-butyldimethylsilyl)oxy)-5-(6-methyl-2,4-dioxo-3,4-dihydropyrimidin-1(2H)-yl)tetrahydrofuran-3-yl (2-cyanoethyl) diisopropylphosphoramidite (Compound am-30) was obtained in the same manner as in Reference Example 1.1 using commercially available 6-methylpyrimidine-2,4(1H,3H)-dione.
$^1$H-NMR (CDCl$_3$, 500 MHz) δ: 7.80 (m, 1H), 7.48-6.78 (m, 13H), 5.55 (s, 1H), 5.50 (m, 1H), 5.10 (m, 1H), 4.31-4.18 (m, 2H), 3.93-3.22 (m, 12H), 2.66-2.28 (m, 5H), 1.18-1.05 (m, 12H), 0.87 (0.86) (s, 9H), 0.07 (0.06) (s, 3H), 0.00 (−0.01) (s, 3H).

Example 36

An siRNA (referred to as 6-Me-dU) having Compound I-34 as X at the 5' end of the antisense strand of 454-Xu shown in Table 38 below was synthesized in the same manner as in Example 1 using Compound am-30 obtained in Reference Example 30.1.
MALDI-TOF/MS (antisense strand): theoretical value: 6680.87 (M−H), actual value: 6681.08

Reference Example 31.0: Compound I-35

Step 1
(2R,3R,4R,5R)-2-(Benzoyloxymethyl)-5-(7-chloro-6-nitro-2,4-dioxo-3, 4-dihydroquinazolin-1(2H)-yl)tetrahydrofuran-3,4-diyl dibenzoate (0.292 g, 34%) was obtained in the same manner as in Step 1 of Reference Example 1.0 using 7-chloro-6-nitroquinazoline-2,4(1H,3H)-dione (0.626 g, 1.24 mmol) synthesized according to the method described in the known method (Organic Process Research & Development, 2001, vol. 5, pp. 426-433).

ESI-MS (m/z): 684 (M−1)

Step 2

7-Chloro-1-(2R,3R,4S,5R)-3,4-dihydroxy-5-(hydroxymethyl)tetrahydrofuran-2-yl)-6-nitroquinazoline-2,4(1H,3H)-dione (1.26 g, 77%) was obtained in the same manner as in Step 2 of Reference Example 7.0 using (2R,3R,4R,5R)-2-(benzoyloxymethyl)-5-(7-chloro-6-nitro-2,4-dioxo-3, 4-dihydroquinazolin-1 (2H)-yl)tetrahydrofuran-3,4-diyl dibenzoate (3.00 g, 4.37 mmol) obtained in Step 1.

ESI-MS (m/z): 372 (M−1)

Step 3

Di-tert-butyl ((3aR,4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate was obtained in the same manner as in Steps 3 to 4 of Reference Example 7.0 using 7-chloro-1-(2R,3R,4S,5R)-3,4-dihydroxy-5-(hydroxymethyl)tetrahydrofuran-2-yl)-6-nitroquinazoline-2,4(1H,3H)-dione obtained in Step 2.

ESI-MS (m/z): 604 (M−1)

Step 4

((2R,3S,4R,5R)-5-(7-Chloro-6-nitro-2,4-dioxo-3,4-dihydroquinazolin-1(2H)-yl)-3,4-dihydroxytetrahydrofuran-2-yl)methyl phosphate (Compound I-35) triethylammonium salt (20.0 mg, 67%) was obtained in the same manner as in Step 5 of Reference Example 1.0 using di-tert-butyl ((3aR, 4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate (32.5 mg, 0.054 mmol) obtained in Step 3. $^1$H-NMR (D$_2$O, 300 MHz) δ: 8.67 (s, 1H), 7.87 (s, 1H), 6.08 (d, J=4.8 Hz, 1H), 4.77 (dd, J=6.6, 4.8 Hz, 1H), 4.42 (t, J=6.4 Hz, 1H), 4.08-3.99 (m, 4H), 3.09 (q, J=7.3 Hz, 6H), 1.17 (t, J=7.3 Hz, 9H).

ESI-MS (m/z): 452 (M−1)

Reference Example 31.1: Compound am-31

Step 1

7-Chloro-1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-nitro quinazoline)-2,4(1H,3H)-dione is obtained in the same manner as in Steps to 2 of Reference Example 1.1 using 7-chloro-1-(2R,3R,4S,5R)-3,4-dihydroxy-5-(hydroxymethyl)tetrahydrofuran-2-yl)-6-nitroquinazoline-2,4(1H,3H)-dione obtained in Step 2 of Reference Example 31.0.

Step 2

((2R,3R,4R,5R)-2-((Bis(4-methoxyphenyl)(phenyl) methoxy)methyl)-4-((tert-butyldimethylsilyl)oxy)-5-(7-chloro-6-nitro-2,4-dioxo-3,4-dihydroquinazolin-1(2H)-yl) tetrahydrofuran-3-yl (2-cyanoethyl) diisopropylphosphoramidite (Compound am-31) is obtained in the same manner as in Steps 3 to 5 of Reference Example 1.1 using 7-chloro-1-((4aR,6R,7R,7aR)-2,2-di-tert-butyl-7-((tert-butyldimethylsilyl)oxy)tetrahydro-4H-furo[3,2-d][1, 3,2]dioxasilin-6-yl)-6-nitro quinazoline)-2,4(1H,3H)-dione obtained in Step 1 of Reference Example 31.1.

Example 37

An siRNA having Compound I-35 at the 5' end of the antisense strand is synthesized in the same manner as in Example 1 using Compound am-31 obtained in Reference Example 31.1.

Reference Example 32.0: Compound I-36

Step 1

Di-tert-butyl ((3aR,4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate (20.0 mg, 0.033 mmol) obtained in Step 3 of Reference Example 10.0 was dissolved in THF (1 mL), and a dimethylamine/THF solution (1 mL, 2.00 mmol) was added thereto, and the mixture was stirred at room temperature for 30 minutes. After the solvent was evaporated under reduced pressure, the residue was purified by preparative thin-layer chromatography (heptane/ethyl acetate=25/75) to obtain di-tert-butyl ((3aR,4R,6R,6aR)-6-(7-(dimethylamino)-6-nitro-2,4-dioxo-3,4-dihydro quinazolin-1(2H)-yl)-2,2-dimethyltetrahydrofuro[3,4-d][1,3]dioxol-4-yl)methyl (14.4 mg, 71%).

ESI-MS (m/z): 613 (M−1)

Step 2

((2R,3S,4R,5R)-5-(7-(Dimethylamino)-6-nitro-2,4-dioxo-3,4-dihydroquinazolin-1(2H)-yl)-3,4-dihydroxytetrahydrofuran-2-yl)methyl phosphate (Compound I-36) triethylammonium salt (12.5 mg, 62%) was obtained in the same manner as in Step 5 of Reference Example 1.0 using di-tert-butyl ((3aR,4R,6R,6aR)-6-(7-(dimethylamino)-6-nitro-2,4-dioxo-3,4-dihydro quinazolin-1(2H)-yl)-2,2-dimethyltetrahydrofuro[3,4-d][1,3]dioxol-4-yl)methyl (22.0 mg, 0.036 mmol) obtained in Step 1.

ESI-MS (m/z): 461 (M−1)

$^1$H-NMR (D$_2$O, 300 MHz) δ: 8.46 (s, 1H), 6.75 (s, 1H), 6.05 (d, J=4.4 Hz, 1H), 4.79 (dd, J=6.6, 4.0 Hz, 1H), 4.38 (t, J=7.0 Hz, 1H), 4.11-3.98 (m, 4H), 3.09 (q, J=7.3 Hz, 6H), 2.92 (s, 6H), 1.17 (t, J=7.3 Hz, 9H).

Reference Example 32.1: Compound am-32

Step 1

1-((4aR,6R,7R,7aR)-2,2-Di-tert-butyl-7-((tert-butyldimethylsilyl)ox y)tetrahydro-4H-furo[3,2-d][1,3,2]dioxasilin-6-yl)-7-(dimethylamino)-6-nitroquinazoline)-2,4(1H,3H)-dione is obtained in the same manner as in Step 1 of Reference Example 32.0 using 7-chloro-1-((4aR,6R,7R,7aR)-2,2-di-tert-butyl-7-((tert-butyldimethylsilyl)oxy)tetrahydro-4H-furo[3,2-d][1,3,2]dioxasilin-6-nitroquinazoline)-2,4(1H,3H)-dione obtained in Step 1 of Reference Example 31.1.

Step 2

((2R,3R,4R,5R)-2-((Bis(4-methoxyphenyl)(phenyl) methoxy)methyl)-4-((tert-butyldimethylsilyl)oxy)-5-(7-(dimethylamino)-6-nitro-2,4-dioxo-3,4-dihydroquinazolin-1 (2H)-yl)tetrahydrofuran-3-yl (2-cyanoethyl) diisopropylphosphoramidite (Compound am-32) is obtained in the same manner as in Steps 3 to 5 of Reference Example 1.1 using 1-((4aR,6R,7R,7aR)-2,2-di-tert-butyl-7-((tert-butyldimethylsilyl)ox y)tetrahydro-4H-furo[3,2-d][1,3,2]dioxasilin-6-yl)-7-(dimethylamino)-6-nitroquinazoline)-2,4(1H, 3H)-dione obtained in Step 1.

Example 38

An siRNA having Compound I-36 at the 5' end of the antisense strand is synthesized in the same manner as in Example 1 using Compound am-32 obtained in Reference Example 32.1.

Reference Example 33.0: Compound I-37

Step 1

1-(2R,3R,4S,5R)-3,4-Dihydroxy-5-(hydroxymethyl)tetrahydrofuran-2-yl)-7-(methylamino)-6-nitroquinazoline 2,4(1H,3H)-dione (110 mg, 71%) was obtained in the same manner as in Step 2 of Reference Example 1.0 using (2R,3R,4R,5R)-2-(benzoyloxymethyl)-5-(7-chloro-6-nitro-2,4-dioxo-3, 4-dihydroquinazolin-1(2H)-yl)tetrahydrofuran-3,4-diyl dibenzoate (292 mg, 0.426 mmol) obtained in Step 1 of Reference Example 31.0.

ESI-MS (m/z): 367 (M−1)

Step 2

((2R,3S,4R,5R)-3,4-Dihydroxy-5-(7-(methylamino)-6-nitro-2,4-dioxo-3,4-dihydroquinazolin-1(2H)-yl)tetrahydrofuran-2-yl)methyl phosphate (Compound I-37) triethylammonium salt was obtained in the same manner as in Steps 3 to 5 of Reference Example 1.0 using 1-(2R,3R,4S,5R)-3,4-dihydroxy-5-(hydroxymethyl)tetrahydrofuran-2-yl)-7-(methylamino)-6-nitroquinazoline-2,4(1H,3H)-dione obtained in Step 1.

ESI-MS (m/z): 447 (M−1)

$^1$H-NMR (D$_2$O, 300 MHz) δ: 8.67 (s, 1H), 6.48 (s, 1H), 6.02 (d, J=4.0 Hz, 1H), 4.78 (dd, J=6.6, 4.0 Hz, 1H), 4.37 (t, J=7.0 Hz, 1H), 4.12 (dt, J=13.9, 5.6 Hz, 1H), 4.03-3.97 (m, 2H), 2.97 (s, 3H) (Amine and amide protons are not observed.).

Reference Example 33.1: Compound am-33

(2R,3R,4R,5R)-2-((Bis(4-methoxyphenyl)(phenyl) methoxy)methyl)-4-((tert-butyldimethylsilyl)oxy)-5-(7-(methylamino)-6-nitro-2,4-dioxo-3, 4-dihydroquinazolin-1 (2H)-yl)tetrahydrofuran-3-yl (2-cyanoethyl) diisopropylphosphoramidite (Compound am-33) was obtained in the same manner as in Reference Example 1.1 using 1-(2R,3R,4S,5R)-3,4-dihydroxy-5-(hydroxymethyl) tetrahydrofuran-2-yl-7-(methylamino)-6-nitroquinazoline-2,4 (1H,3H)-dione obtained in Step 1 of Reference Example 33.0.

$^1$H-NMR (CDCl$_3$, 500 MHz) δ: 9.03 (s, 1H), 8.40 (m, 1H), 7.88 (m, 1H), 7.48-6.73 (m, 13H), 6.64 (s, 1H), 5.88 (m, 1H), 5.13 (5.16) (m, 1H), 4.50-4.29 (m, 2H), 3.93-3.25 (m, 12H), 3.00 (2.96) (d, J=5.1 Hz, 3H), 2.60 (2.32) (m, 2H), 1.20-1.05 (m, 12H), 0.85 (0.82) (s, 9H), 0.07 (0.05) (s, 3H), −0.05 (−0.06) (s, 3H).

Example 39

An siRNA (referred to as 6-NO2,7-Me-dQu) having Compound I-37 as X at the 5' end of the antisense strand of 454-Xu shown in Table 38 below was synthesized in the same manner as in Example 1 using Compound am-33 obtained in Reference Example 33.1.

MALDI-TOF/MS (antisense strand): theoretical value: 6790.94 (M-H), actual value: 6794.76

Reference Example 34.0: Compound I-38

Step 1

((3aR,4R,6R,6aR)-6-(6-(3-Chlorostyryl)-9H-purin-9-yl)-2,2-dimethyltetrahydrofuro[3,4-d][1,3]dioxol-4-yl)methanol (118 mg, 90%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (E)-2-(3-chlorostyryl)-4,4,5,5-tetramethyl-dioxaborolane 1,3,2-(81.0 mg, 0.306 mmol).

ESI-MS (m/z): 429 (M+1) Step 2

Di-tert-butyl ((3aR,4R,6R,6aR)-6-(6-(3-chlorostyryl)-9H-purin-9-yl)-2,2-dimethyltetrahydrofuro[3,4-d][1,3]dioxol-4-yl)methyl phosphate (107 mg, 59.8%) was obtained in the same manner as in Step 3 of Reference Example 6.0 using ((3aR,4R,6R,6aR)-6-(6-(3-chlorostyryl)-9H-purin-9-yl)-2,2-dimethyltetrahydrofuro[3,4-d][1,3]dioxol-4-yl)methanol (115 mg, 0.268 mmol) obtained in Step 1.

ESI-MS (m/z): 621 (M+1)

Step 3

((2R,3S,4R,5R)-5-(6-(3-Chlorostyryl)-9H-purin-9-yl)-3,4-dihydroxytetrahydrofuran-2-yl)methyl phosphate (Compound I-38) triethylammonium salt (28.0 mg, 25.4%) was obtained in the same manner as in Step 5 of Reference Example 1.0 using di-tert-butyl ((3aR,4R,6R,6aR)-6-(6-(3-chlorostyryl)-9H-purin-9-yl)-2,2-dimethyltetrahydrofuro[3,4-d][1,3]dioxol-4-yl)methyl phosphate (120 mg, 0.193 mmol) obtained in Step 2.

$^1$H-NMR (D$_2$O, 400 MHz) δ: 8.45 (1H, s), 8.34 (1H, s), 7.32-7.20 (1H, m), 6.86-6.70 (3H, m), 6.64-6.50 (2H, m), 5.92-5.85 (1H, m), 4.60-4.54 (1H, m), 4.38-4.32 (1H, m), 4.28-4.20 (1H, m), 4.10-3.92 (2H, m), 3.04 (6H, q, J=7.5 Hz), 1.11 (9H, t, J=127.8 Hz).

ESI-MS (m/z): 469 (M+1)

Reference Example 34.1: Compound am-34

Step 1

6-(3-Chlorostyryl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 22.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

Steps 2 to 4

(2R,3R,4R,5R)-2-((Bis(4-methoxyphenyl)(phenyl) methoxy)methyl)-4-(tert-butyldimethylsilyloxy)-5-(6-(3-chlorostyryl)-9H-purin-9-yl)tetra hydrofuran-3-yl 2-cyanoethyl diisopropylphosphoramidite (Compound am-34) is obtained in the same manner as in Steps 3 to 5 of Reference Example 1.1 using 6-(3-chlorostyryl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

Example 40

An siRNA having Compound I-38 at the 5' end of the antisense strand is synthesized in the same manner as in Example 1 using Compound am-34 obtained in Reference Example 34.1.

Reference Example 35.1: Compound am-35

Step 1

6-(benzo[b]thiophen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine was obtained (315 mg, 89.0%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (300 mg, 0.554 mmol) obtained in Step 2 of Reference Example 17.1 and benzo[b]thiophen-2-boronic acid.

Steps 2 to 4

(2R,3R,4R,5R)-5-(6-(benzo[b]thiophen-2-yl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-35) was obtained in the same manner as in Steps 3 to 5 of Reference Example 1.1 using 6-(benzo[b]thiophen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

$^1$H-NMR (CDCl$_3$, 400 MHz) δ: 8.99, 8.98 (1H, 2s), 8.85, 8.83 (1H, 2s), 8.41, 8.38 (1H, 2s), 7.96-7.91 (2H, m), 7.53-7.34 (8H, m), 7.32-7.19 (3H, m), 6.85-6.79 (4H, m), 6.17-6.08 (1H, m), 5.17-5.10 (1H, m), 4.50-4.36 (2H, m), 4.02-3.84 (1H, m), 3.78 (6H, s), 3.68-3.55 (4H, m), 3.38-3.30 (1H, m), 2.69-2.62 (1H, m), 2.33-2.28 (1H, m), 1.23-1.03 (12H, m), 0.76, 0.75 (9H, 2s), −0.01, −0.04, −0.19, −0.19 (6H, 4 s).

Example 41

An siRNA (referred to as 6-benzothiophenyl purine) having Compound I-39 as X at the 5' end of the antisense strand of 454-Xa shown in Table 38 below was synthesized in the same manner as in Example 1 using Compound am-35 obtained in Reference Example 35.1.

ESI-MS (antisense strand): theoretical value: 6807.05, actual value: 6807.89

Reference Example 36.1: Compound am-36

Step 1

6-(6-(benzyloxy)naphthalen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine was obtained (307 mg, 74.9%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (300 mg, 0.554 mmol) obtained in Step 2 of Reference Example 17.1 and 6-benzyloxynapthalene-2-boronic acid.

Steps 2 to 4

(2R,3R,4R,5R)-5-(6-(6-(benzyloxy)naphthalen-2-yl)-9H-purin-9-yl)-2-((bis(4-methoxyphenyl)(phenyl)methoxy)methyl)-4-(tert-butyldimethyl silyloxy)tetrahydrofuran-3-yl 2-cyanoethyl diisopropylphosphoramidite (Compound am-36) was obtained in the same manner as in Steps 3 to 5 of Reference Example 1.1 using 6-(6-(benzyloxy)naphthalen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

$^1$H-NMR (CDCl$_3$, 400 MHz) δ: 9.36 (1H, s), 8.93, 8.91 (1H, 2s), 8.88-8.83 (1H, m), 8.40, 8.37 (1H, 2s), 8.02-7.86 (2H, m), 7.53-7.34 (11H, m), 7.33-7.18 (5H, m), 6.86-6.79 (4H, m), 6.20-6.10 (1H, m), 5.23 (2H, s), 5.17-5.12 (1H, m), 4.50-4.37 (2H, m), 4.03-3.85 (1H, m), 3.76 (6H, s), 3.69-3.55 (4H, m), 3.40-3.30 (1H, m), 2.72-2.61 (1H, m), 2.37-2.25 (1H, m), 1.24-1.03 (12H, m), 0.77, 0.76 (9H, 2s), −0.01, −0.05, −0.18, −0.20 (6H, 4 s).

Example 42

An siRNA (referred to as 6-benzyloxynaphthyl purine) having Compound I-40 as X at the 5' end of the antisense strand of 454-Xa shown in Table 38 below was synthesized in the same manner as in Example 1 using Compound am-36 obtained in Reference Example 36.1.

ESI-MS (antisense strand): theoretical value: 6907.15, actual value: 6909.04

Reference Example 37.1: Compound am-37

Step 1

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(pyren-1-yl)-9H-purine was obtained (202 mg, 51.5%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (300 mg, 0.554 mmol) obtained in Step 2 of Reference Example 17.1 and 1-pyreneboronic acid.

Steps 2 to 4

(2R,3R,4R,5R)-2-((bis(4-methoxyphenyl)(phenyl)methoxy)methyl)-4-(tert-butyldimethylsilyloxy)-5-(6-pyren-1-yl)-9H-purin-9-yl)tetrahydro furan-3-yl 2-cyanoethyl diisopropylphosphoramidite (Compound am-37) was obtained in the same manner as in Steps 3 to 5 of Reference Example 1.1 using 9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(pyren-1-yl)-9H-purine obtained in Step 1.

$^1$H-NMR (CDCl$_3$, 400 MHz) δ: 9.13, 9.11 (1H, 2s), 8.57-8.47 (2H, m), 8.41-8.31 (2H, m), 8.27-8.00 (7H, m), 7.52-7.45 (2H, m), 7.42-7.32 (4H, m), 7.31-7.16 (2H, m), 6.86-6.78 (4H, m), 6.27-6.16 (1H, m), 5.22-5.16 (1H, m), 4.53-4.40 (2H, m), 4.06-3.88 (1H, m), 3.76, 3.75 (6H, 2s), 3.72-3.56 (4H, m), 3.43-3.32 (1H, m), 2.76-2.61 (1H, m), 2.38-2.25 (1H, m), 1.25-1.06 (12H, m), 0.79, 0.78 (9H, 2s), 0.04, 0.02, −0.12, −0.13 (6H, 4 s).

Example 43

An siRNA (referred to as 6-pyrenyl purine) having Compound I-41 as X at the 5' end of the antisense strand of 454-Xa shown in Table 38 below was synthesized in the same manner as in Example 1 using Compound am-37 obtained in Reference Example 37.1.

ESI-MS (antisense strand): theoretical value: 6875.11, actual value: 6875.62

Reference Example 38.1: Compound am-38

Step 1

6-(anthracen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine was obtained (215 mg, 55.0%) in the same manner as in Step of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3, 2]dioxasilin-6-yl)-9H-purine (310 mg, 0.573 mmol) obtained in Step 2 of Reference Example 17.1 and 2-anthraceneboronic acid.

Steps 2 to 4

(2R,3R,4R,5R)-5-(6-(anthracen-2-yl)-9H-purin-9-yl)-2-((bis(4-methoxyphenyl) (phenyl)methoxy)methyl)-4-(tert-butyldimethylsilyloxy)tetrahydrofuran-3-yl 2-cyanoethyl diisopropylphosphoramidite (Compound am-38) was obtained in the same manner as in Steps 3 to 5 of Reference Example 1.1 using 6-(anthracen-2-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

$^1$H-NMR (CDCl$_3$, 500 MHz) δ: 9.69-9.69 (1H, m), 8.98-8.96 (1H, m), 8.83-8.82 (1H, m), 8.71-8.69 (1H, m), 8.46-8.43 (2H, m), 8.18-8.16 (1H, m), 8.05-8.04 (2H, m), 7.50-7.48 (4H, m), 7.41-7.37 (4H, m), 7.31-7.29 (2H, m), 7.24-7.22 (1H, m), 6.84-6.83 (4H, m), 6.20-6.15 (1H, m), 5.17-5.15 (1H, m), 4.47-4.43 (2H, m), 3.99-3.92 (1H, m), 3.80-3.79 (6H, m), 3.68-3.60 (4H, m), 3.40-3.34 (1H, m), 2.67-2.32 (2H, m), 1.19-1.09 (12H, m), 0.77-0.77 (9H, m), 0.01 (−0.02) (3H, s), −0.18 (−0.16) (3H, s).

Example 44

An siRNA (referred to as 6-anthracenyl purine) having Compound I-42 as X at the 5' end of the antisense strand of 454-Xa shown in Table 38 below was synthesized in the same manner as in Example 1 using Compound am-38 obtained in Reference Example 38.1.

ESI-MS (antisense strand): theoretical value: 6851.09, actual value: 6850.63

Reference Example 39.1: Compound am-39

Step 1

(2R,3S,5R)-2-((bis(4-methoxyphenyl)(phenyl)methoxy)methyl)-5-(6-chloro-9H-purin-9-yl)tetrahydrofuran-3-ol (0.287 g, 0.500 mmol) synthesized by the known method described in the literature (J. Am. Chem. Soc., 1991, Vol. 113, pp 4329-4331) was dissolved in THF (2.50 mL). To the mixture were added triethylamine (0.279 mL, 2.00 mmol) and benzylamine (0.164 mL, 1.50 mmol), and the mixture was stirred overnight at 50° C. Saturated sodium bicarbonate solution was added to the reaction mixture, which was then extracted with ethyl acetate, and the organic layer was washed with saturated brine and dried with anhydrous sodium sulfate. The solvent was evaporated under reduced pressure, and the residue was purified by ethyl acetate/hexane silica gel column chromatography to obtain (2R,3S,5R)-5-(6-(benzylamino)-9H-purin-9-yl)-2-((bis(4-methoxyphenyl) (phenyl)methoxy)methyl)tetrahydrofuran-3-ol (0.241 g, 75%).

Step 2

(2R,3S,5R)-5-(6-(benzylamino)-9H-purin-9-yl)-2-((bis(4-methoxyphenyl) (phenyl)methoxy)methyl)tetrahydrofuran-3-ol (0.241 g, 0.374 mmol) obtained in Step 1 was dissolved in THF (3.74 mL). To the mixture were added DIEA (0.196 mL, 1.12 mmol) and 3-(chloro(diisopropylamino)phosphinooxy)propanenitrile (0.100 mL, 0.449 mmol) at 0° C., and the mixture was stirred for 2 hours at room temperature under an argon atmosphere. Saturated sodium bicarbonate solution was added to the reaction mixture, which was then extracted with ethyl acetate, and the organic layer was washed with saturated brine and dried with anhydrous sodium sulfate. The solvent was evaporated under reduced pressure, and the residue was purified by silica gel column chromatography with ethyl acetate and hexane containing 1% triethylamine to obtain (2R,3S,5R)-5-(6-(benzylamino)-9H-purin-9-yl)-2-((bis(4-methoxyphenyl) (phenyl)methoxy)methyl)tetrahydrofuran-3-yl 2-cyanoethyl diisopropylphosphoramidite (am-39, 0.152 g, 48%).

$^1$H-NMR (CDCl$_3$, 500 MHz) δ: 8.35 (1H, s), 7.94-7.92 (1H, m), 7.41-7.16 (14H, m), 6.80-6.77 (4H, m), 6.45-6.42 (1H, m), 6.00 (1H, br s), 4.88 (2H, br s), 4.77-4.75 (1H, m), 4.29-4.27 (1H, m), 3.87-3.57 (4H, m), 3.78-3.76 (6H, m), 3.44-3.31 (2H, m), 2.89-2.86 (1H, m), 2.64-2.59 (2H, m), 2.46-2.45 (1H, m), 1.20-1.11 (12H, m).

Example 45

An siRNA (referred to as N-Bn dA) having Compound I-43 as X at the 5' end of the antisense strand of 454-Xa shown in Table 38 below was synthesized in the same manner as in Example 1 using Compound am-39 obtained in Reference Example 39.1.

ESI-MS (antisense strand): theoretical value: 6864.01, actual value: 6765.02

Reference Example 40.1: Compound am-40

Step 1

(2R,3S,5R)-2-((bis(4-methoxyphenyl)(phenyl)methoxy)methyl)-5-(6-chloro-9H-purin-9-yl)tetrahydrofuran-3-ol (0.287 g, 0.500 mmol) synthesized by the known methods described in the literature (J. Am. Chem. Soc., 1991, Vol. 113, pp 4329-4331) was dissolved in THF (2.50 mL). To the mixture were added triethylamine (0.279 mL, 2.00 mmol) and N-methylbenzylamine (0.193 mL, 1.50 mmol), and the mixture was stirred overnight at 50° C. Saturated sodium bicarbonate solution was added to the reaction mixture, which was then extracted with ethyl acetate, and the organic layer was washed with saturated brine and dried with anhydrous sodium sulfate. The solvent was evaporated under reduced pressure, and the residue was purified by ethyl acetate/hexane silica gel column chromatography to obtain (2R,3S,5R)-5-(6-(benzyl(methyl)amino)-9H-purin-9-yl)-2-((bis(4-meth oxyphenyl)(phenyl)methoxy)methyl)tetrahydrofuran-3-ol (0.187 g, 57%).

Step 2

(2R,3S,5R)-5-(6-(benzyl(methyl)amino)-9H-purin-9-yl)-2-((bis(4-meth oxyphenyl)(phenyl)methoxy)methyl)tetrahydrofuran-3-yl 2-cyanoethyl diisopropylphosphoramidite (am-40, 0.169 g, 69%) was obtained in the same manner as in Step 2 of Reference Example 39.1 using (2R,3S,5R)-5-(6-(benzyl(methyl)amino)-9H-purin-9-yl)-2-((bis(4-meth oxyphenyl)(phenyl)methoxy)methyl)tetrahydrofuran-3-ol (0.187 g, 0.284 mmol) obtained in Step 1.

$^1$H-NMR (CDCl$_3$, 500 MHz) δ: 8.33 (1H, s), 7.91-7.89 (1H, m), 7.40-7.38 (2H, m), 7.30-7.16 (12H, m), 6.79-6.76 (4H, m), 6.48-6.46 (1H, m), 5.34 (2H, br s), 4.73-4.72 (1H, m), 4.29-4.27 (2H, m), 3.87-3.56 (4H, m), 3.76-3.76 (6H, m), 3.44-3.29 (5H, m), 2.84-2.78 (1H, m), 2.65-2.60 (2H, m), 2.46-2.44 (1H, m), 1.20-1.10 (12H, m).

Example 46

An siRNA (referred to as N-Bn-N-Me dA) having Compound I-44 as X at the 5' end of the antisense strand of 454-Xa shown in Table 38 below was synthesized in the same manner as in Example 1 using Compound am-40 obtained in Reference Example 40.1.

ESI-MS (antisense strand): theoretical value: 6778.04, actual value: 6778.19

Reference Example 41.1: Compound am-41

Step 1

8-bromo-9-((4aR,6R,7R,7aR)-2,2-di-tert-butyl-7-((tert-butyldimethyl silyl)oxy)tetrahydro-4H-furo[3,2-d][1,3,2]dioxasilin-6-yl)-6-((E)-styryl)-9H-purine was obtained (4.20 g, 76%) in the same manner as in Step 2 of Reference Example 14.0 using 9-((4aR,6R,7R,7aR)-2,2-di-tert-butyl-7-((tert-butyldimethylsilyl)ox y)tetrahydro-4H-furo[3,2-d][1,3,2]dioxasilin-6-yl)-6-((E)-styryl)-9H-purine (4.90 g, 8.05 mmol) obtained in Step 3 of Reference Example 6.1.

ESI-MS (m/z): 688 (M+1)

Step 2

8-bromo-9-((4aR,6R,7R,7aR)-2,2-di-tert-butyl-7-((tert-butyldimethyl silyl)oxy)tetrahydro-4H-furo[3,2-d][1,3,2]dioxasilin-6-yl)-6-((E)-styryl)-9H-purine (300 mg, 0.436 mmol) obtained in Step 1 was dissolved in ethanol (4.4 mL). To the mixture were added benzylamine (0.304 mL, 2.181 mmol) and triethylamine (0.143 mL, 1.308 mmol), and the mixture was stirred for 3 hours under heated reflux. The reaction solution was cooled to room temperature, and the solvent was evaporated under reduced pressure. The residue was purified by heptane/ethyl acetate column chromatography to obtain N-benzyl-9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-amine (304 mg, 98%).

Step 3

(2R,3R,4R,5R)-5-(8-(benzylamino)-6-((E)-styryl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-41) was obtained in the same manner as in Steps 3 to 5 of Reference Example 1.1 using N-benzyl-9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-amine obtained in Step 2.

$^1$H-NMR (CDCl$_3$, 500 MHz) δ: 8.59-8.56 (m, 1H), 8.21-8.17 (m, 1H), 7.63-7.61 (m, 2H), 7.55-7.50 (m, 1H), 7.37-7.34 (m, 4H), 7.30-7.18 (m, 11H), 7.15-7.13 (m, 2H), 6.74-6.67 (m, 4H), 6.33-6.19 (m, 2H), 5.09 (m, 1H), 4.86-4.75 (m, 1H), 4.40-4.27 (m, 2H), 4.13-3.69 (m, 2H), 3.65-3.50 (m, 4H), 3.39 (m, 1H), 2.77-2.24 (m, 2H), 1.25-1.01 (m, 12H), 0.73 (m, 9H), −0.03 (−0.01) (s, 3H), −0.23 (−0.24) (s, 3H).

Example 47

An siRNA (referred to as 8-BnNH-6-styryl purine) having Compound I-45 as X at the 5' end of the antisense strand of 454-Xa shown in Table 38 below was synthesized in the same manner as in Example 12 using Compound am-41 obtained in Reference Example 41.1.

ESI-MS (antisense strand): theoretical value: 6882.14, actual value: 6882.50

Reference Example 42.1: Compound am-42

Step 1

9-((4aR,6R,7R,7aR)-2,2-di-tert-butyl-7-((tert-butyldimethylsilyl)ox y)tetrahydro-4H-furo[3,2-d][1,3,2]dioxasilin-6-yl)-N-(furan-3-ylmethyl)-6-((E)-styryl)-9H-purin-8-amine was obtained (279 mg, 91%) in the same manner as in Step 2 of Reference Example 41.1 using 8-bromo-9-((4aR,6R,7R,7aR)-2,2-di-tert-butyl-7-((tert-butyldimethyl silyl)oxy)tetrahydro-4H-furo[3,2-d][1,3,2]dioxasilin-6-yl)-6-((E)-styryl)-9H-purine (300 mg, 0.436 mmol) obtained in Step 1 of Reference Example 41.1 and furan-3-ylmethanamine (0.121 mL, 1.308 mmol).

Step 2

(2R,3R,4R,5R)-2-((bis(4-methoxyphenyl)(phenyl)methoxy)methyl)-4-(tert-butyldimethylsilyloxy)-5-(8-(furan-3-ylmethylamino)-6-((E)-styryl)-9H-purin-9-yl)tetrahydrofuran-3-yl (2-cyanoethyl) diisopropylphosphoramidite (Compound am-42) was obtained in the same manner as in Steps 3 to 5 of Reference Example 1.1 using 9-((4aR,6R,7R,7aR)-2,2-di-tert-butyl-7-((tert-butyldimethylsilyl)ox y)tetrahydro-4H-furo[3,2-d][1,3,2]dioxasilin-6-yl)-N-(furan-3-ylmethyl)-6-((E)-styryl)-9H-purin-8-amine obtained in Step 1.

$^1$H-NMR (CDCl$_3$, 400 MHz) δ: 8.58 (m, 1H), 8.28-8.24 (m, 1H), 7.67-7.65 (m, 2H), 7.60-7.56 (m, 1H), 7.41-7.36 (m, 4H), 7.32-7.23 (m, 7H), 7.00 (m, 1H), 6.81-6.76 (m, 4H), 6.35 (m, 1H), 6.29-6.16 (m, 1H), 6.16-6.08 (m, 1H), 5.05-5.01 (m, 1H), 4.51 (m, 1H), 4.34 (m, 1H), 4.24 (m, 1H), 4.11-4.05 (m, 1H), 3.95 (m, 1H), 3.79 (s, 6H), 3.66-3.52 (m, 4H), 3.46 (m, 1H), 3.39-3.35 (m, 1H), 2.74 (m, 1H), 2.24 (m, 1H), 1.32-0.97 (m, 14H), 0.72 (m, 9H), −0.04 (−0.02) (s, 3H), −0.25 (−0.27) (s, 3H).

Example 48

An siRNA (referred to as 8-furanylmethylamino-6-styryl purine) having Compound I-46 as X at the 5' end of the antisense strand of 454-Xa shown in Table 38 below was synthesized in the same manner as in Example 12 using Compound am-42 obtained in Reference Example 42.1.

ESI-MS (antisense strand): theoretical value: 6872.11, actual value: 6872.95

Reference Example 43.1: Compound am-43

Step 1

N-((2H-tetrazol-5-yl)methyl)-9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-amine was obtained (367 mg, 119%) in the same manner as in Step 2 of Reference Example 41.1 using 8-bromo-9-((4aR,6R,7R,7aR)-2,2-di-tert-butyl-7-((tert-butyldimethyl silyl)oxy)tetrahydro-4H-furo[3,2-d][1,3,2]dioxasilin-6-yl)-6-((E)-styryl)-9H-purine (300 mg, 0.436 mmol) obtained in Step 1 of Reference Example 41.1 and (2H-tetrazol-5-yl)methanamine (0.130 mL, 1.308 mmol).

ESI-MS (m/z): 706 (M+1)

Step 2

N-((2H-tetrazol-5-yl)methyl)-9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-amine (366 mg, 0.518 mmol) obtained in Step 1 was dissolved in DMF (5.2 mL). To the mixture were added DBU (0.234 mL, 1.555 mmol) and chloromethyl pivalate (0.150 mL, 1.037 mmol), and the mixture was stirred at 80° C. for 3 hours. Saturated sodium bicarbonate solution was added to the reaction mixture, which was then extracted with ethyl acetate, and the organic layer was washed with saturated brine and dried with anhydrous magnesium sulfate. The solvent was evaporated under reduced pressure, and the residue was purified by ethyl acetate/heptane silica gel column chromatography to obtain a mixture of (5-((9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-

((E)-styryl)-9H-purin-8-ylamino)methyl)-2H-tetrazol-2-yl) methyl pivalate and (5-((9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-ylamino)methyl)-1H-tetrazol-1-yl)methyl pivalate (172 mg, 41%).

ESI-MS (m/z): 821 (M+1)

Step 3

Using the mixture of (5-((9-(((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-((E)-styryl)-9H-purin-8-ylamino)methyl)-2H-tetrazol-2-yl)methyl pivalate and (5-((9-((4aR,6R,7R,7aR)-2,2-di-tert-butyl-7-((tert-butyldimethylsilyl)oxy)tetrahydro-4H-furo[3,2-d][1,3,2] dioxasilin-6-yl)-6-((E)-styryl)-9H-purin-8-ylamino) methyl)-1H-tetrazol-1-yl)methyl pivalate obtained in Step 2, a mixture of (5-((9-((2R,3R,4R,5R)-5-((bis(4-methoxyphenyl)(phenyl)methoxy)methyl)-3-(tert-butyldimethylsilyloxy)-4-((2-cyanoethoxy) (diisopropylamino)phosphinoxy) tetrahydrofuran-2-yl)-6-((E)-styryl)-9H-purin-8-ylamino) methyl)-1H-tetrazol-1-yl)methyl pivalate and (5-((9-(2R, 3R,4R,5R)-5-((bis(4-methoxyphenyl)(phenyl)methoxy) methyl)-3-(tert-butyldimethylsilyloxy)-4-((2-cyanoethoxy) (diisopropylamino)phosphinoxy)tetrahydrofuran-2-yl)-6-((E)-styryl)-9H-purin-8-ylamino) methyl)-2H-tetrazol-2-yl) methyl pivalate (Compound am-43) was obtained in the same manner as in Steps 3 to 5 of Reference Example 1.1.

$^1$H-NMR (CDCl$_3$, 400 MHz) δ: 8.63-8.58 (m, 1H), 8.15-8.07 (m, 1H), 7.64-7.62 (m, 2H), 7.50-7.16 (m, 11H), 6.88-6.86 (m, 1H), 6.80-6.78 (m, 4H), 6.67-6.63 (m, 1H), 6.38-6.19 (m, 1H), 5.10-5.03 (m, 1H), 4.68-4.51 (m, 1H), 4.51-4.30 (m, 3H), 4.20-3.94 (m, 2H), 3.80-3.77 (m, 6H), 3.75-3.52 (m, 4H), 3.45-3.43 (m, 1H), 2.82-2.17 (m, 2H), 1.32-1.14 (m, 12H), 1.09-0.96 (m, 9H), 0.88-0.82 (m, 2H), 0.74-0.71 (m, 9H), −0.02 (0.01) (s, 3H), −0.24 (−0.29) (m, 3H).

Example 49

An siRNA (referred to as 6-styryl-8-tetrazolylmethylamino purine) having Compound I-47 as X at the 5' end of the antisense strand of 454-Xa shown in Table 38 below was synthesized in the same manner as in Example 12 using Compound am-43 obtained in Reference Example 43.1.

ESI-MS (antisense strand): theoretical value: 6874.08, actual value: 6873.91

Reference Example 44.1: Compound am-44

Step 1

9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-(3-methoxy-3-oxopropyl)phenyl)-9H-purine was obtained (905 mg, 81%) in the same manner as in Step 2 of Reference Example 6.0 using 6-chloro-9-((4aR,6R,7R,7aS)-2,2-di-tert-butyl-7-((tert-butyldimethyl silyloxy)tetrahydro-4H-furo[3,2-d][1,3,2]dioxasilin-6-yl)-9H-purine (900 mg, 1.66 mmol) obtained in Step 2 of Reference Example 17.1 and 3-(2-methoxycarbonylethyl)phenylboronic acid.

Steps 2 to 6

(2R,3R,4R,5R)-2-((bis(4-methoxyphenyl)(phenyl) methoxy)methyl)-4-(tert-butyldimethylsilyloxy)-5-(6-(3-(3-(2-cyanoethoxy)-3-oxopropyl)phenyl)-9H-purin-9-yl)tetrahydrofuran-3-yl 2-cyanoethyl diisopropylphosphoramidite (Compound am-44) was obtained in the same manner as in Steps 2 to 6 of Reference Example 26.1 using 9-((4aR,6R, 7R,7aS)-2,2-di-tert-butyl-7-(tert-butyldimethylsilyloxy)tetrahydro-4H-furo[3,2-d][1,3,2]dioxasilin-6-yl)-6-(3-(3-methoxy-3-oxopropyl)phenyl)-9H-purine obtained in Step 1.

$^1$H-NMR (CDCl$_3$, 400 MHz) δ: 8.91, 8.89 (1H, 2s), 8.72-8.57 (2H, m), 8.38, 8.34 (1H, 2s), 7.53-7.45 (3H, m), 7.41-7.33 (5H, m), 7.32-7.19 (3H, m), 6.85-6.79 (4H, m), 6.19-6.09 (1H, m), 5.15-5.09 (1H, m), 4.49-4.35 (2H, m), 4.31-4.24 (2H, m), 4.03-3.84 (1H, m), 3.76 (6H, s), 3.68-3.55 (4H, m), 3.38-3.28 (1H, m), 3.15-3.08 (2H, m), 2.83-2.77 (2H, m), 2.69-2.62 (3H, m), 2.34-2.27 (1H, m), 1.24-1.02 (12H, m), 0.76, 0.75 (9H, 2s), −0.01, −0.05, −0.20, −0.20 (6H, 4 s).

Example 50

An siRNA (referred to as 6-(m-carboxyethylphenyl)purine) having Compound I-48 as X at the 5' end of the antisense strand of 454-Xa shown in Table 38 below was synthesized in the same manner as in Example 1 using Compound am-44 obtained in Reference Example 44.1.

ESI-MS (antisense strand): theoretical value: 6823.03, actual value: 6824.53

Example 51

An siRNA (referred to as 5-furyl dU) having Compound I-49 as X at the 5' end of the antisense strand of 454-Xa shown in Table 38 below was synthesized in the same manner as in Example 1 using commercial 5-(2-furyl)-dU CEP (Berry & Associates, Inc.).

MALDI-TOF/MS (antisense strand): theoretical value: 6717.94, actual value: 6717.65

Example 52

An siRNA (referred to as 2-amino rA) having Compound I-51 as X at the 5' end of the antisense strand of 454-XY shown in Table 38 below and zebularine-5-monophosphate as Y at the third nucleotide from the 3' end of the sense strand was synthesized in the same manner as in Example 12 using commercial 2,6-diaminopurine-TOM-CE phosphoramidite (Glen Research Corporation) and zebularine-CE phosphoramidite (Glen Research Corporation).

MALDI-TOF/MS (antisense strand): theoretical value: 6704.62, actual value: 6704.90

MALDI-TOF/MS (sense strand): theoretical value: 6725.85, actual value: 6725.08

Reference Example 47.1, Compound am-47

Step 1

(2R,3S,5R)-2-((bis(4-methoxyphenyl)(phenyl)methoxy) methyl)-5-(6-((3-(hydroxymethyl)benzyl)amino)-9H-purin-9-yl)tetrahydrofuran-3-ol was obtained (678 mg, 100%) in the same manner as in Step 1 of Reference Example 39.1 using (2R,3S,5R)-2-((bis(4-methoxyphenyl)(phenyl) methoxy)methyl)-5-(6-chloro-9H-purin-9-yl)tetrahydrofuran-3-ol (0.573 g, 1.00 mmol) synthesized by the method described in J. Am. Chem. Soc., 1991, Vol. 113, pp 4329-4331 and (3-(aminomethyl)phenyl)methanol (0.412 g, 3.00 mmol).

ESI-MS (m/z): 675 (M+1)

Step 2

(2R,3S,5R)-2-((bis(4-methoxyphenyl)(phenyl)methoxy) methyl)-5-(6-((3-(tert-butyldimethylsiloxy)methyl)benzylamino)-9H-purin-9-yl)tetrahydrofuran-3-ol was obtained (0.192 g, 39%) in the same manner as in Step of Reference Example 1.1 using (2R,3S,5R)-2-((bis(4-methoxyphenyl)(phenyl)methoxy)methyl)-5-(6-((3-(hydroxymethyl)benzyl)amino)-9H-purin-9-yl)tetrahydrofuran-3-ol (0.337 g, 0.500 mmol) obtained in Step 1.

ESI-MS (m/z): 789 (M+1)

Step 3

(2R,3S,5R)-2-((bis(4-methoxyphenyl)(phenyl)methoxy)methyl)-5-(6-((3-(tert-butyldimethylsiloxy)methyl)benzylamino)-9H-purin-9-yl)tetrahydrofuran-3-yl (2-cyanoethyl) diisopropylphosphoramidite was obtained in the same manner as in Step 2 of Reference Example 39.1 using (2R,3S,5R)-2-((bis(4-methoxyphenyl)(phenyl)methoxy)methyl)-5-(6-((3-(tert-butyldimethylsiloxy)methyl)benzylamino)-9H-purin-9-yl)tetrahydrofuran-3-ol obtained in Step 2, and used in Example 53.

Example 53

An siRNA (referred to as N6-(3-hydroxymethyl)Bn dA) having Compound I-51 as X at the 5' end of the antisense strand of 454-Xa shown in Table 38 below was synthesized in the same manner as in Example 1-1 using Compound am-47 obtained in Reference Example 47.1.

ESI-MS (antisense strand): theoretical value: 6794.04, actual value: 6794.45

Reference Example 48.1, Compound am-48

Step 1

(2R,3S,5R)-2-((bis(4-methoxyphenyl)(phenyl)methoxy)methyl)-5-(6-((3-((bis(4-methoxyphenyl)(phenyl)methoxy)methyl)benzyl)amino)-9H-purin-9-yl)tetrahydrofuran-3-ol was obtained (0.195 g, 40%) in the same manner as in Step 4 of Reference Example 1.1 using (2R,3S,5R)-2-((bis(4-methoxyphenyl)(phenyl)methoxy)methyl)-5-(6-((3-(hydroxymethyl)benzyl)amino)-9H-purin-9-yl)tetrahydrofuran-3-ol (0.337 g, 0.500 mmol) obtained in Step 1 of Reference Example 48.1.

ESI-MS (m/z): 977 (M+1)

Step 2

(2R,3S,5R)-2-((bis(4-methoxyphenyl)(phenyl)methoxy)methyl)-5-(6-((3-((bis(4-methoxyphenyl)(phenyl)methoxy)methyl)benzyl)amino)-9H-purin-9-yl)tetrahydrofuran-3-yl (2-cyanoethyl) diisopropylphosphoramidite was obtained in the same manner as in Step of Reference Example 39.1 using (2R,3S,5R)-2-((bis(4-methoxyphenyl)(phenyl)methoxy)methyl)-5-(6-((3-((bis(4-methoxyphenyl)(phenyl)methoxy)methyl)benzyl)amino)-9H-purin-9-yl)tetrahydrofuran-3-ol obtained in Step 1, and used in Example 54.

Example 54

An siRNA (referred to as N6-(3-phosphonooxymethyl)Bn dA) having Compound I-52 as X at the 5' end of the antisense strand of 454-Xa shown in Table 38 below was synthesized in the same manner as in Example 1-1 using Compound am-48 obtained in Reference Example 48.1.

MALDI-TOF/MS (antisense strand): theoretical value: 6873.01, actual value: 6876.34

Reference Example 49.1: Compound am-49

Step 1

6-chloro-9-((4aR,6R,7aS)-2,2-di-tert-butyltetrahydro-4H-furo[3,2-d][1,3,2]dioxasilin-6-yl)-9H-purine was obtained (2.77 g, 91%) in the same manner as in Step 1 of Reference Example 1.1 using commercial (2R,3S,5R)-5-(6-chloro-9H-purin-9-yl)-2-(hydroxymethyl)tetrahydrofuran-3-ol (2.00 g, 7.39 mmol).

Step 2

9-((4aR,6R,7aS)-2,2-di-tert-butyltetrahydro-4H-furo[3,2-d][1,3,2]dioxasilin-6-yl)-6-((E)-styryl)-9H-purine was obtained (1.74 g, 75%) in the same manner as in Step 2 of Reference Example 6.0 using 6-chloro-9-((4aR,6R,7aS)-2,2-di-tert-butyltetrahydro-4H-furo[3,2-d][1,3,2]dioxasilin-6-yl)-9H-purine (2.00 g, 4.87 mmol) obtained in Step 1.

Steps 3 to 5 (2R,3S,5R)-2-((bis(4-methoxyphenyl)(phenyl)methoxy)methyl)-5-(6-((E)-styryl)-9H-purin-9-yl)tetrahydrofuran-3-yl 2-cyanoethyl diisopropylphosphoramidite (Compound am-49) was obtained in the same manner as in Steps 3 to 5 of Reference Example 1.1 using 9-((4aR,6R,7aS)-2,2-di-tert-butyltetrahydro-4H-furo[3,2-d][1,3,2]dioxasilin-6-yl)-6-((E)-styryl)-9H-purine obtained in Step 2.

ESI-MS (m/z): 841 (M+1)

$^1$H-NMR (CDCl$_3$, 400 MHz) δ: 8.84-8.84 (m, 1H), 8.41-8.37 (m, 1H), 8.28-8.26 (m, 1H), 7.73-7.71 (m, 3H), 7.42-7.39 (m, 6H), 7.31-7.22 (m, 37H), 6.79-6.77 (m, 4H), 6.53-6.52 (m, 1H), 4.82-4.75 (m, 1H), 4.34-4.32 (m, 1H), 3.89-3.56 (m, 14H), 3.49-3.33 (m, 4H), 2.98-2.93 (m, 1H), 2.75-2.62 (m, 2H), 2.48-2.47 (m, 1H), 1.27-1.24 (m, 2H), 1.20-1.19 (m, 9H), 1.14-1.12 (m, 3H).

Example 55

An siRNA (referred to as 6-styrl-dPu) having Compound I-53 as X at the 5' end of the antisense strand of 454-Xa shown in Table 38 below was synthesized in the same manner as in Example 1-1 using Compound am-49 obtained in Reference Example 49.1.

ESI-MS (antisense strand): theoretical value: 6761.01, actual value:
6762.51

Reference Example 50.1: Compound am-50

Step 1

9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine was obtained (6.87 g, 100%) in the same manner as in Step 2 of Reference Example 1.1 using (2R,3S,5R)-2-((bis(4-methoxyphenyl)(phenyl)methoxy)methyl)-5-(6-chloro-9H-purin-9-yl)tetrahydrofuran-3-ol (5.73 g, 10.0 mmol) synthesized by the method described in J. Am. Chem. Soc., 1991, Vol. 113, pp 4329-4331.

Step 2

(3-((bis(4-methoxyphenyl)(phenyl)methoxy)methyl)phenyl)methanol (0.529 g, 1.20 mmol) synthesized by the method described in Bioorg. Med. Chem., 2009, Vol. 17, pp 1974-1981 was dissolved in THF (6.00 mL). Sodium hydride (0.053 g, 1.32 mmol) was added to the mixture at 0° C., and the mixture was stirred for 10 minutes at room temperature. Subsequently, 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.412 g, 0.600 mmol) obtained in Step 1 was added to the mixture at 0° C., and the mixture was stirred at room temperature for 1.5 hours. Water was added to the reaction solution, which was then extracted with ethyl acetate. The organic layer was washed with saturated brine and dried with anhydrous sodium sulfate, and the solvent was evaporated under reduced pressure to obtain crude 9-((2R,4S,5R)-5-((bis(4-methoxyphenyl)(phenyl)methoxy)methyl)-4-

((tert-butyldimethylsilyl)oxy)tetrahydrofuran-2-yl)-6-((3-bis(4-methoxyphenyl) (phenyl)methoxy)methyl)benzyl)oxy)-9H-purine.

Step 3

9-((2R,4S,5R)-5-((bis(4-methoxyphenyl)(phenyl)methyl)-4-((tert-butyldimethylsilyl)oxy)tetrahydrofuran-2-yl)-6-((3-bis(4-methoxyphenyl) (phenyl)methoxy)methyl)benzyl)oxy)-9H-purine obtained in Step 2 was dissolved in THF (6.00 mL). To the mixture was added THF solution of tetrabutylamminoium fluoride (1 mol/L, 1.20 ml, 1.20 mmol), and the mixture was stirred at room temperature for 30 minutes. A saturated ammonium chloride aqueous solution was added to the reaction solution, which was then extracted with ethyl acetate. The organic layer was washed with saturated brine and dried with anhydrous sodium sulfate, the solvent was evaporated under reduced pressure, and the product was purified by hexane/ethyl acetate column chromatography to obtain (2R,3S,5R)-2-((bis(4-methoxyphenyl)(phenyl)methoxy)methyl)-5-(6-((3-bis(4-methoxyphenyl)(phenyl)methoxy)methyl)benzyl)oxy)-9H-purin-9-yl)tetrahydrofuran-3-ol (0.525 g, 90%).

ESI-MS (m/z): 978 (M+1)

Step 4

(2R,3S,5R)-2-((bis(4-methoxyphenyl)(phenyl)methoxy)methyl)-5-(6-((3-bis(4-methoxyphenyl)(phenyl)methoxy)methyl)benzyl)oxy)-9H-purin-9-yl)tetrahydrofuran-3-yl (2-cyanoethyl) diisopropylphosphoramidite (Compound am-50) was obtained (0.475 g, 75%) in the same manner as in Step 2 of Reference Example 39. 1 using (2R,3S,5R)-2-((bis(4-methoxyphenyl)(phenyl)methoxy)methyl)-5-(6-((3-bis(4-methoxyphenyl)(phenyl)methoxy)methyl)benzyl)oxy)-9H-purin-9-yl)tetrahydrofuran-3-ol (0.525 g, 0.537 mmol) obtained in Step 3.

$^1$H-NMR (CDCl$_3$, 400 MHz) δ: 8.47 (1H, d, J=1.3 Hz), 8.09 (1H, d, J=9.1 Hz), 7.52-7.00 (22H, m), 6.85-6.75 (8H, m), 6.49-6.45 (1H, m), 5.66 (2H, s), 4.76 (1H, s), 4.31-4.30 (1H, m), 4.17 (2H, s), 3.88-3.56 (16H, m), 3.41-3.33 (2H, m), 2.89-2.85 (1H, m), 2.62-2.61 (2H, m), 2.47 (1H, t, J=6.2 Hz), 1.20-1.11 (12H, m).

Example 56

An siRNA (referred to as 06-(3-phosphonooxymethyl)Bn dI) having Compound I-54 as X at the 5' end of the antisense strand of 454-Xa shown in Table 38 below was synthesized in the same manner as in Example 1-1 using Compound am-50 obtained in Reference Example 50.1.

ESI-MS (antisense strand): theoretical value: 6875.00, actual value: 6874.56

Reference Example 51.1: Compound am-51

Step 1

9-((4aR,6R,7R,7aR)-2,2-di-tert-butyl-7-(tert-butyldimethylsilyloxy)tetrahydro-4H-furo-[3,2-d][1,3,2]dioxasilin-6-yl)-6-(3-(2-methoxy-2-oxoethyl)phenyl)-9H-purine was obtained (860 mg, 71.1%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (1.00 g, 1.848 mmol) obtained in Step 2 of Reference Example 17.1 and (3-(2-methoxy-2-oxoethyl)phenyl)boronic acid (538 mg, 2.77 mmol).

Steps 2 to 6

(2R,3R,4R,5R)-2-((bis(4-methoxyphenyl)(phenyl)methoxy)methyl)-4-(tert-butyldimethylsilyloxy)-5-(6-(3-(2-(2-cyanoethoxy)-2-oxoethyl)phenyl)-9H-purin-9-yl)tetrahydrofuran-3-yl 2-cyanoethyl diisopropylphosphoramidite (Compound am-51) was obtained in the same manner as in Steps 2 to 6 of Reference Example 26.1 using 9-((4aR,6R,7R,7aR)-2,2-di-tert-butyl-7-(tert-butyldimethylsilyloxy) tetrahydro-4H-furo-[3,2-d][1,3,2]dioxasilin-6-yl)-6-(3-(2-methoxy-2-oxoethyl)phenyl)-9H-purine obtained in Step 1.

$^1$H-NMR (CDCl$_3$, 400 MHz) δ: 8.90, 8.88 (1H, 2s), 8.78-8.66 (1H, m), 8.37, 8.34 (1H, 2s), 7.58-7.42 (4H, m), 7.40-7.31 (4H, m), 7.30-7.16 (3H, m), 6.84-6.77 (4H, m), 6.18-6.07 (1H, m), 5.14-5.08 (1H, m), 4.48-4.35 (2H, m), 4.34-4.28 (2H, m), 4.00-3.86 (1H, m), 3.83 (2H, s), 3.76 (6H, s), 3.68-3.53 (4H, m), 3.37-3.27 (1H, m), 2.72-2.62 (3H, m), 2.32-2.26 (1H, m), 1.23-1.01 (12H, m), 0.75, 0.74 (9H, 2s), −0.03, −0.06, −0.21, −0.23 (6H, 4 s).

Example 57

An siRNA (referred to as 6-(3-(N-methylcarbamoyl)phenyl)-Pu) having Compound I-55 as X at the 5' end of the antisense strand of 454-Xa shown in Table 38 below was synthesized in the same manner as in Example 1-1 using Compound am-51 obtained in Reference Example 51.1 except that AMA (1:1 mixed solution of 40% aqueous methylamine and 28% aqueous ammonia) was used instead of aqueous ammonia when cleaving from the solid-phase resin and deprotecting the protecting groups.

ESI-MS (antisense strand): theoretical value: 6823.09, actual value: 6821.94

Reference Example 52.1: Compound am-52

Step 1

(9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-8-(4-nitrophenyl)-6-((E)-styryl)-9H-purine was obtained (490 mg, 92%) in the same manner as in Step 2 of Reference Example 6.0 using 8-bromo-9-((4aR,6R,7R,7aR)-2,2-di-tert-butyl-7-((tert-butyldimethyl silyl)oxy)tetrahydro-4H-furo[3,2-d][1,3,2]dioxasilin-6-yl)-6-((E)-styryl)-9H-purine (500 mg, 0.727 mmol) obtained in Step 1 of Reference Example 41.1.

Steps 2 to 4

(2R,3R,4R,5R)-2-((bis(4-methoxyphenyl)(phenyl)methoxy)methyl)-4-(tert-butyldimethylsilyloxy)-5-(8-(4-nitrophenyl)-6-((E)-styryl)-9H-purin-9-yl)tetrahydrofuran-3-yl 2-cyanoethyl diisopropylphosphoramidite (Compound am-52) was obtained in the same manner as in Steps 3 to 5 of Reference Example 1.1 using (9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-8-(4-nitrophenyl)-6-((E)-styryl)-9H-purine obtained in Step 1.

$^1$H-NMR (CDCl$_3$, 400 MHz) δ: 8.68, 8.63 (1H, 2s), 8.44-8.38 (m, 3H), 8.15-8.12 (m, 2H), 7.82-7.72 (m, 3H), 7.51-7.43 (m, 10H), 7.20-7.16 (m, 1H), 6.82-6.79 (m, 5H), 5.92-5.83 (m, 2H), 4.54-4.44 (m, 1H), 4.41-4.38 (m, 1H), 3.86-3.78 (m, 7H), 3.65-3.59 (m, 4H), 3.42-3.30 (m, 1H), 2.54-2.52 (m, 1H), 2.29-2.28 (m, 1H), 1.17-1.11 (m, 12H), 0.68, 0.67 (9H, 2s), −0.06, 0.07, −0.32, −0.35 (6H, 4s)

Example 58

An siRNA (referred to as 8-(4-nitro)phenyl-6-styryl-Pu) having Compound I-56 as X at the 5' end of the antisense strand of 454-Xa shown in Table 38 below was synthesized in the same manner as in Example 1-1 using Compound am-52 obtained in Reference Example 52.1.

ESI-MS (antisense strand): theoretical value: 6898.10, actual value: 6897.83

Reference Example 53.1: Compound am-53

Step 1

Crude 2-((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)-N-methylacetamide was obtained in the same manner as in Step 1 of Reference Example 39.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.500 g, 0.727 mmol) obtained in Step 1 of Reference Example 51.1 and 2-amino-N-methylacetamide (0.192 g, 2.18 mmol).

Step 2

2-((9-((2R,4S,5R)-5-((bis(4-methoxyphenyl)(phenyl)methoxy)methyl)-4-hydroxytetrahydrofuran-2-yl)-9H-purin-6-yl)amino)-N-methylacetamide was obtained (0.290 g, 57%) in the same manner as in Step 3 of Reference Example 50.1 using 2-((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)-N-methylacetamide obtained in Step 1.

ESI-MS (m/z): 625 (M+1)

Step 3 (2R,3R,5R)-2-((bis(4-methoxyphenyl)(phenyl)methoxy)methyl)-5-(6-((2-methylamino)-2-oxoethyl)amino)-9H-purin-9-yl)tetrahydrofuran-3-yl (2-cyanoethyl) diisopropylphophoramidite (Compound am-53) was obtained (0.121 g, 25%) in the same manner as in Step 2 of Reference Example 39.1 using 2-((9-((2R,4S,5R)-5-((bis(4-methoxyphenyl)(phenyl)methoxy)methyl)-4-hydroxytetrahydrofuran-2-yl)-9H-purin-6-yl)amino)-N-methylacetamide (0.370 g, 0.592 mmol) obtained in Step 2.

$^1$H-NMR (CDCl$_3$, 400 MHz) δ: 8.35-8.34 (1H, m), 8.01-7.97 (1H, m), 7.42-7.36 (2H, m), 7.31-7.18 (7H, m), 6.81-6.74 (4H, m), 6.47-6.36 (2H, m), 6.27-6.19 (1H, m), 4.82-4.73 (1H, m), 4.35-4.26 (3H, m), 3.90-3.54 (9H, m), 3.46-3.30 (2H, m), 2.95-2.85 (1H, m), 2.84-2.78 (3H, m), 2.71-2.54 (2H, m), 2.46 (1H, t, J=6.4 Hz), 1.21-1.10 (12H, m).

Example 59

An siRNA (referred to as N6-(2-methylamino-2-oxo)ethyl dA) having Compound I-57 as X at the 5' end of the antisense strand of 454-Xa shown in Table 38 below was synthesized in the same manner as in Example 1-1 using Compound am-53 obtained in Reference Example 53.1.

ESI-MS (antisense strand): theoretical value: 6744.97, actual value: 6745.41

Reference Example 54.1: Compound am-54

Step 1

Crude 3-(((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)methyl)pyridin-2(1H)-one was obtained in the same manner as in Step 1 of Reference Example 39.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.500 g, 0.727 mmol) obtained in Step 1 of Reference Example 51.1 and 3-(aminomethyl)pyridin-2(1H)-one (0.256 g, 2.18 mmol).

Step 2

3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)pyridin-2 (1H)-one was obtained (0.370 g, 69%) in the same manner as in Step 3 of Reference Example 50.1 using 3-(((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)methyl)pyridin-2(1H)-one obtained in Step 1.

ESI-MS (m/z): 661 (M+1)

Step 3

(2R,3R,5R)-2-((bis(4-methoxyphenyl)(phenyl)methoxy)methyl)-5-(6-(((2-oxo-1,2-dihydropyridin-3-yl)methyl)amino)-9H-purin-9-yl)tetrahydrofuran-3-yl (2-cyanoethyl) diisopropylphosphoramidite (Compound am-54) was obtained (0.265 g, 63%) in the same manner as in Step 2 of Reference Example 39.1 using 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)pyridin-2 (1H)-one (0.360 g, 0.486 mmol) obtained in Step 2.

$^1$H-NMR (CDCl$_3$, 400 MHz) δ: 8.32 (1H, brs), 7.97, 7.95 (1H, 2s), 7.55 (1H, d, J=6.9 Hz), 7.41-7.37 (2H, m), 7.31-7.15 (9H, m), 6.80-6.75 (4H, m), 6.45-6.41 (1H, m), 6.19-6.13 (1H, m), 4.86-4.70 (3H, m), 4.30-4.23 (1H, m), 3.93-3.51 (10H, m), 3.46-3.27 (2H, m), 2.90-2.80 (1H, m), 2.68-2.54 (2H, m), 2.45 (1H, t, J=6.4 Hz), 1.19-1.09 (12H, m).

$^{31}$P-NMR (CDCl$_3$, 162 MHz) δ: 149.5, 149.4.

Example 60

An siRNA (referred to as N6-(2-oxo-1,2-dihydropyridin-3-yl)methyl dA) having Compound I-58 as X at the 5' end of the antisense strand of 454-Xa shown in Table 38 below was synthesized in the same manner as in Example 1-1 using Compound am-54 obtained in Reference Example 54.1.

ESI-MS (antisense strand): theoretical value: 6781.00, actual value: 6781.94

Reference Example 55.1: Compound am-55

Step 1

(2R,4S,5R)-5-(6-(2-(bis(4-methoxyphenyl)(phenyl)methoxy)ethoxy)-9H-purin-9-yl)-2-((bis(4-methoxyphenyl)(phenyl)methoxy)methyl)tetrahydrofuran-3-ol was obtained (0.305 g, 54%) in the same manner as in Steps to 2 of Reference Example 50.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.500 g, 0.727 mmol) obtained in Step 1 of Reference Example 51.1 and 2-(bis(4-methoxyphenyl)(phenyl)methoxy)ethan-1-ol (0.220 g, 0.602 mmol) synthesized by the method described in J. Org. Chem., 2005, Vol. 70, pp 9198-9206.

Step 2

(2R,4S,5R)-5-(6-(2-(bis(4-methoxyphenyl)(phenyl)methoxy)ethoxy)-9H-purin-9-yl)-2-((bis(4-methoxyphenyl)(phenyl)methoxy)methyl)tetrahydrofuran-3-yl (2-cyanoethyl) diisopropylphophoramidite (Compound am-55) was obtained (0.240 g, 68%) in the same manner as in Step 2 of Reference Example 39.1 using (2R,4S,5R)-5-(6-(2-(bis(4-methoxyphenyl)(phenyl)methoxy)ethoxy)-9H-purin-9-yl)-2-((bis(4-methoxyphenyl)(phenyl)methoxy)methyl)tetrahydrofuran-3-ol (0.300 g, 0.318 mmol) obtained in Step 1.

$^1$H-NMR (CDCl$_3$, 400 MHz) δ: 8.44, 8.43 (1H, 2s), 8.13, 8.10 (1H, 2s), 7.46-7.14 (18H, m), 6.80-6.76 (8H, m), 6.51-6.47 (1H, m), 4.85-4.72 (3H, m), 4.34-4.28 (1H, m), 3.93-3.48 (18H, m), 3.44-3.32 (2H, m), 2.92-2.84 (1H, m), 2.71-2.58 (2H, m), 2.47 (1H, t, J=6.6 Hz), 1.21-1.11 (12H, m).
$^{31}$P-NMR (CDCl$_3$, 162 MHz) δ: 149.6, 149.4.

Example 61

An siRNA (referred to as 06-(2-phosphonooxyethyl) dI) having Compound I-59 as X at the 5' end of the antisense strand of 454-Xa shown in Table 38 below was synthesized in the same manner as in Example 1-1 using Compound am-55 obtained in Reference Example 55.1.
ESI-MS (antisense strand): theoretical value: 6798.91, actual value: 6798.98

Reference Example 56.1: Compound am-56

Step 1
8-bromo-2'-deoxy-adenosine (1 g, 3.03 mmol) was dissolved in ethanol (15.2 mL). To the mixture were added diisopropylethylamine (2.65 mL, 15.2 mmol) and benzylamine (1.32 mL, 12.1 mmol), and the mixture was stirred under reflux for 5 hours. The solvent was evaporated under reduced pressure to obtain crude 8-benzylamino-2'-deoxy-adenosine.
Step 2
8-benzylamino-2'-deoxy-adenosine obtained in Step 1 was dissolved in DMF (15.2 mL). To the mixture was added 1,1-dimethoxy-N,N-dimethylmethanamine (6.04 mL, 45.5 mmol), and the mixture was stirred at room temperature for 2 hours. The solvent was evaporated under reduced pressure, and the residue was purified by chloroform/methanol silica gel column chromatography to obtain (E)-N'-(8-(benzylamino)-9-((2R,4S,5R)-4-hydroxy-5-(hydroxymethyl)tetrahydrofuran-2-yl)-9H-purin-6-yl)-N,N-dimethylformimidamide (0.743 g, 60%).
Step 3
N-(8-(benzylamino)-9-((2R,4S,5R)-5-((bis(4-methoxyphenyl)(phenyl)methoxy)methyl)-4-hydroxytetrahydrofuran-2-yl)-9H-purin-6-yl)formamide was obtained (0.216 g, 17%) in the same manner as in Step 4 of Reference Example 1.1 using (E)-N'-(8-(benzylamino)-9-((2R,4S,5R)-4-hydroxy-5-(hydroxymethyl)tetrahydrofuran-2-yl)-9H-purin-6-yl)-N,N-dimethylformimidamide (0.743 g, 1.81 mmol) obtained in Step 2.
ESI-MS (m/z): 688 (M+1)
Step 4
(2R,4S,5R)-5-(8-(benzylamino)-6-formamide-9H-purin-9-yl)-2-((bis(4-methoxyphenyl)(phenyl)methoxy)methyl) tetrahydrofuran-3-yl (2-cyanoethyl) diisopropylphosphoramidite (Compound am-56) was obtained (0.169 g, 62%) in the same manner as in Step 2 of Reference Example 39.1 using N-(8-(benzylamino)-9-((2R,4S,5R)-5-((bis(4-methoxyphenyl)(phenyl)methoxy)methyl)-4-hydroxytetrahydrofuran-2-yl)-9H-purin-6-yl)formamide (0.210 g, 0.306 mmol) obtained in Step 3.
$^{1}$H-NMR (CDCl$_3$, 400 MHz) δ: 9.79 (1H, d, J=10.6 Hz), 8.30 (1H, d, J=2.5 Hz), 8.13 (1H, d, J=10.6 Hz), 7.33-7.31 (2H, m), 7.24-7.17 (10H, m), 7.08-7.04 (2H, m), 6.73-6.68 (4H, m), 6.50-6.48 (1H, m), 6.34-6.31 (1H, m), 4.86-4.85 (1H, m), 4.35-4.31 (1H, m), 4.21-4.16 (1H, m), 4.04-3.94 (1H, m), 3.88-3.73 (7H, m), 3.65-3.50 (4H, m), 3.39-3.34 (1H, m), 3.04-3.00 (1H, m), 2.64-2.62 (1H, m), 2.56-2.40 (2H, m), 1.21-1.05 (12H, m).

Example 62

An siRNA (referred to as 8-benzylamino dA) having Compound I-60 as X at the 5' end of the antisense strand of 454-Xa shown in Table 38 below was synthesized in the same manner as in Example 1-1 using compound am-56 obtained in Reference Example 56.1.
ESI-MS (antisense strand): theoretical value: 6779.03, actual value: 6779.44

Reference Example 57.1: Compound am-57

Step 1
(3-((bis(4-methoxyphenyl)(phenyl)methoxy)methyl)-5-((tert-butyldiphenylsilyl)oxy)phenyl)methanol was obtained (0.977 g, 55%) in the same manner as in Step 4 of Reference Example 1.1 using (5-((tert-butyldiphenylsilyl)oxy)-1,3-phenylene)dimethanol (1.00 g, 2.55 mmol).
Step 2
Crude 9-((2R,4S,5R)-5-((bis(4-methoxyphenyl)(phenyl)methoxy)methyl)-4-((tert-butyldimethylsilyl)oxy)tetrahydrofuran-2-yl)-6-((3-((bis(4-meth oxyphenyl)(phenyl)methoxy)methyl)-5-((tert-butyldiphenylsilyl)oxy)benzyl) oxy)-9H-purine was obtained in the same manner as in Step 2 of Reference Example 50.1 using (3-((bis(4-methoxyphenyl)(phenyl)methoxy)methyl)-5-((tert-butyldiphenylsilyl)oxy)phenyl)methanol (0.977 g, 1.41 mmol) obtained in Step 1 and 9-((2R,4S,5R)-5-((bis(4-methoxyphenyl)(phenyl) methoxy)methyl)-4-((tert-butyldimethylsilyl)oxy)tetrahydrofuran-2-yl)-6-chloro-9H-purine (0.483 g, 0.703 mmol) obtained in Step 1 of Reference Example 51.1.
Step 3
(2R,3S,5R)-2-((bis(4-methoxyphenyl)(phenyl)methoxy) methyl)-5-(6-((3-((bis(4-methoxyphenyl)(phenyl)methoxy) methyl)-5-hydroxybenzyl)oxy)-9H-purin-9-yl)tetrahydrofuran-3-ol was obtained (0.514 g, 74%) in the same manner as in Step 3 of Reference Example 50.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-((3-((bis(4-meth oxyphenyl)(phenyl)methoxy)methyl)-5-((tert-butyldiphenylsilyl)oxy)benzyl)oxy)-9H-purine obtained in Step 2.
Step 4
(2R,3S,5R)-2-((bis(4-methoxyphenyl(phenyl)methoxy)-5-(6-((3-((bis(4-methoxyphenyl)(phenyl)methoxy)methyl)-5-hydroxybenzyl)oxy)-9H-purin-9-yl)tetrahydrofuran-3-ol (0.186 g, 0.187 mmol) obtained in Step 3 was dissolved in THF (0.935 mL), aqueous sodium hydroxide (1 mol/L, 0.206 mL, 0.206 mmol) and 1-(1H-[1,2,3]triazolo[4,5-b] pyridin-1-yl)ethanone (0.036 g, 0.224 mmol) were added, and the mixture was stirred at room temperature for 4 hours. Saturated sodium chloride aqueous solution was added to the reaction solution, which was then back extracted with ethyl acetate. The organic layer was washed with saturated brine and dried with anhydrous sodium sulfate, and the solvent was evaporated under reduced pressure. The residue was purified by hexane/ethyl acetate silica gel column chromatography to obtain 3-((bis(4-methoxyphenyl)(phenyl)methoxy)methyl)-5-(((9-((2R,4S,5R)-5-((bis(4-methoxyphenyl)(phenyl)methoxy)methyl)-4-hydroxytetrahydro furan-2-yl)-9H-purine-6-yl)oxy)methyl)phenyl acetate (0.082 g, 42%).
ESI-MS (m/z): 1035 (M+1)
Step 5
3-((bis(4-methoxyphenyl)(phenyl)methoxy)methyl)-5-(((9-((2R,4S,5R)-5-((bis(4-methoxyphenyl)(phenyl) methoxy)methyl)-4-(((2-cyanoethoxy) (diisopropylamino) phosphany)oxy)tetrahydrofuran-2-yl)-9H-purin-6-yl)oxy) methyl)phenyl acetate (Compound am-57) was obtained (0.039 g, 41%) in the same manner as in Step 2 of Reference Example 39.1 using 3-((bis(4-methoxyphenyl)(phenyl)

methoxy)methyl)-5-(((9-((2R,4S,5R)-5-((bis(4-methoxyphenyl)(phenyl)methoxy)methyl)-4-hydroxytetrahydrofuran-2-yl)-9H-purine-6-yl)oxy)methyl)phenyl acetate (0.080 g, 0.077 mmol) obtained in Step 4.

$^1$H-NMR (CDCl$_3$, 400 MHz) δ: 8.46 (1H, d, J=1.0 Hz), 8.10 (1H, d, J=8.9 Hz), 7.49-7.47 (2H, m), 7.40-7.17 (18H, m), 7.12-7.10 (1H, m), 6.85-6.75 (8H, m), 6.48-6.46 (1H, m), 5.65 (2H, s), 4.76-4.74 (1H, m), 4.31-4.29 (1H, m), 4.17 (2H, s), 3.78-3.34 (18H, m), 2.61-2.47 (4H, m), 2.29 (3H, s), 1.20-1.11 (12H, m).

Example 63

An siRNA (referred to as 06-(3-hydroxy-5-phosphonooxymethyl)Bn dI) having Compound I-61 as X at the 5' end of the antisense strand of 454-Xa shown in Table 38 below was synthesized in the same manner as in Example 1-1 using Compound am-57 obtained in Reference Example 57.1. ESI-MS (antisense strand): theoretical value: 6890.02, actual value: 6889.9

Reference Example 58.1: Compound am-58

Step 1
(3-(9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)phenyl)methanol was obtained (0.721 g, 84%) in the same manner as in Step 2 of Reference Example 6.0 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.781 g, 1.136 mmol) obtained in Reference Example 51.1. and (3-(hydroxymethyl)phenyl)boronic acid.

Step 2
Crude 9-((2R,4S,5R)-5-((bis(4-methoxyphenyl)(phenyl)methoxy)methyl)-4-((tert-butyldimethylsilyl)oxy)tetrahydrofuran-2-yl)-6-(3-((bis(4-methoxyphenyl)(phenyl)methoxy)phenyl)-9H-purine was obtained in the same manner as in Step 4 of Reference Example 1.1 using (3-(9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)phenyl)methanol (0.721 g, 0.950 mmol) obtained in Step 1.

Step 3
(2R,3S,5R)-2-((bis(4-methoxyphenyl)(phenyl)methoxy)methyl)-5-(6-(3-((bis(4-methoxyphenyl)(phenyl)methoxy)methyl)phenyl)-9H-purin-9-yl)tetrahydrofuran-3-ol was obtained (0.809 g, 90%) in the same manner as in Step 3 of Reference Example 50.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-(3-((bis(4-methoxyphenyl)(phenyl)methoxy)phenyl)-9H-purine obtained in Step 2.
ESI-MS (m/z): 948 (M+1)

Step 4
(2R,3S,5R)-2-((bis(4-methoxyphenyl)(phenyl)methoxy)methyl)-5-(6-(3-((bis(4-methoxyphenyl)(phenyl)methoxy)methyl)phenyl)-9H-purin-9-yl)tetrahydrofuran-3-yl (2-cyanoethyl) diisopropylphosphoramidite (Compound am-58) was obtained (0.154 g, 67%) in the same manner as in Step 2 of Reference Example 39.1 using (2R,3S,5R)-2-((bis(4-methoxyphenyl)(phenyl)methoxy)methyl)-5-(6-(3-((bis(4-methoxyphenyl)(phenyl)methoxy)methyl)phenyl)-9H-purin-9-yl)tetrahydrofuran-3-ol (0.189 g, 0.200 mmol) obtained in Step 3.

$^1$H-NMR (CDCl$_3$, 400 MHz) δ: 8.92 (1H, d, J=1.8 Hz), 8.70 (1H, d, J=7.6 Hz), 8.66 (1H, d, J=1.3 Hz), 8.29 (1H, d, J=9.9 Hz), 7.68 (1H, d, J=7.6 Hz), 7.58-7.52 (3H, m), 7.46-7.38 (6H, m), 7.31-7.15 (10H, m), 6.85-6.83 (4H, m), 6.78-6.75 (4H, m), 6.56-6.53 (1H, m), 4.79-4.77 (1H, m), 4.34-4.32 (3H, m), 3.79-3.68 (16H, m), 3.47-3.32 (2H, m), 2.97-2.94 (1H, m), 2.64-2.62 (2H, m), 2.48-2.47 (1H, m), 1.19-1.14 (12H, m).

Example 64

An siRNA (referred to as 06-(3-hydroxy-5-phosphorylmethyl)Bn dI) having Compound I-62 as X at the 5' end of the antisense strand of 454-Xa shown in Table 38 below was synthesized in the same manner as in Example 1-1 using Compound am-58 obtained in Reference Example 58.1.
ESI-MS (antisense strand): theoretical value: 6844.98, actual value: 6844.96

Reference Example 59.1: Compound am-59

Step 1
Ethyl 3-(3-(9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)phenyl)propanoate was obtained (0.899 g, 90%) in the same manner as in Step 2 of Reference Example 6.0 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.825 g, 1.20 mmol) obtained in Reference Example 51.1 and (3-(3-ethoxy-3-oxopropyl)phenyl)boronic acid (0.400 g, 1.80 mmol).

Steps 2 to 3
2-cyanoethyl 3-(3-(9-((2R,4S,5R)-5-((bis(4-methoxyphenyl)(phenyl)methoxy)methyl)-4-hydroxytetrahydrofuran-2-yl)-9H-purin-6-yl)phenyl)propanoate was obtained in the same manner as in Steps 2 to 3 of Reference Example 26.1 using ethyl 3-(3-(9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)phenyl)propanoate obtained in Step 1.
ESI-MS (m/z): 741 (M+1)

Step 4
2-cyanoethyl 3-(3-(9-((2R,4S,5R)-5-((bis(4-methoxyphenyl)(phenyl)methoxy)methyl)-4-(((2-cyanoethoxy) (diisopropylamino)phosphanyl)oxy)tetrahydrofuran-2-yl)-9H-purin-6-yl)phenyl)propanoate (Compound am-59) was obtained (0.115 g, 61%) in the same manner as in Step 2 of Reference Example 39.1 using 2-cyanoethyl 3-(3-(9-((2R,4S,5R)-5-((bis(4-methoxyphenyl)(phenyl)methoxy)methyl)-4-hydroxytetrahydrofuran-2-yl)-9H-purin-6-yl)phenyl)propanoate (0.148 g, 0.200 mmol) obtained in Step 3.

$^1$H-NMR (CDCl$_3$, 400 MHz) δ: 8.92 (1H, d, J=1.3 Hz), 8.70 (1H, s), 8.68 (1H, s), 8.30 (1H, d, J=10.4 Hz), 7.41-7.40 (4H, m), 7.31-7.18 (7H, m), 6.79-6.76 (4H, m), 6.56-6.54 (1H, m), 4.80-4.79 (1H, m), 4.35-4.27 (3H, m), 3.89-3.58 (10H, m), 3.48-3.33 (2H, m), 3.07-3.05 (2H, m), 2.98-2.93 (1H, m), 2.78-2.61 (6H, m), 2.48-2.47 (1H, m), 1.19-1.14 (12H, m).

Example 65

An siRNA (referred to as 6-(3-carboxyethylphenyl)-Pu) having Compound I-63 as X at the 5' end of the antisense strand of 454-Xa shown in Table 38 below was synthesized in the same manner as in Example 1-1 using Compound am-59 obtained in Reference Example 59.1.

ESI-MS (antisense strand): theoretical value: 6807.03, actual value: 6807.48

Reference Example 60.1: Compound am-60

Step 1

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-(3-methoxy-3-oxopropyl)phenyl)-9H-purine was obtained (620 mg, 45.6%) in the same manner as in Step 2 of Reference Example 6.0 using 6-chloro-9-((4aR,6R,7R,7aS)-2,2-di-tert-butyl-7-(tert-butyldimethyl silyloxy)tetrahydro-4H-furo[3,2-d][1,3,2]dioxasilin-6-yl)-9H-purine (1.10 g, 2.032 mmol) obtained in Step 2 of Reference Example 17.1 and (3-(3-methoxy-3-oxopropyl)phenyl)boronic acid (634 mg, 3.05 mmol).

Step 2

9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-(3-methoxy-3-oxopropyl)phenyl)-9H-purine (620 mg, 0.927=1) obtained in Step 1 was dissolved in tetrahydrofuran (10 mL). To the mixture was added THF solution (3 mol/L) of lithium borohydride (1.545 mL, 4.63 mmol) under ice cooling, and the mixture was stirred at room temperature for 3 hours. Additional THF solution (3 mol/L) of lithium borohydride (1.545 mL, 4.63 mmol) was added, and the mixture was stirred at room temperature for 2 hours. Saturated sodium bicarbonate solution was added under ice cooling to the reaction mixture, which was then extracted with ethyl acetate, the organic layer was washed with saturated brine and dried with anhydrous magnesium sulfate, the solvent was evaporated under reduced pressure, and the residue was purified by ethyl acetate/heptane silica gel column chromatography to obtain 9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-(3-hydroxypropyl)phenyl)-9H-purine (207 mg, 34.8%).

Steps 3 to 5

(2R,3R,4R,5R)-2-((bis(4-methoxyphenyl)(phenyl)methoxy)methyl)-5-(6-(3-(3-(bis(4-methoxyphenyl)(phenyl)methoxy)propyl)phenyl)-9H-purin-9-yl)-4-(tert-butyldimethylsilyloxy)tetrahydrofuran-3-yl 2-cyanoethyl diisopropylphosphoramidite (Compound am-60) was obtained in the same manner as in Steps 3 to 5 of Reference Example 1.1 using 9-((4aR,6R,7R,7aR)-2,2-di-tert-butyl-7-(tert-butyldimethylsilyloxy)tetrahydro-4H-furo[3,2-d][1,3,2]dioxasilin-6-yl)-6-(3-(3-hydroxypropyl)phenyl)-9H-purine obtained in Step 2.

$^1$H-NMR (CDCl$_3$, 400 MHz) δ: 8.90, 8.88 (1H, 2s), 8.68-8.50 (2H, m), 8.35, 8.31 (1H, 2s), 7.53-7.15 (20H, m), 6.85-6.77 (8H, m), 6.18-6.07 (1H, m), 5.16-5.10 (1H, m), 4.46-4.38 (2H, m), 4.02-3.85 (1H, m), 3.80-3.74 (12H, m), 3.70-3.54 (4H, m), 3.38-3.28 (1H, m), 3.17-3.11 (2H, m), 2.91-2.84 (2H, m), 2.69-2.62 (1H, m), 2.34-2.25 (1H, m), 2.07-1.96 (2H, m), 1.23-1.03 (12H, m), 0.75, 0.74 (9H, 2s), −0.02, −0.06, −0.21, −0.23 (6H, 4 s).

Example 66

An siRNA (referred to as 6-(m-phosphonooxypropylphenyl)-Pu) having Compound I-64 as X at the 5' end of the antisense strand of 454-Xa shown in Table 38 below was synthesized in the same manner as in Example 1-1 using Compound am-60 obtained in Reference Example 60.1.

ESI-MS (antisense strand): theoretical value: 6889.03, actual value: 6890.19

Reference Example 61.1: Compound am-61

Step 1

Commercial (2R,3S,5R)-5-(6-chloro-9H-purin-9-yl)-2-(hydroxymethyl)tetrahydrofuran-3-ol (3.00 g, 11.1 mmol) was suspended in pyridine (55 mL). To the mixture was added 4,4'-dimethoxytrityl chloride (4.51 g, 13.3 mmol), and the mixture was stirred at room temperature for 3 hours. Methanol was added to the reaction solution, and the mixture was stirred for 15 minutes. Toluene was added to the mixture, and the solvent was evaporated under reduced pressure. The residue was purified by hexane/ethyl acetate column chromatography to obtain (2R,3S,5R)-2-((bis(4-methoxyphenyl)(phenyl)methoxy)methyl)-5-(6-chloro-9H-purin-9-yl)tetrahydrofuran-3-ol (4.89 g, 82%).

ESI-MS (m/z): 573 (M+1)

Step 2

(2R,3S,5R)-2-((bis(4-methoxyphenyl)(phenyl)methoxy)methyl)-5-(6-chloro-9H-purin-9-yl)tetrahydrofuran-3-ol (250 mg, 0.436 mmol) obtained in Step 1 was dissolved in dimethylformamide (2.5 mL). To the mixture were added water (0.5 mL), tripotassium phosphate (185 mg, 0.872 mmol), indol-2-boronic acid pinacol ester (0.037 mL, 0.523 mmol) and [1,1'-bis(diphenylphosphino)ferrocene]palladiium (II) dichloride dichloromethane adduct (35.6 mg, 0.044 mmol), and the mixture was stirred at 80° C. for 1 hour. The reaction solution was filtered, and the filtrate was extracted with ethyl acetate and dried with anhydrous magnesium sulfate. The reaction solution was evaporated under reduced pressure, and the residue was purified by hexane/ethyl acetate silica gel column chromatography to obtain (2R,3S,5R)-5-(6-(1H-indol-2-yl)-9H-purin-9-yl)-2-((bis(4-methoxyphenyl) (phenyl)methoxy)methyl)tetrahydrofuran-3-ol (151 mg, 53%).

$^1$H-NMR (CDCl$_3$, 400 MHz) δ: 10.38 (s, 1H), 8.84 (s, 1H), 8.28 (s, 1H), 7.83-7.83 (m, 1H), 7.74-7.76 (m, 1H), 7.50-7.52 (m, 1H), 7.39-7.42 (m, 2H), 7.13-7.34 (m, 9H), 6.79-6.83 (m, 4H), 6.53 (t, J=6.4 Hz, 1H), 4.71-4.75 (m, 1H), 4.15-4.19 (m, 1H), 3.76 (d, J=1.3 Hz, 6H), 3.44-3.45 (m, 2H), 2.91-2.97 (m, 1H), 2.57-2.64 (m, 1H).

ESI-MS (m/z): 654 (M+1)

Step 3

(2R,3S,5R)-5-(6-(1H-indol-2-yl)-9H-purin-9-yl)-2-((bis(4-methoxyphenyl) (phenyl)methoxy)methyl)tetrahydrofuran-3-yl 2-cyanoethyl diisopropylphosphoramidite (Compound am-61) was obtained in the same manner as in Reference Example 1.1 using (2R,3S,5R)-5-(6-(1H-indol-2-yl)-9H-purin-9-yl)-2-((bis(4-methoxyphenyl) (phenyl)methoxy)methyl)tetrahydrofuran-3-ol obtained in Step 2. This compound was used in the following step without purification.

Example 67

An siRNA (referred to as 6-(1H-indol-2-yl-dPu) having Compound I-65 as X at the 5' end of the antisense strand of 454-Xa shown in Table 38 below was synthesized in the same manner as in Example 1-1 using Compound am-61 obtained in Reference Example 61.1.

ESI-MS (antisense strand): theoretical value: 6775.01, actual value: 6774.64

Reference Example 62.1: Compound am-62

Step 1

Commercial 9-((2R,4S,5R)-5-((bis(4-methoxyphenyl)(phenyl)methoxy)methyl)-4-hydroxytetrahydrofuran-2-yl)-1H-purin-6(9H)-one (5.02 g, 9.05 mmol) was suspended in THF (250 mL). To the mixture were added diisopropylethylamine (4.74 mL, 27.2 mmol) and 1H-benzotriazol-1-yloxy tris(dimethylamino)phosphonium hexafluorophosphate (4.83 g, 10.9 mmol), and the mixture was stirred at room temperature for 2 days. Additional 1H-benzotriazol-1-yloxy tris(dimethylamino)phosphonium hexafluorophosphate (8.00 g, 18.1 mmol) was added to the mixture, and the mixture was stirred overnight. Saturated sodium bicarbonate solution was added to the reaction solution, and the solvent was evaporated under reduced pressure until the amount of solvent was roughly half. The mixture was extracted with ethyl acetate and dried with anhydrous magnesium sulfate. The solvent was evaporated under reduced pressure, and the residue was purified by hexane/ethyl acetate silica gel column chromatography to obtain (2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (5.77 g, 95%).

$^{1}$H-NMR (CDCl$_3$, 400 MHz) δ: 8.34 (s, 1H), 8.28 (s, 1H), 8.14 (d, J=8.3 Hz, 1H), 7.20-7.56 (m, 12H), 6.79-6.85 (m, 4H), 6.52 (t, J=6.5 Hz, 1H), 4.70-4.73 (m, 1H), 4.16-4.19 (m, 1H), 3.78 (s, 6H), 3.39-3.48 (m, 2H), 2.84-2.91 (m, 1H), 2.58-2.64 (m, 1H).

ESI-MS (m/z): 672 (M+1)

Step 2

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (250 mg, 0.436 mmol) obtained in Step 1 was dissolved in ethanol (5 mL). To the mixture were added diisopropylethylamine (0.152 mL, 0.872 mmol) and 2-mercaptoethanol (0.037 mL, 0.523 mmol), and the mixture was stirred at 60° C. for 1 hour. Additional 2-mercaptoethanol (0.061 mL, 0.872 mmol) was added, and the mixture was stirred at 60° C. for 4 hours. The reaction solution was extracted with ethyl acetate and dried with anhydrous magnesium sulfate. The solvent was evaporated from the reaction solution under reduced pressure, and the residue was purified by hexane/ethyl acetate column chromatography to obtain (2R,3S,5R)-2-((bis(4-methoxphenyl)(phenyl)methoxy)methyl)-5-(6-(2-hydroxyethylthio)-9H-purin-9-yl)tetrahydrofuran-3-ol (207 mg, 77%).

$^{1}$H-NMR (CDCl$_3$, 400 MHz) δ: 8.57 (s, 1H), 8.08 (s, 1H), 7.13-7.47 (m, 18H), 6.77-6.81 (m, 8H), 6.45 (t, J=6.5 Hz, 1H), 4.65-4.70 (m, 1H), 4.09-4.14 (m, 1H), 3.77 (d, J-2.8 Hz), 12H), 3.60-3.64 (m, 2H), 3.35-3.45 (m, 4H), 2.80-2.87 (m, 1H), 2.51-2.57 (m, 1H).

Step 3

(2R,3S,5R)-5-(6-(2-(bis(4-methoxyphenyl)(phenyl)methoxy)ethylthio)-9H-purin-9-yl)-2-((bis(4-methoxyphenyl)(phenyl)methoxy)methyl)tetra hydrofuran-3-yl 2-cyanoethyl diisopropylphosphoramidite (Compound am-62) was obtained in the same manner as in Reference Example 1.1 using (2R,3S,5R)-2-((bis(4-methoxphenyl)(phenyl)methoxy)methyl)-5-(6-(2-hydroxyethylthio)-9H-purin-9-yl)tetrahydrofuran-3-ol obtained in Step 2. This compound was used in the following step without purification.

Example 68

An siRNA (referred to as 6-(phosphonooxyethyl)thio-dPu) having Compound I-66 as X at the 5' end of the antisense strand of 454-Xa shown in Table 38 below was synthesized in the same manner as in Example 1-1 using Compound am-62 obtained in Reference Example 62.1.

ESI-MS (antisense strand): theoretical value: 6815.98, actual value: 6815.44

Reference Example 63.1: Compound am-63

Step 1

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (400 mg, 0.689 mmol) obtained in Step 1 of Reference Example 63 was dissolved in ethanol (8 mL). To the mixture were added diisopropylethylamine (0.247 mL, 1.40 mmol) and 4-mercapto-1-butanol (0.086 mL, 0.838 mmol), and the mixture was stirred at 60° C. for 3 hours. Additional 4-mercapto-1-butanol (0.144 mL, 1.40 mmol) was added, and the mixture was stirred at 60° C. for 4 hours. Additional diisopropyl ethylamine (0.247 mL, 1.40 mmol) and 4-mercapto-1-butanol (0.144 mL, 1.40 mmol) were added to the mixture, and the mixture was stirred at 60° C. overnight. The reaction solution was extracted with ethyl acetate and dried with anhydrous magnesium sulfate. The solvent was evaporated from the reaction solution under reduced pressure, and the residue was purified by hexane/ethyl acetate column chromatography to obtain (2R,3S,5R)-2-((bis(4-methoxphenyl)(phenyl)methoxy)methyl)-5-(6-(4-hydroxybutylthio)-9H-purin-9-yl)tetrahydrofuran-3-ol (341 mg, 76%).

ESI-MS (m/z): 643 (M+1)

Step 2

(2R,3S,5R)-2-((bis(4-methoxyphenyl)(phenyl)methoxy)methyl)-5-(6-(4-hydroxybutylthio)-9H-purin-9-yl)tetrahydrofuran-3-ol (304 mg, 0.530 mmol) obtained in Step 1 was dissolved in dichloromethane (7 mL). To the mixture were added triethylamine (0.369 mL, 2.65 mmol) and 4,4'-dimethoxytrityl chloride (269 mg, 0.795 mmol), and the mixture was stirred overnight at room temperature. Methanol was added to the reaction solution, which was then stirred for 30 minutes. The reaction solution was extracted with chloroform and dried with anhydrous magnesium sulfate. The solvent was evaporated under reduced pressure, and the residue was purified by hexane/ethyl acetate column chromatography to obtain (2R,3S,5R)-5-(6-(4-(bis(4-methoxyphenyl)(phenyl)methoxy)butylthio)-9H-purin-9-yl)-2-((bis(4-methoxyphenyl)(phenyl)methoxy)methyl)tetra hydrofuran-3-ol (437 mg, 87%).

$^{1}$H-NMR (CDCl$_3$, 400 MHz) δ: 8.59 (s, 1H), 8.08 (s, 1H), 7.13-7.44 (m, 18H), 6.78-6.82 (m, 8H), 6.45 (t, J=6.5 Hz, 1H), 4.65-4.70 (m, 1H), 4.11-4.14 (m, 1H), 3.77 (s, 12H), 3.41-3.45 (m, 1H), 3.35-3.39 (m, 3H), 3.10 (t, J=6.2 Hz, 1H), 2.81-2.87 (m, 1H), 1.98-2.01 (m, 1H), 2.51-2.57 (m, 1H), 1.86-1.93 (m, 2H), 1.76-1.83 (m, 2H).

Step 3

(2R,3S,5R)-5-(6-(2-(bis(4-methoxyphenyl)(phenyl)methoxy)butylthio)-9H-purin-9-yl)-2-((bis(4-methoxyphenyl)(phenyl)methoxy)methyl)tetra hydrofuran-3-yl 2-cyanoethyl diisopropylphosphoramidite (Compound am-63) was obtained in the same manner as in Reference Example 1.1 using (2R,3S,5R)-5-(6-(4-(bis(4-methoxyphenyl)(phenyl)methoxy)butylthio)-9H-purin-9-yl)-2-((bis(4-methoxyphenyl)(phenyl)methoxy)methyl)tetra hydrofuran-3-ol obtained in Step 2. This compound was used in the following step without purification.

Example 69

An siRNA (referred to as 6-(phosphonooxybutyl)thio-dPu) having Compound I-67 as X at the 5' end of the antisense strand of 454-Xa shown in Table 38 below was synthesized in the same manner as in Example 1-1 using Compound am-63 obtained in Reference Example 63.1.

ESI-MS (antisense strand): theoretical value: 6844.03, actual value: 6843.73

Reference Example 64.1: Compound am-64

Step 1

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (90.0 mg, 0.134 mmol) obtained in Step 1 of Reference Example 63 was dissolved in ethanol (1 mL). To the mixture were added diisopropyl ethylamine (0.047 mL, 0.268 mmol) and thiophenol (0.012 mL, 0.121 mmol), and the mixture was stirred at 60° C. for 1 hour. The solvent was evaporated under reduced pressure, and the residue was purified by hexane/ethyl acetate silica gel column chromatography to obtain (2R,3S,5R)-2-((bis(4-methoxyphenyl)(phenyl)methoxy)methyl)-5-(6-(phenylthio)-9H-purin-9-yl)tetrahydrofuran-3-ol (70.1 mg, 71%).

$^1$H-NMR (CDCl$_3$, 400 MHz) δ: 8.54 (s, 1H), 8.14 (s, 1H), 7.63-7.69 (m, 2H), 7.45-7.49 (m, 3H) 7.13-7.40 (m, 9H), 6.78-6.82 (m, 4H), 6.46 (t, J=6.4 Hz, 1H), 4.67-4.71 (m, 1H), 4.11-4.15 (m, 1H), 3.78 (s, 6H), 3.34-3.45 (m, 2H), 2.84-2.90 (m, 1H), 2.51-2.58 (m, 1H).

Step 2

(2R,3S,5R)-2-((bis(4-methoxyphenyl)(phenyl)methoxy)methyl)-5-(6-(phenylthio)-9H-purin-9-yl)tetrahydrofuran-3-yl 2-cyanoethyl diisopropylphosphoramidite (Compound am-64) was obtained in the same manner as in Reference Example 1.1 using (2R,3S,5R)-2-((bis(4-methoxyphenyl)(phenyl)methoxy)methyl)-5-(6-(phenylthio)-9H-purin-9-yl)tetrahydrofuran-3-ol obtained in Step 1. This compound was used in the following step without purification.

Example 70

An siRNA (referred to as 6-phenylthio-dPu) having Compound I-68 as X at the 5' end of the antisense strand of 454-Xa shown in Table 38 below was synthesized in the same manner as in Example 1-1 using Compound am-64 obtained in Reference Example 64.1.

ESI-MS (antisense strand): theoretical value: 6768.04, actual value: 6767.68

Reference Example 65.1: Compound am-65

Step 1

(2R,3S,5R)-5-(6-chloro-9H-purin-9-yl)-2-(hydroxymethyl)tetrahydrofuran-3-ol obtained in Step 1 of Reference Example 62 (250 mg, 0.436 mmol) was dissolved in dimethylformamide (2.5 mL). To the mixture were added water (0.5 mL), tripotassium phosphate (185 mg, 0.872 mmol), 4-(hydroxymethyl)phenylboronic acid (99.4 mg, 0.648 mmol) and [1,1'-bis(diphenylphosphino)ferrocene]palladium (II) dichloride dichloromethane adduct (35.6 mg, 0.044 mmol), and the mixture was stirred at 80° C. for 1 hour. The reaction solution was filtered, and the filtrate was extracted with ethyl acetate and dried with anhydrous magnesium sulfate. The solvent was evaporated from the reaction solution under reduced pressure, and the residue was purified by hexane/ethyl acetate column chromatography to obtain (2R,3S,5R)-2-((bis(4-methoxyphenyl)(phenyl)methoxy)methyl)-5-(6-(4-(hydroxymethyl)phenyl)-9H-purin-9-yl)tetrahydrofuran-3-ol (166 mg, 61%).

ESI-MS (m/z): 654 (M+1)

Step 2

(2R,3S,5R)-2-((bis(4-methoxyphenyl)(phenyl)methoxy)methyl)-5-(6-(4-(hydroxymethyl)phenyl)-9H-purin-9-yl)tetrahydrofuran-3-ol (165 mg, 0.256 mmol) obtained in Step 1 was dissolved in dichloromethane (3 mL). To the mixture were added triethylamine (0.178 mL, 1.28 mmol) and 4,4'-dimethoxytrityl chloride (130 mg, 0.384 mmol), and the mixture was stirred overnight at room temperature. Methanol was added to the reaction solution, which was then stirred for 30 minutes. The reaction solution was extracted with chloroform and dried using anhydrous magnesium sulfate. The solvent was evaporated under reduced pressure, and the residue was purified by hexane/ethyl acetate silica gel column chromatography to obtain (2R,3S,5R)-2-((bis(4-methoxyphenyl)(phenyl)methoxy)methyl)-5-(6-(4-((bis(4-methoxyphenyl)(phenyl)methoxy)methyl)phenyl)-9H-purin-9-yl)tetrahydrofuran-3-ol (yield 180 mg, 74%).

$^1$H-NMR (CDCl$_3$, 400 MHz) δ: 8.93 (s, 1H), 8.73-8.75 (d, J=8.4 Hz, 2H), 8.26 (s, 1H), 7.59 (d, J=8.6 Hz, 2H), 7.52-7.54 (m, 2H), 7.39-7.44 (m, 6H), 7.14-7.33 (m, 11H), 6.83-6.87 (m, 4H), 6.78-6.82 (m, 4H), 6.55 (t, J=6.5 Hz, 1H), 4.70-4.74 (m, 1H), 4.15-4.18 (dd, J=3.8 Hz, 1H), 3.76-3.80 (m, 12H), 3.40-3.48 (m, 2H), 2.90-2.96 (m, 1H), 2.57-2.63 (m, 1H).

ESI-MS (m/z): 947 (M+1)

Step 3

(2R,3S,5R)-2-((bis(4-methoxyphenyl)(phenyl)methoxy)methyl)-5-(6-(4-((bis(4-methoxyphenyl)(phenyl)methoxy)methyl)phenyl)-9H-purin-9-yl)tetrahydrofuran-3-yl 2-cyanoethyl diisopropylphosphoramidite (Compound am-65) was obtained in the same manner as in Reference Example 1.1 using (2R,3S,5R)-2-((bis(4-methoxyphenyl)(phenyl)methoxy)methyl)-5-(6-(4-((bis(4-methoxyphenyl)(phenyl)methoxy)methyl)phenyl)-9H-purin-9-yl)tetrahydrofuran-3-ol obtained in Step 2. This compound was used in the following step without purification.

Example 71

An siRNA (referred to as 6-(4-phosphonooxymethyl)phenyl-dPu) having Compound I-69 as X at the 5' end of the antisense strand of 454-Xa shown in Table 38 below was synthesized in the same manner as in Example 1-1 using Compound am-65 obtained in Reference Example 65.1.

ESI-MS (antisense strand): theoretical value: 6845.98, actual value: 6845.62

Example 72

An siRNA (referred to as 6-(3-carboxymethylphenyl)-Pu) having Compound I-70 as X at the 5' end of the antisense strand of 454-Xa shown in Table 38 below was synthesized in the same manner as in Example 1-1 using Compound am-51 obtained in Reference Example 51.1.

ESI-MS (antisense strand): theoretical value: 6809.00, actual value: 6804.3

Reference Example 66.1: Compound am-66

Step 1

4-((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)buta-2-yn-1-ol was obtained (0.280 g, 52%) in the same manner as in Step 1 of Reference Example 53.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.500 g, 0.727 mmol) obtained in Step 1 of Reference Example 51.1 and 4-aminobuta-2-yn-1-ol hydrochloride (0.265 g, 2.18 mmol).

Steps 2 to 3

(2R,3S,5R)-5-(6-((4-(bis(4-methoxyphenyl)(phenyl)methoxy)buta-2-yn-1-yl)amino)-9H-purin-9-yl)-2-((bis(4- methoxyphenyl)(phenyl)methoxy)methyl)tetrahydrofuran-3-ol was obtained (0.240 g, 68%) in the same manner as in Step 4 of Reference Example 1.1 and Step 3 of Reference Example 50.1 using 4-((9-((2R,4S,5R)-5-((bis(4-methoxyphenyl)(phenyl)methoxy)methyl)-4-((tert-butyldimethylsilyl)oxy)tetrahydrofuran-2-yl)-9H-purin-6-yl)amino)buta-2-yn-1-ol (0.280 g, 0.380 mmol) obtained in Step 1.

ESI-MS (m/z): 924 (M+1)

Step 4

(2R,3S,5R)-5-(6-((4-(bis(4-methoxyphenyl)(phenyl)methoxy)buta-2-yn-1-yl)amino)-9H-purin-9-yl)-2-((bis(4-methoxyphenyl)(phenyl)methoxy)methyl)tetrahydrofuran-3-yl (2-cyanoethyl) diisopropylphosphoramidite (Compound am-66) was obtained (0.168 g, 57%) in the same manner as in Step 2 of Reference Example 39.1 using (2R,3S,5R)-5-(6-((4-(bis(4-methoxyphenyl)(phenyl)methoxy)buta-2-yn-1-yl)amino)-9H-purin-9-yl)-2-((bis(4-methoxyphenyl)(phenyl)methoxy)methyl)tetrahydrofuran-3-ol (0.240 g, 0.260 mmol) obtained in Step 3.

$^1$H-NMR (CDCl$_3$, 400 MHz) δ: 8.35 (1H, s), 7.97, 7.95 (1H, 2s), 7.46-7.17 (18H, m), 6.84-6.76 (8H, m), 6.45-6.41 (1H, m), 5.82 (1H, brs), 4.78-4.71 (1H, m), 4.47 (2H, brs), 4.30-4.26 (1H, m), 3.95-3.54 (18H, m), 3.44-3.30 (2H, m), 2.91-2.83 (1H, m), 2.68-2.55 (2H, m), 2.46 (1H, t, J=6.4 Hz), 1.20-1.11 (12H, m).

Example 73

An siRNA (referred to as N6-(4-phosphonooxy-2-butynyl) dA) having Compound I-71 as X at the 5' end of the antisense strand of 454-Xa shown in Table 38 below was synthesized in the same manner as in Example 1-1 using Compound am-66 obtained in Reference Example 66.1.

ESI-MS (antisense strand): theoretical value: 6821.66, actual value: 6823.08

Reference Example 67.1: Compound am-67

Step 1

Crude 4,4'-(((2-iodobenzyl)oxy)(phenyl)methylene)bis(methoxybenzene) was obtained (7.67 g) in the same manner as in Step 4 of Reference Example 1.1 using (2-iodophenyl)methanol (3.00 g, 12.8 mmol).

Step 2

4,4'-(((2-iodobenzyl)oxy)(phenyl)methylene)bis(methoxybenzene) (2.00 g) obtained in Step 1 was dissolved in THF (19.0 mL). To the mixture were added triethylamine (19 mL), propargylamine (1.43 mL, 22.4 mmol) and copper iodide (71.8 mg, 0.337 mmol). Argon gas was blown in for 10 minutes to degass the system. Tetrakis triphenyl phosphine palladium (0.216 g, 0.187 mmol) was added to the mixture, which was then stirred at room temperature for 23 hours. The reaction solution was filtered with Celite, and the filtrate was concentrated under reduced pressure. The residue was dissolved in dichloromethane and washed with water, and the water layer was further extracted with dichloromethane, after which the organic layers were combined, dried with anhydrous sodium sulfate and concentrated under reduced pressure. The resulting crude product was purified by silica gel column chromatography (developing solvent: 100% chloroform containing 1% triethylamine) to obtain 3-(2-((bis(4-methoxyphenyl)(phenyl)methoxy)methyl)phenyl)propan-2-yn-1-amine (0.650 g, 35%).

Steps 3 to 4

(2R,3S,5R)-2-((bis(4-methoxyphenyl)(phenyl)methoxy)methyl)-5-(6-((3-(2-((bis(4-methoxyphenyl)(phenyl)methoxy)methyl)phenyl)propa-2-yn-1-yl)amino)-9H-purin-9-yl)tetrahydrofuran-3-ol was obtained (0.240 g, 36%) in the same manner as in Step 1 of Reference Example 53.1 and Step of Reference Example 50.1 using 9-((2R,4S,5R)-5-((bis(4-methoxyphenyl)(phenyl)methoxy)methyl)-4-((tert-butyldimethylsilyl)oxy)tetrahydrofuran-2-yl)-6-chloro-9H-purine (0.400 g, 0.582 mmol) obtained in Step 1 of Reference Example 51.1 and 3-(2-((bis(4-methoxyphenyl)(phenyl)methoxy)methyl)phenyl)propan-2-yn-1-amine (0.650 g, 1.40 mmol) obtained in Step 2.

ESI-MS (m/z): 1000 (M+1)

Step 5

(2R,3S,5R)-2-((bis(4-methoxyphenyl)(phenyl)methoxy)methyl)-5-(6-((3-(2-((bis(4-methoxyphenyl)(phenyl)methoxy)methyl)phenyl)propa-2-yn-1-yl)amino)-9H-purin-9-yl)tetrahydrofuran-3-yl (2-cyanoethyl) diisopropylphosphoramidite (Compound am-67) was obtained (0.106 g, 42%) in the same manner as in Step 2 of Reference Example 39.1 using (2R,3S,5R)-2-((bis(4-methoxyphenyl)(phenyl)methoxy)methyl)-5-(6-((3-(2-((bis(4-methoxyphenyl)(phenyl)methoxy)methyl)phenyl)propa-2-yn-1-yl)amino)-9H-purin-9-yl)tetrahydrofuran-3-ol (0.240 g, 0.211 mmol) obtained in Step 4.

$^1$H-NMR (CDCl$_3$, 400 MHz) δ: 8.33 (1H, s), 7.97, 7.95 (1H, 2s), 7.73, 7.71 (1H, 2 brs), 7.52-7.48 (2H, m), 7.42-7.35 (8H, m), 7.31-7.16 (11H, m), 6.85-6.75 (8H, m), 6.48-6.42 (1H, m), 5.76 (1H, brs), 4.80-4.71 (1H, m), 4.54 (2H, brs), 4.29 (3H, brs), 3.94-3.31 (18H, m), 3.04-2.56 (3H, m), 2.46 (1H, t, J=6.4 Hz), 1.29-1.11 (12H, m).

Example 74

An siRNA (referred to as N6-(2-phosphonooxymethyl)phenylpropargyl dA) having Compound I-72 as X at the 5' end of the antisense strand of 454-Xa shown in Table 38 below was synthesized in the same manner as in Example 1-1 using Compound am-67 obtained in Reference Example 67.1.

ESI-MS (antisense strand): theoretical value: 6897.76, actual value: 6898.86

Reference Example 68.1: Compound am-68

Steps 1 to 5

(2R,3S,5R)-2-((bis(4-methoxyphenyl)(phenyl)methoxy)methyl)-5-(6-((3-(3-((bis(4-methoxyphenyl)(phenyl)methoxy)methyl)phenyl)propa-2-yn-1-yl)amino)-9H-purin-9-yl)tetrahydrofuran-3-yl (2-cyanoethyl) diisopropylphosphoramidite (Compound am-68) was obtained in the same manner as in Steps 1 to 5 of Reference Example 67.1 using (3-iodophenyl) methanol.

(CDCl$_3$, 400 MHz) δ: 8.38 (1H, s), 7.98, 7.96 (1H, 2s), 7.51-7.16 (22H, m), 6.85-6.76 (8H, m), 6.46-6.42 (1H, m), 5.96 (1H, brs), 4.79-4.65 (3H, m), 4.32-4.26 (1H, m), 4.15-4.10 (2H, m), 3.96-3.32 (18H, m), 2.92-2.84 (1H, m), 2.69-2.56 (2H, m), 2.46 (1H, t, J=6.6 Hz), 1.20-1.10 (12H, m).

Example 75

An siRNA (referred to as N6-(3-phosphonooxymethyl)phenylpropargyl dA) having Compound I-73 as X at the 5' end of the antisense strand of 454-Xa shown in Table 38 below was synthesized in the same manner as in Example 1-1 using Compound am-68 obtained in Reference Example 68.1. ESI-MS (antisense strand): theoretical value: 6897.76, actual value: 6898.90

Reference Example 69.1: Compound am-69

Steps 1 to 5

(2R,3S,5R)-2-((bis(4-methoxyphenyl)(phenyl)methoxy)methyl)-5-(6-((3-(4-((bis(4-methoxyphenyl)(phenyl)methoxy)methyl)phenyl)propa-2-yn-1-yl)amino)-9H-purin-9-yl)tetrahydrofuran-3-yl (2-cyanoethyl) diisopropylphosphoramidite (Compound am-69) was obtained in the same manner as in Steps 1 to 5 of Reference Example 67.1 using (4-iodophenyl)methanol.

$^1$H-NMR (CDCl$_3$, 400 MHz) δ: 8.38 (1H, s), 7.99, 7.96 (1H, 2s), 7.51-7.47 (2H, m), 7.40-7.18 (20H, m), 6.85-6.76 (8H, m), 6.46-6.42 (1H, m), 5.96 (1H, brs), 4.80-4.64 (3H, m), 4.31-4.26 (1H, m), 4.15 (2H, s), 3.96-3.31 (18H, m), 2.93-2.56 (3H, m), 2.46 (1H, t, J=6.4 Hz), 1.20-1.11 (12H, m).

Example 76

An siRNA (referred to as N6-(4-phosphonooxymethyl)phenylpropargyl dA) having Compound I-74 as X at the 5' end of the antisense strand of 454-Xa shown in Table 38 below was synthesized in the same manner as in Example 1-1 using Compound am-69 obtained in Reference Example 69.1. ESI-MS (antisense strand): theoretical value: 6897.76, actual value: 6899.02

Reference Example 70.1: Compound am-70

Step 1

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (350 mg, 0.521 mmol) obtained in Step 1 of Reference Example 63 was dissolved in ethanol (5.2 mL). To the mixture were added diisopropyl ethylamine (0.273 mL, 1.56 mmol) and 4-hydroxybenzenethiol (78.9 mg, 0.625 mmol), and the mixture was stirred at 60° C. for 1 hour. Additional 4-hydroxybenzenethiol (32.9 mg, 0.261 mmol) was added to the mixture, and the mixture was stirred for 1 hour. The solvent was evaporated from the reaction solution under reduced pressure, and the precipitate was filtered. The solvent was evaporated from the filtrate under reduced pressure, and the residue was purified by amino silica gel column chromatography (chloroform/methanol) to obtain (2R,3S,5R)-2-((bis(4-methoxyphenyl)(phenyl)methoxy)methyl)-5-(6-(4-hydroxyphenylthio)-9H-purin-9-yl)tetrahydrofuran-3-ol (282 mg, 82%).

$^1$H-NMR (CDCl$_3$, 400 MHz) δ: 8.55 (s, 1H), 8.15 (s, 1H), 7.45-7.49 (m, 2H), 7.36-7.39 (m, 2H), 7.18-7.30 (m, 7H), 6.83-6.87 (m, 2H), 6.78-6.82 (m, 4H), 6.46 (t, J=6.5 Hz, 1H), 6.40 (s, 1H), 4.66-4.71 (m, 1H), 4.12-4.15 (m, 1H), 3.78 (s, 6H), 3.35-3.45 (m, 2H), 2.82-2.89 (m, 1H), 2.52-2.58 (m, 1H).

ESI-MS (m/z): 663 (M+1)

Step 2

(2R,3S,5R)-2-((bis(4-methoxyphenyl)(phenyl)methoxy)methyl)-5-(6-(4-hydroxyphenylthio)-9H-purin-9-yl)tetrahydrofuran-3-ol obtained in Step 1 (280 mg, 0.422 mmol) was dissolved in dichloromethane (4.2 mL). To the mixture were added triethylamine (0.178 mL, 1.27 mmol) and pivaloyl chloride (0.078 mL, 0.643 mmol), and the mixture was stirred at room temperature for 1 hour. Saturated sodium bicarbonate solution (4 mL) was added to the reaction solution, which was then stirred for 30 minutes. The reaction solution was extracted with chloroform and dried with anhydrous magnesium sulfate. The solvent was evaporated under reduced pressure, and the residue was purified by hexane/ethyl acetate column chromatography to obtain 4-(9-((2R,4S,5R)-5-((bis(4-methoxyphenyl)(phenyl)methoxy)methyl)-4-hydroxytetrahydrofuran-2-yl)-9H-purin-6-ylthio)phenyl pivalate (304 mg, 78%).

ESI-MS (m/z): 747 (M+1)

Step 3

4-(9-((2R,4S,5R)-5-((bis(4-methoxyphenyl)(phenyl)methoxy)methyl)-4-((2-cyanoethoxy) (diisopropylamino)phosphinooxy)tetrahydrofuran-2-yl)-9H-purin-6-ylthio)phenyl pivalate (Compound am-70) was obtained in the same manner as in Reference Example 1.1 using 4-(9-((2R,4S,5R)-5-((bis(4-methoxyphenyl)(phenyl)methoxy)methyl)-4-hydroxytetrahydrofuran-2-yl)-9H-purin-6-ylthio)phenyl pivalate obtained in Step 2. This compound was used in the following step without purification.

Example 77

An siRNA (referred to as 6-(4-hydroxy)phenylthio-dPu) having Compound I-75 as X at the 5' end of the antisense strand of 454-Xa shown in Table 38 below was synthesized in the same manner as in Example 1-1 using Compound am-70 obtained in Reference Example 70.1.

ESI-MS (antisense strand): theoretical value: 6784.04, actual value: 6784.15

Reference Example 71.1: Compound am-71

Step 1

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (350 mg, 0.521 mmol) obtained in Step 1 of Reference Example 63 was dissolved in ethanol (5.2 mL). To the mixture were added diisopropylethylamine (0.273 mL, 1.56 mmol) and 3-hydroxybenzenethiol (0.063 mL, 0.625 mmol), and the mixture was stirred at 60° C. for 1 hour. Additional 3-hydroxybenzenethiol (0.026 mL, 0.261 mmol) was added to the mixture, and the mixture was stirred for 1 hour. The solvent was evaporated from the reaction solution under reduced pressure, and the resulting precipitate was filtered. The solvent was evaporated from the filtrate under reduced pressure, and the residue was purified by chloroform/methanol NH column chromatography to obtain (2R,3S,5R)-2-((bis(4-methoxyphenyl)(phenyl)methoxy)methyl)-5-(6-(3-hydroxyphenylthio)-9H-purin-9-yl)tetrahydrofuran-3-ol (267 mg, 77%).

$^1$H-NMR (CDCl$_3$, 400 MHz) δ: 8.55 (s, 1H), 8.15 (s, 1H), 7.16-7.39 (m, 11H), 7.07-7.08 (m, 1H), 6.88-6.91 (m, 1H), 6.77-6.82 (m, 4H), 6.64 (bs, 1H), 6.45 (t, J=6.4 Hz, 1H), 4.69-4.72 (m, 1H), 4.11-4.15 (m, 1H), 3.78 (s, 6H), 3.35-3.44 (m, 2H), 2.85-2.91 (m, 1H), 2.53-2.59 (m, 1H).

ESI-MS (m/z): 663 (M+1)

Step 2

(2R,3S,5R)-2-((bis(4-methoxyphenyl)(phenyl)methoxy)methyl)-5-(6-(3-hydroxyphenylthio)-9H-purin-9-yl)tetrahydrofuran-3-ol (265 mg, 0.400 mmol) obtained in Step 1 was dissolved in dichloromethane (4 mL). To the mixture were added triethylamine (0.167 mL, 1.20 mmol) and pivaloyl chloride (0.073 mL, 0.600 mmol), and the mixture was stirred at room temperature for 1 hour. Saturated sodium bicarbonate solution (4 mL) was added to the reaction solution, which was then stirred for 30 minutes. The reaction solution was extracted with chloroform and dried with anhydrous magnesium sulfate. The solvent was evaporated under reduced pressure, and the residue was purified by hexane/ethyl acetate silica gel column chromatography to obtain 3-(9-((2R,4S,5R)-5-((bis(4-methoxyphenyl)(phenyl)

methoxy)methyl)-4-hydroxytetrahydrofuran-2-yl)-9H-purin-6-ylthio)phenyl pivalate (263 mg, 88%).

$^1$H-NMR (CDCl$_3$, 400 MHz) δ: 8.55 (s, 1H), 8.14 (s, 1H), 7.20-7.56 (m, 13H), 6.78-6.82 (m, 4H), 6.46 (t, J=6.5 Hz, 1H), 4.66-4.71 (m, 1H), 4.11-4.15 (m, 1H), 3.78 (s, 6H), 3.35-3.45 (m, 2H), 2.84-2.90 (m, 1H), 2.52-2.58 (m, 1H), 1.35 (s, 9H).

ESI-MS (m/z): 747 (M+1)

Step 3

3-(9-((2R,4S,5R)-5-((bis(4-methoxyphenyl)(phenyl)methoxy)methyl)-4-((2-cyanoethoxy) (diisopropylamino)phosphinooxy)tetrahydrofuran-2-yl)-9H-purin-6-ylthio)phenyl pivalate (Compound am-71) was obtained in the same manner as in Reference Example 1.1 using 3-(9-((2R,4S,5R)-5-((bis(4-methoxyphenyl)(phenyl)methoxy)methyl)-4-hydroxytetrahydrofuran-2-yl)-9H-purin-6-ylthio)phenyl pivalate obtained in Step 2. This compound was used in the following step without purification.

Example 78

An siRNA (referred to as 6-(3-hydroxyphenyl)thio-dPu) having Compound I-76 as X at the 5' end of the antisense strand of 454-Xa shown in Table 38 below was synthesized in the same manner as in Example 1-1 using Compound am-71 obtained in Reference Example 71.1.

ESI-MS (antisense strand): theoretical value: 6784.04, actual value: 6783.69

Reference Example 72.1: Compound am-72

Step 1

(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol (350 mg, 0.521 mmol) obtained in Step 1 of Reference Example 63 was dissolved in ethanol (5.2 mL). To the mixture were added diisopropyl ethylamine (0.273 mL, 1.56 mmol) and 2-mercaptobenzyl alcohol (124 mg, 0.886 mmol), and the mixture was stirred at 60° C. for 1 hour. The solvent was evaporated from the reaction solution under reduced pressure, and the resulting residue was filtered. The solvent was evaporated from the filtrate under reduced pressure, and the residue was purified by chloroform/methanol NH column chromatography to obtain (2R,3S,5R)-2-((bis(4-methoxyphenyl)(phenyl)methoxy)methyl)-5-(6-(3-(hydroxymethyl)phenylthio)-9H-purin-9-yl)tetrahydrofuran-3-ol (310 mg, 98%).

ESI-MS (m/z): 677 (M+1)

Step 2

(2R,3S,5R)-2-((bis(4-methoxyphenyl)(phenyl)methoxy)methyl)-5-(6-(3-(hydroxymethyl)phenylthio)-9H-purin-9-yl)tetrahydrofuran-3-ol (304 mg, 0.449 mmol) obtained in Step 1 was dissolved in dichloromethane (4.5 mL). To the mixture were added triethylamine (0.313 mL, 2.46 mmol) and 4,4'-dimethoxytrityl chloride (305 mg, 0.898 mmol), and the mixture was stirred at room temperature for 2 hours. Methanol was added to the reaction solution, which was then stirred for 30 minutes. The reaction solution was extracted with chloroform and dried with anhydrous magnesium sulfate. The solvent was evaporated under reduced pressure, and the residue was purified by hexane/ethyl acetate silica gel column chromatography to obtain (2R,3S,5R)-2-((bis(4-methoxyphenyl)(phenyl)methoxy)methyl)-5-(6-(3-((bis(4-methoxyphenyl)(phenyl)methoxy)methyl)phenylthio)-9H-purin-9-yl)tetrahydrofuran-3-ol (301 mg, 59%).

$^1$H-NMR (CDCl$_3$, 400 MHz) δ: 8.55 (s, 1H), 8.14 (s, 1H), 7.14-7.66 (m, 22H), 6.78-6.84 (m, 8H), 6.46 (t, J=6.5 Hz, 1H), 4.66-4.70 (m, 1H), 4.22 (s, 2H), 4.12-4.15 (m, 1H), 3.78 (d, J=2.5 Hz, 12H), 3.34-3.45 (m, 2H), 2.83-2.89 (m, 1H), 2.52-2.58 (m, 1H).

ESI-MS (m/z): 979 (M+1)

Step 3

(2R,3S,5R)-2-((bis(4-methoxyphenyl)(phenyl)methoxy)methyl)-5-(6-(3-((bis(4-methoxyphenyl)(phenyl)methoxy)methyl)phenylthio)-9H-purin-9-yl)tetrahydrofuran-3-yl 2-cyanoethyl diisopropylphosphoramidite (Compound am-72) was obtained in the same manner as in Reference Example 1.1 using (2R,3S,5R)-2-((bis(4-methoxyphenyl)(phenyl)methoxy)methyl)-5-(6-(3-((bis(4-methoxyphenyl)(phenyl)methoxy)methyl)phenylthio)-9H-purin-9-yl)tetrahydrofuran-3-ol obtained in Step 2. This compound was used in the following step without purification.

Example 79

An siRNA (referred to as 6-(3-phosphonooxymethyl)phenylthio-dPu) having Compound I-77 as X at the 5' end of the antisense strand of 454-Xa shown in Table 38 below was synthesized in the same manner as in Example 1-1 using Compound am-72 obtained in Reference Example 72.1.

ESI-MS (antisense strand): theoretical value: 6878.05, actual value: 6877.67

Reference Example 73.1: Compound am-73

Step 1

Methyl 3-(9-((2R,4S,5R)-5-((bis(4-methoxyphenyl)(phenyl)methoxy)methyl)-4-hydroxytetrahydrofuran-2-yl)-9H-purin-6-yl)benzoate was obtained (0.275 g, 57%) in the same manner as in Step 2 of Reference Example 6.0 using (2R,3S,5R)-2-((bis(4-methoxyphenyl)(phenyl)methoxy)methyl)-5-(6-chloro-9H-purin-9-yl)tetrahydrofuran-3-ol (0.400 g, 0.698 mmol) synthesized by the method described in J. Am. Chem. Soc., 1991, Vol. 113, pp 4329-4331 and 3-(methoxycarbonyl)benzeneboronic acid (0.380 g, 2.09 mmol).

ESI-MS (m/z): 673 (M+1)

Step 2

Methyl 3-(9-((2R,4S,5R)-5-((bis(4-methoxyphenyl)(phenyl)methoxy)methyl)-4-(((2-cyanoethoxy) (diisopropylamino)phosphanyl)oxy)tetrahydrofuran-2-yl)-9H-purin-6-yl)benzoate (Compound am-73) was obtained (97.0 mg, 28%) in the same manner as in Step 2 of Reference Example 39.1 using methyl 3-(9-((2R,4S,5R)-5-((bis(4-methoxyphenyl)(phenyl)methoxy)methyl)-4-hydroxytetrahydrofuran-2-yl)-9H-purin-6-yl)benzoate (0.275 g, 0.401 mmol) obtained in Step 1.

$^1$H-NMR (CDCl$_3$, 400 MHz) δ: 9.41 (1H, brs), 9.03, 9.01 (1H, 2 brs), 8.97, 8.97 (1H, 2s), 8.34, 8.31 (1H, 2s), 8.23-8.19 (1H, m), 7.65 (1H, t, J=8.0 Hz), 7.42-7.38 (2H, m), 7.32-7.16 (7H, m), 6.82-6.75 (4H, m), 6.58-6.54 (1H, m), 4.84-4.76 (1H, m), 4.38-4.31 (1H, m), 3.98 (3H, s), 3.93-3.56 (10H, m), 3.49-3.34 (2H, m), 3.01-2.93 (1H, m), 2.78-2.61 (2H, m), 2.48 (1H, t, J=6.4 Hz), 1.22-1.13 (12H, m).

Example 80

An siRNA (referred to as 6-(3-carbamoyl)phenyl Pu) having Compound I-78 as X at the 5' end of the antisense strand of 454-Xa shown in Table 38 below was synthesized in the same manner as in Example 1-1 using Compound am-73 obtained in Reference Example 73.1.

ESI-MS (antisense strand): theoretical value: 6777.71, actual value: 6778.90

Example 81

An siRNA (referred to as 6-(3-(N-methylcarbamoyl))phenyl-Pu) having Compound I-79 as X at the 5' end of the antisense strand of 454-Xa shown in Table 38 below was synthesized in the same manner as in Example 57 using Compound am-73 obtained in Reference Example 73.1.

ESI-MS (antisense strand): theoretical value: 6791.74, actual value: 6793.01

Reference Example 74: Compound am-74

Steps 1 to 2

(2R,3S,5R)-2-((bis(4-methoxyphenyl)(phenyl)methoxy)methyl)-5-(6-(3-(methylsulfonyl)phenyl)-9H-purin-9-yl)tetrahydrofuran-3-yl (2-cyanoethyl) diisopropylphosphoramidite (Compound am-74) was obtained in the same manner as in Steps 1 to 2 of Reference Example 73.1 using 3-(methylsulfonyl)phenylboronic acid.

$^1$H-NMR (CDCl$_3$, 400 MHz) δ: 9.43 (1H, brs), 9.20-9.17 (1H, m), 8.98, 8.98 (1H, 2s), 8.37, 8.34 (1H, 2s), 8.12, 8.10 (1H, 2 brs), 7.78 (1H, dd, J=8.0, 8.0 Hz), 7.45-7.15 (9H, m), 6.83-6.75 (4H, m), 6.60-6.55 (1H, m), 4.89-4.76 (1H, m), 4.39-4.32 (1H, m), 3.95-3.56 (10H, m), 3.52-3.33 (2H, m), 3.17 (3H, s), 3.02-2.94 (1H, m), 2.80-2.62 (2H, m), 2.49 (1H, t, J=6.4 Hz), 1.25-1.14 (12H, m).

Example 82

An siRNA (referred to as 6-(3-methylsulfonyl)phenyl-Pu) having Compound I-80 as X at the 5' end of the antisense strand of 454-Xa shown in Table 38 below was synthesized in the same manner as in Example 1-1 using Compound am-74 obtained in Reference Example 74.1.

ESI-MS (antisense strand): theoretical value: 6812.78, actual value: 6814.23

Reference Example 75: Compound am-75

Steps 1 to 2

(2R,3S,5R)-2-((bis(4-methoxyphenyl)(phenyl)methoxy)methyl)-5-(6-(3-(cyanomethyl)phenyl)-9H-purin-9-yl)tetrahydrofuran-3-yl (2-cyanoethyl) diisopropylphosphoramidite (Compound am-75) was obtained in the same manner as in Steps 1 to 2 of Reference Example 73.1 using 3-cyanomethylphenylboronic acid.

$^1$H-NMR (CDCl$_3$, 400 MHz) δ: 8.95, 8.94 (1H, 2s), 8.80, 8.78 (1H, 2 brs), 8.72 (1H, brs), 8.34, 8.32 (1H, 2s), 7.61-7.52 (2H, m), 7.41-7.38 (2H, m), 7.31-7.16 (7H, m), 6.80-6.77 (4H, m), 6.58-6.54 (1H, m), 4.85-4.76 (1H, m), 4.38-4.31 (1H, m), 3.90 (2H, s), 3.90-3.58 (10H, m), 3.49-3.34 (2H, m), 3.00-2.93 (1H, m), 2.78-2.61 (2H, m), 2.48 (1H, t, J=6.4 Hz), 1.22-1.13 (12H, m).

Example 83

An siRNA (referred to as 6-(3-cyanomethyl)phenyl-Pu) having Compound I-81 as X at the 5' end of the antisense strand of 454-Xa shown in Table 38 below was synthesized in the same manner as in Example 1-1 using Compound am-75 obtained in Reference Example 75.1.

ESI-MS (antisense strand): theoretical value: 6773.72, actual value: 6775.60

Reference Example 76.1: Compound am-76

Step 1

1,2,4-benzenetrimethanol (4.55 g, 27.1 mmol) was suspended in 2,2-dimethoxypropane (14.0 mL) in an argon atmosphere, and p-toleuenesulfonic acid monohydrate (0.256 g, 1.35 mmol) was added to the mixture. The mixture was stirred at room temperature for 35 minutes. Triethylamine (0.250 mL, 1.79 mmol) was added to stop the reaction, and the reaction solution was concentrated under reduced pressure. The resulting crude product was purified by silica gel column chromatography (chloroform containing 1% triethylamine/methanol=1/10 to 10/1) to obtain (3,3-dimethyl-1,5-dihydrobenzo[e][1,3]dioxepin-7-yl)methanol (2.73 g, 48%).

Step 2

9-((2R,4S,5R)-4-((tert-butyldimethylsilyl)oxy)-5-(((tert-butyldimethylsilyl)oxy)methyl)tetrahydrofuran-2-yl)-6-((3,3-dimethyl-1,5-dihydrobenzo[e][1,3]dioxepin-7-yl)methoxy)-9H-purine was obtained (1.37 g, 68%) in the same manner as in Step 2 of Reference Example 50.1 using (3,3-dimethyl-1,5-dihydrobenzo[e][1,3]dioxepin-7-yl)methanol (1.18 g, 5.65 mmol) obtained in Step 1 and 6-chloro-9-(2'-deoxy-3',5'-bis-O-(tert-butyldimethylsilyl)-β-D-erythropentofuranosyl) purine (1.50 g, 3.01 mmol) synthesized by the method described in Org. Lett., 2005, Vol. 7, pp 999-1002.

Step 3

9-((2R,4S,5R)-4-((tert-butyldimethylsilyl)oxy)-5-(((tert-butyldimethylsilyl)oxy)methyl)tetrahydrofuran-2-yl)-6-((3,3-dimethyl-1,5-dihydrobenzo[e][1,3]dioxepin-7-yl)methoxy)-9H-purine (1.30 g, 1.94 mmol) obtained in Step 2 was ice cooled. To the mixture was added 80% (v/v) aqueous acetic acid solution (26.0 mL), and the mixture was stirred at room temperature for 20 minutes. The reaction solution was added little by little to ice cooled saturated sodium bicarbonate solution for 20 minutes to stop the reaction and extracted with ethyl acetate. The organic layer was washed with saturated brine, dried with anhydrous sodium sulfate, and concentrated under reduced pressure to obtain crude (4-(((9-((2R,4S,5R)-4-((tert-butyldimethylsilyl)oxy)-5-(((tert-butyldimethylsilyl)oxy)methyl)tetrahydrofuran-2-yl)-9H-purin-6-yl)oxy)methyl)-1,2-phenylene)dimethanol.

Step 4

Crude 6-((3,4-bis((bis(4-methoxyphenyl)(phenyl)methoxy)methyl)benzyl)oxy)-9-((2R,4S,5R)-4-((tert-butyldimethylsilyl)oxy)-5-(((tert-butyldimethylsilyl)oxy)methyl)tetrahydrofuran-2-yl)-9H-purine was obtained in the same manner as in Step 4 of Reference Example 1.1 using the crude (4-(((9-((2R,4S,5R)-4-((tert-butyldimethylsilyl)oxy)-5-(((tert-butyldimethylsilyl)oxy)methyl)tetrahydrofuran-2-yl)-9H-purin-6-yl)oxy)methyl)-1,2-phenylene)dimethanol obtained in Step 3.

Step 5

(2R,3S,5R)-5-(6-((3,4-bis((bis(4-methoxyphenyl)(phenyl)methoxy)meth yl)benzyl)oxy)-9H-purin-9-yl)-2-(hydroxymethyl)tetrahydrofuran-3-ol was obtained (1.22 g, 56%) in the same manner as in Step 3 of Reference Example 50.1 using the crude 6-((3,4-bis((bis(4-methoxyphenyl)(phenyl)methoxy)methyl)benzyl)oxy)-9-((2R,4S,5R)-4-((tert-butyldimethylsilyl)oxy)-5-(((tert-butyldimethylsilyl)oxy)methyl)tetrahydrofuran-2-yl)-9H-purine obtained in Step 4.

Step 6

(2R,3S,5R)-5-(6-((3,4-bis((bis(4-methoxyphenyl)(phenyl)methoxy)meth yl)benzyl)oxy)-9H-purin-9-yl)-2-((bis(4-methoxyphenyl)(phenyl)methoxy)methyl)tetrahydrofuran-3-ol was obtained (0.732 g, 48%) in the same manner as in Step 4 of Reference Example 1.1 using (2R,3S,5R)-5-(6-((3,4-bis((bis(4-methoxyphenyl)(phenyl)methoxy)

meth yl)benzyl)oxy)-9H-purin-9-yl)-2-(hydroxymethyl)tetrahydrofuran-3-ol (1.22 g, 1.10 mmol) obtained in Step 5.

$^1$H-NMR (CDCl$_3$, 400 MHz) δ: 8.50 (1H, s), 8.06 (1H, s), 7.71 (1H, d, J=1.6 Hz), 7.61 (1H, d, J=7.8 Hz), 7.53 (1H, dd, J=7.8, 1.6 Hz), 7.41-7.16 (27H, m), 6.81-6.79 (4H, m), 6.74-6.69 (8H, m), 6.48 (1H, t, J=6.4 Hz), 5.74 (2H, s), 4.70-4.66 (1H, m), 4.16-4.12 (1H, m), 4.03 (4H, s), 3.77 (6H, s), 3.76 (6H, s), 3.76 (6H, s), 3.45 (1H, dd, J=10.3, 4.8 Hz), 3.38 (1H, dd, J=10.3, 5.3 Hz), 2.84 (1H, ddd, J=13.7, 6.4, 6.4 Hz), 2.57-2.52 (1H, m).

Step 7

(2R,3S,5R)-5-(6-((3,4-bis((bis(4-methoxyphenyl)(phenyl)methoxy)meth yl)benzyl)oxy)-9H-purin-9-yl)-2-((bis(4-methoxyphenyl)(phenyl)methoxy)methyl)tetrahydrofuran-3-yl (2-cyanoethoxy) diisopropylphosphoramidite (Compound am-76) was obtained (0.566 g, 71%) in the same manner as in Step 2 of Reference Example 39.1 using (2R,3S,5R)-5-(6-((3,4-bis((bis(4-methoxyphenyl)(phenyl)methoxy)meth yl)benzyl)oxy)-9H-purin-9-yl)-2-((bis(4-methoxyphenyl)(phenyl)methoxy)methyl)tetrahydrofuran-3-ol (0.732 g, 0.525 mmol) obtained in Step 6.

$^1$H-NMR (CDCl$_3$, 400 MHz) δ: 8.45 (1H, s), 8.11, 8.09 (1H, 2s), 7.70 (1H, brs), 7.60 (1H, d, J=7.8 Hz), 7.53 (1H, dd, J=7.8, 1.8 Hz), 7.40-7.15 (27H, m), 6.79-6.75 (4H, m), 6.73-6.68 (8H, m), 6.50-6.46 (1H, m), 5.73 (2H, s), 4.80-4.72 (1H, m), 4.33-4.29 (1H, m), 4.02 (4H, s), 3.93-3.55 (22H, m), 3.43-3.32 (2H, m), 2.92-2.84 (1H, m), 2.70-2.57 (2H, m), 2.47 (1H, t, J=6.4 Hz), 1.21-1.11 (12H, m).

Example 84

An siRNA (referred to as 06-(3,4-diphosphonooxymethyl)Bn dI) having Compound I-82 as X at the 5' end of the antisense strand of 454-Xa shown in Table 38 below was synthesized in the same manner as in Example 1-1 using Compound am-76 obtained in Reference Example 76.1.

ESI-MS (antisense strand): theoretical value: 6984.72, actual value: 6986.66

Reference Example 77.1: Compound am-77

Step 1

(3-((bis(4-methoxyphenyl)(phenyl)methoxy)methyl)-5-fluorophenyl)methanol was obtained (0.898 g, 48%) in the same manner as in Step 4 of Reference Example 1.1 using 5-fluoro-1,3-benzene trimethanol (0.638 g, 4.09 mmol).

Step 2

(2R,3S,5R)-2-((bis(4-methoxyphenyl(phenyl)methoxy)methyl)-5-(6-(3-((bis(4-methoxyphenyl)(phenyl)methoxy)methyl)-5-fluorobenzyl)oxy)-9H-purin-9-yl)(tetrahydrofuran-3-ol was obtained (0.180 g, 31%) in the same manner as in Step 2 of Reference Example 50.1 using (3-((bis(4-methoxyphenyl)(phenyl)methoxy)methyl)-5-fluorophenyl) methanol (0.400 g, 0.872 mmol) obtained in Step 1 and (2R,3S,5R)-2-((bis(4-methoxyphenyl)(phenyl)methoxy) methyl)-5-(6-chloro-9H-purin-9-yl)tetrahydrofuran-3-ol (0.333 g, 0.582 mmol) synthesized by the method described in J. Am. Chem. Soc., 1991, Vol. 113, pp 4329-4331.

ESI-MS (m/z): 995 (M+1)

Step 3

(2R,3S,5R)-2-((bis(4-methoxyphenyl)(phenyl)methoxy) methyl)-5-(6-(3-((bis(4-methoxyphenyl)(phenyl)methoxy) methyl)-5-fluorobenzyl)oxy)-9H-purin-9-yl)(tetrahydrofuran-3-yl (2-cyanoethoxy) diisopropylphosphoramidite (Compound am-77) was obtained (0.135 g, 62%) in the same manner as in Step 2 of Reference Example 39.1 using (2R,3S,5R)-2-((bis(4-methoxyphenyl(phenyl)methoxy) methyl)-5-(6-(3-((bis(4-methoxyphenyl)(phenyl)methoxy) methyl)-5-fluorobenzyl)oxy)-9H-purin-9-yl)tetrahydrofuran-3-ol (0.180 g, 0.181 mmol) obtained in Step 2.

$^1$H-NMR (CDCl$_3$, 400 MHz) δ: 8.46, 8.45 (1H, 2s), 8.12, 8.09 (1H, 2s), 7.50-7.12 (21H, m), 6.85-6.76 (8H, m), 6.49-6.45 (1H, m), 5.63 (2H, s), 4.80-4.72 (1H, m), 4.33-4.28 (1H, m), 4.16 (2H, s), 3.96-3.55 (16H, m), 3.42-3.32 (2H, m), 2.92-2.84 (1H, m), 2.70-2.57 (2H, m), 2.47 (1H, t, J=6.4 Hz), 1.20-1.11 (12H, m).

Example 85

An siRNA (referred to as 06-(3-fluoro-5-phosphonooxymethyl)Bn dI) having Compound I-83 as X at the 5' end of the antisense strand of 454-Xa shown in Table 38 below was synthesized in the same manner as in Example 1-1 using Compound am-77 obtained in Reference Example 77.1.

ESI-MS (antisense strand): theoretical value: 6892.71, actual value: 6894.36

Reference Example 78.1: Compound am-78

Steps 1 to 3

(3-((bis(4-methoxyphenyl)(phenyl)methoxy)methyl)-5-((tert-butyldiphenylsilyl)oxy)phenyl)methanol (2.60 g, 3.74 mmol) obtained in Step 1 of Reference Example 58.1 was dissolved in dichloromethane (37.0 mL). Triethylamine (1.04 mL, 7.48 mmol) was added to the mixture, followed by ice cooling. Methanesulfonyl chloride (0.347 mL, 4.49 mmol) was added slowly dropwise to the mixture, and the mixture was stirred for 50 minutes under ice cooling. Water was added to the reaction solution under ice cooling to stop the reaction, followed by extraction with dichloromethane. The organic layer was washed with saturated brine (50 mL), dried with anhydrous sodium sulfate, and concentrated under reduced pressure to obtain crude 3-((bis(4-methoxyphenyl)(phenyl)methoxy)methyl)-5-((tert-butyldiphenylsilyl)oxy)benzyl methanesulfonate. The resulting crude product was dissolved in DMF (37.0 mL), and stirred at 60° C. for 4 hours after addition of sodium azide (0.291 g, 4.49 mmol). Ethyl acetate was added to the reaction solution, which was then washed twice with saturated brine. The organic layer was dried with anhydrous sodium sulfate and concentrated under reduced pressure. Methanol (37.0 mL) was added to the mixture to suspend the resulting crude product. To the mixture was added triphenylphosphine (0.980 g, 3.74 mmol), and the mixture was then refluxed for 55 minutes. The reaction solution was cooled and concentrated under reduced pressure, heptane (50.0 mL) and triethylamine (0.100 mL) were added to the residue, which was suspended and washed at 40° C. and then filtered, and the filtrate was concentrated under reduced pressure. This was suspended and washed by addition of heptane and triethylamine, and the operations from addition of heptane and triethylamine, and followed by suspending and washing up to concentration under reduced pressure were repeated 3 more times. The resulting residue was purified by silica gel column chromatography (developing solvent: n-heptane containing 1% triethylamine/chloroform=1/0→0/1→chloroform/methanol=1/0→10/1) to obtain (3-((bis(4-methoxyphenyl)(phenyl)methoxy)methyl)-5-((tert-butyldiphenylsilyl)oxy)phenyl)methanamine (1.62 g, including triphenylphosphine oxide).

Step 4

(2R,3S,5R)-2-((bis(4-methoxyphenyl)(phenyl)methoxy) methyl)-5-(6-((3-((bis(4-methoxyphenyl)(phenyl)methoxy)

methyl)-5-((tert-butyldiphenylsilyl)oxy)benzyl)amino)-9H-purin-9-yl)tetrahydrofuran-3-ol was obtained (0.285 g, 58%) in the same manner as in Step 1 of Reference Example 39.1 using (3-((bis(4-methoxyphenyl)(phenyl)methoxy)methyl)-5-((tert-butyldiphenylsilyl)oxy)phenyl)methanamine (0.784 g, including triphenylphosphine oxide) obtained in Step 3.

ESI-MS (m/z): 1230 (M+1)

Step 5

(2R,3S,5R)-2-((bis(4-methoxyphenyl)(phenyl)methoxy)methyl)-5-(6-((3-((bis(4-methoxyphenyl)(phenyl)methoxy)methyl)-5-((tert-butyldiphenylsilyl)oxy)benzyl)amino)-9H-purin-9-yl)tetrahydrofuran-3-yl (2-cyanoethoxy) diisopropylphosphoramidite (Compound am-78) was obtained (0.240 g, 72%) in the same manner as in Step 2 of Reference Example 39.1 using (2R,3S,5R)-2-((bis(4-methoxyphenyl)(phenyl)methoxy)methyl)-5-(6-((3-((bis(4-methoxyphenyl)(phenyl)methoxy)methyl)-5-((tert-butyldiphenylsilyl)oxy)benzyl)amino)-9H-purin-9-yl)tetrahydrofuran-3-ol (0.285 g, 0.232 mmol) obtained in Step 4.

$^1$H-NMR (CDCl$_3$, 400 MHz) δ: 8.28 (1H, s), 7.93, 7.90 (1H, 2s), 7.69 (4H, d, J=6.4 Hz), 7.42-7.15 (24H, m), 6.82-6.72 (11H, m), 6.46-6.42 (1H, m), 5.84 (1H, brs), 4.79-4.57 (3H, m), 4.31-4.26 (1H, m), 3.94 (2H, s), 3.89-3.31 (16H, m), 3.45-3.31 (2H, m), 2.90-2.81 (1H, m), 2.68-2.54 (2H, m), 2.46 (1H, t, J=6.6 Hz), 1.20-1.11 (12H, m), 1.09 (9H, s).

Example 86

An siRNA (referred to as N6-(3-hydroxy-5-phosphonooxymethyl)Bn dA) having Compound I-84 as X at the 5' end of the antisense strand of 454-Xa shown in Table 38 below was synthesized in the same manner as in Example 1-1 using Compound am-78 obtained in Reference Example 78.1. ESI-MS (antisense strand): theoretical value: 6889.73, actual value: 6891.42

Reference Example 79.1: Compound am-79

Step 1

The (2R,3S,5R)-2-((bis(4-methoxyphenyl)(phenyl)methoxy)methyl)-5-(6-((3-(hydroxymethyl)benzyl)amino)-9H-purin-9-yl)tetrahydrofuran-3-ol (0.337 g, 0.500 mmol) obtained in Step 1 of Reference Example 48.1 was dissolved in DMF (11.7 mL). To the mixture were added diisopropylethylamine (1.02 mL, 5.86 mmol), levulinic acid (0.144 mL, 1.41 mmol) and 1-[bis(dimethylamino)methylene]-1H-1,2,3-triazolo[4,5-b]pyridinium 3-oxide hexafluorophosphate (HATU) (0.892 g, 2.35 mmol), and the mixture was stirred overnight at room temperature. Saturated sodium bicarbonate solution was added to the reaction solution, which was then extracted with ethyl acetate. The organic layer was washed with water and saturated brine, dried with anhydrous sodium sulfate, and concentrated under reduced pressure. The residue was purified by chloroform/methanol silica gel column chromatography to obtain 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzyl 4-oxopentanoate (0.350 g, 39%).

ESI-MS (m/z): 772 (M+1)

Step 2

3-(((9-((2R,4S,5R)-5-((bis(4-methoxyphenyl)(phenyl)methoxy)methyl)-4-(((2-cyanoethoxy) (diisopropylamino)phosphanyl)oxy)tetrahydrofuran-2-yl)-9H-purin-6-yl)amino)methyl)benzyl 4-oxopentanoate (Compound am-79) was obtained (0.110 g, 25%) in the same manner as in Step 2 of Reference Example 39.1 using 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzyl 4-oxopentanoate (0.350 g, 0453 mmol) obtained in Step 1.

$^1$H-NMR (CDCl$_3$, 400 MHz) δ: 8.35 (1H, s), 7.94 (1H, d, J=9.4 Hz), 7.41-7.16 (13H, m), 6.79-6.77 (4H, m), 6.46-6.42 (1H, m), 6.02 (1H, br s), 5.09 (2H, s), 4.88 (2H, br s), 4.78-4.71 (1H, m), 4.29-4.27 (1H, m), 4.23-3.30 (13H, m), 2.91-2.44 (7H, m), 2.17 (3H, s), 1.17-1.12 (12H, m).

Example 87

An antisense strand was synthesized by solid-phase synthesis using Compound am-79 in the same manner as in Example 1, immersed in hydrazine solution (0.5 mol/L in acetic acid/pyridine=3:2, 500 μL), and allowed to stand for 20 minutes at room temperature. The resin was washed with acetonitrile, and coupled successively with commercial 2-(bis(4-methoxyphenyl)(phenyl)methoxy)ethyl (2-cyanoethyl) diisopropylphosphoramidite and a phosphorylation reagent in a nucleic acid synthesizer. The resulting solid-phase resin was post-treated in the same manner as in Reference Example 1 to synthesize siRNA having Compound I-85 as X at the 5' end of the antisense strand of 454-Xa shown in Table 38 below.

ESI-MS (antisense strand): theoretical value: 6998.05, actual value: 6998.23

Reference Example 80.1: Compound am-80

Step 1

Commercial 3-aminobenzyl alcohol (500 mg, 4.06 mmol) was dissolved in DMF (40 mL). To the mixture were added imidazole (415 mg, 6.09 mmol) and tert-butyldimethylsilyl chloride (734 mg, 4.87 mmol), and the mixture was stirred for 1 hour at room temperature. Water was added to the reaction solution, which was then stirred for 15 minutes. The reaction solution was extracted with ethyl acetate and dried with anhydrous magnesium sulfate, and the solvent was evaporated under reduced pressure. The residue was purified by hexane/ethyl acetate silica gel column chromatography to obtain 3-((tert-butyldimethylsilyloxy)methyl)aniline (893 mg, 93%).

ESI-MS (m/z): 238 (M+1)

Step 2

Commercial 9-((2R,4S,5R)-4-hydroxy-5-(hydroxymethyl)tetrahydrofuran-2-yl)-1H-purin-6(9H)-one (500 mg, 1.98 mmol) was suspended in DMF (13 mL). To the mixture were added imdazole (944.7 mg, 13.9 mmol) and tert-butyldimethylsilyl chloride (1.20 g, 7.93 mmol), and the mixture was stirred overnight at room temperature. Water was added to the reaction solution, which was then stirred for 30 minutes. The reaction solution was extracted with ethyl acetate and dried with anhydrous magnesium sulfate. The solvent was evaporated under reduced pressure, the residue was dissolved in tert-butylmethyl ether, and hexane was added to the solution. The precipitate was filtered out to obtain 9-((2R,4S,5R)-4-(tert-butyldimethylsilyloxy)-5-((tert-butyldimethyl silyloxy)methyl)tetrahydrofuran-2-yl)-1H-purin-6(9H)-one (886 mg, 93%).

ESI-MS (m/z): 481 (M+1)

Step 3

9-((2R,4S,5R)-4-(tert-butyldimethylsilyloxy)-5-((tert-butyldimethyl silyloxy)methyl)tetrahydrofuran-2-yl)-1H-purin-6(9H)-one (878 mg, 1.83 mmol) obtained in Step 2 was dissolved in THF (44 mL). To the mixture were added diisopropyl ethylamine (956 mL, 5.48 mmol) and 1H-benzotriazole-1-yloxytris(dimethylamino)phosphonium hexafluorophosphate (2.42 g, 5.48 mmol), and the mixture was stirred at room temperature for 2 days. Saturated sodium bicarbonate solution was added to the reaction solution, which was then filtered. The filtrate was extracted with ethyl acetate and dried with anhydrous magnesium sulfate. The solvent was evaporated under reduced pressure, and the residue was filtered out. The solvent was evaporated under reduced pressure, and the residue was purified by hexane/ethyl acetate column chromatography to obtain 6-(1H-benzo[d][1,2,3]triazol-1-yloxy)-9-((2R,4S,5R)-4-(tert-butyldimethylsilyloxy)-5-((tert-butyldimethylsilyloxy)methyl) tetrahydrofuran-2-yl)-9H-purine (535 mg, 49%).

$^1$H-NMR (CDCl$_3$, 400 MHz) δ: 8.54 (s, 1H), 8.41 (s, 1H), 8.13-8.16 (m, 1H), 7.44-7.56 (m, 3H), 6.55 (t, J=6.3 Hz, 1H), 4.63-4.66 (m, 1H), 4.05-4.08 (m, 1H), 3.90-3.94 (m, 1H), 3.78-3.82 (m, 1H), 2.62-2.68 (m, 1H), 2.45-2.55 (m, 1H), 0.91-0.94 (m, 18H), 0.10-0.12 (m, 18H).

Step 4

6-(1H-benzo[d][1,2,3]triazol-1-yloxy)-9-((2R,4S,5R)-4-(tert-butyldimethylsilyloxy)-5-((tert-butyldimethylsilyloxy) methyl)tetrahydrofuran-2-yl)-9H-purine (179 mg, 0.300 mmol) obtained in Step 3 and the 3-((tert-butyldimethylsilyloxy)methyl)aniline (142 mg, 0.600 mmol) obtained in Step 1 were dissolved in ethanol (3 mL), and diisopropyl ethylamine (0.104 mL, 0.600 mmol) was added to the mixture. The mixture was stirred overnight at 60° C. and then for 5 hours at 80° C. The solvent was evaporated from the reaction solution under reduced pressure, and the residue was purified by hexane/ethyl acetate silica gel column chromatography to obtain 9-((2R,4S,5R)-4-((tert-butyldimethylsilyloxy)5-((tert-butyldimethyl silyloxy)methyl)tetrahydrofuran-2-yl)-N-(3-((tert-butyldimethylsilyloxy)methyl) phenyl)-9H-purin-6-amine (164 mg, 78%).

$^1$H-NMR (CDCl$_3$, 400 MHz) δ: 8.52 (s, 1H), 8.18 (s, 1H), 7.83 (bs, 1H), 7.66-7.69 (m, 2H), 7.34 (t, J=7.9 Hz, 1H), 7.04-4.07 (m, 1H), 6.49 (t, J=6.5 Hz, 1H), 4.79 (s, 2H), 4.61-4.64 (m, 1H), 4.01-4.05 (m, 1H), 3.88-3.91 (m, 1H), 3.77-3.81 (m, 1H), 2.63-2.70 (m, 1H), 2.43-2.49 (m, 1H), 0.91-0.97 (m, 27H), 0.14-0.09 (m, 18H).

Step 5

9-((2R,4S,5R)-4-((tert-butyldimethylsilyloxy) 5-((tert-butyldimethyl silyloxy)methyl)tetrahydrofuran-2-yl)-N-(3-((tert-butyldimethylsilyloxy)methyl)phenyl)-9H-purin-6-amine (162 mg, 0.231 mmol) obtained in Step 4 was dissolved in THF (2.3 mL). To the mixture was added tetrabutylammonium fluoride (1.00 mol/L THF solution, 0.810 mL), and the mixture was stirred at room temperature for 2 hours. The solvent was evaporated from the reaction solution under reduced pressure, and the residue was purified by chloroform/methanol column chromatography to obtain (2R,3S,5R)-2-(hydroxymethyl)-5-(6-(3-(hydroxymethyl)phenylamino)-9H-purin-9-yl)tetrahydrofuran-3-ol (88.9 mg, 107%).

ESI-MS (m/z): 358 (M+1)

Step 6

(2R,3S,5R)-2-(hydroxymethyl)-5-(6-(3-(hydroxymethyl) phenylamino)-9H-purin-9-yl)tetrahydrofuran-3-ol (88.9 mg, 0.231 mmol) obtained in Step 5 was dissolved in pyridine (2.3 mL), and 4,4'-dimethoxytrityl chloride (196 mg, 0.577 mmol) was added to the mixture. The mixture was stirred overnight at room temperature. Additional 4,4'-dimethoxytrityl chloride (78.3 mg, 0.231 mmol) was added, and the mixture was stirred for several hours at room temperature. Methanol was added to the reaction solution, which was then stirred for 15 minutes. Toluene was added thereto, and the solvent was evaporated under reduced pressure. A suitable amount of water was added to the residue, which was then extracted with ethyl acetate, and the organic layer was dried with anhydrous magnesium sulfate. The solvent was evaporated under reduced pressure, and the residue was purified by hexane/ethyl acetate silica gel column chromatography to obtain (2R,3S,5R)-2-((bis(4-methoxyphenyl) (phenyl)methoxy)methyl)-5-(6-(3-((bis(4-methoxyphenyl) (phenyl)methoxy)methyl)phenylamino)-9H-purin-9-yl) tetrahydrofuran-3-ol (95.4 mg, 43%).

$^1$H-NMR (CDCl$_3$, 400 MHz) δ: 8.47 (s, 1H), 8.00 (s, 1H), 7.90 (bs, 1H), 7.71-7.75 (m, 2H), 7.52-7.56 (m, 2H), 7.10-7.45 (m, 18H), 6.79-6.87 (m, 8H), 6.46 (t, J=6.4 Hz, 1H), 4.68-4.74 (m, 1H), 4.21 (s, 2H), 4.11-4.16 (m, 1H), 3.78 (d, J=11.3 Hz, 12H), 3.38-3.47 (m, 2H), 2.86-2.92 (m, 1H), 2.53-2.59 (m, 1H).

Step 7

(2R,3S,5R)-2-((bis(4-methoxyphenyl)(phenyl)methoxy) methyl)-5-(6-(3-((bis(4-methoxyphenyl)(phenyl)methoxy) methyl)phenylamino)-9H-purin-9-yl)tetrahydrofuran-3-yl 2-cyanoethyl diisopropylphosphoramidite (Compound am-80) was obtained in the same manner as in Reference Example 1.1 using (2R,3S,5R)-2-((bis(4-methoxyphenyl) (phenyl)methoxy)methyl)-5-(6-(3-((bis(4-methoxyphenyl) (phenyl)methoxy)methyl)phenylamino)-9H-purin-9-yl)tetrahydrofuran-3-ol obtained in Step 6. This compound was used in the following step without purification.

Example 88

An siRNA (referred to as N6-(3-phosphonooxymethyl) phenyl dA) having Compound I-86 as X at the 5' end of the antisense strand of 454-Xa shown in Table 38 below was synthesized in the same manner as in Example 1-1 using Compound am-80 obtained in Reference Example 80.1.

ESI-MS (antisense strand): theoretical value: 6861.00, actual value: 6862.08

Reference Example 81.1: Compound am-81

Step 1

(2R,3S,5R)-5-(6-(1H-benzo[d][1,2,3]triazol-1-yloxy)-9H-purin-9-yl)-2-((bis(4-methoxyphenyl)(phenyl)methoxy) methyl)tetrahydrofuran-3-ol (250 mg, 0.372 mmol) obtained in Step 1 of Reference Example 63 was dissolved in ethanol (3.7 mL), and diisopropyl ethylamine (0.194 mL, 1.12 mmol) and 8-mercapto-1-octanol (0.077 mL, 0.447 mmol) were added to the mixture. The mixture was stirred at 80° C. for 1 hour. Additional 8-mercapto-1-octanol (0.032 mL, 0.186 mmol) was added, and the mixture was stirred for 1 hour and then further stirred overnight at room temperature. The solvent was evaporated from the reaction solution under reduced pressure, and the residue was purified by hexane/ethyl acetate column chromatography to obtain (2R,3S,5R)-2-((bis(4-methoxyphenyl)(phenyl)methoxy)methyl)-5-(6-(8-hydroxyoctylthio)-9H-purin-9-yl)tetrahydrofuran-3-ol (186 mg, 71%). ESI-MS (m/z): 699 (M+1)

Step 2

(2R,3S,5R)-2-((bis(4-methoxyphenyl)(phenyl)methoxy) methyl)-5-(6-(8-hydroxyoctylthio)-9H-purin-9-yl)tetrahydrofuran-3-ol (183 mg, 0.262 mmol) obtained in Step 1 was dissolved in dichloromethane (3.7 mL), and triethylamine (0.182 mL, 1.31 mmol) and 4,4'-dimethoxytrityl chloride (133 mg, 0.393 mmol) were added thereto. The mixture was stirred overnight at room temperature. Additional 4,4'-dimethoxytrityl chloride (17.8 mg, 0.052 mmol) was added, and the mixture was stirred at room temperature for 2 hours. Methanol was added to the reaction solution, which was then stirred for 30 minutes. The reaction solution was extracted with chloroform, the organic layer was dried with anhydrous magnesium sulfate, the solvent was evaporated under reduced pressure, and the residue was purified by hexane/ethyl acetate silica gel column chromatography to obtain (2R,3S,5R)-5-(6-(6-(bis(4-methoxyphenyl)(phenyl) methoxy) octylthio)-9H-purin-9-yl)-2-((bis(4-methoxyphenyl)(phenyl)methoxy)methyl)tetra hydrofuran-3-ol (208 mg, 79%).

$^1$H-NMR (CDCl$_3$, 400 MHz) δ: 8.61 (s, 1H), 8.07 (s, 1H), 7.14-7.44 (m, 18H), 6.78-6.84 (m, 8H), 6.45 (t, J=6.5 Hz, 1H), 4.66-4.70 (m, 1H), 4.11-4.14 (m, 1H), 3.78 (s, 12H), 3.34-3.45 (m, 4H), 3.02 (t, J=6.6 Hz, 2H), 2.81-2.88 (m, 1H), 2.51-2.57 (m, 1H), 1.73-1.80 (m, 2H), 1.56-1.63 (m, 2H), 1.42-1.45 (m, 2H), 1.22-1.39 (m, 6H).

Step 3

(2R,3S,5R)-5-(6-(6-(bis(4-methoxyphenyl)(phenyl) methoxy)octylthio)-9H-purin-9-yl)-2-((bis(4-methoxyphenyl)(phenyl)methoxy)methyl)tetra hydrofuran-3-yl 2-cyanoethyl diisopropylphosphoramidite (Compound am-81) was obtained in the same manner as in Reference Example 1.1 using (2R,3S,5R)-5-(6-(6-(bis(4-methoxyphenyl)(phenyl)methoxy)octylthio)-9H-purin-9-yl)-2-((bis(4-methoxyphenyl)(phenyl)methoxy)methyl)tetra hydrofuran-3-ol obtained in Step 2. This compound was used in the following step without purification.

Example 89

An siRNA (referred to as 6-(8-phosphonooxyoctyl)thio-dPu) having Compound I-87 as X at the 5' end of the antisense strand of 454-Xa shown in Table 38 below was synthesized in the same manner as in Example 1-1 using Compound am-81 obtained in Reference Example 81.1.

ESI-MS (antisense strand): theoretical value: 6900.14, actual value: 6899.92

Reference Example 82.1: Compound am-82

Step 1

2-(3-aminophenoxy)ethanol (300 mg, 1.96 mmol) was dissolved in DMF (20 mL), and imidazole (200 mg, 1.94 mmol) and tert-butyldimethylsilyl chloride (354 mg, 2.35 mmol) were added to the mixture. The mixture was stirred at room temperature for 90 minutes. Water was added to the reaction solution, which was then stirred for 30 minutes. The reaction solution was extracted with ethyl acetate and dried with anhydrous magnesium sulfate, the solvent was evaporated under reduced pressure, and the residue was purified by hexane/ethyl acetate silica gel column chromatography to obtain 3-(2-(tert-butyldimethylsilyloxy)ethoxy)aniline (522 mg, 99%).

ESI-MS (m/z): 268 (M+1)

Step 2

The 3-(2-(tert-butyldimethylsilyloxy)ethoxy)aniline (382 mg, 1.43 mmol) obtained in Step 1 and the 6-(1H-benzo[d][1,2,3]triazol-1-yloxy)-9-((2R,4S,5R)-4-(tert-butyldimethylsilyloxy)-5-((tert-butyldimethylsilyloxy)methyl)tetrahydrofuran-2-yl)-9H-purine (427 mg, 0.714 mmol) obtained in Step 3 of Reference Example 83 were dissolved in ethanol (7.1 mL), and diisopropyl ethylamine (0.249 mL, 1.43 mmol) was added to the mixture. The mixture was stirred overnight at 80° C. Additional 6-(1H-benzo[d][1,2,3]triazol-1-yloxy)-9-((2R,4S,5R)-4-(tert-butyldimethylsilyloxy)-5-((tert-butyldimethylsilyloxy)methyl)tetrahydrofuran-2-yl)-9H-purine (139 mg, 0.520 mmol) and ethanol (0.9 mL) were added, and the mixture was stirred for 2.5 hours. The solvent was evaporated from the reaction solution under reduced pressure, and the residue was purified by hexane/ethyl acetate silica gel column chromatography to obtain 9-((2R,4S,5R)-4-(tert-butyldimethylsilyloxy)-5-((tert-butyldimethyl silyloxy)methyl)tetrahydrofuran-2-yl)-N-(3-(2-(tert-butyldimethylsilyloxy) ethoxy)phenyl)-9H-purin-6-amine (326 mg, 63%).

$^1$H-NMR (CDCl$_3$, 400 MHz) δ: 8.53 (s, 1H), 8.19 (s, 1H), 7.66 (bs, 1H), 7.56 (t, J=2.2 Hz, 1H), 7.30-7.33 (m, 2H), 6.66-6.68 (m, 1H), 6.49 (t, J=6.4 Hz, 1H), 4.61-4.64 (m, 1H), 3.98-4.10 (m, 5H), 3.88-3.92 (m, 1H), 3.77-3.82 (m, 1H), 2.63-2.71 (m, 1H), 2.43-2.49 (m, 1H), 0.91-0.93 (m, 27H), 0.09-0.12 (m, 18H).

ESI-MS (m/z): 730 (M+1)

Step 3

9-((2R,4S,5R)-4-(tert-butyldimethylsilyloxy)-5-((tert-butyldimethyl silyloxy)methyl)tetrahydrofuran-2-yl)-N-(3-(2-(tert-butyldimethylsilyloxy) ethoxy)phenyl)-9H-purin-6-amine (324 mg, 0.446 mmol) obtained in Step 2 was dissolved in THF (4.5 mL), and tetrabutylammonium fluoride (1.00 mol/L THF solution, 1.56 mL) was added to the mixture. The mixture was stirred at room temperature for 2 hours. The solvent was evaporated from the reaction solution under reduced pressure, and the residue was purified by chloroform/methanol silica gel column chromatography to obtain (2R,3S,5R)-5-(6-(3-(2-hydroxyethoxy)phenylamino)-9H-purin-9-yl)-2-(hydroxymethyl)tetrahydrofuran-3-ol (194 mg, 113%).

ESI-MS (m/z): 388 (M+1).

Step 4

(2R,3S,5R)-5-(6-(3-(2-hydroxyethoxy)phenylamino)-9H-purin-9-yl)-2-(hydroxymethyl)tetrahydrofuran-3-ol (0.446 mmol) obtained in Step 3 was dissolved in pyridine (4.5 mL), and 4,4'-dimethoxytrityl chloride (378 mg, 1.12 mmol) was added to the mixture. The mixture was stirred overnight at room temperature. Methanol was added to the reaction solution, which was then stirred for 15 minutes. Toluene was added, the solvent was evaporated under reduced pressure, and a suitable amount of water was added to the residue, which was then extracted with ethyl acetate and dried with anhydrous magnesium sulfate. The solvent was evaporated under reduced pressure, and the residue was purified by hexane/ethyl acetate silica gel column chromatography to obtain (2R,3S,5R)-5-(6-(3-(2-(bis(4-methoxyphenyl)(phenyl)methoxy)ethoxy)phenylamino)-9H-purin-9-yl)-2-((bis(4-methoxyphenyl)(phenyl)methoxy)methyl) tetrahydrofuran-3-ol (167 mg, 38%).

$^1$H-NMR (CDCl$_3$, 400 MHz) δ: 8.47 (s, 1H), 8.00 (s, 1H), 7.62-7.68 (m, 2H), 7.14-7.41 (m, 20H), 6.78-6.85 (m, 8H), 6.68-6.71 (m, 1H), 6.46 (t, J=6.5 Hz, 1H), 4.68-4.73 (m, 1H), 4.19 (t, J=5.1 Hz, 2H), 4.12-4.15 (m, 1H), 3.77 (d, J=5.5 Hz, 12H), 3.37-3.50 (m, 4H), 2.86-2.92 (m, 1H), 2.51-2.59 (m, 1H).

ESI-MS (m/z): 992 (M+1)

Step 5

(2R,3S,5R)-5-(6-(3-(2-(bis(4-methoxyphenyl)(phenyl) methoxy)ethoxy)phenylamino)-9H-purin-9-yl)-2-((bis(4-methoxyphenyl)(phenyl) methoxy)methyl)tetrahydrofuran-3-yl 2-cyanoethyl diisopropylphosphoramidite (Compound am-82) was obtained in the same manner as in Reference Example 1.1 using (2R,3S,5R)-5-(6-(3-(2-(bis(4-methoxyphenyl)(phenyl)methoxy)ethoxy)phenylamino)-9H-purin-9-yl)-2-((bis(4-methoxyphenyl)(phenyl) methoxy)methyl)tetrahydrofuran-3-ol obtained in Step 4. This compound was not purified and used in the next step.

Example 90

An siRNA (referred to as N6-(3-phosphonooxyethoxy) phenyl dA) having Compound I-88 as X at the 5' end of the antisense strand of 454-Xa shown in Table 38 below was synthesized in the same manner as in Example 1-1 using Compound am-82 obtained in Reference Example 82.1.

ESI-MS (antisense strand): theoretical value: 6891.02, actual value: 6892.22

Reference Example 83.1: Compound am-83

Step 1
(2R,3S,5R)-5-(6-(1H-benzo[d][1,2,3]triazol-1-yloxy)-9H-purin-9-yl)-2-((bis(4-methoxyphenyl)(phenyl)methoxy) methyl)tetrahydrofuran-3-ol (250 mg, 0.372 mmol) obtained in Step 1 of Reference Example 63 was dissolved in ethanol (3.7 mL), and diisopropyl ethylamine (0.194 mL, 1.12 mmol) and 6-mercapto-1-hexanol (0.061 mL, 0.447 mmol) were added. The mixture was stirred at 80° C. for 1 hour. Additional 6-mercapto-1-hexanol (0.025 mL, 0.186 mmol) was added, and the mixture was stirred for 1 hour. Additional 6-mercapto-1-hexanol (0.025 mL, 0.186 mmol) was again added, and the mixture was stirred for 2 hours. The solvent was evaporated from the reaction solution under reduced pressure, and the residue was purified by hexane/ethyl acetate silica gel column chromatography to obtain (2R,3S,5R)-2-((bis(4-methoxyphenyl)(phenyl)methoxy)methyl)-5-(6-(6-hydroxyhexylthio)-9H-purin-9-yl)tetrahydrofuran-3-ol (198 mg).

Step 2
(2R,3S,5R)-2-((bis(4-methoxyphenyl)(phenyl)methoxy) methyl)-5-(6-(6-hydroxyhexylthio)-9H-purin-9-yl)tetrahydrofuran-3-ol (0.372 mmol) obtained in Step 1 was dissolved in dichloromethane (3.7 mL), triethylamine (0.259 mL, 1.861 mmol) and 4,4'-dimethoxytrityl chloride (252 mg, 0.744 mmol) were added to the mixture. The mixture was stirred at room temperature for 2 hours, and methanol was added to the reaction solution, which was then stirred for 30 minutes. The reaction solution was extracted with chloroform, the organic layer was dried with anhydrous magnesium sulfate, the solvent was evaporated under reduced pressure, and the residue was purified by hexane/ethyl acetate column chromatography to obtain (2R,3S,5R)-5-(6-(6-(bis(4-methoxyphenyl)(phenyl)methoxy)hexylthio)-9H-purin-9-yl)-2-((bis(4-methoxyphenyl)(phenyl) methoxy)methyl)tetra hydrofuran-3-ol (231 mg, 59%).

$^1$H-NMR (CDCl$_3$, 400 MHz) δ: 8.61 (s, 1H), 8.08 (s, 1H), 7.14-7.44 (m, 18H), 6.78-6.83 (m, 8H), 6.45 (t, J=6.5 Hz, 1H), 4.66-4.70 (m, 1H), 4.11-4.14 (m, 1H), 3.78 (s, 12H), 3.32-3.45 (m, 4H), 3.04 (t, J=6.6 Hz, 2H), 2.81-2.88 (m, 1H), 2.51-2.57 (m, 1H), 1.73-1.80 (m, 2H), 1.57-1.66 (m, 2H), 1.50-1.37 (m, 4H).

Step 3
(2R,3S,5R)-5-(6-(6-(bis(4-methoxyphenyl)(phenyl) methoxy)hexylthio)-9H-purin-9-yl)-2-((bis(4-methoxyphenyl)(phenyl)methoxy)methyl)tetra hydrofuran-3-yl 2-cyanoethyl diisopropylphosphoramidite (Compound am-83) was obtained in the same manner as in Reference Example 1.1 using (2R,3S,5R)-5-(6-(6-(bis(4-methoxyphenyl)(phenyl)methoxy)hexylthio)-9H-purin-9-yl)-2-((bis(4-methoxyphenyl)(phenyl)methoxy)methyl)tetra hydrofuran-3-ol obtained in Step 2. This compound was used in the following step without purification.

Example 91

An siRNA (referred to as 6-(6-phosphonooxy)hexylthio-dPu) having Compound I-89 as X at the 5' end of the antisense strand of 454-Xa shown in Table 38 below was synthesized in the same manner as in Example 1-1 using Compound am-83 obtained in Reference Example 83.1.

ESI-MS (antisense strand): theoretical value: 6872.08, actual value: 6871.82

Reference Example 84.1: Compound am-84

Step 1
8-bromo-9-((4aR,6R,7aS)-2,2-di-tert-butyltetrahydro-4H-furo[3,2-d][1,3,2]dioxasilin-6-yl)-6-((E)-styryl)-9H-purine was obtained (922 mg, 56%) in the same manner as in Step 2 of Reference Example 14.0 using 9-((4aR,6R,7R,7aS)-2,2-di-tert-butyltetrahydro-4H-furo[3,2-d][1,3,2]dioxasilin-6-yl)-6-((E)-styryl)-9H-purin (1.38 g, 2.87 mmol) obtained in Step 2 of Reference Example 50.1.

Step 2
N-benzyl-9-((4aR,6R,7aS)-2,2-di-tert-butyltetrahydro-4H-furo[3,2-d][1,3,2]dioxasilin-6-yl)-6-((E)-styryl)-9H-purin-8-amine was obtained (342 mg, 109%) in the same manner as in Step 2 of Reference Example 41.1 using 8-bromo-9-((4aR,6R,7aS)-2,2-di-tert-butyltetrahydro-4H-furo[3,2-d][1,3,2]dioxasilin-6-yl)-6-((E)-styryl)-9H-purine (300 mg, 0.538 mmol) obtained in Step 1.

ESI-MS (m/z): 584 (M+1)

Steps 3 to 5
(2R,3S,5R)-5-(8-(benzylamino)-6-((E)-styryl)-9H-purin-9-yl)-2-((bis(4-methoxyphenyl)(phenyl)methoxy)methyl) tetrahydrofuran-3-yl 2-cyanoethyl diisopropylphosphoramidite (Compound am-84) was obtained in the same manner as in Steps 3 to 5 of Reference Example 1.1 using N-benzyl-9-((4aR,6R,7aS)-2,2-di-tert-butyltetrahydro-4H-furo[3,2-d][1,3,2]dioxasilin-6-yl)-6-((E)-styryl)-9H-purin-8-amine obtained in Step 2.

$^1$H-NMR (CDCl$_3$, 400 MHz) δ: 8.58, 8.58 (1H, 2s), 8.22, 8.18 (1H, 2s), 7.63-7.61 (m, 2H), 7.53-7.49 (m, 1H), 7.37-7.21 (m, 14H), 6.72-6.70 (m, 5H), 6.54-6.48 (m, 1H), 6.36-6.32 (m, 1H), 4.87-4.78 (m, 1H), 4.57-4.51 (m, 1H), 4.20-4.06 (m, 3H), 3.92-3.74 (m, 7H), 3.64-3.49 (m, 4H), 3.36-3.34 (m, 2H), 3.10-2.99 (m, 1H), 2.58, 2.46 (m, 3H), 1.21-1.04 (m, 12H).

Example 92

An siRNA (referred to as 8-BnNH-6-styryl-dPu) having Compound I-90 as X at the 5' end of the antisense strand of 454-Xa shown in Table 38 below was synthesized in the same manner as in Example 1-1 using Compound am-84 obtained in Reference Example 84.1.

ESI-MS (antisense strand): theoretical value: 6866.14, actual value: 6866.99

Reference Example 85.1: Compound am-85

Steps 1 to 4 (2R,3S,5R)-5-(6-((3,5-bis((bis(4-methoxyphenyl)(phenyl)methoxy)meth yl)benzyl)oxy)-9H-purin-9-yl)-2-((bis(4-methoxyphenyl)(phenyl)methoxy)methyl)tetrahydrofuran-3-yl (2-cyanoethyl) diisopropylphosphoramidite (Compound am-85) was obtained in the same manner as in Steps 1 to 4 of Reference Example 50.1 using benzenetrimethanol.

$^1$H-NMR (CDCl$_3$, 400 MHz) δ: 8.48-8.45 (1H, m), 8.09-8.07 (1H, m), 7.52-7.50 (5H, m), 7.42-7.37 (12H, m), 7.29-7.14 (13H, m), 6.83-6.75 (12H, m), 6.49-6.45 (1H, m), 5.65 (2H, s), 4.76-4.73 (1H, m), 4.31-4.30 (1H, m), 4.18

(4H, s), 3.87-3.56 (22H, m), 3.41-3.33 (2H, m), 2.87-2.84 (1H, m), 2.62-2.45 (3H, m), 1.18-1.13 (12H, m).

Example 93

An siRNA (referred to as 06-(3,5-diphosphonooxymethyl)Bn dI having Compound I-91 as X at the 5' end of the antisense strand of 454-Xa shown in Table 38 below was synthesized in the same manner as in Example 1-1 using Compound am-85 obtained in Reference Example 85.1.

ESI-MS (antisense strand): theoretical value: 6985.01, actual value: 6985.44

Reference Example 86.1: Compound am-86

Steps 1 to 4
(2R,3S,5R)-2-((bis(4-methoxyphenyl)(phenyl)methoxy)methyl)-5-(6-((3-((bis(4-methoxyphenyl)(phenyl)methoxy)methyl)-5-nitrobenzyl)oxy)-9H-purin-9-yl)tetrahydrofuran-3-yl (2-cyanoethyl) diisopropylphosphoramidite (am-86) was obtained in the same manner as in Steps 1 to 4 of Reference Example 50.1 using (5-nitro-1,3-phenylene)dimethanol.

$^1$H-NMR (CDCl$_3$, 400 MHz) δ: 8.47-8.45 (1H, m), 8.27 (1H, brs), 8.18 (1H, brs), 8.13, 8.11 (1H, 2 brs), 7.80 (1H, brs), 7.50-7.45 (2H, m), 7.42-7.34 (6H, m), 7.32-7.15 (10H, m), 6.87-6.75 (8H, m), 6.50-6.46 (1H, m), 5.72 (2H, s), 4.81-4.72 (1H, m), 4.34-4.27 (3H, m), 3.96-3.55 (16H, m), 3.43-3.32 (2H, m), 2.92-2.84 (1H, m), 2.72-2.57 (2H, m), 2.88 (1H, t, J=6.6 Hz), 1.20-1.11 (12H, m).

Example 94

An siRNA (referred to as 06-(3-nitro-5-phosphonooxymethyl)Bn dI) having Compound I-92 as X at the 5' end of the antisense strand of 454-Xa shown in Table 38 below was synthesized in the same manner as in Example 1-1 using Compound am-86 obtained in Reference Example 86.1.

ESI-MS (antisense strand): theoretical value: 6920.00, actual value: 6920.75

Reference Example 87.1: Compound am-87

Step 1
3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzoic acid was obtained (153 mg, 37%) in the same manner as in Step 1 of Reference Example 39.1 using (2R,3S,5R)-5-(6-((1H-benzo[d][1,2,3]triazol-1-yl)oxy)-9H-purin-9-yl)-2-((bis(4-methoxyphenyl)(phenyl)methoxy)methyl)tetrahydrofuran-3-ol (0.403 g, 0.600 mmol) synthesized by the method described in J. Am. Chem. Soc., 2007, Vol. 129, pp 782-789 and 3-(aminomethyl)benzoic acid (0.181 g, 1.20 mmol).

ESI-MS (m/z): 689 (M+1)

Step 2
2-cyanoethyl 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzoate was obtained (97.0 mg, 61%) in the same manner as in Step 2 of Reference Example 26.1 using 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzoic acid (153 mg, 0.222 mmol) obtained in Step 1.

ESI-MS (m/z): 742 (M+1)

Step 3
2-cyanoethyl 3-(((9-((2R,4S,5R)-5-((bis(4-methoxyphenyl)(phenyl)methoxy)methyl)-4-(((2-cyanoethoxy)(diisopropylamino)phosphanyl)oxy)tetrahydrofuran-2-yl)-9H-purin-6-yl)amino)methyl)benzoate (Compound am-87) was obtained (60.0 mg, 79%) in the same manner as in Step 2 of Reference Example 39.1 using 2-cyanoethyl 3-(((9-((2R,4S,5R)-5-((bis(4-methoxyphenyl)(phenyl)methoxy)methyl)-4-hydroxytetrahydrofuran-2-yl)-9H-purin-6-yl)amino)methyl)benzoate (97.0 mg, 0.131 mmol) synthesized in Step 2.

$^1$H-NMR (CDCl$_3$, 400 MHz) δ: 8.35 (1H, s), 8.07 (1H, s), 7.99-7.95 (2H, m), 7.64-7.62 (1H, m), 7.42-7.40 (3H, m), 7.31-7.17 (7H, m), 6.80-6.77 (4H, m), 6.45-6.43 (1H, m), 6.05 (1H, s), 4.93 (2H, s), 4.78-4.75 (1H, m), 4.52-4.50 (2H, m), 4.29-4.28 (1H, m), 3.78-3.69 (10H, m), 3.45-3.31 (2H, m), 2.90-2.59 (5H, m), 2.47-2.45 (1H, m), 1.20-1.10 (12H, m).

Example 95

An siRNA (referred to as N6-(3-carboxy)Bn dA) having Compound I-93 as X at the 5' end of the antisense strand of 454-Xa shown in Table 38 below was synthesized in the same manner as in Example 1-1 using Compound am-87 obtained in Reference Example 87.1.

ESI-MS (antisense strand): theoretical value: 6808.02, actual value Reference example 88.1: Compound am-88

Step 1
(2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-yl 2-cyanoethyl diisopropylphosphoramidite (Compound am-88) was obtained in the same manner as in Reference Example 1.1 using (2R,3S,5R)-5-(6-(1H-benzo[d][1,2,3]triazol-1-yloxy)-9H-purin-9-yl)-2-((bis(4-methoxyphenyl)(phenyl)methoxy)methyl)tetrahydrofuran-3-ol obtained in Step 1 of Reference Example 63.

$^1$H-NMR (CDCl$_3$, 400 MHz) δ: 8.34 (d, J=2.2 Hz, 1H), 8.32 (d, J=10.2 Hz, 1H), 8.13-8.15 (m, 1H), 7.56-7.13 (m, 12H), 6.77-6.82 (m, 4H), 6.51-6.55 (m, 1H), 4.76-4.84 (m, 1H), 4.32-4.38 (m, 1H), 3.78-3.79 (m, 6H), 3.34-3.47 (m, 2H), 2.89-2.96 (m, 1H), 2.66-2.78 (m, 1H), 2.47-2.63 (m, 2H), 2.36 (s, 2H) 1.13-1.32 (m, 14H).

ESI-MS (m/z): 872 (M+1)

Example 96

Step 1
A single-stranded oligonucleotide having diethyl 2-(((((2R,3S,5R)-5-(6-(1H-benzo[d][1,2,3]triazol-1-yloxy)-9H-purin-9-yl)-3-hydroxytetrahydrofuran-2-yl)methoxy)(hydroxy)phosphoryloxy)methyl)-2-(hydroxymethyl)malonate as X at the 5' end of the antisense strand was synthesized in the same manner as in Example 1 using Compound am-88 obtained in Reference Example 88.

Step 2
An siRNA having Compound I-94 as X at the 5' end of the antisense strand of 454-Xa-dT shown in Table 39 below was synthesized by reacting a DMSO solution of 10 mmol/L 2-(3-mercaptophenyl)acetic acid and a DMSO solution of 50 mmol/L triethylamine for 5 hours at 65° C. with the single-stranded oligonucleotide obtained in Step 1.

ESI-MS (antisense strand): theoretical value: 6824.10, actual value: 6824.00

Example 97

Step 1

An siRNA having Compound I-95 as X at the 5' end of the antisense strand of 454-Xa-dT shown in Table 39 below was synthesized in the same manner as in Example 96 using Compound am-88 obtained in Reference Example 88 and 3-amino-1-propanesulfonic acid.

ESI-MS (antisense strand): theoretical value: 6795.07, actual value: 6794.00

Reference Example 89.1: Compound am-89

Steps 1 to 4

2-cyanoethyl 4-(3-(9-((2R,4S,5R)-5-((bis(4-methoxyphenyl)(phenyl)methoxy)methyl) 4-(((2-cyanoethoxy) (diisopropylamino)phosphanyl)oxy)tetrahydrofuran-2-yl)-9H-purin-6-yl)phenyl)butanoate (am-89) was obtained in the same manner as in Steps 1 to 4 of Reference Example 59.1 using (3-(4-methoxy-4-oxobutyl)phenyl)boronic acid.

$^1$H-NMR (CDCl$_3$, 400 MHz) δ: 8.94-8.94 (1H, m), 8.66-8.64 (1H, m), 8.54 (1H, s), 8.32-8.30 (1H, m), 7.51-7.48 (1H, m), 7.41-7.39 (2H, m), 7.36-7.34 (1H, m), 7.31-7.16 (7H, m), 6.78-6.77 (4H, m), 6.58-6.54 (1H, m), 4.83-4.76 (1H, m), 4.36-4.32 (1H, m), 4.26-4.24 (2H, m), 3.91-3.56 (10H, m), 3.47-3.42 (1H, m), 3.36-3.34 (1H, m), 2.98-2.93 (1H, m), 2.82-2.80 (2H, m), 2.76-2.61 (4H, m), 2.47-2.43 (3H, m), 2.09-2.05 (2H, m), 1.17 (12H, dt, J=21.9, 7.9 Hz).

Example 98

An siRNA (referred to as 6-(3-carboxypropylphenyl)-dPu) having Compound I-96 as X at the 5' end of the antisense strand of 454-Xa shown in Table 38 below was synthesized in the same manner as in Example 1-1 using Compound am-89 obtained in Reference Example 89.1.

ESI-MS (antisense strand): theoretical value: 6822.10, actual value: 6816.08

Reference Example 90.1: Compound am-90

Steps 1 to 2

(2R,3S,5R)-5-(6-((2-(bis(2-(bis(4-methoxyphenyl)(phenyl)methoxy)ethyl)amino)-9H-purin-9-yl)-2-((bis(4-methoxyphenyl)(phenyl)methoxy)methyl)tetrahydrofuran-3-ol was obtained in the same manner as in Steps to 3 of Reference Example 62.1 using N,N-bis(2-hydroxyethyl)ethylenediamine.

ESI-MS (m/z): 1290.04 (M+1)

Step 3

(2R,3S,5R)-5-(6-((2-(bis(2-(bis(4-methoxyphenyl)(phenyl)methoxy)ethyl)amino)ethyl)amino-9H-purin-9-yl)-2-((bis(4-methoxyphenyl)(phenyl) methoxy)methyl)tetrahydrofuran-3-yl (2-cyanoethyl) diisopropylphosphoramidite (am-90) was obtained in the same manner as in Step 2 of Reference Example 39.1 using (2R,3S,5R)-5-(6-((2-(bis(2-(bis(4-methoxyphenyl)(phenyl)methoxy)ethyl)amino)-9H-purin-9-yl)-2-((bis(4-methoxyphenyl)(phenyl)methoxy)methyl)tetrahydrofuran-3-ol obtained in Step 2.

$^1$H-NMR (CDCl$_3$, 400 MHz) δ: 8.38 (1H, s), 7.98-7.95 (1H, m), 7.70-7.16 (30H, m), 6.84-6.76 (12H, m), 6.45-6.43 (1H, m), 5.91 (1H, s), 4.76-4.73 (3H, m), 4.30-4.28 (1H, m), 4.13-4.12 (4H, m), 3.89-3.54 (24H, m), 3.41-3.34 (2H, m), 2.90-2.87 (1H, m), 2.69-2.55 (2H, m), 2.47-2.45 (1H, m), 1.20-1.10 (12H, m).

Example 99

An siRNA (referred to as N6-(N,N-diphosphonooxyethyl)aminoethyl dA) having Compound I-97 as X at the 5' end of the antisense strand of 454-Xa shown in Table 38 below was synthesized in the same manner as in Example 1-1 using Compound am-90 obtained in Reference Example 90.1. ESI-MS (antisense strand): theoretical value: 6966.06, actual value: 6965.21

Reference Example 91.1: Compound am-91

Steps 1 to 4

(2R,3S,5R)-5-(6-((3-(3,5-bis((bis(4-methoxyphenyl)(phenyl)methoxy)methyl)phenyl)propa-2-yn-1-yl)amino)-9H-purin-9-yl)-2-((bis(4-methoxyphenyl) (phenyl) methoxy)methyl)tetrahydrofuran-3-yl (2-cyanoethyl) diisopropylphosphoramidite (am-91) was obtained in the same manner as in Steps 1 to 4 of Reference Example 67.1 using (5-iodo-1,3-phenylene)dimethanol.

$^1$H-NMR (CDCl$_3$, 400 MHz) δ: 8.26 (1H, s), 7.84-7.82 (1H, m), 7.52-7.00 (27H, m), 6.80-6.72 (12H, m), 6.42-6.40 (1H, m), 6.03 (1H, br s), 4.75-4.69 (1H, m), 4.28-4.27 (1H, m), 3.90-3.54 (24H, m), 3.44-3.29 (2H, m), 3.16-3.15 (4H, m), 2.84-2.78 (7H, m), 2.65-2.54 (2H, m), 2.46-2.44 (1H, m), 1.20-1.10 (12H, m).

Example 100

An siRNA (referred to as N6-(3,5-diphosphonooxymethyl)phenylpropargyl dA) having Compound I-98 as X at the 5' end of the antisense strand of 454-Xa shown in Table 38 below was synthesized in the same manner as in Example 1-1 using Compound am-91 obtained in Reference Example 91.1. ESI-MS (antisense strand): theoretical value: 7009.08, actual value: 7009.53

Reference Example 92.1: Compound am-92

Steps 1 to 3

(2R,3S,5R)-5-(6-((3-(bis(2-(bis(4-methoxyphenyl)(phenyl)methoxy)ethyl)amino)propyl)amino-9H-purin-9-yl)-2-((bis(4-methoxyphenyl)(phenyl) methoxy)methyl)tetrahydrofuran-3-yl (2-cyanoethyl) diisopropylphosphoramidite (am-92) was obtained in the same manner as in Steps 1 to 3 of Reference Example 90.1 using N,N-bis(2-hydroxyethyl)-1,3-propylendiamine.

$^1$H-NMR (CDCl$_3$, 400 MHz) δ: 8.27 (1H, s), 7.79, 7.77 (1H, 2s), 7.42-7.36 (6H, m), 7.31-7.11 (21H, m), 6.79-6.73 (12H, m), 6.42-6.38 (1H, m), 6.32 (1H, brs), 4.78-4.70 (1H, m), 4.30-4.25 (1H, m), 3.91-3.30 (26H, m), 3.18 (4H, t, J=6.2 Hz), 2.90-2.81 (1H, m), 2.71 (4H, t, J=6.0 Hz), 2.66-2.52 (4H, m), 2.45 (1H, t, J=6.4 Hz), 1.76-1.69 (2H, m), 1.20-1.11 (12H, m).

Example 101

An siRNA (referred to as N6-(N,N-diphosphonooxyethyl) aminopropyl dA) having Compound I-99 as X at the 5' end of the antisense strand of 454-Xa shown in Table 38 below was synthesized in the same manner as in Example 1-1 using Compound am-92 obtained in Reference Example 92.1. ESI-MS (antisense strand): theoretical value: 6980.08, actual value: 6979.20

Reference Example 93.1: Compound am-93

Steps 1 to 3

2-Cyanoethyl 2-(1-(((9-((2R,4S,5R)-5-((bis(4-methoxyphenyl)(phenyl)methoxy)methy 1)-4-(((2-cyanoethoxy) (diisopropylamino)phosphanyl)oxy)tetrahydrofuran-2-yl)-9H- purin-6-yl)thio)(methyl)cyclopropyl acetate (am-93) was obtained in the same manner as in Steps 1 to 3 of Reference Example 87.1 using 2-(1-(mercaptomethyl)cyclopropyl) acetic acid.

$^1$H-NMR (CDCl$_3$, 400 MHz) δ: 8.57 (1H, s), 8.16, 8.14 (1H, 2s), 7.40-7.38 (2H, m), 7.31-7.17 (7H, m), 6.80-6.77 (4H, m), 6.48-6.44 (1H, m), 4.80-4.72 (1H, m), 4.33-4.27 (1H, m), 4.30 (2H, t, J=6.4 Hz), 3.90-3.30 (14H, m), 2.93-2.86 (1H, m), 2.70-2.58 (4H, m), 2.49 (2H, s), 2.47 (1H, t, J=6.4 Hz), 1.20-1.11 (12H, m), 0.80 (2H, t, J=5.5 Hz), 0.63 (2H, t, J=5.5 Hz).

Example 102

An siRNA (referred to as 6-(1-carboxymethyl)cyclopropylmethyl-dPu) having Compound I-100 as X at the 5' end of the antisense strand of 454-Xa shown in Table 38 below was synthesized in the same manner as in Example 1-1 using Compound am-93 obtained in Reference Example 93.1.
ESI-MS (antisense strand): theoretical value: 6804.10, actual value: 6798.26

Reference Example 94.1: Compound am-94

Steps 1 to 3
3-((9-((2R,4S,5R)-5-((bis(4-methoxyphenyl)(phenyl)methoxy)methyl)-4-(((2-cyanoethoxy) (diisopropylamino)phosphanyl)oxy)tetrahydrofuran-2-yl)-9H-purin-6-yl)thio)benzoic acid (am-94) was obtained in the same manner as in Steps 1 to 3 of Reference Example 87.1 using 3-mercaptobenzoic acid.

$^1$H-NMR (CDCl$_3$, 400 MHz) δ: 8.53 (1H, s), 8.34 (1H, s), 8.22, 8.20 (1H, 2 s), 8.16 (1H, d, J=7.8 Hz), 7.88 (1H, d, J=7.8 Hz), 7.57 (1H, t, J=7.8 Hz), 7.41-7.36 (2H, m), 7.29-7.17 (7H, m), 6.80-6.77 (4H, m), 6.50-6.45 (1H, m), 4.80-4.72 (1H, m), 4.54 (2H, t, J=6.4 Hz), 4.34-4.28 (1H, m), 3.89-3.31 (12H, m), 2.95-2.88 (1H, m), 2.84 (2H, t, J=6.4 Hz), 2.73-2.67 (1H, m), 2.62 (1H, t, J=6.4 Hz), 2.47 (1H, t, J=6.4 Hz), 1.20-1.11 (12H, m).

Example 103

An siRNA (referred to as 6-(3-carboxy)phenylthio-dPu) having Compound I-101 as X at the 5' end of the antisense strand of 454-Xa shown in Table 38 below was synthesized in the same manner as in Example 1-1 using Compound am-94 obtained in Reference Example 94.1.
ESI-MS (antisense strand): theoretical value: 6812.07, actual value: 6811.50

Example 104

SiRNAs having Compound I-1 as X at the 5' end of the antisense strands of Table 40 below were synthesized in the same manner as in Example 1-1.

Test Example 6

The affinity of the luciferase-targeting siRNAs introduced an unnatural nucleotide residue at the 5' end of the antisense strand obtained in Examples 1 to 4 for AGO2 was evaluated by measuring the competition with the 5' end of an oligo DNA immobilized on the surface of a substrate which immobilizes the affinity of the siRNA and an AGO2-MID domain using Biacore T100 and T200 systems (GE Healthcare Sciences (GE) Company) as described below.

(1) Preparation of Sample

A running buffer stock solution (HBS-EP+10λ, GE Company, BR-1006-69) was diluted to 10-fold with pure water, followed by filtration through a filter, and then HPS-EP+(10 mM HEPES (4-(2-hydroxyethyl)-1-piperazineethanesulfonic acid), 150 mM NaCl, 3 mM EDTA, 0.05% (v/v) Surfactant P20, pH 7.4) was prepared and used as a running buffer.

To HBS-EP+, dithiothreitol (DTT) was added to give a final concentration of 2 mM, and the siRNA solution was diluted to 200 nM, 100 nM, 50 nM, and 25 nM, and each of the diluted siRNA solutions was mixed with an equal amount of a 5 μg/mL AGO2-MID domain solution obtained by dilution in the same manner, whereby 2.5 μg/mL AGO2-MID domain solutions containing the siRNA at 100 nM, 50 nM, 25 nM, and 12.5 nM, respectively, were prepared.

(2) Measurement Method (2-1) Immobilization of Biotinylated Oligo

A biotinylated single-stranded DNA (dT(16)-Biotin) was immobilized on a chip (Series S Sensor Chip SA, GE Company, BR-1005-31). The flow rate was set to a constant rate of 10 μL/min, and the biotinylated single-stranded DNA solution diluted to 100 nM with HBS-EP+ was used to immobilize on Fc2 or Fc4 according to the following program. At the same time, a blank immobilization operation was performed on Fc1 and Fc3.

1. 1 M NaCl/50 mM NaOH, 60 seconds (INJECT command), 3 times

2. Running buffer (WASH command)

3. Running buffer 120 seconds (INJECT command)

4. Aim for Immobilized Level was set to 750 RU and immobilized (LIGAND INJECT command)

5. 1 M NaCl/50 mM NaOH/50% isopropyl alcohol (WASH command)

In the immobilized cells, an immobilization level of about 700 RU was confirmed.

(2-2) Competition Experiments on Oligonucleotide (siRNA)

A competition experiment by the siRNA was performed using the chip immobilized the biotinylated single-stranded DNA thereon. The flow rate is set to 30 μL/minute throughout the experiment, and one cycle is performed as follows: binding for 60 seconds, dissociation for 5 seconds, and regeneration 1 M NaCl for 5 seconds.

In order to stabilize the machine, the first 10 cycles are performed by adding only HBS-EP+, and thereafter, the measurement is performed for each siRNA in the order of HBS-EP+(BLANK), a 2.5 μg/mL AGO2-MID domain solution (CONTROL), and 2.5 μg/mL AGO2-MID domain solutions (Sample) containing the siRNA at 100 nM, 50 nM, 25 nM, and 12.5 nM, respectively. In the analysis, the binding level of the graph obtained by subtracting the graph for blank immobilization from the graph for the immobilized cell is used, and the residual binding ratio (%) is calculated according to the formula: ([Sample]−[BLANK])/([CONTROL]−[BLANK])×100, and the inhibition ratio (%) is calculated according to 100-(residual binding ratio).

Further, for comparison, siRNAs having a corresponding natural nucleotide at the 5' end of the antisense strand of each of the siRNAs were also tested in the same manner.

In Table 35, the respective inhibition ratios (%) are shown.

TABLE 35

|  | inhibition rate (%) (50 nM AGO2-MID domain solutions) |
|---|---|
| 874-A | 21.33 |
| 874-8-Br-dA | 75.67 |
| 874-8-oxo-dA | 31.77 |
| 874-U | 38.94 |
| 874-5-Br-dU | 45.07 |
| 454-5-U | 60.59 |
| 454-5-F-dU | 66.67 |
| 1556-5-U | 51.43 |
| 1556-5-F-dU | 57.63 |

From the results of Test Example 6, it was revealed that the luciferase-targeting siRNAs (874-8-Br-dA, 874-8-oxo-dA, 874-5-Br-dU, 454-5-F-dU, and 1556-5-F-dU) introduced an unnatural nucleotide residue at the 5' end of the antisense strand obtained in Examples 1 to 4 have a higher inhibition ratio (%) than the siRNAs (874-A and 874-U) having adenosine monophosphate or uridine monophosphate, which is a corresponding natural nucleotide, at the 5' end thereof, and therefore have a higher affinity for AGO2.

Test Example 7: Biacore of Nucleotide (Monomer)

The affinity of 8-Br-dA (Compound I-1) and 5-fluoro-2'-deoxyuridine monophosphate (Compound I-4), which are unnatural nucleotides at the 5' end of the siRNAs obtained in Examples 1 and 4, respectively, for AGO2 was evaluated by measuring the affinity between each of the siRNAs and an AGO2-MID domain with respect to competition with the 5' end of an oligo DNA immobilized on the surface of a substrate which immobilizes the affinity of the siRNA and an AGO2-MID domain using Biacore T100 and T200 systems (GE Company) as described below.

(1) Preparation of Sample

HBS-EP+ 10× was diluted to 10-fold with pure water, and DTT was added thereto to give a final concentration of 2 mM, followed by filtration through a filter to prepare an HBS-EP+ 2 mM DTT aqueous solution. To this solution, dimethyl sulfoxide (DMSO) was added to give a final concentration of 1%, whereby a running buffer was prepared.

A monomer solution dissolved in DMSO or distilled water was diluted to 200 µM, 40 µM, 8 µM, and 1.6 µM/(2% DMSO, HBS-EP+, 2 mM DTT), and each of the diluted solutions was mixed with an equal amount of a 5 µg/mL AGO2-MID domain solution diluted with the HBS-EP+2 mM DTT solution, whereby 2.5 µg/mL AGO2-MID domain solutions containing the monomer at 100 µM, 20 µM, 4 µM, and 0.8 µM, respectively, were prepared as the HBS-EP+, 2 mM DTT, 1% DMSO solution.

(2) Competition Experiment on Nucleotide (Monomer)

A competition experiment by the siRNA was performed using a chip immobilized dT(16)-Biotin oligo thereon in the same manner as in Test Example 6. The flow rate is set to 30 µL/minute throughout the experiment, and one cycle is performed as follows: binding for 60 seconds, dissociation for 5 seconds, and regeneration 1 M NaCl for 5 seconds.

In order to stabilize the machine, the first 10 cycles are performed by adding only HBS-EP+, and thereafter, the measurement is performed for each monomer in the order of HBS-EP+(BLANK), a 2.5 µg/mL AGO2-MID domain solution (CONTROL), and 2.5 µg/mL AGO2-MID domain solutions (Sample) containing the monomer at 100 µM, 20 µM, 4 µM, and 0.8 µM, respectively, and a 2.5 µg/mL AGO2-MID domain solution (CONTROL). In the analysis, the binding level of the graph obtained by subtracting the graph for blank immobilization from the graph for the immobilized cell is used, and the residual binding ratio (%) is calculated according to ([Sample]−[BLANK])/([CONTROL]−[BLANK])×100, and the inhibition ratio (%) is calculated according to 100−(residual binding ratio).

In Table 36, the inhibition ratios (%) of 8-Br-dA (Compound I-1) and 5-fluoro-2'-deoxyuridine monophosphate (Compound I-4), and for comparison thereof, the inhibition ratios (%) of adenosine monophosphate (AMP) and uridine monophosphate (UMP) are shown.

TABLE 36

|  | inhibition rate (%) (100 µM AGO2-MID domain solutions) |
|---|---|
| compound I-1 | 68.6 |
| compound I-4 | 42.7 |
| AMP | 27.1 |
| UMP | 35.9 |

From the results of Test Example 7, it was revealed that 8-Br-dA and 5-fluoro-2'-deoxyuridine monophosphate, which are unnatural nucleotides introduced at the 5' end of the antisense strands of the siRNAs of the present invention, have a higher inhibition ratio (%) than adenosine monophosphate or uridine monophosphate, which is a natural nucleotide, and therefore have a higher affinity for AGO2.

Test Example 8: Biacore of Monomer

The affinity of Compounds I-5 to I-31, and I-33 to I-38, which are unnatural nucleotides at the 5' end of the siRNAs obtained in Examples 7 to 33, and 35 to 40 for AGO2 was evaluated in the same manner as in Test Example 7.

The respective inhibition ratios (%) determined are shown in Table 37.

TABLE 37

|  | inhibition rate (%) (100 µM AGO2-MID domain solutions) |
|---|---|
| compound I-5 | 87.4 |
| compound I-6 | 70.0 |
| compound I-7 | 71.7 |
| compound I-8 | 77.1 |
| compound I-9 | 70.9 |
| compound I-10 | 73.5 |
| compound I-11 | 60.9 |
| compound I-12 | 74.2 |
| compound I-13 | 63.4 |
| compound I-14 | 63.3 |
| compound I-15 | 73.0 |
| compound I-16 | 65.6 |
| compound I-17 | 86.0 |
| compound I-18 | 97.8 |
| compound I-19 | 89.7 |
| compound I-20 | 76.9 |
| compound I-21 | 78.2 |
| compound I-22 | 91.6 |
| compound I-23 | 85.2 |
| compound I-24 | 88.4 |
| compound I-25 | 33.9 |
| compound I-26 | 82.4 |
| compound I-27 | 92.4 |
| compound I-28 | 77.0 |
| compound I-29 | 77.9 |
| compound I-30 | 73.2 |

TABLE 37-continued

| | inhibition rate (%) (100 μM AGO2-MID domain solutions) |
|---|---|
| compound I-31 | 73.6 |
| compound I-33 | 82.9 |
| compound I-34 | 31.8 |
| compound I-35 | 88.0 |
| compound I-36 | 91.6 |
| compound I-37 | 92.3 |
| compound I-38 | 78.9 |

From the results of Test Example 8, it was revealed that all Compounds I-5 to I-31, and I-33 to I-38, which are unnatural nucleotides at the 5' end of the siRNAs obtained in Examples 7 to 33, and 35 to 40 have a high inhibition ratio (%), and therefore have a high affinity for AGO2. Accordingly, the siRNAs obtained in Examples 7 to 33, and 35 to 40 are oligonucleotides having an improved affinity for AGO2, and therefore are expected to be oligonucleotides having a high knockdown activity against a target mRNA.

Test Example 9: Knockdown Activity of Luciferase-Targeting siRNA

The activity of an siRNA having each compound at the 5' end of the antisense strand obtained in Example 39, 23, 36, or 27 was measured and evaluated in the same manner as in Test Example 1 except that the number of cells per well was set to 7500, the final concentration of the siRNA was set to the following five levels: 10000 pmol/L, 1000 pmol/L, 100 pmol/L, 10 pmol/L, and 1 pmol/L, and N was set to 5. The knockdown activity of each of siRNAs having 1-37 (6-NO2, 7-Me-dQu), 1-21 (6-napht-2-yl-dPu), 1-34 (6-Me-dU), or I-25 (6-napht-1-yl-dPu) at the 5' end of the antisense strand is shown in FIG. 4.

Incidentally, an siRNA having 8-Br-dA as X at the 5' end of the antisense strand of 454-Xa in Table 38 (referred to as 454-BrdA) was synthesized in the same manner as in Example 1 using 8-Br-dA, and the activity of the siRNA was measured and evaluated. Further, also for an siRNA having a natural nucleotide which contains adenosine monophosphate or uridine monophosphate, at the 5' end of the antisense strand (referred to as 454-A or 454-U), the activity of the siRNA was measured and evaluated in the same manner.

From the results of Test Example 9, it is found that the siRNA having a high affinity base analog for Ago2 at the 5' end of the antisense strand shows a higher knockdown activity than the siRNA having a natural nucleotide at the 5' end of the antisense strand.

Test Example 10: Knockdown Activity of Luciferase-Targeting siRNA

The activity of an siRNA having each compound at the 5' end of the antisense strand obtained in Example 34 and 21 was measured and evaluated in the same manner as in Test Example 1 except that the number of cells per well was set to 7500, the final concentration of the siRNA was set to the following five levels: 10000 pmol/L, 1000 pmol/L, 100 pmol/L, 10 pmol/L, and 1 pmol/L, and N was set to 5. The knockdown activity of siRNAs having 1-32 (2'-OMe-6-styryl-dA) or I-19 (di-Me-thienyl-dU) at the 5' end of the antisense strand is shown in FIG. 5.

From the results of Test Example 10, it is found that the siRNA having a high affinity base analog for Ago2 at the 5' end of the antisense strand shows a higher knockdown activity than the siRNA having a corresponding natural nucleotide at the 5' end of the antisense strand.

TABLE 38

| | sense strand | | antisense strand | |
|---|---|---|---|---|
| | sequence (5'→3') | SEQ ID NO | sequence (5'→3') | SEQ ID NO |
| 454-U | GGAUAGCAAGACCGACUAACA | 25 | UUAGUCGGUCUUGCUAUCCAU | 28 |
| 454-A | GGAUAGCAAGACCGACUAUCA | 65 | AUAGUCGGUCUUGCUAUCCAU | 66 |
| 454-Xu | GGAUAGCAAGACCGACUAACA | 25 | XUAGUCGGUCUUGCUAUCCAU | 26 |
| 1454-Xa | GGAUAGCAAGACCGACUAUCA | 65 | XUAGUCGGUCUUGCUAUCCAU | 26 |
| 1454-XY | GGAUAGCAAGACCGACUAYCA | 67 | XUAGUCGGUCUUGCUAUCCAU | 26 |

TABLE 39

| | sense strand | | antisense strand | |
|---|---|---|---|---|
| | sequence (5'→3') | SEQ ID NO | sequence (5'→3') | SEQ ID NO |
| 454-A-dT | GGAUAGCAAGACCGACUAUCA | 65 | AUAGUCGGUCUUGCUAUCCAdT | 68 |
| 454-Xa-dT | GGAUAGCAAGACCGACUAUCA | 65 | XUAGUCGGUCUUGCUAUCCAdT | 69 |

TABLE 40

| | sense strand | | antisense strand | |
|---|---|---|---|---|
| | sequence (5'→3') | SEQ ID NO | sequence (5'→3') | SEQ ID NO |
| 1203-BrdA | UUAACAACCCCGAGGCUAUAA | 9 | AUAGCCUCGGGGUUGUUAACG | 10 |
| 1556-BrdA | GACGAGGUGCCUAAAGGAUUG | 11 | AUCCUUUAGGCACCUCGUCCA | 12 |

Test Example 11: Knockdown Activity of Luciferase-Targeting siRNAs

The activity of siRNAs having compounds obtained in Examples 32 and 41 to 51 at the 5' end of the antisense strand was measured and evaluated in the same manner as in Test Example 1 except that the number of cells per well was set to 7500, the final concentration of the siRNA was set to the following five levels: 1000 pmol/L, 100 pmol/L, 10 pmol/L, 1 pmol/L and 0.1 pmol/L, and N was set to 5. FIG. 6 shows the knockdown activity of siRNAs having I-45 (8-BnNH-6-styryl purine), I-44 (N-Bn-N-Me dA) or I-46 (8-furanyl-methylamino-6-styryl purine) at the 5' end of the antisense strand. FIG. 7 shows the knockdown activity of siRNAs having I-39 (6-benzothiophenyl purine), I-41 (6-pyrenyl purine), I-43 (N-Bn dA) or I-40 (6-benzyloxynaphthyl purine) at the 5' end of the antisense strand; FIG. 8 shows the knockdown activity of an siRNA having I-42 (6-anthracenyl purine) at the 5' end of the antisense strand; FIG. 9 shows the knockdown activity of an siRNA having I-47 (6-styryl-8-tetrazolylmethylamino purine) at the 5' end of the antisense strand; FIG. 10 shows the knockdown activity of an siRNA having I-30 (6-(m-carboxyphenyl) purine) at the 5' end of the antisense strand; FIG. 11 shows the knockdown activity of an siRNA having I-48 (6-(m-carboxyethylphenyl) purine) at the 5' end of the antisense strand; and FIG. 12 shows the knockdown activity of an siRNA having I-49 (5-furyl dU) at the 5' end of the antisense strand. The siRNA activity of a natural-type siRNA (454-A) having adenosine monophosphate as the 5' end of the antisense strand of 454-Xa shown in Table 38 was also measured and evaluated under the same conditions.

The results of Test Example 11 show that an siRNA having a high affinity base analog for Ago2 at the 5' end of the antisense strand exhibits higher knockdown activity than an siRNA having a natural-type nucleotide corresponding to the 5' end of the antisense strand.

Test Example 12: Knockdown Activity of Luciferase-Targeting siRNA

The activity of an siRNA having a compound obtained in Example 52 at the 5' end of the antisense strand was measured and evaluated in the same manner as in Test Example 1 except that the number of cells per well was set to 7500, the final concentration of the siRNA was set to the following five levels: 500 pmol/L, 100 pmol/L, 20 pmol/L, 4 pmol/L and 0.8 pmol/L, and N was set to 5. FIG. 13 shows the knockdown activity of an siRNA having I-50 (2-amino rA) at the 5' end of the antisense strand. The siRNA activity of a natural-type siRNA (454-A) having adenosine monophosphate as the 5' end of the antisense strand of 454-Xa shown in Table 38 was also measured and evaluated under the same conditions.

The results of Test Example 12 show that an siRNA having a high affinity base analog for Ago2 at the 5' end of the antisense strand exhibits higher knockdown activity than an siRNA having a natural-type nucleotide corresponding to the 5' end of the antisense strand.

From the results of Test Examples 9 to 12 above, it is anticipated that with medical application of the siRNA of the present invention having enhanced activity, dosages will be reduced in comparison with applications using natural siRNA.

Test Example 13: RNAi Activity of Luciferase-Targeting siRNA

The RNAi activity of luciferase-targeting siRNAs obtained in Examples 24 and 53 having I-22 or I-51 at the 5' end of the antisense strand was measured using the level of inhibition of luciferase luminescence as an index as described below.

The Hela cells with an introduced luciferase expression vector used in Test Example 1 were suspended in RPMI 1640 medium (RPMI 1640 Medium (ATCC Modification), Invitrogen Life Technologies, A10491-01) containing 10% fetal bovine serum, and 50 µL of the cell suspension was inoculated into each well of a culture dish (CulturPlatem 96 cell culture microplate, 6005688) to give 7500 cells per well.

The siRNA was diluted with OPTI-MEM (Invitrogen Life Technologies, 31985-070). Lipofectamine RNAiMAX (Invitrogen Life Technologies, 13778-150) was diluted with OPTI-MEM. The dilutions were mixed together, forming a complex of siRNA and Lipofectamine RNAiMAX. 10 µL of the prepared siRNA-Lipofectamine RNAiMAX complex solution was added to each well containing the cell suspension, thereby introducing the siRNA into the Hela cells. The final concentration of the siRNA was set to five levels: 1000 pmol/L, 100 pmol/L, 10 pmol/L, 1 pmol/L and 100 fmol/L, and N was set to 5. Cells were also inoculated with Lipofectamine RNAiMAX only as a negative control. For purposes of comparison, the same test was also performed with 454-A having adenosine monophosphate in the location of each siRNA corresponding to I-22 or I-51.

After siRNA introduction, the cells were cultured for 24 hours under conditions of 37° C., 5% $CO_2$.

Forty microliter of Steady-Glo Luciferase Assay System (Promega, E2520), a commercial luciferase assay reagent for cultured cells, was added to each well in accordance with the attached protocols, and the luminescence (cps) per 0.5 seconds in each well was measured by ARVO (PerkinElmer) in accordance with the protocols.

The luminescence of the negative control was measured at the same time as the luminescence of the group treated with luciferase-targeting siRNA, and the RNAi results for the siRNA-introduced sample were calculated as a relative ratio given 1 as the luminescence of the siRNA-unintroduced group (negative control group).

The results of this test are shown in FIG. 14. FIG. 14 shows the knockdown activity of siRNAs having I-22 and I-51 of the invention, as well as 454-A having adenosine monophosphate in the position corresponding to I-22 and I-51 in the sequence. The ordinate represents the 50% inhibitory concentration ($IC_{50}$ (pM)), and the abscissa represents the siRNAs used. Statistical analysis software (SAS, Release 9.2, SAS Institute Inc.) was used for the statistical analysis.

The results of Test Example 13 show that an siRNA having I-22 or I-51 at the 5' end of the antisense strand exhibits higher knockdown activity than an siRNA having a natural-type nucleotide corresponding to the 5' end of the antisense strand.

Test Example 14: Knockdown Activity of Luciferase-Targeting siRNAs

The activity of siRNAs having the compounds obtained in Examples 54, 57 and 58 at the 5' end of the antisense strand was measured and evaluated in the same manner as in Test Example 13 except that the luminescence of each well was measured in 0.8 second increments using a 2104 EnVision™ Multilabel Counter (PerkinElmer) as the luminescence measurement device. FIG. 15 shows the knockdown activity of siRNAs having I-52, I-55 or I-56 at the 5' end of the antisense strand, as well as the knockdown activity of 454-A having natural adenosine monophosphate in the position corresponding to I-52, I-55 or I-56 in the sequence.

The results of Test Example 14 show that an siRNA having I-52, I-55 or I-56 at the 5' end of the antisense strand exhibits higher knockdown activity than an siRNA having a natural-type nucleotide corresponding to the 5' end of the antisense strand.

Test Example 15: Knockdown Activity of Luciferase-Targeting siRNAs

The activity of siRNAs having the compounds obtained in Examples 56, 59, 60 and 61 at the 5' end of the antisense strand was measured and evaluated in the same manner as in Test Example 13. FIG. 16 shows the knockdown activity of siRNAs having I-54, I-57, I-58 or I-59 at the 5' end of the antisense strand, as well as the knockdown activity of 454-A having natural adenosine monophosphate in the position corresponding to I-54, I-57, I-58 or I-59 in the sequence.

The results of Test Example 15 show that an siRNA having I-54, I-57, I-58 or I-59 at the 5' end of the antisense strand exhibits higher knockdown activity than an siRNA having a natural-type nucleotide corresponding to the 5' end of the antisense strand.

Test Example 16: Knockdown Activity of Luciferase-Targeting siRNAs

The activity of siRNAs having the compounds obtained in Examples 55, 62, 63, 64, 65, 66 and 72 at the 5' end of the antisense strand was measured and evaluated in the same manner as in Test Example 13. FIG. 17 shows the knockdown activity of siRNAs having I-53, I-60, I-61, I-62, I-63, I-64 or I-70 at the 5' end of the antisense strand, as well as the knockdown activity of 454-A having natural adenosine monophosphate in the position corresponding to I-53, I-60, I-61, I-62, I-63, I-64 or I-70 in the sequence.

The results of Test Example 16 show that an siRNA having I-53, I-60, I-61, I-62, I-63, I-64 or I-70 at the 5' end of the antisense strand exhibits higher knockdown activity than an siRNA having a natural-type nucleotide corresponding to the 5' end of the antisense strand.

Test Example 17: Knockdown Activity of Luciferase-Targeting siRNAs

The activity of siRNAs having the compounds obtained in Examples 73, 74, 75 and 76 at the 5' end of the antisense strand was measured and evaluated in the same manner as in Test Example 13. FIG. 18 shows the knockdown activity of siRNAs having I-71, I-72, I-73 or I-74 at the 5' end of the antisense strand, as well as the knockdown activity of 454-A having natural adenosine monophosphate in the position corresponding to I-71, I-72, I-73 or I-74 in the sequence.

The results of Test Example 17 show that an siRNA having I-71, I-72, I-73 or I-74 at the 5' end of the antisense strand exhibits higher knockdown activity than an siRNA having a natural-type nucleotide corresponding to the 5' end of the antisense strand.

Test Example 18: Knockdown Activity of Luciferase-Targeting siRNAs

The activity of siRNAs having the compounds obtained in Examples 67, 68, 69, 70 and 71 at the 5' end of the antisense strand was measured and evaluated in the same manner as in Test Example 13. FIG. 19 shows the knockdown activity of siRNAs having I-65, I-66, I-67, I-68 or I-69 at the 5' end of the antisense strand, as well as the knockdown activity of 454-A having natural adenosine monophosphate in the position corresponding to I-65, I-66, I-67, I-68 or I-69 in the sequence.

The results of Test Example 18 show that an siRNA having I-65, I-66, I-67, I-68 or I-69 at the 5' end of the antisense strand exhibits higher knockdown activity than an siRNA having a natural-type nucleotide corresponding to the 5' end of the antisense strand.

Test Example 19: Knockdown Activity of Luciferase-Targeting siRNA

The activity of siRNAs having the compounds obtained in Examples 80, 81, 82 and 83 at the 5' end of the antisense strand was measured and evaluated in the same manner as in Test Example 13. FIG. 20 shows the knockdown activity of siRNAs having I-78, I-79, I-80 or I-81 at the 5' end of the antisense strand, as well as the knockdown activity of 454-A having natural adenosine monophosphate in the position corresponding to I-78, I-79, I-80 or I-81 in the sequence.

The results of Test Example 19 show that an siRNA having I-78, I-79, I-80 or I-81 at the 5' end of the antisense strand exhibits higher knockdown activity than an siRNA having a natural-type nucleotide corresponding to the 5' end of the antisense strand.

Test Example 20: Knockdown Activity of Luciferase-Targeting siRNA

The activity of siRNAs having the compounds obtained in Examples 77, 78 and 79 at the 5' end of the antisense strand was measured and evaluated in the same manner as in Test Example 13. FIG. 21 shows the knockdown activity of siRNAs having I-75, I-76 or I-77 at the 5' end of the antisense strand, as well as the knockdown activity of 454-A having natural adenosine monophosphate in the position corresponding to I-75, I-76 or I-77 in the sequence.

The results of Test Example 20 show that an siRNA having I-75, I-76 or I-77 at the 5' end of the antisense strand exhibits higher knockdown activity than an siRNA having a natural-type nucleotide corresponding to the 5' end of the antisense strand.

Test Example 21: Knockdown Activity of Luciferase-Targeting siRNA

The activity of siRNAs having the compounds obtained in Examples 84 and 85 at the 5' end of the antisense strand was measured and evaluated in the same manner as in Test Example 13. FIG. 22 shows the knockdown activity of siRNAs having I-82 or I-83 at the 5' end of the antisense strand, as well as the knockdown activity of 454-A having natural adenosine monophosphate in the position corresponding to I-82 or I-83 in the sequence.

The results of Test Example 21 show that an siRNA having I-82 or I-83 at the 5' end of the antisense strand exhibits higher knockdown activity than an siRNA having a natural-type nucleotide corresponding to the 5' end of the antisense strand.

Test Example 22: Knockdown Activity of Luciferase-Targeting siRNAs

The activity of siRNAs having the compounds obtained in Examples 86 and 87 at the 5' end of the antisense strand was measured and evaluated in the same manner as in Test Example 13. FIG. 23 shows the knockdown activity of siRNAs having I-84 or I-85 at the 5' end of the antisense strand, as well as the knockdown activity of 454-A having natural adenosine monophosphate in the position corresponding to I-84 or I-85 in the sequence.

The results of Test Example 22 show that an siRNA having I-84 or I-85 at the 5' end of the antisense strand exhibits higher knockdown activity than an siRNA having a natural-type nucleotide corresponding to the 5' end of the antisense strand.

Test Example 23: Knockdown Activity of Luciferase-Targeting siRNAs

The activity of siRNAs having the compounds obtained in Examples 88, 89, 90 and 91 at the 5' end of the antisense strand was measured and evaluated in the same manner as in Test Example 13. FIG. 24 shows the knockdown activity of siRNAs having I-86, I-87, I-88 or I-89 at the 5' end of the antisense strand, as well as the knockdown activity of 454-A having natural adenosine monophosphate in the position corresponding to I-86, I-87, I-88 or I-89 in the sequence.

The results of Test Example 23 show that an siRNA having I-86, I-87, I-88 or I-89 at the 5' end of the antisense strand exhibits higher knockdown activity than an siRNA having a natural-type nucleotide corresponding to the 5' end of the antisense strand.

Test Example 24: Knockdown Activity of Luciferase-Targeting siRNAs

The activity of siRNAs having the compounds obtained in Examples 29, 31, 92, 93, 94 and 95 at the 5' end of the antisense strand was measured and evaluated in the same manner as in Test Example 13. FIG. 25 shows the knockdown activity of siRNAs having I-27, I-29, I-90, I-91, I-92 or I-93 at the 5' end of the antisense strand, as well as the knockdown activity of 454-A having natural adenosine monophosphate in the position corresponding to I-27, I-29, I-90, I-91, I-92 or I-93 in the sequence.

The results of Test Example 24 show that an siRNA having I-27, I-29, I-90, I-91, I-92 or I-93 at the 5' end of the antisense strand exhibits higher knockdown activity than an siRNA having a natural-type nucleotide corresponding to the 5' end of the antisense strand.

Test Example 25: Knockdown Activity of Luciferase-Targeting siRNAs

The activity of siRNAs having the compounds obtained in Examples 96 and 97 at the 5' end of the antisense strand was measured and evaluated in the same manner as in Test Example 13. FIG. 26 shows the knockdown activity of siRNAs having I-94 or I-95 at the 5' end of the antisense strand, as well as the knockdown activity of 454-A having natural adenosine monophosphate in the position corresponding to I-94 or I-95 in the sequence.

The results of Test Example 25 show that an siRNA having I-94 or I-95 at the 5' end of the antisense strand exhibits higher knockdown activity than an siRNA having a natural-type nucleotide corresponding to the 5' end of the antisense strand.

Test Example 26: Knockdown Activity of Luciferase-Targeting siRNAs

The activity of an siRNA having the compound obtained in Example 98 at the 5' end of the antisense strand was measured and evaluated in the same manner as in Test Example 13. FIG. 27 shows the knockdown activities of an siRNA having I-96 at the 5' end of the antisense strand, as well as 454-A having natural adenosine monophosphate in the position corresponding to I-96 in the sequence.

The results of Test Example 26 show that an siRNA having I-96 at the 5' end of the antisense strand exhibits higher knockdown activity than an siRNA having a natural-type nucleotide corresponding to the 5' end of the antisense strand.

Test Example 27: Knockdown Activity of Luciferase-Targeting siRNAs

The activity of siRNAs having the compounds obtained in Examples 99, 100, 101, 102 and 103 at the 5' end of the antisense strand was measured and evaluated in the same manner as in Test Example 13. FIG. 28 shows the knockdown activity of siRNAs having I-97, I-98, I-99, I-100 or I-101 at the 5' end of the antisense strand, as well as the knockdown activity of 454-A having natural adenosine monophosphate in the position corresponding to I-97, I-98, I-99, I-100 or I-101 in the sequence.

The results of Test Example 27 show that an siRNA having I-97, I-98, I-99, I-100 or I-101 at the 5' end of the antisense strand exhibits higher knockdown activity than an siRNA having a natural-type nucleotide corresponding to the 5' end of the antisense strand.

INDUSTRIAL APPLICABILITY

According to the present invention, an oligonucleotide having an improved affinity for AGO2 and the like are provided.

The invention claimed is:

1. An oligonucleotide, comprising a nucleotide residue or a nucleoside residue represented by formula (I) at the 5' end thereof, wherein the nucleotide residue or the nucleoside residue binds to an adjacent nucleotide residue through the oxygen atom at position 3:

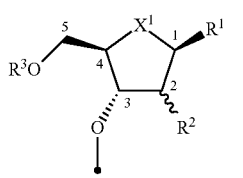
(I)

{wherein $X^1$ is an oxygen atom, a sulfur atom, a selenium atom, or $NR^4$ (wherein $R^4$ is a hydrogen atom, optionally substituted lower alkyl, optionally substituted lower alkenyl, optionally substituted lower alkynyl, optionally substituted lower alkanoyl, optionally substituted lower alkyl sulfonyl, optionally substituted aralkyl, optionally substituted aryl, optionally substituted aroyl, or optionally substituted aromatic heterocyclic carbonyl), $R^1$ is formula (II):

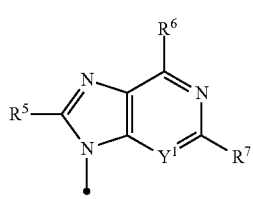
(II)

{wherein $Y^1$ is a nitrogen atom or $CR^8$ [wherein $R^8$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted aryl, optionally substituted aralkyl, an optionally substituted aromatic heterocyclic group, optionally substituted aromatic heterocyclic alkyl, —$NR^{9a}R^{9b}$ (wherein $R^{9a}$ and $R^{9b}$ may be the same or different, and each is a hydrogen atom, optionally substituted lower alkyl, or optionally substituted aralkyl), or —$CONR^{9c}R^{9d}$ (wherein $R^{9c}$ and $R^{9d}$ may be the same or different, and each is a hydrogen atom or optionally substituted lower alkyl)], R[5] is a hydrogen atom, halogen, cyano, carboxy, optionally substituted lower alkyl, optionally substituted cycloalkyl, optionally substituted lower alkenyl, optionally substituted lower alkynyl, optionally substituted lower alkoxy, optionally substituted lower alkoxycarbonyl, optionally substituted lower alkylthio, optionally substituted lower alkanoyl, optionally substituted aryl, an optionally substituted aromatic heterocyclic group, an optionally substituted aliphatic heterocyclic group, —NR[10a]R[10b] (wherein R[10a] and R[10b] have the same meanings as R[9a] and R[9b] described above, respectively), —CONR[10c]R[10d] (wherein R[10c] and R[10d] have the same meanings as R[9c] and R[9d] described above, respectively), —N=C—R[10e] (wherein R[10e] is a hydrogen atom or optionally substituted lower alkyl), —C=N—R[10f] (wherein R[10f] is a hydrogen atom or optionally substituted lower alkyl), or —N=N—R[10g] (wherein R[10g] is a hydrogen atom or optionally substituted lower alkyl), R[6] is an aralkyloxy substituted with a substituent or substituents containing an acidic functional group, a lower alkylthio substituted with a substituent or substituents containing an acidic functional group, or an arylthio substituted with a substituent or substituents containing an acidic functional group, R[7] is a hydrogen atom, an isostere of a hydrogen atom in the nucleic acid field, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR[11a]R[11b] (wherein R[11a] and R[11b] may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkyl sulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), —CONR[11c]R[11d] (wherein R[11c] and R[11d] may be the same or different, and each is a hydrogen atom, optionally substituted lower alkyl, optionally substituted aryl, or an optionally substituted aromatic heterocyclic group), —NHCONR[11e]R[11f] (wherein R[11e] and R[11f] may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO₂R[11g] (wherein R[11g] is optionally substituted lower alkyl, optionally substituted aralkyl, optionally substituted aromatic heterocyclic alkyl, optionally substituted aryl, or an optionally substituted aromatic heterocyclic group), provided that when Y[1] is a nitrogen atom, R[5] is a hydrogen atom, R[6] is —NR[11a]R[11b] and R[7] is a hydrogen atom, R[11a] and R[11b] are not simultaneously hydrogen atoms}, R[2] is a hydrogen atom, and R[3] is a hydrogen atom or

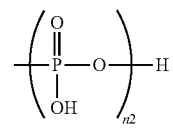

(wherein n2 is 1, 2, or 3)}.

2. An oligonucleotide, comprising a nucleotide residue or a nucleoside residue represented by formula (I) at the 5' end thereof, wherein the nucleotide residue or the nucleoside residue binds to an adjacent nucleotide residue through the oxygen atom at position 3:

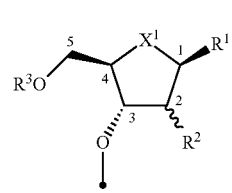

{wherein X[1] is an oxygen atom, a sulfur atom, a selenium atom, or NR[4] (wherein R[4] is a hydrogen atom, optionally substituted lower alkyl, optionally substituted lower alkenyl, optionally substituted lower alkynyl, optionally substituted lower alkanoyl, optionally substituted lower alkyl sulfonyl, optionally substituted aralkyl, optionally substituted aryl, optionally substituted aroyl, or optionally substituted aromatic heterocyclic carbonyl), R[1] is formula (II):

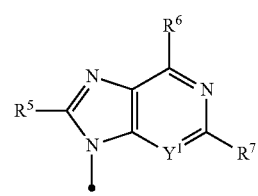

{wherein Y[1] is a nitrogen atom or CR[8] [wherein R[8] is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted aryl, optionally substituted aralkyl, an optionally substituted aromatic heterocyclic group, optionally substituted aromatic heterocyclic alkyl, —NR[9a]R[9b] (wherein R[9a] and R[9b] may be the same or different, and each is a hydrogen atom, optionally substituted lower alkyl, or optionally substituted aralkyl), or —CONR[9c]R[9d] (wherein R[9c] and R[9d] may be the same or different, and each is a hydrogen atom or optionally substituted lower alkyl)], R⁵ is a hydrogen atom, halogen, cyano, carboxy, optionally substituted lower alkyl, optionally substituted cycloalkyl, optionally substituted lower alkenyl, optionally substituted lower alkynyl, optionally substituted lower alkoxy, optionally substituted lower alkoxycarbonyl, optionally substituted lower alkylthio, optionally substituted lower alkanoyl, optionally substituted aryl, an optionally substituted aromatic heterocyclic group, an optionally substituted aliphatic heterocyclic group, —NR$^{10a}$R$^{10b}$ (wherein R$^{10a}$ and R$^{10b}$ have the same meanings as R$^{9a}$ and R$^{9b}$ described above, respectively), —CONR$^{10c}$R$^{10d}$ (wherein R$^{10c}$ and R$^{10d}$ have the same meanings as R$^{9c}$ and R$^{9d}$ described above, respectively), —N=C—R$^{10e}$ (wherein R$^{10e}$ is a hydrogen atom or optionally substituted lower alkyl), —C=N—R$^{10f}$ (wherein R$^{10f}$ is a hydrogen atom or optionally substituted lower alkyl), or —N=N—R$^{10g}$ (wherein R$^{10g}$ is a hydrogen atom or optionally substituted lower alkyl), R⁶ is an aralkyloxy substituted with a substituent or substituents containing an acidic functional group, a lower alkylthio substituted with a substituent or substituents containing an acidic functional group, or an arylthio substituted with a substituent or substituents containing an acidic functional group, R⁷ is a hydrogen atom, an isostere of a hydrogen atom in the nucleic acid field, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR$^{11a}$R$^{11b}$ (wherein R$^{11a}$ and R$^{11b}$ may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkyl sulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), —CONR$^{11c}$R$^{11d}$ (wherein R$^{11c}$ and R$^{11d}$ may be the same or different, and each is a hydrogen atom, optionally substituted lower alkyl, optionally substituted aryl, or an optionally substituted aromatic heterocyclic group), —NHCONR$^{11e}$R$^{11f}$ (wherein R$^{11e}$ and R$^{11f}$ may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO₂R$^{11g}$ (wherein R$^{11g}$ is optionally substituted lower alkyl, optionally substituted aralkyl, optionally substituted aromatic heterocyclic alkyl, optionally substituted aryl, or an optionally substituted aromatic heterocyclic group), provided that when Y¹ is a nitrogen atom, R⁵ is a hydrogen atom, R⁶ is —NR$^{11a}$R$^{11b}$, and R⁷ is a hydrogen atom, R$^{11a}$ and R$^{11b}$ are not simultaneously hydrogen atoms}, R² is a hydrogen atom, hydroxy, halogen, or optionally substituted lower alkoxy, and R³ is a hydrogen atom or

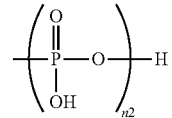

(wherein n2 is 1, 2, or 3).

3. The oligonucleotide according to claim 1 or 2, wherein the acidic functional group is carboxy and/or —OP(=O)(OH)₂.

4. The oligonucleotide according to claim 1 or 2, wherein X¹ is an oxygen atom.

5. The oligonucleotide according to claim 1 or 2, wherein Y¹ is a nitrogen atom.

6. The oligonucleotide according to claim 5,
wherein R⁵ is a hydrogen atom, halogen, cyano, optionally substituted lower alkyl, optionally substituted cycloalkyl, optionally substituted lower alkenyl, optionally substituted lower alkynyl, optionally substituted lower alkoxy, optionally substituted lower alkanoyl, optionally substituted aryl, an optionally substituted aromatic heterocyclic group, an optionally substituted aliphatic heterocyclic group,
—NR$^{10a}$R$^{10b}$ (wherein R$^{10a}$ and R$^{10b}$ have the same meanings as described above, respectively), —CONR$^{10c}$R$^{10d}$ (wherein R$^{10c}$ and R$^{10d}$ have the same meanings as described above, respectively), —N=C—R$^{10e}$ (wherein R$^{10e}$ is a hydrogen atom or optionally substituted lower alkyl), —C=N—R$^{10f}$ (wherein R$^{10f}$ is a hydrogen atom or optionally substituted lower alkyl), or —N=N—R$^{10g}$ (wherein R$^{10g}$ is a hydrogen atom or optionally substituted lower alkyl).

7. The oligonucleotide according to claim 5, wherein R⁵ is a hydrogen atom, halogen, optionally substituted lower alkyl, optionally substituted lower alkenyl, cyano, or —NR$^{10a}$R$^{10b}$ (wherein R$^{10a}$ and R$^{10b}$ have the same meanings as described above, respectively).

8. The oligonucleotide according to claim 5, wherein R⁵ is optionally substituted lower alkenyl or cyano.

9. The oligonucleotide according to claim 1 or 2, wherein R³ is

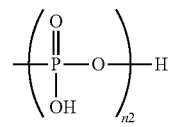

(wherein n2 has the same meaning as described above).

10. The oligonucleotide according to claim 9, wherein n2 is 1.

11. The oligonucleotide according to claim 2, wherein R² is a hydrogen atom, hydroxy, a fluorine atom, or methoxy.

12. The oligonucleotide according to claim 2, wherein R² is hydroxy.

13. The oligonucleotide according to claim 2, wherein R² is a hydrogen atom, or a fluorine atom.

14. The oligonucleotide according to claim 2, wherein $X^1$ is an oxygen atom, and $R^2$ is a hydrogen atom, hydroxy, a fluorine atom, or methoxy.

15. The oligonucleotide according to claim 14, wherein $R^1$ is formula (IIA):

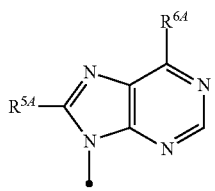

(IIA)

(wherein $R^{5A}$ and $R^{6A}$ have the same meanings as $R^5$ and $R^6$ described above, respectively).

16. The oligonucleotide according to claim 15, wherein $R^{5A}$ is halogen, carbamoyl, optionally substituted lower alkyl, optionally substituted cycloalkyl, optionally substituted lower alkenyl, optionally substituted lower alkynyl, optionally substituted lower alkoxy, optionally substituted lower alkanoyl, optionally substituted lower alkylamino, optionally substituted di-lower alkylamino, optionally substituted lower alkylcarbamoyl, optionally substituted di-lower alkylcarbamoyl, optionally substituted aryl, an optionally substituted aromatic heterocyclic group, an optionally substituted aliphatic heterocyclic group, or —$NR^{10a}R^{10b}$ (wherein $R^{10a}$ and $R^{10b}$ have the same meanings as described above, respectively).

17. The oligonucleotide according to claim 15, wherein $R^{5A}$ is halogen, optionally substituted lower alkyl, optionally substituted lower alkenyl, cyano, or —$NR^{10a}R^{10b}$ (wherein $R^{10a}$ and $R^{10b}$ have the same meanings as described above, respectively).

18. The oligonucleotide according to claim 14, wherein $R^3$ is

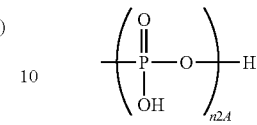

(wherein n2A has the same meaning as described above).

19. The oligonucleotide according to claim 18, wherein n2A is 1.

20. The oligonucleotide according to claim 1 or 2, wherein the oligonucleotide has a length of 10 to 80 bases.

21. The oligonucleotide according to claim 1 or 2, wherein the oligonucleotide has a length of 20 to 50 bases.

22. The oligonucleotide according to claim 1 or 2, wherein the oligonucleotide has a length of 20 to 30 bases.

23. The oligonucleotide according to claim 1 or 2, wherein the oligonucleotide has a length of 21 to 25 bases.

24. The oligonucleotide according to claim 1 or 2, wherein the oligonucleotide is a double-stranded oligonucleotide.

25. The oligonucleotide according to claim 1 or 2, wherein the oligonucleotide is a single-stranded oligonucleotide.

26. The oligonucleotide according to claim 1 or 2, wherein the oligonucleotide is a small interfering RNA (siRNA).

* * * * *